(12) United States Patent
Kuvaeva et al.

US009051591B2

(10) Patent No.: US 9,051,591 B2
(45) Date of Patent: Jun. 9, 2015

(54) BACTERIUM OF ENTEROBACTERIACEAE FAMILY PRODUCING L-ASPARTIC ACID OR L-ASPARTIC ACID-DERIVED METABOLITES AND A METHOD FOR PRODUCING L-ASPARTIC ACID OR L-ASPARTIC ACID-DERIVED METABOLITES

(75) Inventors: Tatyana Mikhailovna Kuvaeva, Moscow (RU); Sergey Vasilievich Smirnov, Moscow (RU); Olga Nikolaevna Ivanova, Moscow (RU); Aleksandr Dmitrievich Kivero, Moscow (RU); Joanna Yosifovna Katashkina, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 13/543,360

(22) Filed: Jul. 6, 2012

(65) Prior Publication Data

US 2012/0329105 A1 Dec. 27, 2012

Related U.S. Application Data

(63) Continuation of application No. PCT/JP2011/050797, filed on Jan. 12, 2011.

(30) Foreign Application Priority Data

Jan. 15, 2010 (RU) .............................. 2010101135

(51) Int. Cl.
| | |
|---|---|
| *C12N 9/06* | (2006.01) |
| *C12N 9/88* | (2006.01) |
| *C12N 1/21* | (2006.01) |
| *C12P 13/10* | (2006.01) |
| *C12P 13/20* | (2006.01) |
| *C12P 13/06* | (2006.01) |
| *C12P 13/08* | (2006.01) |
| *C12P 13/12* | (2006.01) |
| *C12N 9/00* | (2006.01) |

(52) U.S. Cl.
CPC ......... *C12P 13/20* (2013.01); *C12Y 104/01021* (2013.01); *C12P 13/06* (2013.01); *C12P 13/08* (2013.01); *C12P 13/12* (2013.01); *C12N 9/88* (2013.01); *C12N 9/93* (2013.01); *C12N 9/0016* (2013.01); *C12P 13/10* (2013.01)

(58) Field of Classification Search
None
See application file for complete search history.

(56) References Cited

U.S. PATENT DOCUMENTS

| | | | |
|---|---|---|---|
| 4,000,040 A | 12/1976 | Tsuchida et al. | |
| 4,278,765 A | 7/1981 | Debabov et al. | |
| 4,346,170 A | 8/1982 | Sano et al. | |
| 5,661,012 A | 8/1997 | Sano et al. | |
| 6,040,160 A | 3/2000 | Kojima et al. | |
| 6,071,728 A | 6/2000 | Eyal et al. | |
| 7,604,979 B2 | 10/2009 | Katashkina et al. | |
| 7,670,822 B2 | 3/2010 | Smirnov et al. | |
| 7,785,858 B2 | 8/2010 | Kozlov et al. | |
| 8,114,651 B2 | 2/2012 | Kodera et al. | |
| 2010/0267094 A1 | 10/2010 | Kozlov et al. | |
| 2010/0323409 A1 | 12/2010 | Smirnov et al. | |
| 2010/0330622 A1 | 12/2010 | Smirnov et al. | |
| 2011/0183382 A1* | 7/2011 | Schmalisch et al. ......... 435/109 |

FOREIGN PATENT DOCUMENTS

| | | |
|---|---|---|
| EP | 1 057 893 | 12/2000 |
| EP | 1 172 433 | 1/2002 |
| JP | 2006-254730 | 9/2006 |
| JP | 2006-254795 | 9/2006 |
| JP | 2010-183860 | 8/2010 |
| RU | 2337959 | 11/2008 |
| WO | WO 2007/017710 | 2/2007 |
| WO | 2007/083789 | 7/2007 |
| WO | WO 2009/022754 | 2/2009 |
| WO | WO 2010/038905 | 4/2010 |
| WO | WO 2011/087139 | 7/2011 |

OTHER PUBLICATIONS

U.S. Appl. No. 61/286,729, filed Dec. 15, 2009.*
Japanese Published Patent Application 2006-254795, English-language machine translation, published Sep. 28, 2006.*
Kretovich et al., The synthesis of aspartic acid in Rhizobium lupine bacteroids, Plant and Soil, 1981, 61, 145-56.*
Yoneda et al., The first archael L-aspartate dehydrogenase from the hyperthermophile Archaeoglobus fulgidus: Gene cloning and enzymological characterization, Biochim. Biophys. Acta, 2006, 1764, 1087-93.*
UniProt, Accession No. Q89FY1, Dec. 2009, www.uniprot.org.*
Cooper, THE CELL: A MOLECULAR APPROACH, Chapter 2, ASM Press, 1997.*
Emmerling et al.,Metabolic Flux Responses to Pyruvate Kinase Knockout in *Escherichia coli*, J. Bacteriol., 2002, 184, 152-64.*
Cunin et al., Biosynthesis and metabolism of arginine in bacteria, Microbiol. Reviews, 1986, 50, 314-352.*
Helling, Why Does *Escherichia coli* Have Two Primary Pathways for Synthesis of Glutamate?, J. Bacteriol., 1994, 176, 4664-68.*
U.S. Appl. No. 13/344,110, Kodera et al., filed Jan. 5, 2012.
U.S. Appl. No. 13/344,170, Kodera et al., filed Jan. 5, 2012.
U.S. Appl. No. 13/344,200, Kodera et al., filed Jan. 5, 2012.
DATABASE WPI, Week 200673, Thomson Scientific, London, GB; AN2006-700717 (Mar. 17, 2005).
DATABASE WPI, Week 200674, Thomson Scientific, London, GB; AN2006-711889 (Mar. 15, 2005).

(Continued)

*Primary Examiner* — Rebecca Prouty
*Assistant Examiner* — Todd M Epstein
(74) *Attorney, Agent, or Firm* — Shelly Guest Cermak; Cermak Nakajima & McGowan LLP

(57) ABSTRACT

The presently disclosed subject matter provides a bacterium of Enterobacteriaceae family producing L-aspartic acid or an L-aspartic acid-derived metabolite modified to have aspartate dehydrogenase and a method for producing L-aspartic acid or an L-aspartic acid-derived metabolite, such as L-threonine, L-lysine, L-arginine, L-methionine and L-homoserine, using such bacterium.

7 Claims, 23 Drawing Sheets

(56) References Cited

OTHER PUBLICATIONS

Katashkina, J. I., et al., "Use of the λ Red-recombineering method for genetic engineering of *Pantoea ananatis*," BMC Mol. Biol. 2009;10(1):1-11.

Kuznetsova, E., et al., "Enzyme genomics: Application of general enzymatic screens to discover new enzymes," FEMS Microbiol. Rev. 2005;29:263-279.

Yang, Z., et al., "Aspartate Dehydrogenase, a Novel Enzyme Identified from Structural and Functional Studies of TM1643," J. Biol. Chem. 2003;278(10):8804-8808.

Yoneda, K., et al., "The first archaeal L-aspartate dehydrogenase from the hyperthermophile *Archaeoglobus fulgidus*: Gene cloning and enzymological characterization," Biochimica et Biophysica Acta 2006;1764:1087-1093.

International Search Report and Written Opinion for PCT Patent App. No. PCT/JP2011/050797 (Aug. 1, 2011).

Li, Y., et al., "A Non-NadB Type L-Aspartate Dehydrogenase from *Ralstonia eutropha* Strain JMP134: Molecular Characterization and Physiological Functions," Biosci. Biotechnol. Biochem. 2011;75(8):1524-1532.

Li, Y., et al., "A novel L-aspartate dehydrogenase from the mesophilic bacterium *Pseudomonas aeruginosa* PAO1: molecular characterization and application for L-aspartate production," Appl. Microbiol. Biotechnol. 2011;90:1953-1962.

Li, Y., et al., "L-Aspartate dehydrogenase: features and applications," Appl. Microbiol. Biotechnol. 2012;93:503-516.

Office Action from Japanese Patent App. No. 2012-532187 (Apr. 7, 2015) with English translation.

\* cited by examiner

Fig. 3

```
GENE ID: 4013636 Bpro_3686 | L-aspartate dehydrogenase [Polaromonas sp.
JS666]

Score =  114 bits (286),  Expect = 5e-24, Method: Compositional matrix
adjust.
 Identities = 75/259 (28%), Positives = 125/259 (48%), Gaps = 26/259 (10%)

Query 1     MTVLIIGMGNIGKKLVELGNFEKIYAYDRI--------------SKDIPGVVRLDEFQVP  46
            + + +IG G IG  ++EL + +     DR+              ++  P    L+
Sbjct 2     LKIAMIGCGAIGASVLELLHGDSDVVVDRVITVPEARDRTEIAVARWAPRARVLEVLAAD  61

Query 47    SDVSTVVECASPEAVKEYSLQILKNPVNYIIISTSAFADEVFRERFFSELKNSPARVFFP  106
                 VVECA   A+ + +  L+ + ++ S  A +       +      +V
Sbjct 62    DAPDLVVECAGHGAIAAHVVPALERGIPCVVTSVGALSAPGMAQLLEQAARRGKTQVQLL  121

Query 107   SGAIGGLDVLSSIK-DFVKNVRIETIKPPKSLG-------LDLKGKTV---VFEGSVEEA  155
            SGAIGG+D L++ +  + +V    KPP +          DL    TV   +F+GS E+A
Sbjct 122   SGAIGGIDALAAARVGGLDSVVYTGRKPPMAWKGTPAEAVCDLDSLTVAHCIFDGSAEQA  181

Query 156   SKLFPRNINVASTIGLI-VGFEKVKVTIVADPAMDHNIHIVRISSAIGNYEFKIENIPSP  214
            ++L+P+N NVA+T+ L  +G ++ +V + ADP + N+H V    A G++E  +    P
Sbjct 182   AQLYPKNANVAATLSLAGLGLKRTQVQLFADPGVSENVHHVAAHGAFGSFELTMRGRPLA  241

Query 215   ENPKTSMLTVYSILRTLRN  233
            NPKTS LTVYS++R L N
Sbjct 242   ANPKTSALTVYSVVRALLN  260
```

Fig. 7

```
     Polaromonas sp. JS666    (1) ----------MLKIAMIGCGAIGASVLELLHGDSDVVVDR
         Delftia acidovorans  (1) ---------MTMNIAVIGCGAIGASVLELLKGHAAVQVG-
       Comamonas testosteroni (1) ----------MKNIALIGCGAIGSSVLELLSGDTRLQVG-
           Ralstonia eutropha (1) --------MSMLHVSMVGCGAIGRGVLELLKADPDVAFDV
       Pseudomonas aeruginosa (1) ----------MLNIVMIGCGAIGAGVLELLENDPQLRVDA
     Burkholderia cenocepacia (1) MHNGQKRARAPVDVAMIGFGAIGAAVYRAVEHDASLRVAH
           R. palustris RPB_3108 (1) -----------MKIAVIGYGAIGRFLIEQLDAVPDFEIAA
           R. palustris RPB_0147 (1) ----MRSGRAPQRVAIAGLGAIGKAIARELDRGLDGLTLG
                       TM1643  (1) ----------MTVLIIGMGNIGKKLVELGNFEKIYAYD-
                    Consensus  (1)           L IAMIGCGAIGASVLELL GD   L V 41                                         80
     Polaromonas sp. JS666   (31) VITVPEARDRTEIAVARWAPRARVLEVLAADDAPDLVVEC
         Delftia acidovorans (31) WVLVPEVTDAVRATLARHAPQARALPALTIEDRPDLIVEC
       Comamonas testosteroni(30) WILVPEITPAVRETVARLAPQAQLLQALPGDAVPDLLVEC
           Ralstonia eutropha(33) VIVPEGQMDEARSALSALAPNVRVATGLDGQ-RPDLLVEC
       Pseudomonas aeruginosa(31) VIVPRDSETQVRHRLASLRRPPRVLSALPAGERPDLLVEC
     Burkholderia cenocepacia(41) VIVPEHQRAAVQRELGGAVEVVSSVDALARR--PEFALEC
           R. palustris RPB_3108(30) VYSVPAPPDRAERVVDDLD---ALLATR--P---DLVVEC
           R. palustris RPB_0147(37) -AVASGDPEKHRAFLDGLRTTPPVVPLDQLHAHADLVIEA
                       TM1643 (29) -----------RISKDIP-GVVRLDEFQVPSDVSTVVEC
                    Consensus (41) VIV     D R  LA L      VL AL      PDLVVEC 81                                        120
     Polaromonas sp. JS666   (71) AGHGAIAAHVVPALERGIPCVVTSVGALSAPGMAQLLEQA
         Delftia acidovorans (71) AGHTAIEEHVLPALRRGIPAVVASIGALSAPGMAEAVQAA
       Comamonas testosteroni(70) AGHAAIEEHVLPALTRGIPAVIASIGALSAPGMAERVQAA
           Ralstonia eutropha(72) AGHQALEEHIVPALERGIPCMVVSVGALSEPGLVERLEAA
       Pseudomonas aeruginosa(71) AGHRAIEQHVLPALAQGIPCLVVSVGALSEPGLVERLEAA
     Burkholderia cenocepacia(79) AGHGALVDHVVPLLKAGTDCAVASIGALSDLALLDVLSQA
           R. palustris RPB_3108(62) AGHRALSECGEAVLRSGVDLLVVSVGALADPALEQQLRTA
           R. palustris RPB_0147(76) APSRLLRAIVEPFVSRGRTAIVLSAAALLQN---EDLIDL
                       TM1643 (56) ASPEAVKEYSLQILKNPVNYIIISTSAFADEVFRERFFSE
                    Consensus (81) AGH AI EHVLPAL RGIP VVVSVGALSDPGL E L AA 121                                       160
     Polaromonas sp. JS666  (111) ARRGKTQVQLLSGAIGGIDALAAARVGGLDSVVYTGRKPP
         Delftia acidovorans(111) AEAGGTQVQLLSGAIGGVDALAAARIGGLDEVVYTGRKPP
       Comamonas testosteroni(110) AEAGKTQAQLLSGAIGGIDALAAARVGGLETVVYTGRKPP
           Ralstonia eutropha(112) ARRGNTQVQLLSGAIGAIDALAAARVGGLDEVIYTGRKPA
       Pseudomonas aeruginosa(111) AQAGGSRIELLPGAIGAIDALSAARVGGLESVRYTGRKPA
     Burkholderia cenocepacia(119) ADEGGTTVTLLSGAIGGIDALASAKEGGLDEVRYGRKPP
           R. palustris RPB_3108(102) ARHGG-RLLIAAGALSGLDALSTAREAGLDSVSYVGKKAP
           R. palustris RPB_0147(113) ANLNGGQIIVPTGALIGLDAVTAAAVGTIHSVRMITRKPV
                       TM1643 (96) LKNSPARVFFPSGAIGGLDVLSSIKDFVKNVRIETIKPPK
                    Consensus(121) A  GGTQV LLSGAIGGIDALAAARVGGLDSVVYTGRKPP
```

Fig. 8

```
                              161                                    200
    Polaromonas sp. JS666  (151) MAWKGTPAEAV--CDLDSLTVAHCIFDGSAEQAAQLYPKN
       Delftia acidovorans (151) LAWTGTPAEQR--CDLASLKEAFCIFEGSAREAAQLYPKN
     Comamonas testosteroni (150) KAWSGTPAEQV--CDLDGLTEAFCIFEGSAREAAQLYPKN
         Ralstonia eutropha (152) RAWTGTPAAEL--FDLEALTEPTVIFEGTARDAARLYPKN
      Pseudomonas aeruginosa (151) SAWLGTPGETV--CDLQRLEKARVIFDGSAREAARLYPKN
    Burkholderia cenocepacia (159) LGWLGTPAEEL--CDLRAMTEEKVIFEGSARDAARLYPKN
          R. palustris RPB_3108 (141) AAWTNTPAEDM--VDLTSITSAVTFLECDARTAALRFPQN
          R. palustris RPB_0147 (153) DGLRGAPFIVDNGIDLDGLREPLKLFEGTAREAGKGFPAN
                       TM1643 (136) SLGLDLKG------------KTVVFEGSVEEASKLFPRN
                    Consensus (161)  AW GTPAE V  CDL SLTEA  IFEGSAREAARLYPKN 201                                    240
    Polaromonas sp. JS666  (189) ANVAATLSLAGLGLKRTQVQLFADPGVSENVHHVAAHGAF
       Delftia acidovorans (189) ANVAATLSLAGMGLDRTTVRLYADPAVDENVHHVAARGAF
     Comamonas testosteroni (188) ANVAATLSLAGLGLDKTMVRLFADPGVHENVHQVEARGAF
         Ralstonia eutropha (190) ANVAATVSLAGLGLDRTSVRLLADPNAVENVHHIEARGAF
      Pseudomonas aeruginosa (189) ANVAATLSLAGLGLDRTQVRLIADPESCENVHQVEASGAF
    Burkholderia cenocepacia (197) ANVAATVALAGLGLDATHVRLIADPAVERNVHRITARGAF
          R. palustris RPB_3108 (179) ANVVAAIALAGLGFERTQVSLVVDPASNGNNHSFVARGAF
          R. palustris RPB_0147 (193) LNVAVALSLAGIGPDRTMVEIWADPGVTRNTHRIEVDADS
                       TM1643 (163) INVASTIG-LIVGFEKVKVTIVADPAMDHNIHIVRISSAI
                    Consensus (201) ANVAATLSLAGLGLDRT VRLIADPAV ENVH V ARGAF 241                                    280
    Polaromonas sp. JS666  (229) GSFELTMRGRPLAANPKTSALTVYSVVRALLNRGRALVI-
       Delftia acidovorans (229) GSMELTMRGKPLEANPKTSALTVYSVVRAVLNQATAIAI-
     Comamonas testosteroni (228) GAMELTMRGKPLAANPKTSALTVYSVVRSVLNNVAPLAI-
         Ralstonia eutropha (230) GGFELTMRGKPLAANPKTSALTVFSVVRALGNRAHAVSI-
      Pseudomonas aeruginosa (229) GGFELTLRGKPLAANPKTSALTVYSVVRALGNHAHAISI-
    Burkholderia cenocepacia (237) GEMSLEMSGKPLPDNPKTSALTAYSAIRALRNRAACCVI-
          R. palustris RPB_3108 (219) GEIAMTTRSATLPANPKTSMLAPYSLVQTIKKHAGLIIV-
          R. palustris RPB_0147 (233) ARFAMTIENVP-SDNPRTGLITPLSVIALLRKQSAALRVG
                       TM1643 (202) GNYEFKIENIPSPENPKTSMLTVYSILRTLRNLESKIIFG
                    Consensus (241) G FELTMRGKPLAANPKTSALTVYSVVRAL N A AI I
```

Fig. 12
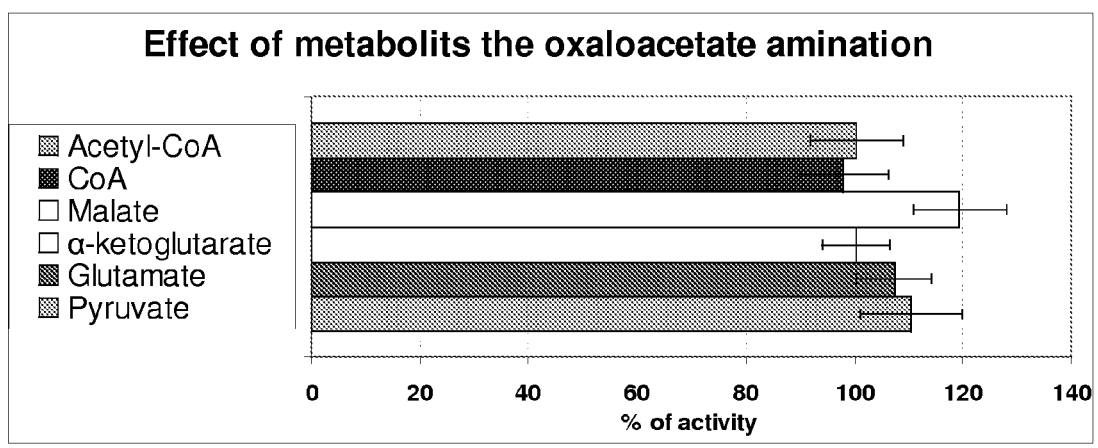
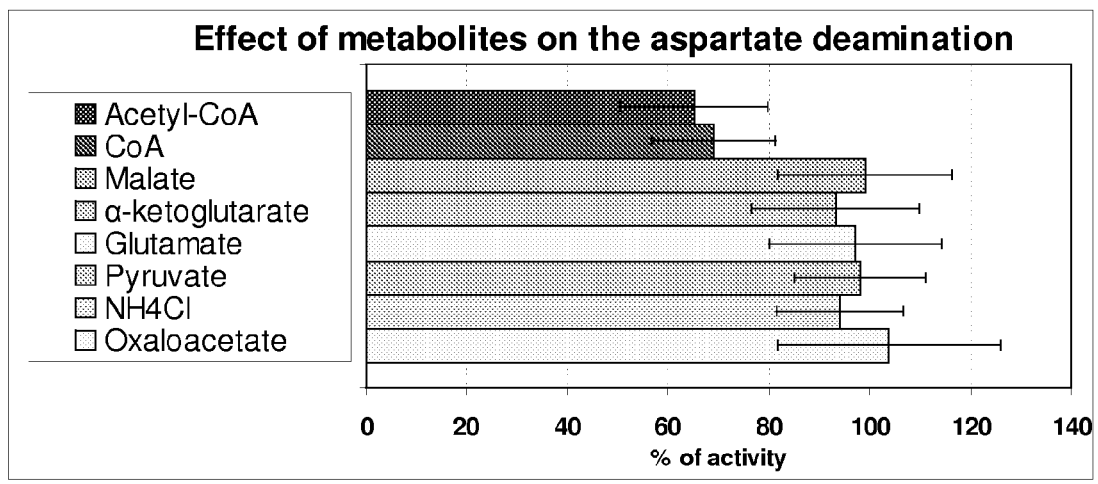

BACTERIUM OF ENTEROBACTERIACEAE FAMILY PRODUCING L-ASPARTIC ACID OR L-ASPARTIC ACID-DERIVED METABOLITES AND A METHOD FOR PRODUCING L-ASPARTIC ACID OR L-ASPARTIC ACID-DERIVED METABOLITES

This application is a Continuation of, and claims priority under 35 U.S.C. §120 to, International Application No. PCT/JP2011/050797, filed Jan. 12, 2011, and claims priority therethrough under 35 U.S.C. §119 to Russian Patent Application No. 2010101135, filed Jan. 15, 2010, the entireties of which are incorporated by reference herein. Also, the Sequence Listing filed electronically herewith is hereby incorporated by reference (File name: 2012-07-06T_US-407_Seq_List; File size: 192 KB; Date recorded: Jul. 6, 2012).

BACKGROUND OF THE INVENTION

1. Field of the Invention

The present invention relates to the microbiological industry, and specifically to a method for producing L-aspartic acid or L-aspartic acid-derived metabolites using a bacterium of Enterobacteriaceae family which has been modified to have aspartate dehydrogenase.

2. Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (U.S. Pat. No. 4,278,765). Other techniques for enhancing production yields include increasing the activities of enzymes involved in amino acid biosynthesis and/or desensitizing the target enzymes to feedback inhibition by the resulting L-amino acid (U.S. Pat. Nos. 4,346,170, 5,661,012 and 6,040,160).

L-aspartic acid is a useful metabolite having different applications (aspartame sweetener, biodegradable polymers, etc.). In the currently used industrial process, aspartic acid is produced enzymatically from fumarate using aspartase. In turn, fumarate can be obtained by chemical synthesis, as a product of oil distillation or from hydrocarbons in bacterial fermentation process.

A known three-step production process includes the steps of: 1) production of calcium-fumarate in fermentation of a bacterial strain; 2) conversion of the calcium-fumarate to diammonium fumarate by addition of ammonia, ammonium carbonate or ammonia in combination with $CO_2$; and 3) enzymatic conversion of the obtained diammonium fumarate to ammonium aspartate by aspartase (U.S. Pat. No. 6,071,728).

Direct methods for producing L-aspartic acid from carbohydrates or hydrocarbons in bacterial fermentation have been previously developed using bacteria belonging to the genus *Corynebacterium* or *Brevibacterium* (U.S. Pat. No. 4,000,040). Some wild-type strains of these genera are the natural producers of L-aspartic acid. These methods and bacteria relate to the process of selecting the induced mutants with increased producing ability.

It has been shown by Yang Zh. et al (J. Biol. Chem., 278 (10): 8804-8808 (2003)), that aspartate dehydrogenase isolated from *Thermotaoga maritima* can catalyze the forward reaction of aspartate synthesis from oxaloacetate and ammonia in vitro. Use of this reaction for aspartate synthesis could help to avoid the glutamate by-production. On the other hand, the authors have proposed that the role of this enzyme in vivo is the conversion of aspartic acid to iminoaspartic acid, the precursor of NAD biosynthesis. Moreover, it has been shown that the aspartate dehydrogenase from *T. maritima* has a high optimum temperature (+70° C.) and saves only low residual activity at +30° C.-+40° C.

But currently, there have been no reports of using a bacterium of Enterobacteriaceae family modified to have aspartate dehydrogenase for producing L-aspartic acid or L-aspartic acid-derived metabolites.

SUMMARY OF THE INVENTION

Aspects of the presently disclosed subject matter can include enhancing the productivity of L-aspartic acid-producing strains and providing a method for producing L-aspartic acid or L-aspartic acid-derived metabolites using these strains.

The above aspects can be achieved by modifying a bacterium of Enterobacteriaceae family to have aspartate dehydrogenase, which can enhance production of L-aspartic acid by the bacterium.

The presently disclosed subject matter can include a bacterium of Enterobacteriaceae family which has an increased ability to produce L-aspartic acid or an L-aspartic acid-derived metabolite and a method for producing L-aspartic acid or an L-aspartic acid-derived metabolite using the bacterium.

It is an aspect of the presently disclosed subject matter to provide a bacterium of Enterobacteriaceae family which produces L-aspartic acid or an L-aspartic acid-derived metabolite, wherein the bacterium can be modified to have aspartate dehydrogenase.

It is a further aspect of the presently disclosed subject matter to provide the bacterium as described above, wherein the bacterium can be modified by introducing the gene coding for aspartate dehydrogenase.

It is a further aspect of the presently disclosed subject matter to provide the bacterium as described above, wherein the gene coding for aspartate dehydrogenase can be derived from *Thermotaoga maritima*.

It is a further aspect of the presently disclosed subject matter to provide the bacterium as described above, wherein said gene coding for aspartate dehydrogenase can be derived from *Polaromonas* sp.

It is a further aspect of the presently disclosed subject matter to provide the bacterium as described above, wherein said gene coding for aspartate dehydrogenase can be derived from *Rhodopseudomonas palustris*.

It is a further aspect of the presently disclosed subject matter to provide the bacterium as described above, wherein said gene coding for aspartate dehydrogenase can be derived from *Ralstonia eutropha*.

It is a further aspect of the presently disclosed subject matter to provide the bacterium as described above, wherein said gene coding for aspartate dehydrogenase can be derived from *Azorhizobium caulinodans*.

It is a further aspect of the presently disclosed subject matter to provide the bacterium as described above, wherein said gene coding for aspartate dehydrogenase can be derived from *Bradyrhizobium japonicum*.

It is a further aspect of the presently disclosed subject matter to provide the bacterium as described above, wherein said gene coding for aspartate dehydrogenase can be derived from *Mesorhizobium* sp.

It is a further aspect of the presently disclosed subject matter to provide the bacterium as described above, wherein said gene coding for aspartate dehydrogenase can be derived from *Corynebacterium glutamicum*.

It is a further aspect of the presently disclosed subject matter to provide the bacterium as described above, wherein said gene coding for aspartate dehydrogenase can be derived from *Nitrosopumilus maritimus*.

It is a further aspect of the presently disclosed subject matter to provide the bacterium as described above, wherein said gene coding for aspartate dehydrogenase can be derived from *Oceanicola granulosus*.

It is a further aspect of the presently disclosed subject matter to provide the bacterium as described above, wherein the bacterium can be the bacterium belonging to the genus *Pantoea*.

It is a further aspect of the presently disclosed subject matter to provide the bacterium as described above, wherein the bacterium is *Pantoea ananatis*.

It is a further aspect of the presently disclosed subject matter to provide the bacterium as described above, wherein the bacterium can be the bacterium belonging to the genus *Escherichia*. It is a further aspect of the presently disclosed subject matter to provide the bacterium as described above, wherein the bacterium is *Escherichia coli*.

It is a further aspect of the presently disclosed subject matter to provide the bacterium as described above, wherein wherein the bacterium produces L-aspartic acid.

It is a further aspect of the presently disclosed subject matter to provide the bacterium as described above, wherein wherein the bacterium produces an L-aspartic acid-derived metabolite.

It is a further aspect of the presently disclosed subject matter to provide the bacterium as described above, wherein the L-aspartic acid-derived metabolites can include L-threonine, L-lysine, L-arginine, L-methionine and L-homoserine.

It is a further aspect of the presently disclosed subject matter to provide the bacterium as described above, wherein said L-aspartic acid-derived metabolite is L-arginine.

It is a further aspect of the presently disclosed subject matter to provide the bacterium as described above, wherein the bacterium has been further modified to have at least:
- decreased activity of α-ketoglutarate dehydrogenase;
- decreased activity of citrate synthase;
- increased activity of phosphoenolpyruvate carboxylase or pyruvate carboxylase;
- decreased activity of aspartate ammonia-lyase;
- decreased activity of pyruvate kinase.

It is a further aspect of the presently disclosed subject matter to provide the bacterium as described above, wherein the bacterium has been further modified to have decreased activity of malate dehydrogenase.

It is a further aspect of the presently disclosed subject matter to provide a method for producing L-aspartic acid or an L-aspartic acid-derived metabolite that can include:
- cultivating any of the bacterium described above in a culture medium, and
- collecting the L-aspartic acid or the L-aspartic acid-derived metabolite from the medium.

It is a further aspect of the presently disclosed subject matter to provide the method as described above, by which L-aspartic acid is produced.

It is a further aspect of the presently disclosed subject matter to provide the method as described above, by which an L-aspartic acid-derived metabolite is produced.

It is a further aspect of the presently disclosed subject matter to provide the method as described above, wherein the L-aspartic acid-derived metabolites can include L-threonine, L-lysine, L-arginine, L-methionine and L-homoserine.

It is a further aspect of the presently disclosed subject matter to provide the method as described above, wherein said L-aspartic acid-derived metabolite is L-arginine.

BRIEF DESCRIPTION OF THE DRAWINGS

FIG. 3 shows alignments of the aspartate dehydrogenase from *T. maritima* (nucleotides 1 to 233 of SEQ ID NO: 2) and its homolog from *Polaromonas* sp. JS666 (nucleotides 2 to 260 of SEQ ID NO: 4).

FIG. 7 shows alignment of several homologues of the aspartate dehydrogenase from *Polaromonas* sp. JS666.
*Polaromonas* sp. JS666 (SEQ ID NO: 4)
*Delftia acidovorans* (SEQ ID NO: 100)
*Comamonas testosteroni* (SEQ ID NO: 102)
*Ralstonia eutropha* (SEQ ID NO: 104)
*Pseudomonas aeruginosa* (SEQ ID NO: 106)
*Burkholderia cenocepacia* (SEQ ID NO: 108)
*Rhodopseudomonas palustris* RPB_3108 (SEQ ID NO: 110)
*Rhodopseudomonas palustris* RPB_0147 (SEQ ID NO: 112)
Consensus (SEQ ID NO: 113)

FIG. 8 shows alignment of several homologues of the aspartate dehydrogenase from *Polaromonas* sp. JS666 (continued).

FIG. 12 shows regulatory properties of the *Polaromonas* sp. aspartate dehydrogenase.

K: BL21(DE3)/pET15b
M: protein marker SM0431
Lanes 7, 8: BL21(DE3)/pET15-ADH1-Rp, clones 7 and 8.

Figure 17:
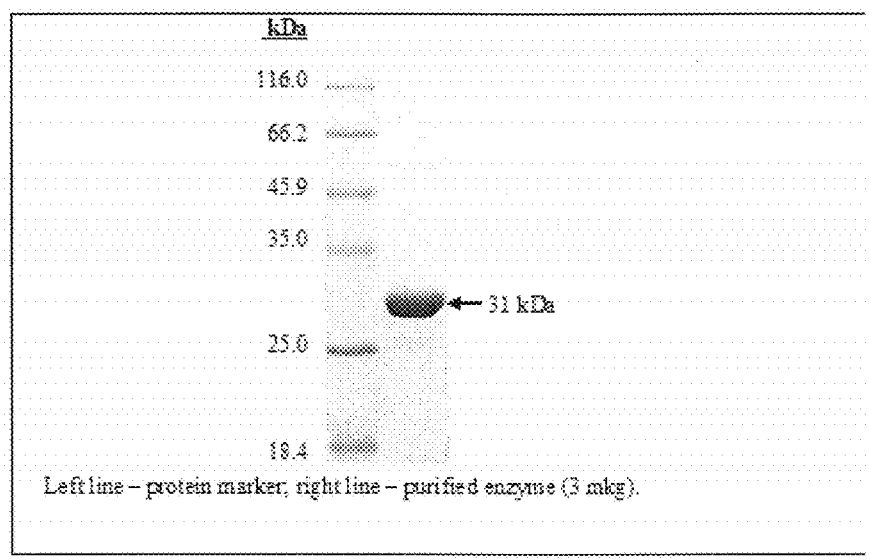

FIG. 17 is a photograph of SDS-PAGE of the purified *Rhodopseudomonas palustris* aspartate dehydrogenase (ADH1-Rp).

Figure 18:
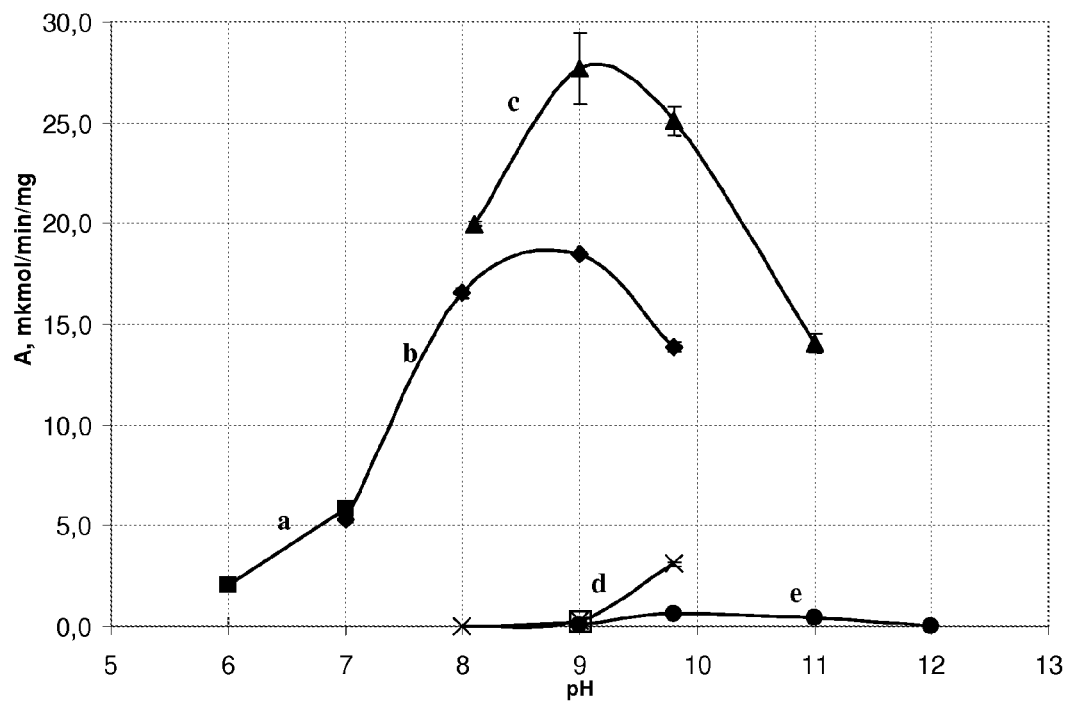

FIG. 18 shows effect of pH on catalysis of *Rhodopseudomonas palustris* ADH1-Rp.

Figure 19:
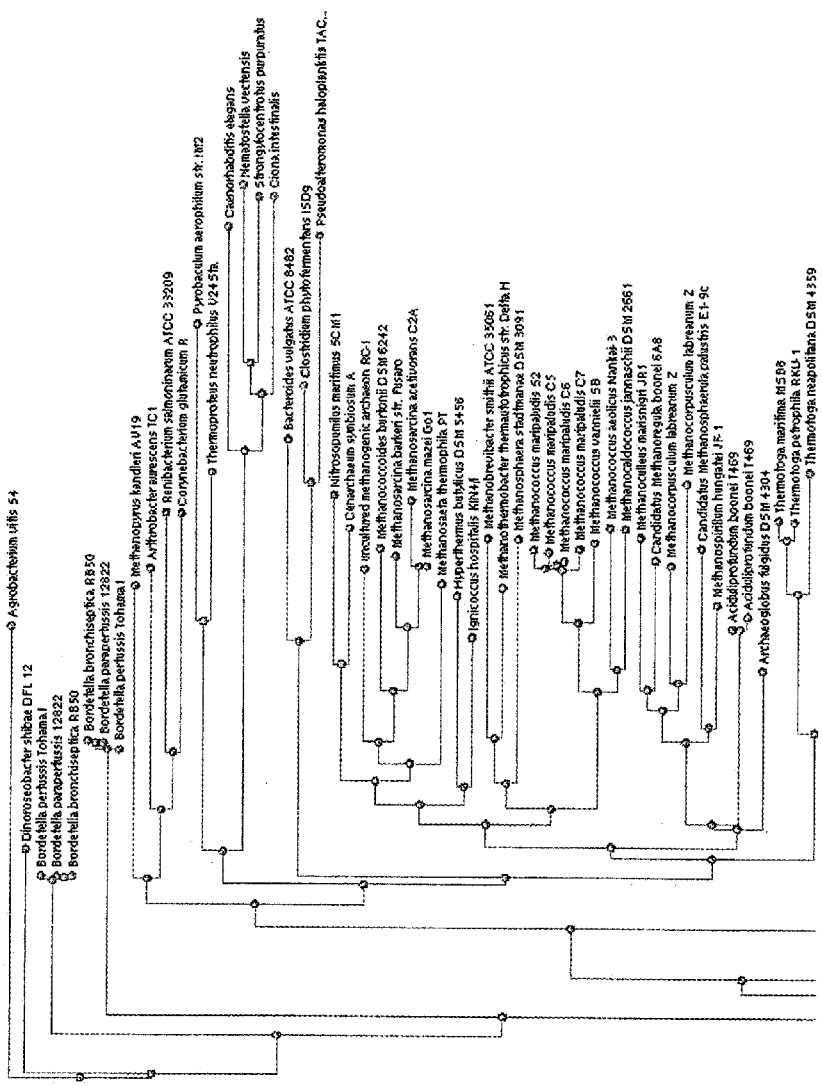

FIG. 19 is a distance tree of the full-length homologues of the aspartate dehydrogenase from *Polaromonas* sp.

Figure 20:
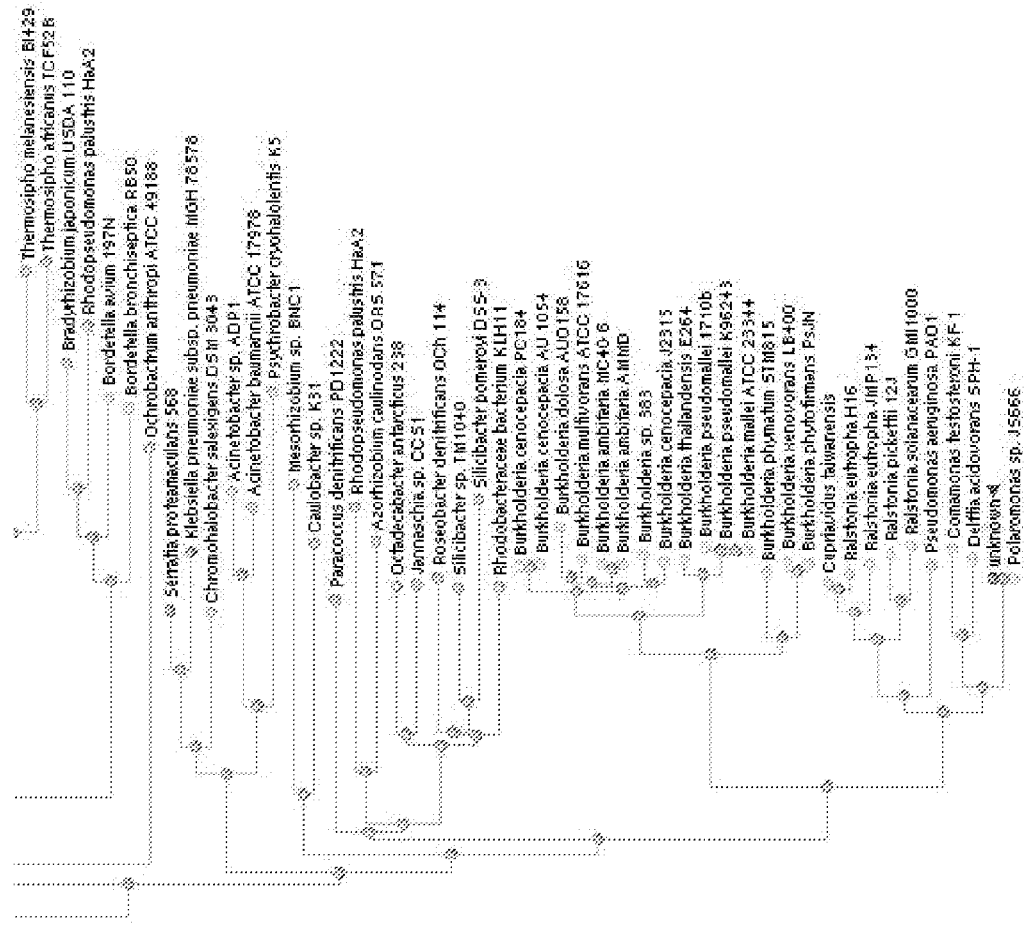

FIG. 20 is a distance tree of the full-length homologues of the aspartate dehydrogenase from *Polaromonas* sp (continued).

Figure 21:
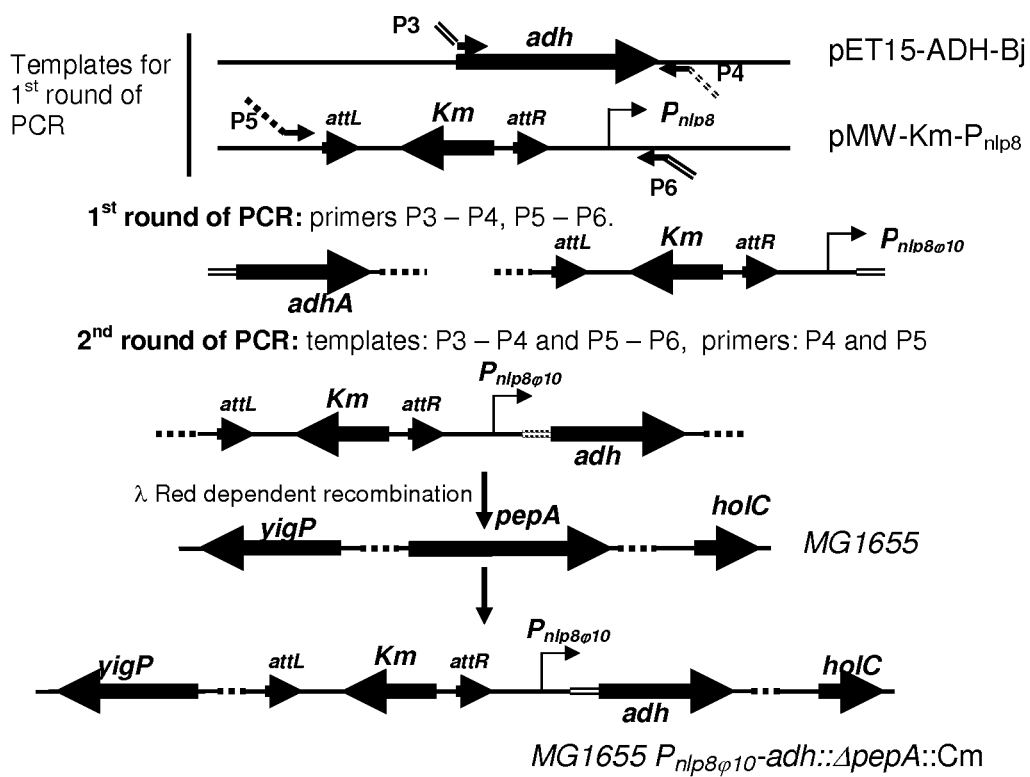

FIG. 21 shows the integration of the aspartate dehydrogenase gene from *Bradyrhizobium japonicum* into the chromosome of the strain *E. coli* MG1655.

Figure 22:
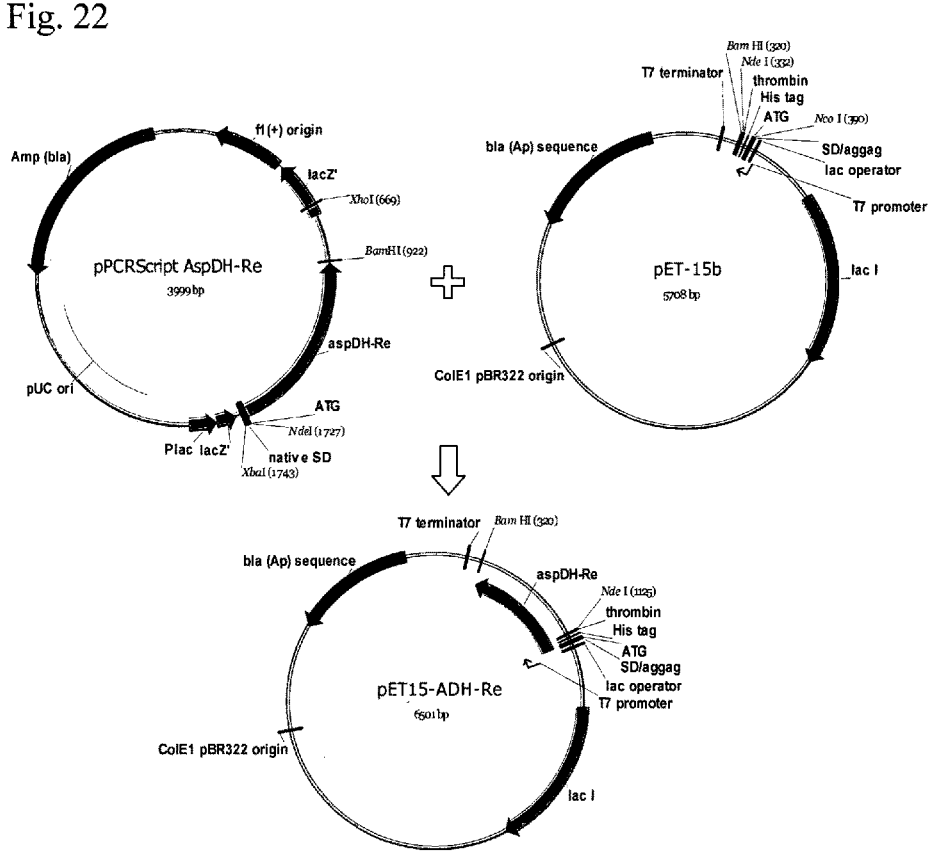

FIG. 22 shows construction of the pET15-ADH-Re plasmid comprising the putative aspartate dehydrogenase gene h16_B0736 from *Ralstonia eutropha* H16.

Figure 23:
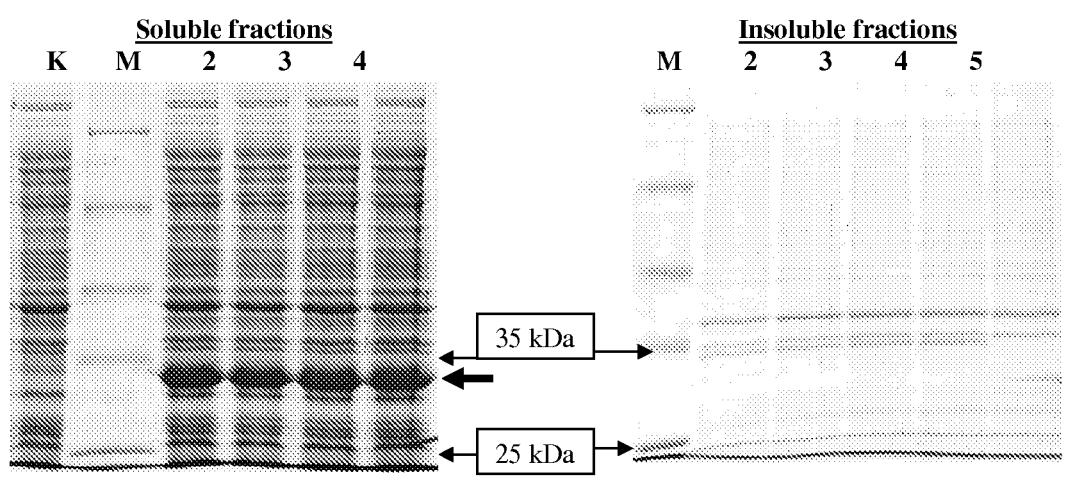

FIG. 23 is a photograph of SDS/PAAG (10%) electrophoresis of the soluble and insoluble fractions prepared from the crude extracts of the BL21(DE3) strain harboring the pET15-ADH-Re plasmid.

K: pET15b
M: protein marker SM0431
Lane 2: pET15-ADH-Re, clone 2
Lane 3: pET15-ADH-Re, clone 3
Lane 4: pET15-ADH-Re, clone 4
Lane 5: pET15-ADH-Re, clone 5

Figure 24:
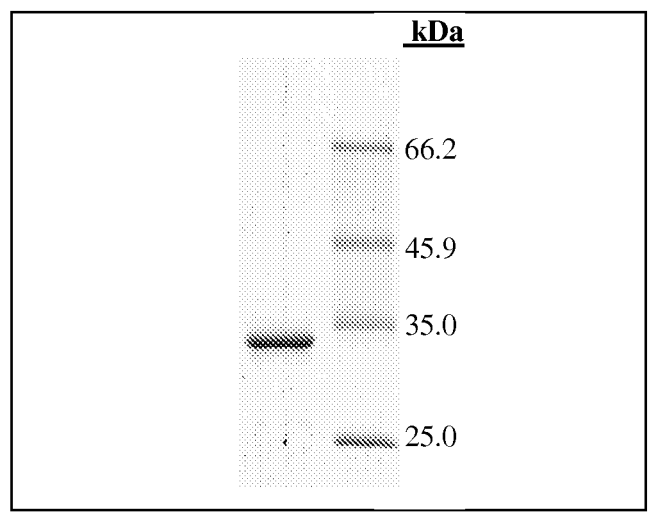

FIG. 24 is a photograph of SDS-PAGE of the purified *Ralstonia eutropha* ADH-Re.

Left lane: purified enzyme (1 mkg); right lane: protein marker

Figure 25:
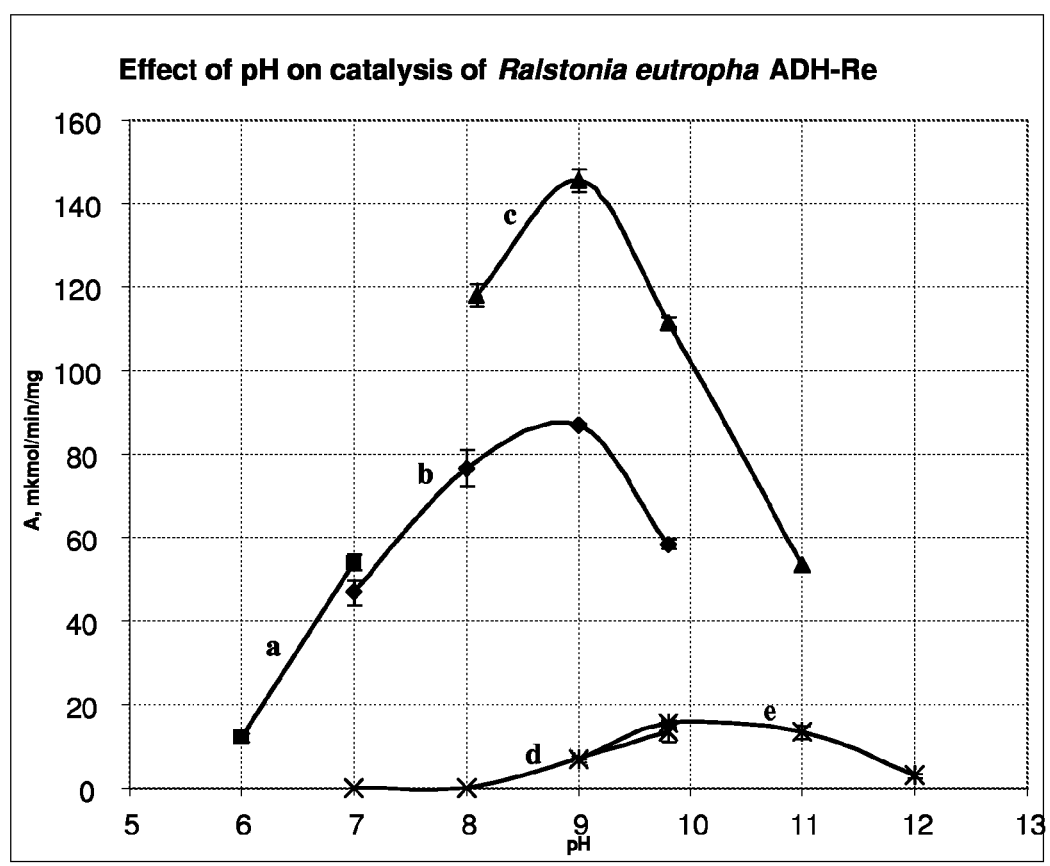

FIG. 25 shows effect of pH on catalysis of *Ralstonia eutropha* ADH-Re of the amination and deamination reactions.

Figure 26:
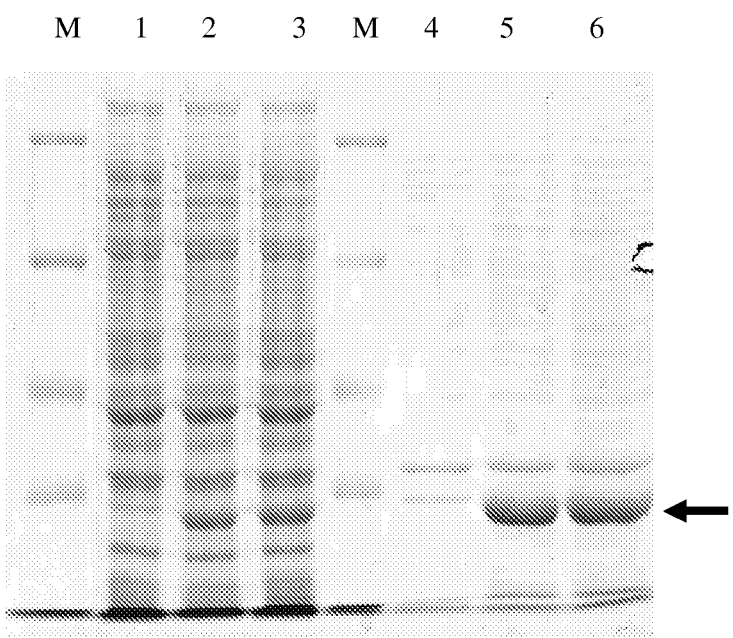

FIG. 26 is a photograph of SDS/PAAG (10%) electrophoresis of the soluble and insoluble fractions prepared from the crude extracts of the BL21(DE3) strain harboring the pET15-ADH-Bj plasmid.

M: SM0431 marker
Lane 1: soluble fraction of BL21(DE3)/pET15b
Lanes 2, 3: soluble fraction of BL21(DE3)/pET15-ADH-Bj, clone 1, 2
Lane 4: insoluble fraction of BL21(DE3)/pET15b
Lanes 5, 6: insoluble fraction of BL21(DE3)/pET15-ADH-Bj, clone 1, 2

Figure 27:
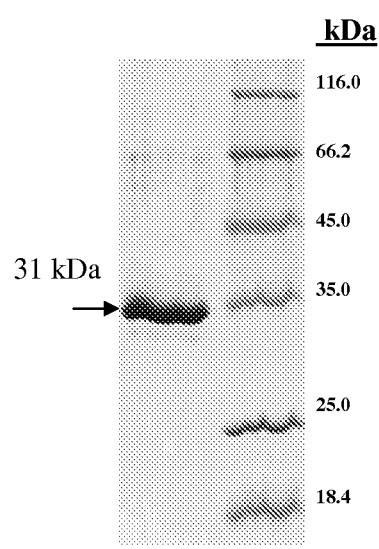

FIG. 27 is a photograph of SDS-PAGE (12%) of the purified *Bradyrhizobium japonicum* ADH-Bj.

Left lane: purified enzyme (2 mkg); right lane: protein marker.

Figure 28:
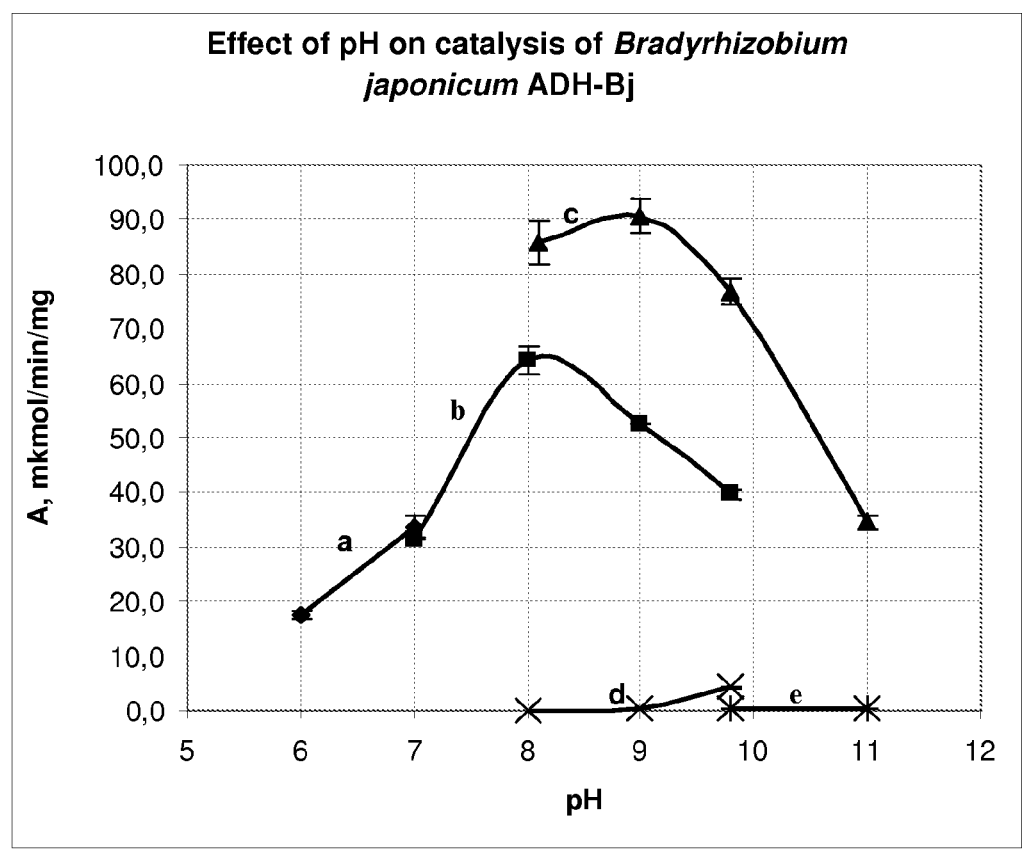

FIG. 28 shows effect of pH on catalysis *Bradyrhizobium japonicum* ADH-Bj of the amination and deamination reactions.

DETAILED DESCRIPTION OF THE PREFERRED EMBODIMENTS

Bacterium in Accordance with the Presently Disclosed Subject Matter

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, those classified into the Enterobacteriaceae according to the taxonomy used by the NCBI (National Center for Biotechnology Information) database (www.ncbi.nlm.nih.gov/htbin-post/Taxonomy/wgetorg?mode=Tree&id=1236&lvl=3&keep=1&srchmode=1&unlock) can be used. A bacterium belonging to the genus *Escherichia* or *Pantoea* are particular examples.

The phrase "a bacterium belonging to the genus *Pantoea*" can mean that the bacterium can be classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on nucleotide sequence analysis of 16S rRNA, etc (International Journal of Systematic Bacteriology, July 1989, 39(3). p. 337-345). Furthermore, some bacteria belonging to the genus *Erwinia* were re-classified as *Pantoea ananatis* or *Pantoea stewartii* (International Journal of Systematic Bacteriology, January 1993, 43(1), pp. 162-173). Typical strains of the *Pantoea* bacteria can include, but are not limited to, *Pantoea ananatis, Pantoea stewartii, Pantoea agglomerans*, and *Pantoea citrea*. Specific examples include the following strains: *Pantoea ananatis* AJ13355 (FERM BP-6614, European Patent Publication No. 0952221), *Pantoea ananatis* AJ13356 (FERM BP-6615, European Patent Publication No. 0952221), *Pantoea ananatis* AJ13601 (FERM BP-7207, European Patent Publication No. 0952221). In an exemplary embodiment of the presently disclosed subject matter, *Pantoea ananatis* SC17(0) can be used as a λ-Red resistant bacterium (VKPM B-9246, RU application 2006134574).

The phrase "a bacterium belonging to the genus *Escherichia*" can mean that the bacterium is classified into the genus *Escherichia* according to the classification known to a person skilled in the art of microbiology. Examples of a bacterium belonging to the genus *Escherichia* include, but are not limited to, *Escherichia coli* (*E. coli*).

The bacterium belonging to the genus *Escherichia* is not particularly limited; however, e.g., bacteria described by Neidhardt, F. C. et al. (*Escherichia coli* and *Salmonella typhimurium*, American Society for Microbiology, Washington D.C., 1208, Table 1) are encompassed by the present invention.

The phrase "bacterium producing L-aspartic acid or an L-aspartic acid-derived metabolite" can refer to the ability to produce L-aspartic acid and/or one or more of L-aspartic acid-derived metabolites and cause accumulation of L-aspartic acid and/or L-aspartic acid-derived metabolites in a medium or cells of the bacterium in accordance with the presently disclosed subject matter to such a degree that L-aspartic acid or L-aspartic acid-derived metabolites can be collected from the medium or cells when the bacterium is cultured in the medium. Alternatively, the phrase "bacterium producing L-aspartic acid or an L-aspartic acid-derived metabolite" can mean a bacterium which is able to cause accumulation of a target L-aspartic acid and/or one or more of L-aspartic acid derived-metabolites in culture medium in an amount larger than the wild-type or parental strain. In an exemplary embodiment of the presently disclosed subject matter, the microorganism can cause accumulation in a medium of a first exemplary amount of not less than 0.4 g/L, or of a second exemplary amount of not less than 1.0 g/L of aspartic acid and/or L-aspartic acid-derived metabolites. The ability to produce L-aspartic acid or L-aspartic acid-derived metabolites in the bacterium can be a native ability, or it can be imparted by modifying the bacterium using mutagenesis or recombinant DNA techniques.

In accordance with the presently disclosed subject matter, the term "L-aspartic acid" refers to free L-aspartic acid or to any salt thereof called as aspartic acid. The L-aspartic acid-derived metabolites can include L-threonine, L-lysine, L-arginine, L-methionine and L-homoserine. L-aspartic acid and/or the L-aspartic acid-derived-metabolites are also referred to as target amino acids. The target amino acid can be a free L-amino acid, or may be a salt such as sulfate salt, hydrochloride salt, carbonate salt, ammonium salt, sodium salt, or potassium salt.

Earlier authors of subject matter related to the presently disclosed subject matter explored producing L-aspartic acid or L-aspartic acid-derived metabolites by a bacterium belonging to the genus *Pantoea*, and if it may be necessary to modify the bacterium to have at least:

decreased activity of α-ketoglutarate dehydrogenase;

decreased activity of citrate synthase;

increased activity of phosphoenolpyruvate carboxylase or pyruvate carboxylase; and increased activity of glutamate dehydrogenase or glutamate synthase.

The bacterium may also be modified to have attenuated expression of a gene coding for aspartate ammonia-lyase (aspartase) (WO/2010/038905).

The bacterium may also be modified to have attenuated expression of a gene coding for pyruvate kinase.

The bacterium may also be modified to have attenuated expression of a gene coding for malate dehydrogenase.

Furthermore, the inventors of the presently disclosed subject matter realized that production of L-aspartic acid or L-aspartic acid-derived metabolites by a bacterium belonging to the genus *Pantoea* can be enhanced when the bacterium is modified to have aspartate dehydrogenase.

Activity of aspartate dehydrogenase means the activity of catalyzing the forward reaction of direct aspartic acid synthesis from oxaloacetate and ammonia. Use of this reaction for aspartic acid synthesis can help to avoid the glutamate by-production. And in this case it may not be necessary to increase activity of glutamate dehydrogenase or glutamate synthase.

A bacterium according to the presently disclosed subject matter can be obtained by introducing a gene encoding aspartate dehydrogenase (ad gene) using methods widely known to the person skilled in the art. For example, the bacterium can be transformed with a DNA fragment containing the gene encoding aspartate dehydrogenase. The gene can be introduced into the bacterial chromosome using integration/recombination systems under the control of a promoter suitable for expression in a bacterium of Enterobacteriaceae family such as a bacterium belonging to the genus *Pantoea*. For example, a method for constructing recombinant bacterium belonging to the genus *Pantoea* is described in detail in Russian patent application 2006134574. Alternatively, a bacterium can be transformed with a plasmid containing gene encoding aspartate dehydrogenase, etc. The copy number of the adh gene in the bacterium may be one or more.

The nucleotide sequence of the gene coding for aspartate dehydrogenase and the amino acid sequence of aspartate dehydrogenase from *Thermotaoga maritima* are shown in SEQ ID NO: 1 and SEQ ID NO: 2, respectively.

Further, the inventors of the presently disclosed subject matter first identified and cloned the aspartate dehydrogenase gene from *Polaromonas* sp. JS5666 coding for aspartate dehydrogenase with a low optimum temperature. The nucleotide sequence of the gene coding for aspartate dehydrogenase and the amino acid sequence of aspartate dehydrogenase from *Polaromonas* sp. JS666 are shown in SEQ ID NO: 3 and SEQ ID NO: 4, respectively.

An alignment of several homologues of the aspartate dehydrogenase from *Polaromonas* sp. JS666 (*Polaromonas* sp. JS666, *Delftia acidovorans*, *Comamonas testosterone*, *Ralstonia eutropha*, *Pseudomonas aeruginosa*, *Burkholderia cenocepacia*, *Rhodopseudomonas palustris* RPB_3108, *R. palustris* RPB_0147, *T. maritima*) is shown on FIGS. 7 and 8. Consensus sequence of these homologues is also shown in FIGS. 7 and 8.

Further, the inventors of the presently disclosed subject matter selected group of genes from several microorganisms to find, clone and characterize the other aspartate dehydrogenases.

The nucleotide sequence of the RPB_0147 gene coding for aspartate dehydrogenase from *Rhodopseudomonas palustris* HaA2 is shown in SEQ ID NO: 64.

The nucleotide sequence of the RPB_3108 gene coding for aspartate dehydrogenase from *Rhodopseudomonas palustris* HaA2 is shown in SEQ ID NO: 65.

The nucleotide sequence of the H16_B0736 gene coding for putative aspartate dehydrogenase from *Ralstonia eutropha* H16 is shown in SEQ ID NO: 66.

The nucleotide sequence of the AZC_4388 gene coding for putative aspartate dehydrogenase from *Azorhizobium caulinodans* ORS 571 is shown in SEQ ID NO: 67.

The nucleotide sequence of the bl16567 gene coding for putative aspartate dehydrogenase from *Bradyrhizobium japonicum* USDA 110 is shown in SEQ ID NO: 68.

The nucleotide sequence of the Meso_0824 gene coding for putative aspartate dehydrogenase from *Mesorhizobium* sp. is shown in SEQ ID NO: 69.

The nucleotide sequence of the cgR_1126 gene coding for putative aspartate dehydrogenase from *Corynebacterium glutamicum* R is shown in SEQ ID NO: 70.

The nucleotide sequence of the Nmar_1240 gene coding for putative aspartate dehydrogenase from *Nitrosopumilus maritimus* is shown in SEQ ID NO: 71.

The nucleotide sequence of the OG2516_00504 gene coding for putative aspartate dehydrogenase from *Oceanicola granulosus* is shown in SEQ ID NO: 72.

Above-described microoraganisms are available from ATCC (American Type Culture Collection, 12301 Parklawn Drive, Rockville, Md. 20852, P.O. Box 1549, Manassas, Va. 20108, United States of America), or JCM (Japan Collection of Microorganisms (RIKEN BioResource Center, 2-1 Hirosawa, Wako, Saitama 351-0198, Japan).

The phrase "activity of enzyme is increased" can mean that the activity of an enzyme in the cell is higher as compared to the non-modified microorganism, for example, a parental or wild-type strain. The activity of the enzyme can be increased in the cell by enhancing the expression of the gene encoding the enzyme. Examples of such modification can include increasing the copy number of expressed gene per cell, increasing the expression level of the gene, and so forth. The quantity of the copy number of an expressed gene can be measured, for example, by restricting the chromosomal DNA followed by Southern blotting using a probe based on the gene sequence, fluorescence in situ hybridization (FISH), and the like. The level of gene expression can be measured by various known methods including Northern blotting, quantitative RT-PCR, and the like. Furthermore, wild-type strains that can act as a control can include, for example, *Pantoea ananatis* FERM BP-6614.

The nucleotide sequence of the aspA gene and the amino acid sequence of aspartate ammonia-lyase (AspA, aspartase) from *P. ananatis* are shown in SEQ ID NO: 5 and SEQ ID NO: 6, respectively.

The nucleotide sequence of the sucA gene and the amino acid sequence of α-ketoglutarate dehydrogenase (SucA, 2-oxoglutarate dehydrogenase) from *P. ananatis* are shown in SEQ ID NO: 7 and SEQ ID NO: 8, respectively.

The nucleotide sequence of the gltA gene and the amino acid sequence of citrate synthase (GltA, citrogenase, oxalaoacetate transacetylase) from *P. ananatis* are shown in SEQ ID NO: 9 and SEQ ID NO: 10, respectively.

*P. ananatis* has two isozymes coding for pyruvate kinase: PykA and PykF. The nucleotide sequence of pykA gene and the amino acid sequence of pyruvate kinase (PykA) from *P. ananatis* are shown in SEQ ID NO: 11 and SEQ ID NO: 12, respectively. The nucleotide sequence of pykF gene and the amino acid sequences of pyruvate kinase (PykF) from *P. ananatis* are shown in SEQ ID NO: 13 and SEQ ID NO: 14, respectively.

The ppc gene encoding phosphoenolpyruvate carboxylase from *E. coli* is known (nucleotides complementary to nucleotides in positions from 4,148,470 to 4,151,121; GenBank accession no. NC_000913.2; gi: 49175990) The ppc gene is located between the yijP and the argE genes on the chromosome of *E. coli* K-12. The nucleotide sequence of the ppc gene and the amino acid sequence of Ppc encoded by the ppc gene from *E. coli* are shown in SEQ ID NO: 15 and SEQ ID NO: 16, respectively.

The pycA gene encoding pyruvate carboxylase from *Sinorhizobium meliloti* is known (WO/2010/038905).

Since there may be some differences in DNA sequences between the genera or strains, the adh, aspA, sucA, gltA, pykA, pykF or ppc gene which is modified to increase or attenuate expression is not limited to the gene shown in SEQ ID NO:1, SEQ ID NO:3, SEQ ID NO:5, SEQ ID NO:7, SEQ ID NO:9, SEQ ID NO:11, SEQ ID NO:13, or SEQ ID NO:15, respectively, but can include genes homologous to SEQ ID SEQ ID NO:1, SEQ ID NO:3, NO:5, SEQ ID NO:7, SEQ ID NO:9, SEQ ID NO:11, SEQ ID NO:13, or SEQ ID NO:15, respectively. Therefore, the protein variant encoded by the adh, aspA, sucA, gltA, pykA, pykF or ppc gene can have exemplary homologies of not less than 80%, not less than 90%, not less than 95%, not less than 98%, or not less than 99% with respect to the entire amino acid sequence shown in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, respectively, as long as the activity of the corresponding protein is maintained. The phrase "protein variant" as used in the presently disclosed subject matter means proteins which have changes in the sequences, whether they are deletions, insertions, additions, or substitutions of amino acids. The number of changes in the variant proteins can depend on the position in the three dimensional structure of the protein or the type of amino acid residues. Exemplary embodiments can be 1 to 30, 1 to 15, or 1 to 5 in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, respectively. These changes in the variants can occur in regions of the protein which are not critical for the three dimensional structure of the protein. This is because some amino acids have high homology to one another so the three dimensional structure is not affected by such a change. In this specification, "homology" can mean "identity".

Homology between two amino acid sequences can be determined using the well-known methods, for example, the computer program BLAST 2.0, which calculates three parameters: score, identity and similarity.

The substitution, deletion, insertion or addition of one or several amino acid residues are conservative mutation(s) so that the activity is maintained. The representative conservative mutation is a conservative substitution. Examples of conservative substitutions can include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Therefore, the adh, aspA, sucA, gltA, pykA, pykF or ppc gene can be a variant which hybridizes under stringent conditions with the nucleotide sequence shown in SEQ ID NO:1, SEQ ID NO:3, SEQ ID NO:5, SEQ ID NO:7, SEQ ID NO:9, SEQ ID NO:11, SEQ ID NO:13, or SEQ ID NO:15, respectively, or a probe which can be prepared from the nucleotide sequence, provided that it encodes a functional protein. "Stringent conditions" can include those under which a specific hybrid, for example, a hybrid having homology of not less than 60%, is formed and a non-specific hybrid, for example, a hybrid having homology lower than the above, is not formed. Other exemplary homologies can include not less than 70%, not less than 80%, not less than 90%, not less than 95%, not less than 98%, and not less than 99%. For example, stringent conditions are exemplified by washing one time or more, such as two or three times, at a salt concentration of 1×SSC, 0.1% SDS. Another exemplary salt concentration can include 0.1×SSC, 0.1% SDS at 60° C. Duration of washing depends on the type of membrane used for blotting and, as a rule, it can be what is recommended by the manufacturer. For example, the recommended duration of washing for the Hybond™ N+ nylon membrane (Amersham) under stringent conditions is 15 minutes. By way of example, washing can be performed 2 to 3 times. The length of the probe can be suitably selected depending on the hybridization conditions, and can be 100 bp to 1 kbp, for example.

The phrase "bacterium has been modified to attenuate expression of the gene" can mean that the bacterium has been modified in such a way that a modified bacterium contains a reduced amount of the protein encoded by the gene as compared with an unmodified bacterium, for example, a parental or wild-type strain, or is unable to synthesize the protein encoded by the gene.

The phrase "inactivation of the gene" can mean that the modified gene encodes a completely non-functional protein. It is also possible that the modified DNA region is unable to naturally express the gene due to a deletion of a part of the gene or the entire gene, shifting of the reading frame of the gene, introduction of missense/nonsense mutation(s), or modification of an adjacent region of the gene, including sequences controlling gene expression, such as a promoter, enhancer, attenuator, ribosome-binding site, etc.

The presence or absence of the aspA, sucA, gltA, pykA or pykF gene in the chromosome of a bacterium can be detected by well-known methods, including PCR, Southern blotting and the like. In addition, the levels of expression of genes can be estimated by measuring the amounts of mRNA transcribed from the genes using various known methods including Northern blotting, quantitative RT-PCR, and the like. The amounts or molecular weights of the proteins coded by the genes can be measured by known methods including SDS-PAGE followed by immunoblotting assay (Western blotting analysis), and the like.

Expression of the gene can be attenuated by introducing a mutation into the gene on the chromosome so that the intracellular amount of the protein encoded by the gene is decreased as compared to an unmodified strain. Such a mutation can be introduction of insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods can be employed to introduce a mutation by gene recombination. A mutant gene is prepared, and the bacterium to be modified is transformed with a DNA fragment containing the mutant gene. Then, the native gene on the chromosome is replaced with the mutant gene by homologous recombination, and the resulting strain is selected. Such gene replacement by homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication (U.S. Pat. No. 6,303,383 or JP 05-007491A). An exemplary strain to be used in accordance with the presently disclosed subject matter can be Pantoea ananatis strain which can be modified to be resistant to the product of the λ-Red genes. The example of such strain can include, but is not limited to, the Pantoea ananatis strain SC17(0) (VKPM B-9246, RU application 2006134574).

Furthermore, the incorporation of a site-specific mutation by gene substitution using homologous recombination such as set forth above can also be conducted with a plasmid which is unable to replicate in the host.

Expression of the gene also can be attenuated by insertion of a transposon or an IS factor into the coding region of the gene (U.S. Pat. No. 5,175,107), or by conventional methods, such as mutagenesis with UV irradiation or nitrosoguanidine (N-methyl-N'-nitro-N-nitrosoguanidine).

Inactivation of the gene also can be performed by conventional methods, such as by mutagenesis with UV irradiation or nitrosoguanidine (N-methyl-N'-nitro-N-nitrosoguanidine), site-directed mutagenesis, gene disruption using homologous recombination, or/and insertion-deletion mutagenesis (Yu, D. et al., Proc. Natl. Acad. Sci. USA, 2000, 97:12: 5978-83 and Datsenko, K. A. and Wanner, B. L., Proc. Natl. Acad. Sci. USA, 2000, 97:12: 6640-45) also called "Red-driven integration".

Methods for preparation of plasmid DNA, digestion and ligation of DNA, transformation, selection of an oligonucleotide as a primer and the like are well known to one skilled in the art. These methods are described, for instance, in Sambrook, J., Fritsch, E. F., and Maniatis. T., "Molecular Cloning A Laboratory Manual, Second Edition"; Cold Spring Harbor Laboratory Press (1989).

Bacteria Producing L-Aspartic Acid or L-Aspartic Acid-Derived Metabolites

As a bacterium in accordance with the presently disclosed subject matter which is able to produce L-aspartic acid or L-aspartic acid-derived metabolites, the bacterium modified to have decreased activity of α-ketoglutarate dehydrogenase; decreased activity of citrate synthase; increased activity of phosphoenolpyruvate carboxylase or pyruvate carboxylase; and increased activity of glutamate dehydrogenase or glutamate synthase can be used. It is also possible to further modify the bacterium to have attenuated expression of gene coding for aspartate ammonia-lyase (aspartase).

L-Threonine-Producing Bacteria

Examples of parent strains which can be used to derive L-threonine-producing bacteria in accordance with the presently disclosed subject matter can include strains in which expression of one or more genes encoding an L-threonine biosynthetic enzyme is/are enhanced. In an exemplary embodiment, the bacterium in accordance with the presently disclosed subject matter can be modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase).

Genes from Escherichia coli bacterium can be used. The thrA gene which encodes aspartokinase homoserine dehydrogenase I of Escherichia coli has been elucidated (nucleotide positions 337 to 2799, GenBank accession no. NC_000913.2, gi: 49175990). The thrA gene is located between the thrL and thrB genes on the chromosome of E. coli K-12. The thrB gene which encodes homoserine kinase of Escherichia coli has been elucidated (nucleotide positions 2801 to 3733, GenBank accession no. NC_000913.2, gi: 49175990). The thrB gene is located between the thrA and thrC genes on the chromosome of E. coli K-12. The thrC gene which encodes threonine synthase of Escherichia coli has been elucidated (nucleotide positions 3734 to 5020, GenBank accession no. NC_000913.2, gi: 49175990). The thrC gene is located between the thrB gene and the yaaX open reading frame on the chromosome of E. coli K-12. All three genes can function as a single threonine operon. To enhance expression of the threonine operon, the attenuator region which affects the transcription can be removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from well-known plasmid pVIC40 which is present in the threonine producing E. coli strain VKPM B-3996. Plasmid pVIC40 is described in detail in U.S. Pat. No. 5,705,371.

The rhtA gene exists at 18 min on the E. coli chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position-1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi:16128895), and can be obtained by PCR. The aspC genes of other microorganisms can be obtained in a similar manner.

L-Lysine-Producing Bacteria

Examples of parent strains for deriving L-lysine-producing bacteria in accordance with the presently disclosed subject matter can include strains in which expression of one or more genes encoding an L-lysine biosynthetic enzyme are enhanced. Examples of such genes can include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogeneaase (asd), and aspartase (aspA) (EP 1253195 A). In addition, the parent strains can have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria in accordance with the presently disclosed subject matter also can include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine can include homoserine dehydrogenase, lysine decarboxylase (U.S. Pat. No. 5,827,698), and the malic enzyme (WO2005010175).

L-Arginine-Producing Bacteria

Examples of parent strains for deriving L-arginine-producing bacteria in accordance with the presently disclosed subject matter can include strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria of the present invention also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Methionine-Producing Bacteria

Examples of L-methionine-producing bacteria and parent strains for deriving L-methionine producing bacteria include, but are not limited to, L-threonine-auxotrophic mutant strain and norleucine-resistant mutant strain (JP 2000-139471 A). Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as parent strains.

L-Homoserine-Producing Bacteria

L-homoserine resistance can be imparted to bacteria by increasing the copy number of the rhtB gene, and the production of L-homoserine, L-threonine, L-alanine, L-valine, and L-isoleucine is increased (EP994190A2). Furthermore, resistance to L-homoserine and L-threonine can be imparted to bacteria by increasing the copy number of the rhtC gene, and the production of L-homoserine, L-threonine, and L-leucine is increased (EP994190A2). Examples of parent strain for deriving L-lysine-producing bacteria in accordance with the presently disclosed subject matter include *E. coli* 44 strain which has been deposited in the Russian National Collection of Industrial Microorganisms (VKPM) (Russia, 117545 Moscow, $1^{st}$ Dorozhny proezd, 1) on Sep. 1, 1980 under accession number VKPM B-2175 and then converted to a deposit under the Budapest Treaty on Sep. 1, 2000.

2. Method in Accordance with the Presently Disclosed Subject Matter

The method in accordance with the presently disclosed subject matter can be a method for producing L-aspartic acid or L-aspartic acid derived metabolites that includes cultivating the bacterium in accordance with the presently disclosed subject matter in a culture medium to produce and excrete the target amino acid into the medium, and collecting the produced amino acid from the medium.

In accordance with the presently disclosed subject matter, the cultivation, collection, and purification of target amino acid from the medium and the like may be performed in a manner similar to conventional fermentation methods wherein an amino acid is produced using a bacterium.

A medium used for culture can be either a synthetic or natural medium, so long as the medium includes a carbon source and a nitrogen source and minerals and, if necessary, appropriate amounts of nutrients which the bacterium requires for growth. The carbon source can include various carbohydrates such as glucose and sucrose, and various organic acids. Depending on the assimilation mode of the chosen microorganism, alcohol including ethanol and glycerol can be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as by shaking and/or stirring with aeration, at a first exemplary temperature of 30 to 36° C., or at a second exemplary temperature of 32 to 34° C. A first exemplary pH of the culture can be between 5.0 and 7.0, and a second exemplary pH can be between 6.0 and 6.5. The pH of the culture can be adjusted with ammonia, calcium carbonate, various acids, various bases, and buffers. A 1 to 5-day cultivation can lead to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

The collected L-amino acid may contain bacterial cells, medium components, moisture, and by-product metabolites of the bacterium in addition to the L-amino acid. Purity of the collected L-amino acid can be 50% or higher, 85% or higher, or even 95% or higher (Japanese Patent No. 1214636, U.S. Pat. Nos. 5,431,933, 4,956,471, 4,777,051, 4,946,654, 5,840, 358, 6,238,714, U.S. Patent Published Application No. 2005/ 0025878).

EXAMPLES

The presently disclosed subject matter will be more concretely explained below with reference to the following non-limiting examples.

Example 1

Introduction of the TM1643 Gene from *Thermotaoga maritima* to the Aspartic Acid-Producing Strain The well-studied TM1643 gene from *Thermotaoga maritima* coding for aspartic acid dehydrogenase (Yang Zh. et al, J Biol Chem, 278(10): 8804-8808(2003)) was cloned and over-expressed in *E. coli*. A strain of *Thermotaoga maritima* can be available from ATCC.

Coding part of this gene contained 18 codons that are rare in *E. coli*. To provide efficient translation of the cloned gene in *E. coli*, the chemical synthesis and cloning of the DNA fragment containing the coding part of the aspartic acid dehydrogenase gene from *T. maritima*, in which all rare codons were substituted by the synonymous frequent codons, was ordered from Sloning BioTechnology, GmbH (German). This cloning technology is disclosed in WO2005071077. The nucleotide sequence of the TM1643 gene that contained substitutions of all rare codons and the amino acid sequences the protein encoded by this gene are shown in SEQ ID NO: 17 and SEQ ID NO: 18, respectively.

To provide translation, the modified coding part of the TM1643 gene that contained substitutions of all rare codons has been sub-cloned into the pET-22b ("Novagen") vector under control of the PT7 promoter and RBSΦ10. For that, the pUC-TM1643-All plasmid provided by Sloning BioTechnology GmbH (German) was digested with NdeI and BamHI restrictases. The plasmid fragment comprising the variant of the TM1643 gene with substituted rare codons was ligated with the pET-22b(+) vector (Novagen) digested with NdeI and BamHI restrictases. To deliver from the initial pUC-TM1643-All plasmid the ligated mixture was digested with KpnI restrictase and was then electrotransformed to *E. coli* TG1 strain at electric field intensity of 15 kV/cm and pulse time of 5 msec. The TG1 strain can be available, for example, from Zymo Research Corporation.

Figure 1:
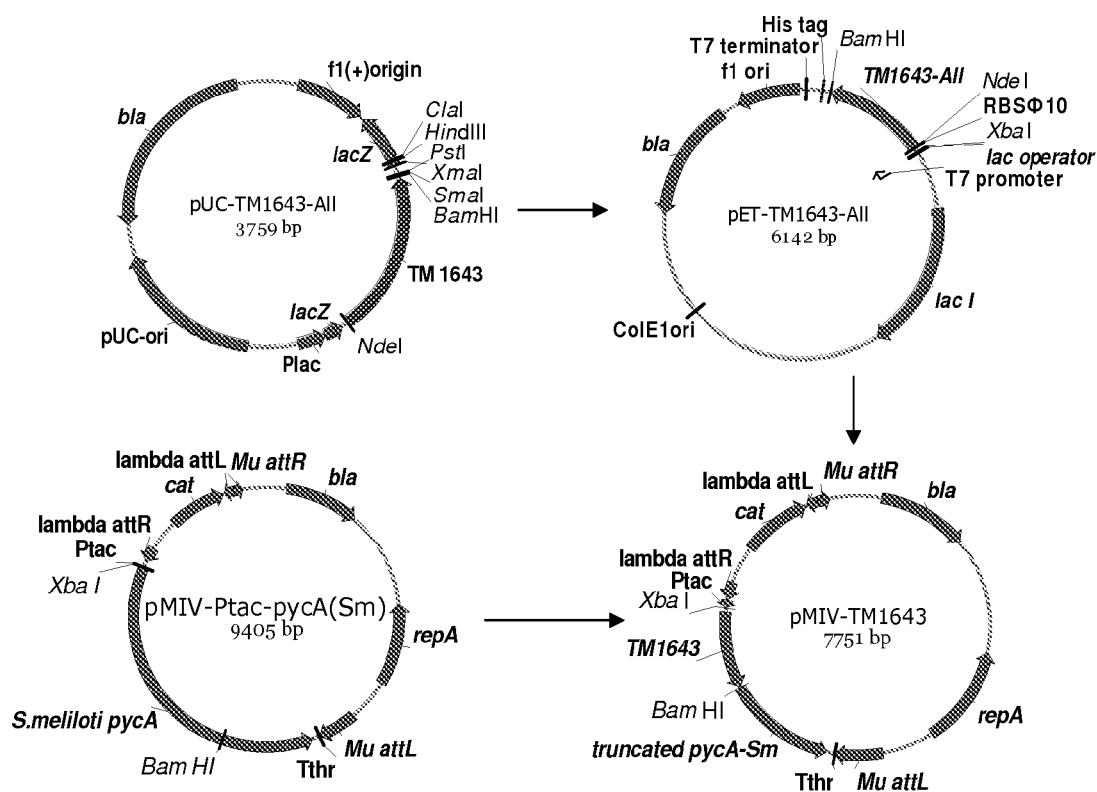
FIG. 1 shows cloning of the TM1643 gene from *Thermotaoga maritima*.

Plasmid DNA was isolated from the clones grown on LB plates with ampicillin (100 mg/L) and the plasmids of the expected structure have been selected using restriction analysis. The resulting plasmid was designated pET-TM1643-All (FIG. 1).

The pET-TM1643-All plasmid and the pET-22b plasmid (as a control) were each introduced into the *E. coli* BL21 (DE3) ("Novagen") strain carrying the gene of T7 RNA polymerase in its chromosome. *E. coli* BL21(DE3)/pET-TM1643-All and BL21(DE3)/pET-22b strains were grown overnight at 37° C. in LB medium, and the culture was diluted 100 times with fresh LB medium and incubated at +37° C. with aeration up to $OD_{595}$=1.0. After that, IPTG was added up to 1 mM concentration in the appropriate cultures and incubated at +37° C. for 1 hour. Analysis of samples of bacterial cultures using PAAG electrophoresis showed that after induction by IPTG, high level accumulation of the protein of the expected size (27 kDa) was observed in the insoluble fraction. The soluble fraction also contained significant amounts of the protein (see FIG. 2). Aspartic acid dehydrogenase activity in the crude extracts of grown cells was also assayed. Cells from 45 ml of the culture were harvested by centrifugation, re-suspended in 50 mM TRIS pH 7.5 with addition of 2 mM DTT and disrupted using French Press. Lysates were centrifuged for 10 min at 13000 rpm and the obtained crude extracts were transferred to new vials. A reaction mixture contained 100 mM TRIS pH 9.8, 1 mM $NAD^+$ or $NADP^+$ and 5 mM aspartic acid. Assay of aspartate dehydrogenase activity in the crude extracts (Table 1) showed that $NADP^+$ is a preferable co-factor, at least in the reverse reaction. Activity at +34° C. has proved to be detectable, but it was 30 times lower than at +70° C.

TABLE 1

Assay of aspartate dehydrogenase activity in crude extracts of BL21(DE3) strain harboring pET-TM1643-All plasmid.
Aspartate dehydrogenase activity, nmol/mg * min

| | Co-factor | |
|---|---|---|
| Temperature | $NADP^+$ | $NAD^+$ |
| +70° C. | 650 | <8 |
| +34° C. | 2 | <4 |

The gene linked to $RBS_{\Phi 10}$ has been sub-cloned into the integrative vector pMIV5-JS (RU patent application 2006132818, EP1942183) under control of the $P_{tac}$ promoter. The resulting plasmid pMIV-TM1643 (FIG. 1) was introduced into the *P. ananatis* 5ΔP2-36S strain (construction of the strain 5ΔP2R is described in Reference example 1). The *P. ananatis* 5ΔP2-36S and 5ΔP2-36S/pMIV-TM1643 strains were each grown for 7 hours in LB-M91/2 medium with addition of 50 mg/L chloramphenicol for the haboring plasmid strains were diluted 30 times with the standard medium for test tube fermentations and were cultivated for 15 hours with aeration in flasks (30 ml of the culture in 750 ml flask). Cells from 6 ml of the culture were harvested by centrifugation, washed with 50 mM TRIS, pH 7.5 and frozen. The pellets were re-suspended in the buffer of 50 mM TRIS, pH 7.4, and 2 mM DTT and cells were disrupted by sonication. The reaction mixture contained 100 mM TRIS, pH 9.8, 1 mM NADP, 5 mM aspartic acid and 2.5 μg of the total protein. The probes were incubated for 30 min at +70° C. The probes that were not incubated and the probes without aspartic acid were used as controls. Assay of aspartate dehydrogenase activity in the crude extracts of 5ΔP2-36S/pMIV-TM1643 showed a high level of aspartate dehydrogenase activity comparable with the specific activities measured in *E. coli* BL21(DE3)/ pET-TM1643-All strain in 6 independent the transformants (Table 2).

TABLE 2

Assay of aspartate dehydrogenase activity in crude extracts of the 5ΔP2-36 strain harboring pMIV-TM1643.

| Strain | ADH sp. activity, nmol/mg * min |
|---|---|
| 5ΔP2-36S | 0 |
| 5ΔP2-36S./pMIV-TM1643 | 620 ± 30 |

Mu-dependent integration of the TM1643 gene to the chromosome of the 5ΔP2R strain has been performed as described in Reference Example 1 for *E. coli* ppc$^{K620S}$ gene. Test tube cultivation (standard protocol for test-tube cultivation (T=+34° C., initial glucose 40 g/L, initial L-Glu (L-glutamic acid) 3 g/L, 48-hour cultivation was applied) showed significant (up to 2.8-fold) increase of aspartic acid accumulation by the strain harboring TM1643 gene (Table 3, Average data for 2 independent cultures are represented).

TABLE 3

Test-tube cultivation of the 5ΔP2R strain and the 5ΔP2R-TM1643 integrants.

| Strain | Clone | OD$_{595}$ | Asp, g/L | Residual Glu, g/L |
|---|---|---|---|---|
| 5ΔP2R | | 5.5 | 0.25 | 1.7 |
| 5ΔP2R-TM1643 | 1 | 3.5 | 0.70 | 2.1 |
| | 2 | 4.4 | 0.55 | 1.9 |
| | 3 | 5.3 | 0.35 | 1.8 |

Aspartate dehydrogenase specific activity in the crude extracts of the 5ΔP2R-TM1643 integrant carrying the aspartate dehydrogenase gene from *T. maritima* was assayed. Cultures were grown in 9 hours in LB-M91/2 medium containing 5 g/L glucose with addition of 50 mg/L chloramphenicol for the integrants. Then, they were diluted 1:30 up to a final volume of 10 ml by the standard medium for test tube fermentations (Table 4, pH 6, without CaCO$_3$) containing 10 g/L glucose and 3 g/L L-Glu. Resulting cultures were cultivated at +34° C. in 16 hours with aeration in tubes. Then cells were harvested by centrifugation, washed with 50 mM TRIS, pH 7.4 and frozen. The pellets were re-suspended in the buffer containing 50 mM TRIS, pH 7.4, and 2 mM DTT and cells were disrupted by sonication. Reaction mixture contained 100 mM TRIS, pH 9.8, 1 mM NADP+ and 5 mM aspartic acid. The probes were incubated in 30 min at +70° C. The probes without aspartic acid were used as controls. The results are presented in Table 5. These results show direct correlation of the enzymatic activity and aspartic acid accumulation.

TABLE 4

Medium for test-tube cultivation.

| Section | Component | Concentration, g/L |
|---|---|---|
| A | Glucose | 40.0 |
| | MgSO$_4$7H$_2$0 | 1.0 |
| B | (NH4)$_2$SO$_4$ | 16.0 |
| | KH$_2$PO$_4$ | 0.3 |
| | KCl | 1.0 |
| | MES | 10.0 |
| | Pantothenate Ca | 0.01 |
| | Betaine | 1.0 |
| | FeSO$_4$7H$_2$0 | 0.01 |
| | MnSO$_4$5H$_2$0 | 0.01 |
| | (Lys, Met, DAP) | 0.1 |
| | L-Glu | 3.0 |
| C | CaCO$_3$ | 30.0 |
| | Antibiotics (if necessary): | |
| | Cm | 50.0 mg/L |
| | Tc | 10.0 mg/L |
| | Km | 40.0 mg/L |
| | Ap | 800 mg/L |

Section B was adjusted by NaOH to have pH 6.5. Sections B and C were sterilized separately.

TABLE 5

Aspartate dehydrogenase specific activity in the crude extracts of the 5ΔP2R-TM1643 integrant carrying the aspartate dehydrogenase gene from *T. maritima*.

| Strain | Clone | Aspartate dehydrogenase sp. activity, nmol/min/mg | Asp, g/L |
|---|---|---|---|
| 5ΔP2R | | 0 | 0.25 |
| 5ΔP2R-TM1643 | 1 | 360 ± 30 | 0.70 |
| | 2 | 220 ± 4 | 0.55 |

Example 2

Cloning of the Putative Aspartate Dehydrogenase Genes

*Polaromonas* sp. J5666, bacterial species of biosafety level 1 living in an environment similar to that of *P. ananatis*, was selected as donor of the candidate aspartate dehydrogenase gene. Alignments of the aspartate dehydrogenase from *T. maritima* and its homolog (GENE ID: 4013636 Bpro_3686) from *Polaromonas* sp. J5666 is presented on FIG. 3. The strain *Polaromonas* sp. J5666 can be available from ATCC.

Figure 14:
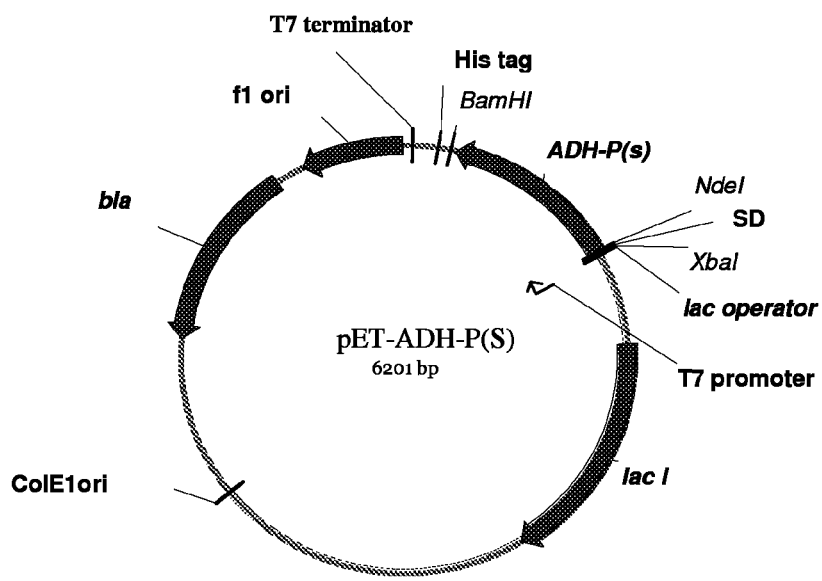
FIG. 14 shows construction of the pET-ADH-P(S) plasmid.

First, the putative aspartate dehydrogenase gene from *Polaromonas* sp. Bpro_3686 was cloned to the pET-22b(+) vector under control of the PT7 promoter and canonical SD-sequence AGGAGG. To construct pET-ADH-P(S) plasmid (FIG. 14), the DNA fragment including a coding part of the *Polaromonas* sp. Bpro_3686 putative aspartate dehydrogenase gene linked with canonical SD-sequence AGGAGG was generated in PCR with the primers AspP5S-Xba (SEQ ID NO: 21) and AspP3-BH(SEQ ID NO: 22). Chromosome DNA isolated from the *Polaromonas* sp. J5666 strain (ATCC BAA-500) was used as the template in the reaction. The obtained fragment was digested with XbaI and BamHI restrictases and ligated with the pET-22b(+) vector which had been digested with the same endonucleases. The ligated mixture was transformed to *E. coli* TG1 strain and plasmid DNA was isolated from the clones grown on LB plates with ampicillin (100 mg/L). The plasmids of the expected structure have been selected using restriction analysis. The resulting plasmid was designated pET-ADH-P(S). Precision of DNA sequence of the cloned fragment has been proved by Sanger method using the primers Seq-adh-P5 (SEQ ID NO: 23), Seq-adh-P3(SEQ ID NO: 24) and Seq-adh-Pm (SEQ ID NO: 25).

The constructed plasmid was named pET-ADH-P(S). Specific aspartate dehydrogenase activity in crude extracts of the BL21(DE3) strain harboring pET-ADH-P(S) at +25° C. was determined. Cells were cultivated in M9 medium (5 g/L glucose) at +37° C. up to OD595=0.9. After that, 1 mM IPTG was added and cells were cultivated for 2 hours. Assay was performed at room temperature. A reaction mixture for the forward reaction contained 100 mM TRIS-HCl, pH 8.0, 100 mM NH$_4$Cl, 0.15 mM NAD(P)H, 5 mM oxaloacetate (pH 7.0 by NaOH). A reaction mixture for the reverse reaction contained 100 mM TRIS-HCl, pH 9.8, 1 mM NAD(P)$^+$ and 5 mM sodium aspartate (pH 7.0). The results are presented in Table 6. These results show that the plasmid provides high-level NAD/NADP-dependent aspartate dehydrogenase activity at room temperature.

TABLE 6

Assay of aspartate dehydrogenase activity in crude extracts of the BL21(DE3) strain harboring the pET-ADH-P(S) plasmid carrying the gene from *Polaromonas* sp. at 25° C.

| Strain | Clone | Specific activity, nmol/min/mg | | | |
|---|---|---|---|---|---|
| | | ADP+ | AD+ | ADPH | ADH |
| BL21(DE3)/pET22b(+) | | | | | |
| BL21(DE3)/pET- | | | 070 | 60 | 600 |
| ADH-P(S) | | 90 | 050 | 60 | 200 |

The coding region of the *Polaromonas* sp. Bpro_3686 gene contained 9 codons that are rare in *E. coli*. To provide efficient translation, the ORF with substituted rare codons was chemically synthesized by Sloning BioTechnology GmbH (German). The nucleotide sequence of the Bpro_3686 gene that contained substitutions of all rare codons and the amino acid sequences the protein encoded by this gene are shown in SEQ ID NO: 19 and SEQ ID NO: 20, respectively. The native Bpro_3686 gene and the variant of the gene without rare codons were cloned into the pMIV5-JS-like vector under control of the $P_{tac}$ promoter and canonical SD-sequence AGGAGG. The constructed plasmids were named pMIV-ADH-P(S) and pMIV-ADH-P(S)-all respectively. Specific aspartate dehydrogenase activity provided by the plasmids carrying the wild-type aspartate dehydrogenase gene from *Polaromonas* sp. JS666 and the gene with substituted rare codons were assayed. Overnight cultures of the *E. coli* MG1655 (ATCC 47076, ATCC 700926)) transformed with each of the above-mentioned vectors grown in LB broth with addition of chloramphenicol (50 mg/L) were diluted up to $OD_{595}$=0.1 and a final volume of 10 ml in M9 medium containing 5 g/L glucose and chloramphenicol (50 mg/L). The MG1655 strain can be available from the American Type Culture Collection (Address: 12301 Parklawn Drive, Rockville, Md. 20852, P.O. Box 1549, Manassas, Va. 20108, United States of America). Cultures of the *P. ananatis* 5ΔP2RMG transformed with each of the above-mentioned vectors grown for 9 hours in LB-M91/2 medium containing 5 g/L glucose and chloramphenicol (50 mg/L) were diluted 1:30 up to a final volume of 10 ml by the standard medium for test tube fermentations (pH 6, without $CaCO_3$) containing 10 g/L glucose, 3 g/L L-Glu and chloramphenicol (50 mg/L). Resulting cultures were cultivated at +34° C. with aeration up to $OD_{595}$=1.0. Cells from 5 ml of each culture were harvested by centrifugation, washed in TRIS-HCl (pH 7.4, 50 mM) and frozen at −70° C. The pellets were re-suspended in 450 μl of the buffer containing TRIS-HCl (pH 7.4, 50 mM) and DTT (2 mM) and disrupted by sonication. Assay of the activity was performed in the reverse reaction at room temperature. The reaction mixture contained 100 mM TRIS, pH=9.8, 1 mM $NAD^+$ and 5 mM aspartic acid. Average data for three independent clones are represented in Table 7. These data show that the codon substitution led to some increase of the specific activity in *E. coli*, but not in *P. ananatis*.

TABLE 7

Specific aspartate dehydrogenase activity provided by the plasmids carrying the wild-type aspartate dehydrogenase gene from *Polaromonas* sp. JS666 and the gene with substituted rare codons.

| | Aspartate dehydrogenase sp. activity, nmol/mg/min | |
|---|---|---|
| Plasmid | *E. coli* MG1655 | *P. ananatis* 5ΔP2RMG |
| pMIV5-JS | 0 | 0 |
| pMIV-ADH-P(S) | 17 ± 1 | 84 ± 10 |
| pMIV-ADH-P(S)-all | 23 ± 1 | 94 ± 4 |

The putative aspartate dehydrogenase genes from *Ralstonia eutropha* (orf h16_B0736, SEQ ID NO: 75) and *Rhodopseudomonas palustris* (ORF1 RPB_0147, SEQ ID NO: 73 and ORF2 RPB_3108, SEQ ID NO: 74) with substituted rare codons were also chemically synthesized by Sloning BioTechnology and cloned to the pMIV5-JS-like vector under control of the $P_{tac}$ promoter. The constructed plasmids were named pMIV-ADH-Re, pMIV-ADH1-Rp and pMIV-ADH2-Rp, respectively. Comparative assay of the aspartate dehydrogenase activity in crude extracts of the *E. coli* MG1655 strain harboring all constructed plasmids was performed. Overnight cultures of the strains were grown in LB broth with addition of chloramphenicol (50 mg/L). The cultures were diluted up to $OD_{595}$=0.1 in M9 medium containing 5 g/L glucose, 1 mM IPTG and chloramphenicol (50 mg/L) and incubated at +34° C. with aeration up to $OD_{595}$=1.0. Cells from 5 ml of each culture were harvested by centrifugation, washed in TRIS-HCl (pH 7.4, 50 mM) and frozen at −70° C. The pellets were re-suspended in 450 μl of the buffer containing TRIS-HCl (pH 7.4, 50 mM) and DTT (2 mM) and disrupted by sonication. Assay of the activity was performed in the reverse reaction at room temperature. The reaction mixture contained 100 mM TRIS, pH=9.8, 1 mM $NAD^+$ and 5 mM aspartic acid. Average data for two independent clones are represented in Table 8. These data show that, apart from the plasmids carrying the genes from *Polaromonas* sp. J5666, only the plasmid carrying one of genes from *Rhodopseudomonas palustris* (ORF2 RPB_3108) provided detectable levels of the aspartate dehydrogenase activity. Thus, the aspartate dehydrogenase gene found in *Polaromonas* sp. providing a higher activity level was chosen for further analysis.

TABLE 8

Aspartate dehydrogenase specific activity at +25° C. in the crude extracts of the *E. coli* MG1655 strain harboring different plasmids containing putative aspartate dehydrogenase genes and pMIV5-JS as a negative control.

| Strain | Aspartate dehydrogenase sp. activity, nmol/min/mg |
|---|---|
| MG1655/pMIV5-JS | 0 |
| MG1655/pMIV-ADH-P(S) | 34 ± 2 |
| MG1655/pMIV-ADH-P(S)-all | 39 ± 2 |
| MG1655/pMIV-ADH-Re | 0 |
| MG1655/pMIV-ADH1-Rp | 0 |
| MG1655/pMIV-ADH2-Rp | 11 ± 2 |

Further investigation showed that aspartate dehydrogenase genes from *Rhodopseudomonas palustris* (ADH1-Rp) and *Ralstonia eutropha* (ADH-Re) being cloned on the pMIV5-JS-like vector did not express in the *E. coli*. Recloning the genes to pET vector optimized for transcription and translation of these enzymes led to their successful expression. See Example 5 and Example 9, respectively.

Example 3

Purification and Characterization of the Aspartate Dehydrogenase from *Polaromonas* sp. JS666

Figure 2:
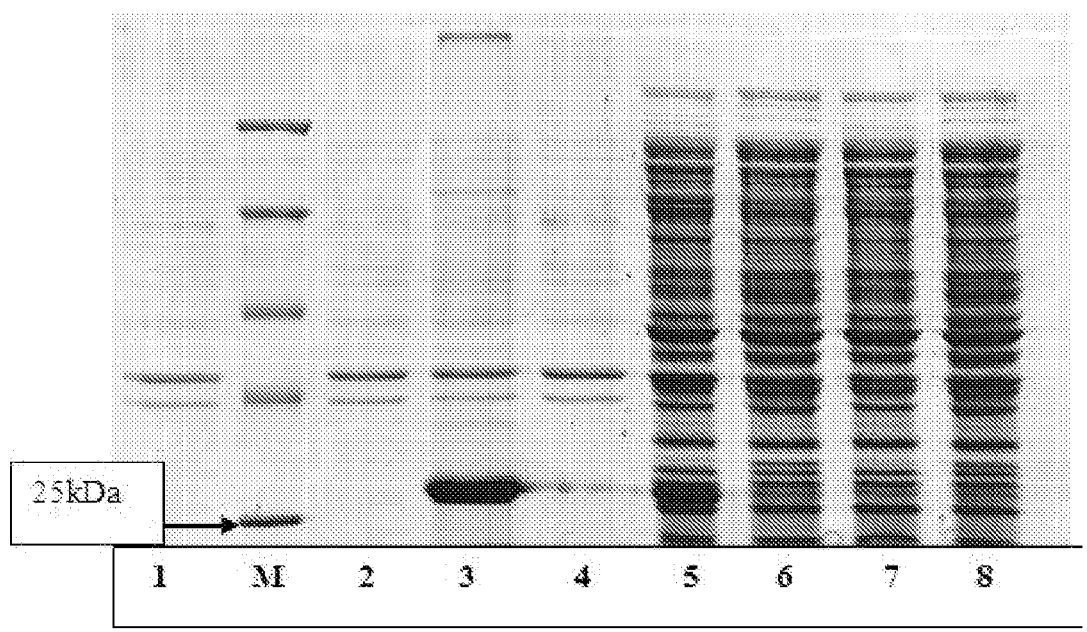
FIG. 2 is a photograph of PAAG electrophoretic pattern for insoluble and soluble fractions of BL21(DE3) strain harboring pET-TM1643-All plasmid or pET-22b as a control.
Lanes 1, 2, 3, 4: insoluble fraction
Lanes 6, 7, 8, 9: soluble fraction
M: protein marker.
Lane 1: pET-22b plasmid+IPTG
Lane 2: pET-22b plasmid
Lane 3: pET-TM1643-All+IPTG
Lane 4: pET-TM1643-All
Lane 5: pET-TM1643-All+IPTG
Lane 6: pET-TM1643-All
Lane 7: pET-22b plasmid+IPTG
Lane 8: pET-22b plasmid

The corresponding protein designated hereinafter as ADH was purified from BL21(DE3) strain harboring pET-ADH-P(S) plasmid. The procedure for ADH purification from soluble fraction of crude cell extracts was developed using precipitation in ammonium sulfate solution, anion-exchange chromatography and affinity chromatography. The ADH activity was determined spectrophometrically by measuring the absorbance increase at 340 nm at 29° C. The assay mixture contained 0.1M TRIS-HCl buffer, pH 9.8, 1 mM $NAD^+$, 5 mM aspartic acid in 1 ml of final volume. The results are presented in Table 9. These data show that the implemented procedure resulted in 77-fold ADH purification with 20% yield. The homogeneity of the purified ADH was assessed by SDS/PAGE and a major band with molecular mass of about (30±3) kDa was obtained (FIG. 2). The determined molecular mass of the ADH corresponds to the value predicted from its sequence (27.6 kDa). The molecular weight of the native ADH was determined about (49±12) kDa by gel-filtration, suggesting that the active form of the enzyme exists as a homodimer.

TABLE 9

Purification of the *Polaromonas* sp. aspartate dehydrogenase from BL21(DE3) strain harboring pET-ADH-P(S) plasmid.

| Purification step | Total protein (mg) | Total activity (μmol/min) | Specific activity (μmol/min/mg) | Yield (%) | Purification fold |
|---|---|---|---|---|---|
| Cell extract | 375.28 | 127.355 | 0.339 | 100 | 1 |
| Ammonium sulfate | 38.19 | 101.192 | 2.650 | 79 | 8 |
| anion-exchange chromatography | 2.95 | 43.304 | 14.679 | 34 | 43 |
| affinity chromatography | 1.00 | 26.150 | 26.150 | 20 | 77 |

Purified protein was extracted from the gel and digested by trypsin. Mass spectrometry analysis proved that the purified enzyme is a protein product of the Bpro_3686 aspartate dehydrogenase gene from *Polaromonas* sp. JS666.

HPLC analysis showed that in vitro L-aspartic acid is the only product of the direct reaction of oxaloacetate reductive amination catalyzed by the purified aspartate dehydrogenase.

Temperature Stability

To check temperature stability of the purified protein, its aliquots were incubated at 20, 30, 34, 40, 50, 60 or 70° C. for one hour. Thermostability of the protein was evaluated via assay of residual activity in standard forward reaction (0.1M TRIS-HCl buffer, pH 9.8, 0.15 mM NADH, 100 mM $NH_4Cl$ and 20 mM oxaloacetate at 29° C.) using the protein aliquot pre-incubated at the various temperatures indicated on the x axis during one hour. The results are presented in FIG. 11 as the percentages of activity measured with the protein incubated at the various temperatures in relation to the activity measured with the protein kept at 0° C. The assays were done at least in duplicate, and the error bars indicate deviations between the measurements.

Figure 11:
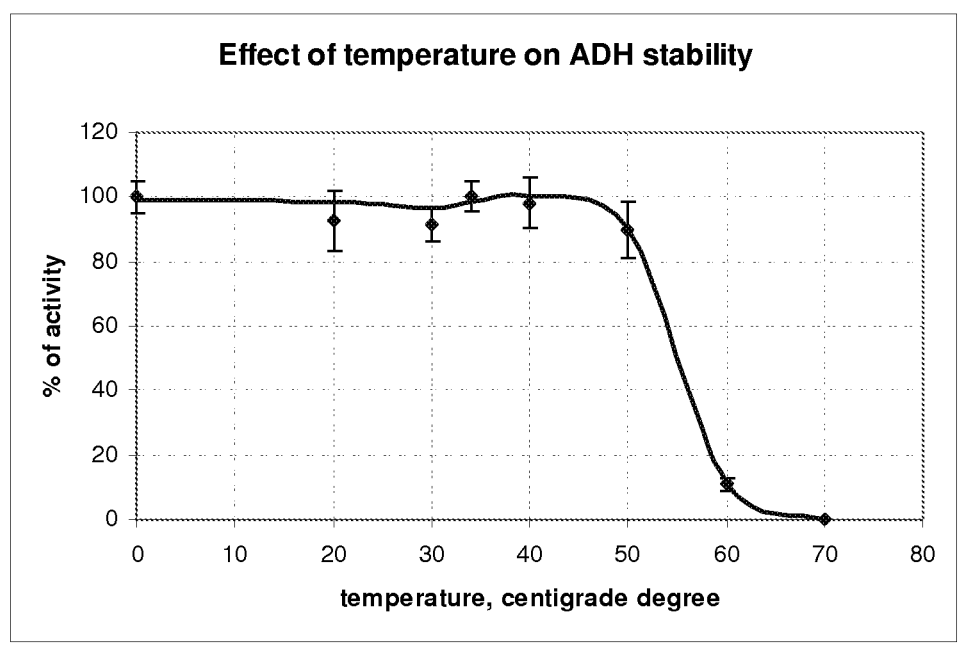
FIG. 11 shows effect of temperature on stability of the *Polaromonas* sp. aspartate dehydrogenase.

As presented in FIG. 11, after incubation at a temperature range from 20° C. to 50° C., significant decrease of the enzyme activity was not observed. After incubation at 60° C., the enzyme lost about 90% of its activity. After incubation at 70° C., 100% loss of the enzyme activity was observed. So, the purified enzyme is rather stable at temperature up to 50° C.

pH Optimum and Substrate Specificity for ADH Catalysis

The effect of pH on ADH catalysis of forward and reverse reactions was determined. The results are presented in FIG. 10. The forward reaction was performed in (a) 0.1M MES-NaOH buffer, pH 6 to 7 or (b) 0.1M TRIS-HCl buffer, pH 7 to 9.8 or (c) 0.05M Gly-NaOH buffer, pH 8 to 11 with 0.15 mM NADH, 50 mM $NH_4Cl$ and 10 mM oxaloacetate. The reverse reaction was performed in (d) 0.1M TRIS-HCl buffer, pH 8 to 9.8 or (e) 0.1M Gly-NaOH buffer, pH 9.8 to 12 with 1 mM $NAD^+$ and 10 mM aspartic acid.

Figure 10:
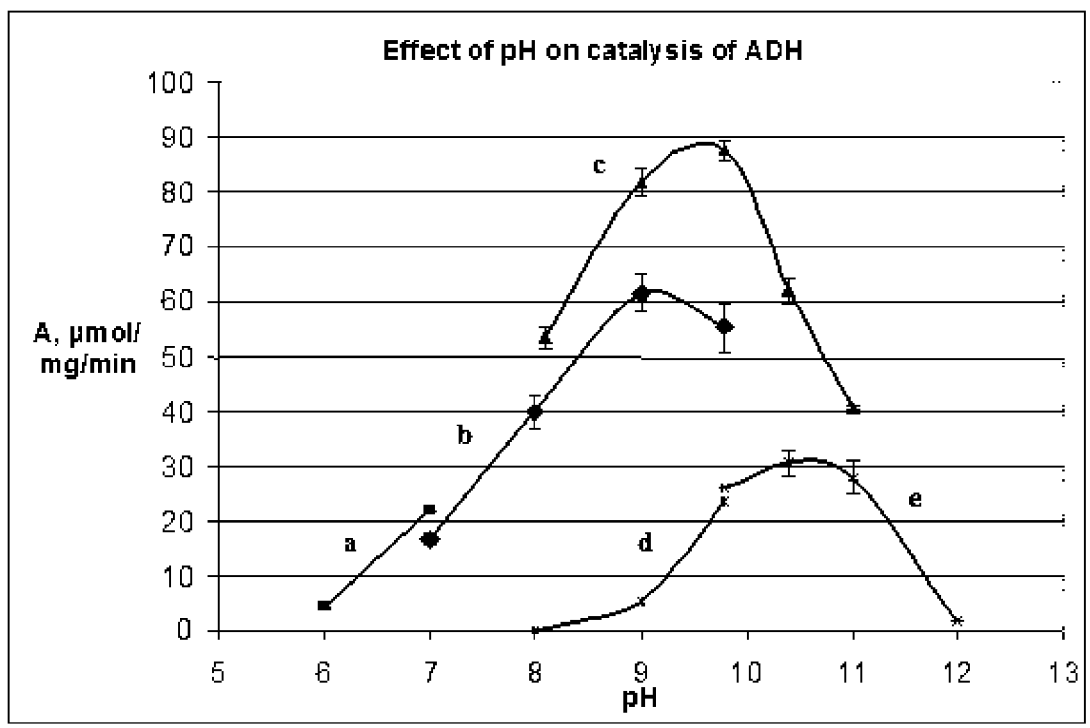
FIG. 10 shows effect of pH on ADH catalysis of forward and reverse reactions.

As follows from FIG. 10, the pH optimum for ADH catalysis of forward and reverse reactions (the aspartate synthesis and the oxidative deamination of aspartic acid, respectively) was observed in alkaline region. The purified ADH showed maximum activity for forward reaction at pH from 9 to 10. The maximum ADH activity for reverse reaction occurred at pH from 9.8 to 11. So 0.1 M TRIS-HCl buffer at pH 9.8 was used for further characterization of the purified ADH.

To identify alternative substrates for the purified ADH in the forward and reverse reactions, screening of substrate specificity was performed. Pyruvate, α-ketoglutarate, α-ketobutyrate, ketoisovaleriate and ketomethylvaleriate, all at 10 mM, were examined for their ability to replace oxaloacetate in forward reaction with 0.15 mM NADH, 50 mM $NH_4Cl$ at 29° C. Glutamate, alanine, α-aminobutyrate, valine, isoleucine, asparagine, all at 10 mM, were examined for their ability to replace aspartic acid in reverse reaction with 1 mM $NAD^+$ at 29° C. No activity was found with all of these substances, the enzyme is strictly specific for oxaloacetate and L-aspartic acid.

Kinetic Parameters

A detailed kinetic characterization was performed for the purified native ADH in forward and reverse reactions. The kinetic analysis of ADH in the forward reaction was carried out by varying the substrate (oxaloacetate) concentration from 0.5 to 20 mM at 0.15 mM NADH and 100 mM $NH_4Cl$, and by varying the ammonium ($NH_4Cl$) concentration from 6 to 125 mM at 0.15 mM NADH and 20 mM oxaloacetate, and by varying the concentration of coenzyme (NADH or NADPH) from 0.017 to 0.35 mM at 20 mM oxaloacetate and 100 mM $NH_4Cl$. The kinetic analysis of ADH in reverse reaction was carried out by varying the substrate (aspartic acid) concentration from 0.1 to 40 mM at 2 mM $NAD^+$, and by varying the concentration of coenzyme ($NAD^+$ or $NADP^+$) from 0.06 to 4 mM at 20 mM aspartic acid. The results are presented in Table 10. As follows from Table 10, with regard to coenzyme specificity, the catalytic efficiency ($k_{cat}K_m$) of ADH for NADH was nearly three times higher than that one for NADPH, and the catalytic efficiency for $NAD^+$ was nearly five times higher than that one for $NADP^+$. So the ADH has a better affinity for NADH than for NADPH in the forward reaction and for $NAD^+$ than $NADP^+$ in reverse reaction. When the forward and the reverse reaction were compared, the ADH catalyzed the oxaloacetate amination with the oxidation of NADH or NADPH at rates nearly three times or 10 times higher than those for the aspartic acid deanination.

TABLE 10

Kinetic parameters of the *Polaromonas* sp. ADH.

| Substrate | $V_{max}$ (μmol/min/mg) | $K_m$ (mM) | $k_{cat}$ (1/min) | $k_{cat}/K_m$ (1/min/mM) |
|---|---|---|---|---|
| Oxaloacetate reductive amination | | | | |
| Oxaloacetate[a] | 74 ± 3 | 2.2 ± 0.3 | 2030 ± 90 | 900 ± 200 |
| NH$_4$Cl[a] | 83 ± 3 | 33 ± 3 | 2280 ± 80 | 70 ± 9 |
| NADH[a] | 140 ± 20 | 0.190 ± 0.040 | 3800 ± 500 | 21000 ± 7000 |
| NADH[b] | 80 ± 3 | 0.068 ± 0.005 | 2210 ± 90 | 33000 ± 4000 |
| NADPH[a] | 97 ± 10 | 0.400 ± 0.060 | 2700 ± 300 | 7000 ± 2000 |
| NADPH[b] | 54 ± 4 | 0.150 ± 0.020 | 1490 ± 100 | 10000 ± 2000 |
| Aspartic acid oxidative deamination | | | | |
| Aspartic acid[a] | 26.2 ± 0.9 | 1.3 ± 0.2 | 720 ± 20 | 560 ± 90 |
| NAD$^{+}$[a] | 32.0 ± 0.2 | 0.424 ± 0.010 | 881 ± 6 | 2080 ± 60 |
| NADP$^{+}$[a] | 7.5 ± 0.2 | 0.510 ± 0.030 | 208 ± 4 | 400 ± 30 |
| Oxaloacetate reductive amination | | | | |
| Oxaloacetate[a] | 74 ± 3 | 2.2 ± 0.3 | 2030 ± 90 | 900 ± 200 |
| NH$_4$Cl[a] | 83 ± 3 | 33 ± 3 | 2280 ± 80 | 70 ± 9 |
| NADH[a] | 140 ± 20 | 0.190 ± 0.040 | 3800 ± 500 | 21000 ± 7000 |
| NADH[b] | 80 ± 3 | 0.068 ± 0.005 | 2210 ± 90 | 33000 ± 4000 |
| NADPH[a] | 97 ± 10 | 0.400 ± 0.060 | 2700 ± 300 | 7000 ± 2000 |
| NADPH[b] | 54 ± 4 | 0.150 ± 0.020 | 1490 ± 100 | 10000 ± 2000 |
| Aspartic acid oxidative deamination | | | | |
| Aspartic acid[a] | 26.2 ± 0.9 | 1.3 ± 0.2 | 720 ± 20 | 560 ± 90 |
| NAD$^{+}$[a] | 32.0 ± 0.2 | 0.424 ± 0.010 | 881 ± 6 | 2080 ± 60 |
| NADP$^{+}$[a] | 7.5 ± 0.2 | 0.510 ± 0.030 | 208 ± 4 | 400 ± 30 |

[a]The $K_m$ and $V_{max}$ parameters were determined from Michaelis-Menten kinetic equation plots.
[b]The kinetic parameters were determined from Hill kinetic equation plots because of sigmoidal curves were observed for these reaction. The calculated Hill coefficients were as follows: 1.71 ± 0.13 for NADH and 1.37 ± 0.08 for NADPH.
All data-fitting procedures were performed with the Sigma Plot 8.0 program. The $k_{cat}$ and $k_{cat}/K_m$ values were calculated according to the molecular mass of the ADH is equal to 27.57 kDa.

Regulatory Properties of the ADH

The ADH activity was not significantly affected by the addition of 1 mM of pyruvate, α-ketoglutarate, glutamate, malate, coenzyme A or acetyl-coenzyme A in forward and reverse reactions. Aspartate dehydrogenase assay was measured at 29° C. in the forward reaction (0.1M TRIS-HCl buffer, pH 9.8, 0.15 mM NADH, 100 mM NH$_4$Cl and 20 mM oxaloacetate) and reverse reaction (0.1M TRIS-HCl buffer, pH 9.8, 2 mM NAD$^+$ and 20 mM aspartic acid) in the presence of 1 mM of each metabolite indicated on the y axes. The results are presented in FIG. 12 as the percentages of activity in the presence of the metabolites in relation to the activity measured in the absence of the metabolites. The assays were done at least in duplicate, and the error bars indicate deviations between the measurements.

Figure 13:
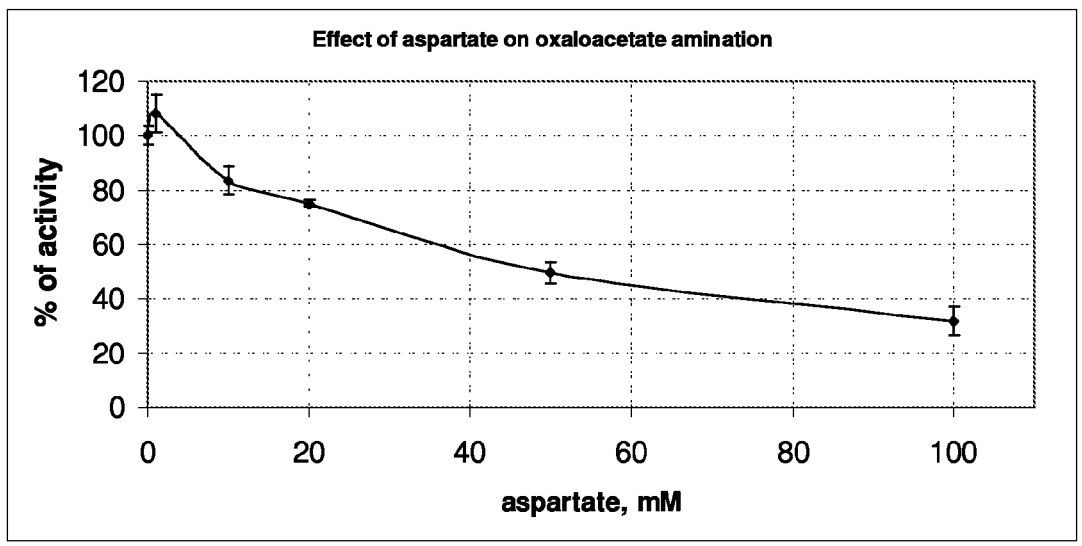
FIG. 13 shows effect of aspartic acid on ADH catalysis of the oxaloacetate amination reaction.

Addition of 1 mM oxaloacetate or NH$_4$Cl did not significantly inhibit the reverse reaction of aspartic acid deamination. Aspartic acid was examined for its ability to inhibit forward reaction of the aspartic acid synthesis in a concentration range from 1 to 100 mM. Aspartate dehydrogenase assay was measured at 29° C. in 0.1M TRIS-HCl buffer, pH 9.8, 0.15 mM NADH, 100 mM NH$_4$Cl and 20 mM oxaloacetate with addition of aspartic acid or without it. The results are presented in FIG. 13 as the percentages of activity in the presence of aspartic acid in relation to the activity measured in the absence of aspartic acid. The assays were done at least in duplicate, and the error bars indicate deviations between the measurements. As presented in FIG. 13, the addition of 100 mM aspartic acid decreased the enzyme activity only by 3 times.

Study of Biological Role of the Aspartate Dehydrogenase from *Polaromonas* sp.

To elucidate the in vivo function of the aspartate dehydrogenase from *Polaromonas* sp., the experiment on complementation of *E. coli* ΔaspCΔtyrB mutations was conducted. ΔaspCΔtyrB strain is auxotrophic for L-aspartic acid and L-tyrosine. The constructed pMIV-ADH-P(S) plasmid carrying the Bpro_3686 aspartate dehydrogenase gene from *Polaromonas* sp. and pMIV5-JS vector were introduced to the *E. coli* MG1655ΔaspCΔtyrB strain. The *E. coli* MG1655 strain harboring pMIV5-JS vector was used as a positive control. To test the complementation the obtained plasmid strains were re-streaked on M-9 medium containing glucose (10 g/L) as sole carbon source, Tyr (0.1 g/L) and chloramphenicol (50 mg/L). The pMIV-ADH-P(S) plasmid recovered growth of MG1655ΔaspCΔtyrB strain on M9 medium indicated above.

As for the reverse reaction, complementation of ΔaspA mutation in *E. coli* was tested. ΔaspA strain cannot utilize L-aspartic acid as a sole carbon source. Introduction of the pMIV-ADH-P(S) plasmid into the *E. coli* MG1655ΔaspA-PL-gltS provided growth of this strain on M-9 medium containing aspartic acid (10 g/L) as sole carbon source and chloramphenicol (50 mg/L). MG1655ΔaspA-PL-gltS/pMIV5-JS was used as a negative control.

Thus, complementation of ΔaspCΔtyrB and ΔaspA mutations by the plasmid carrying aspartate dehydrogenase gene from *Polaromonas* sp. was proved in *E. coli*. The resulting aspartate dehydrogenase seems to take part both in biosynthesis and in catabolism of aspartic acid.

Example 4

Introducing the Aspartate Dehydrogenase Gene from *Polaromonas* sp. JS666 to the Aspartic Acid Producing Strain of *P. ananatis*

The aspartate dehydrogenase gene from *Polaromonas* sp. JS666 was integrated to 5ΔP2RMG-S strain via miniMu-dependent procedure using the integrative pMIV-ADH-P(S)-all plasmid. Construction of 5Δ2RMG-S strain is described in the Reference Example 1. Assay of aspartate dehydrogenase activity in the crude extracts of the best RMG::ADH(P) integrant was performed. Cultures were grown for 9 hours in LB-M91/2 medium containing 5 g/L glucose with addition of 50 mg/L chloramphenicol for the integrants. Then, they were diluted 1:30 up to final volume of 10 ml by the standard medium for test tube fermentations (pH 6, without CaCO$_3$) containing 10 g/L glucose and 3 g/L L-Glu with addition of 0.1 mM IPTG.

Resulting cultures were cultivated at +34° C. in 16 hours with aeration in tubes. Then cells were harvested by centrifugation, washed with 50 mM TRIS, pH 7.4 and frozen. The pellets were re-suspended in the buffer containing 50 mM TRIS, pH 7.4, and 2 mM DTT and cells were disrupted by sonication. Assay of the aspartate dehydrogenase activity was performed in forward and reverse reactions at +26° C. One reaction mixture contained 100 mM TRIS, pH 9.8, 2 mM NAD+ and 10 mM aspartic acid. Another reaction mixture contained 100 mM TRIS, pH 9.8, 0.15 mM NADH, 100 mM NH4Cl and 20 mM oxaloacetate. The probes without aspartic acid were used as controls in forward reaction. The probes without NH$_4$Cl were used as controls in reverse reaction. Results are presented in Table 11. Data in Table 11 show high level of aspartate dehydrogenase activity comparable with the specific activities measured in *E. coli* BL21(DE3)/pET-ADH-P(S) strain.

TABLE 11

Aspartate dehydrogenase specific activity in the crude extracts of the RMG::ADH(P) integrant carrying the aspartate dehydrogenase gene from *Polaromonas* sp. JS666.

| | Aspartate dehydrogenase sp. activity, nmol/min/mg | |
|---|---|---|
| Strain | NAD$^+$ | NADH |
| 5ΔP2RMG-S | 0 | 0 |
| RMG::ADH(P) | 1080 ± 30 | 1160 ± 50 |

Test-tube cultivation of the RMG::ADH(P) integrants was performed. Standard medium (initial glucose 40 g/L, initial L-Glu 3 g/L) was supplemented with 0.1 mM IPTG for induction of expression of the aspartate dehydrogenase gene. 72-hour cultivation at +34° C. was applied. Average data for three independent cultures are represented in Table 12. As presented in Table 12, aspartic acid accumulation by the best integrant was about 2-fold higher than for the control. Therefore, the aspartate dehydrogenase from *Polaromonas* sp. JS666 can be exploited for oxaloacetate amination in aspartic acid fermentation.

TABLE 12

Test-tube cultivation of the RMG::ADH(P) integrants.

| Strain | OD$_{595}$ | Res. Glucose, g/L | Asp, g/L | Res. Glu, g/L |
|---|---|---|---|---|
| 5ΔP2RMG-S (control) | 8.7 ± 0.2 | 0.0 | 0.8 ± 0.1 | 1.8 |
| RMG::ADH(P) | 8.2 ± 0.1 | 0.4 | 1.4 ± 0.4 | 1.5 |

Example 5

Purification and Characterization of the Aspartate Dehydrogenase from *Rhodoseudomonas palustris* HaA2

Cloning of the Putative Aspartate Dehydrogenase Gene RPB_0147 from *Rhodoseudomonas palustris* HaA2

As described above (see, Example 2), the RPB_0147 gene from *Rhodoseudomonas palustris* HaA2 was selected for analysis as the putative aspartate dehydrogenase gene. Its protein product has 28% of homology to the known TM1643 aspartate dehydrogenase from *Thermotoga maritma* and the similar level of homology (34% identity) to the found aspartate dehydrogenase from *Polaromonas* sp. The RPB_0147 gene localized near to the genes coding for a transporter and a putative monovalent cation/H$^+$ antiporter. So, the gene surroundings of the *R. palustris* RPB_0147 differ from the gene surroundings of aspartate dehydrogenase genes from *T. maritma* and *Polaromonas* sp. It was assumed, that the enzyme from *R. palustris* may possess new features.

Figure 15:
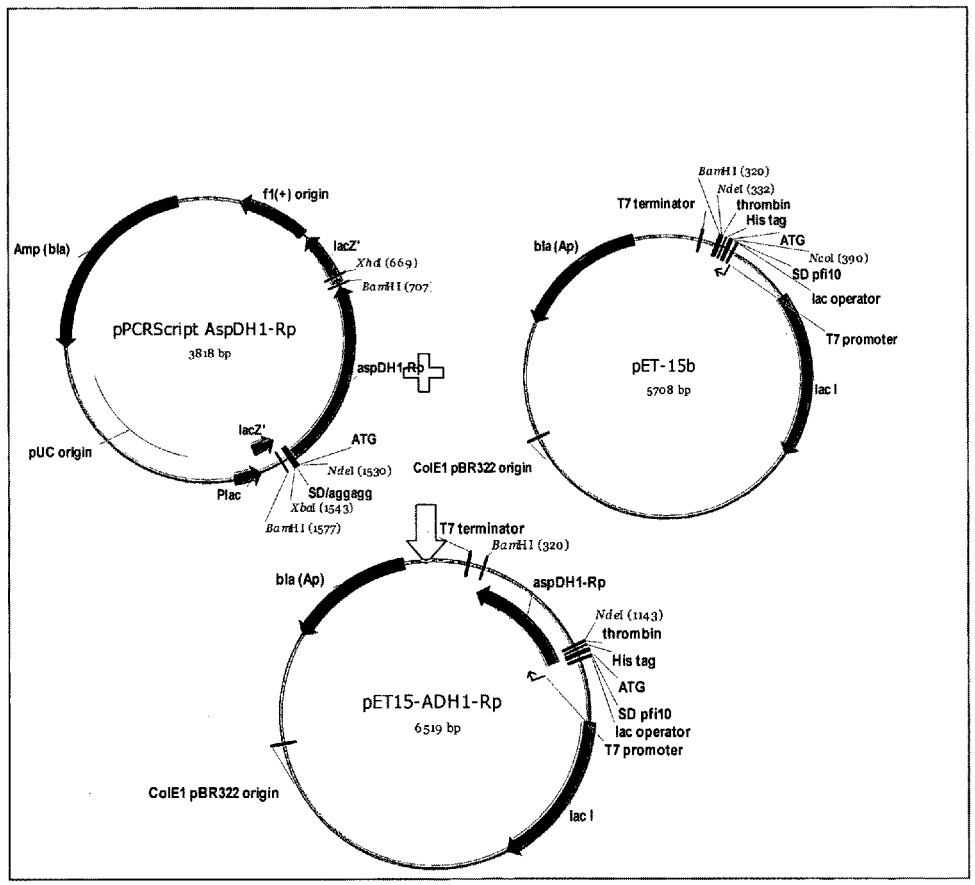
FIG. 15 shows scheme of construction of the pET15-ADH1-Rp plasmid comprising the putative aspartate dehydrogenase gene RPB_0147 from *Rhodosevdomonas palustris* HaA2.

To provide an effective translation of mRNA of the RPB_0147 gene from *R. palustris*, the variant of the gene with substituted rare codons (SEQ ID NO: 73) was ordered from Sloning BioTechnology, GmbH (German) and further subcloned into the pET-15b vector under the T7 expression region containing a P$_{T7}$ promoter, a T7 transcription start, a RBS$_{Φ10}$, a His-Tag coding sequence followed by a thrombin site. For that, the NdeI-BamHI fragment of the pPCR-Script_AspDH1-Rp plasmid comprising the ORF of the *R. palustris* RPB_0147 gene with substituted rare codons was ligated with the pET-15b vector digested with the same NdeI and BamHI endonucleases. The resulting plasmid was designated pET15-ADH1-Rp. The scheme of construction of the pET15-ADH1-Rp plasmid is represented in FIG. 15. To check precision of DNA sequence of the cloned fragment, the nucleotide sequence of the cloned gene being in composition of the constructed plasmid was determined by Vostok limited (Russia) using Sanger's method (Sanger F., Nicklen S., Coulson A. R. 1977. DNA sequencing with chain-terminating inhibitors. Proc. Natl. Acad. Sci. USA. 74, 5463-5467). As a result, pET15-ADH1-Rp clones 7 and 8 comprised the cloned gene having the expected DNA sequence.

Figure 16:
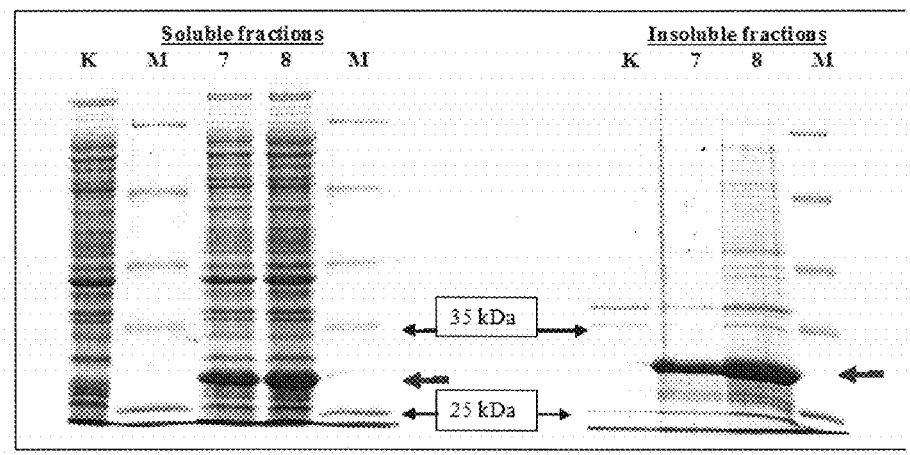
FIG. 16 is a photograph of SDS/PAAG (10%) electrophoresis of the soluble and insoluble fractions prepared from the crude extracts of the BL21(DE3) strain harboring the pET15-ADH1-Rp plasmid.

The obtained pET15-ADH1-Rp plasmid was transformed to the BL21(DE3) strain carrying the gene of T7 RNA polymerase in its chromosome. The strain harboring pET-15b vector was used as a negative control. Cells were cultivated in LB medium with ampicillin (120 mg/L) at +37° C. up to OD595=0.9. After that, 1 mM IPTG was added and cells were cultivated for 2 hours. Cells from 1.5 ml were disrupted by sonication in the buffer containing 50 mM TRIS pH 7.5, 1 mM DTT and 1 mM EDTA. After induction by IPTG, high level accumulation of the protein of the expected size (30.6 kDa) was observed in the soluble and insoluble fractions (FIG. 16).

Cells were cultivated in LB medium with ampicillin (120 mg/L) at +37° C. up to OD$_{595}$=0.9. After that, 1 mM IPTG was added and cells were cultivated for 2 hours. Assay was performed at room temperature (+30° C.). Reaction mixture for the deamination reaction contained 100 mM TRIS-HCl, pH 9.8, 2 mM NAD(P)$^+$ and 10 mM sodium aspartate (pH 7.0). Reaction mixture for the amination reaction contained 100 mM TRIS-HCl, pH 9.8, 100 mM NH$_4$Cl 0.15 mM NAD(P)H and 20 mM oxaloacetate (pH 7.0). Assay of specific aspartate dehydrogenase activity in crude extracts showed high level of NADP(H)-dependent aspartate dehydrogenase activity at room temperature (+30° C.) (Table 13). So, the cloned RPB_0147 gene from *Rhodosevdomonas palustris* encoded a novel aspartate dehydrogenase (ADH1-Rp) active at room temperature.

TABLE 13

Assay for aspartate dehydrogenase activity in crude extracts of the BL21(DE3) strain harboring the pET15b vector or the pET15-ADH1-Rp plasmid carrying the gene from *Rhodopseudomonas palustris* at +30° C.

| | | Sp. ADH activity, nmol/min/mg | | | |
|---|---|---|---|---|---|
| Strain | Clone | NAD$^+$ | NADP$^+$ | NADH | NADPH |
| BL21(DE3)/pET15b | | 0 | 0 | 0 | 0 |
| BL21(DE3)/pET15-ADH1-Rp | 7 | 35 ± 5 | 290 ± 40 | nd | 1960 |
| | 8 | 35 ± 8 | 350 ± 40 | nd | 1880 |

Purification and Characterization of the Found Aspartate Dehydrogenase 1 from *Rhodoseudomonas palustris*

Novel aspartate dehydrogenase (ADH1-Rp) cloned from *Rhodoseudomonas palustris* was purified from *E. coli* BL21 (DE3) strain harboring pET15-ADH1-Rp plasmid clone 8. Overnight culture grown in 30 ml LB broth supplemented with ampicillin (120 mg/L) was diluted 1:100 in 200 ml of the same medium and cultivated in flask at +37° C. up to OD$_{595}$=1. The cells were then induced by addition of 1 mM IPTG. After 2 h of cultivation the cells from 1 L culture were harvested by centrifugation and stored at −70° C. until used. Frozen cells were thawed, suspended in 10 ml of buffer A (20 mM sodium phosphate, pH 7.0, 0.5 M NaCl, 20 mM imidazole) and disrupted by two passages through French pressure cell (Thermo Spectronic) at p=2000 psi and by sonication followed by centrifugation to remove debris. The recombinant aspartate dehydrogenase expressed with a hexa-histidine fusion tag at the N terminus was purified using HisTrap HP column (Amersham Pharmacia Biotech, UK) according to manufacture's recommendation. The elution was carried out with a linear gradient from 20 to 500 mM imidazole in buffer B (20 mM sodium phosphate, pH 7.0, 0.5 M NaCl). Active fractions were pooled and desalted by gel-filtration on the PD-10 desalting column (Amersham Pharmacia Biotech, UK) equilibrated with buffer C (20 mM sodium phosphate, pH 7.0, 1 mM DTT, 1 mM EDTA, 15% glycerol). The purified enzyme was aliquoted and stored at −70° C. until used.

The used procedure resulted in 5-fold *Rhodoseudomonas palustris* ADH1-Rp purification with 19% yield. The homogeneity of the purified ADH was assessed by SDS/PAGE and a major band with molecular mass of about 31 kDa was obtained (FIG. 17). The determined molecular mass of the ADH1-Rp corresponds to the value predicted from its sequence (30.6 kDa).

pH Optimum

The amination reaction was performed in (a) 0.1M MES-NaOH buffer, pH 6 to 7 or (b) 0.1M TRIS-HCl buffer, pH 7 to 9.8 or (c) 0.05M Gly-NaOH buffer, pH 8 to 11 with 0.15 mM NADPH, 100 mM $NH_4Cl$ and 20 mM oxaloacetate. The deamination reaction was performed in (d) 0.1 M TRIS-HCl buffer, pH 8 to 9.8 or (e) 0.05M Gly-NaOH buffer, pH 9 to 12 with 1 mM $NADP^+$ and 10 mM aspartate. The assays were done at least in duplicate, and the error bars indicate deviations between the measurements.

The pH optimum for *Rhodoseudomonas palustris* ADH1-Rp catalysis of the oxaloacetate amination and the aspartic acid deamination reactions was observed in alkaline region (FIG. 18). The purified ADH1-Rp showed maximum activity for amination reaction at pH 9.0. The maximum ADH1-Rp activity for deamination reaction occurred at pH 9.8. So, 0.1 M TRIS-HCl buffers at pH 9.0 and 9.8 were used for further characterization of the purified ADH1-Rp in amination and deamination reactions, respectively.

Kinetic Parameters

A detailed kinetic characterization was performed for the purified *Rhodoseudomonas palustris* ADH1-Rp in amination and deamination reactions. The kinetic analysis of ADH1-Rp in amination reaction was carried out by varying the substrate (oxaloacetate) concentration from 1.3 to 20 mM at 0.15 mM NADPH and 100 mM $NH_4Cl$, and by varying the ammonium ($NH_4Cl$) concentration from 1 to 100 mM at 0.15 mM NADPH and 20 mM oxaloacetate, and by varying the concentration of NADPH from 0.025 to 0.400 mM at 20 mM oxaloacetate and 100 mM $NH_4Cl$, and by varying the concentration of NADH from 0.050 to 5 mM at 20 mM oxaloacetate and 100 mM $NH_4Cl$. The kinetic analysis of ADH1-Rp in deamination reaction was carried out by varying the substrate (aspartic acid) concentration from 1 to 60 mM at 1 mM $NADP^+$, and by varying the concentration of NADP from 0.015 to 1 mM at 40 mM aspartic acid, and by varying the concentration of $NAD^+$ from 0.5 to 12 mM at 40 mM aspartic acid. All data-fitting procedures were performed with the Sigma Plot 8.0 program. The $k_{cat}$ and $k_{cat}/K_m$ values were calculated according to the molecular mass of the ADH1-Rp which is equal to 30.63 kDa. Obtained data are shown in Table 14. The $K_m$ and $V_{max}$ parameters were determined from Michaelis-Menten kinetic equation plots. With regard to coenzyme specificity, the catalytic efficiency ($k_{cat}/K_m$) of ADH1-Rp for NADPH was nearly 72 times higher than for NADH, and the catalytic efficiency for NADP was nearly 103 times higher than for $NAD^+$. So the ADH1-Rp has much better affinity for NADPH than for NADH in forward reaction and for $NADP^+$ than $NAD^+$ in reverse reaction. When the amination and the deamination reactions were compared, the ADH1-Rp catalyzed the oxaloacetate amination with the oxidation of NADPH or NADH at rates nearly 4 times or 5 times higher than for the aspartic acid deamination.

TABLE 14

Kinetic parameters of the *Rhodopseudomonas palustris* AspDH 1

| Substrate | $V_{max}$ (µmol/min/mg) | $K_m$ (mM) | $k_{cat}$ (1/min) | $k_{cat}/K_m$ (1/min/mM) |
|---|---|---|---|---|
| Oxaloacetate reductive amination ||||
| Oxalocetate | 27.9 ± 1.4 | 9.2 ± 0.9 | 850 ± 40 | 92 ± 13 |
| $NH_4Cl$ | 20.2 ± 0.6 | 11.3 ± 1.1 | 620 ± 20 | 55 ± 7 |
| NADH | 10.1 ± 0.6 | 4.5 ± 0.4 | 310 ± 20 | 69 ± 11 |
| NADPH | 37 ± 4 | 0.210 ± 0.050 | 1150 ± 120 | 5000 ± 2000 |
| Aspartic acid oxidative deamination ||||
| Aspartic acid | 5.61 ± 0.08 | 13.4 ± 0.5 | 172 ± 2 | 12.8 ± 0.7 |
| $NAD^+$ | 3.11 ± 0.06 | 7.0 ± 0.3 | 95 ± 2 | 13.6 ± 0.9 |
| $NADP^+$ | 4.57 ± 0.14 | 0.102 ± 0.011 | 140 ± 4 | 1400 ± 200 |

Summary

1. Reaction of aspartic acid synthesis in vitro is catalyzed by the *Rhodoseudomonas palustris* ADH1-Rp more efficiently (4-5 times) than reverse reaction of aspartic acid deamination under alkaline conditions (at pH 9.0 and 9.8). Moreover, only amination reaction was detected under physiological conditions at pH 7.0.

2. The determined $K_m$ value for ammonium ($NH_4Cl$) is 11 mM. This value is 3 times lower than $K_m$ value for $NH_4Cl$ (33 mM) determined for *Polaromonas* sp. ADH.

3. NADPH and NADP are more preferable (in 70-100 times) cofactors for *Rhodoseudomonas palustris* ADH1-Rp in vitro.

4. The determined $K_m$ values for NADPH and NADH are 0.210 and 4.5 mM, respectively. At the same time, the typical concentrations of corresponding pyridine nucleotides within *E. coli* cells are 0.15 mM NADPH and 0.02 mM NADH (T Penfound & J W Faster, 1996. Biosynthesis and Recycling of NAD. In: Neidhardt, F. C. (ed), *Escherichia coli* and *Salmonella typhimurium*: Cellular and Molecular Biology. ASM Press, Washington, D.C., pp. 721-730). So, it could be proposed that in vivo ADH1-Rp from *Rhodoseudomonas palustris* could use only NADPH as a cofactor in the oxaloacetate amination reaction.

Example 6

Searching for the Putative Aspartate Dehydrogenase Genes Based on the Analysis of Homologues for the Known ADH1-Rp and their Gene Surroundings As described above in Example 2, the Bpro_3686 gene from *Polaromonas* sp. JS666 coding for aspartate dehydrogenase active at moderate temperature (+29° C.) was found. To find new enzymes optimal for aspartic acid biosynthesis, Blastp (protein-protein BLAST) analysis of the *Polaromonas* sp. aspartate dehydrogenase was carried out. Full-length homologs of this protein were found in many groups of bacteria and arhaea (FIGS. 19 and 20). Close homologs of the protein (identity 50-71%) were found in *Ralstonia, Burholderia, Comamonas testosteroni, Delftia acidovorans, Cupriavidus taiwanensis* and *Pseudomonas aeruginosa*.

All found homologs of novel aspartate dehydrogenase from *Polaromonas* sp. JS666 were classified on the basis of functional chromosomal surroundings of the gene encoding such homolog.

The aspartate dehydrogenase gene from *Polaromonas* sp. was localized near to the genes coding for thiamine pyrophosphate enzyme and betaine-aldehyde dehydrogenase. First group included putative aspartate dehydrogenase genes having the same gene surroundings. The known TM1643 gene from *Thermotaoga maritima* (Yang Zh, Savchenko A, Yakunin A, Zhang R, Edwards A, Arrowsmith C, Tong L. Aspartate dehydrogenase, a novel enzyme identified from structural and functional studies of TM1643. 2003. J Biol Chem, 278(10): 8804-8808) organizes operon with nadA and nadC genes coding for quinolinate synthethase A and nicotinate-nucleotide pyrophosphorylase, respectively. So, second group included putative aspartate dehydrogenase genes organized as the gene from *T. maritima*. Third group included putative aspartate dehydrogenase genes localized near to the gene coding for a transporter. Fourth group included putative aspartate dehydrogenase genes localized near to the gene from lysR family. A set of weak homologues had different gene surroundings and was unclassified.

The Meso_0824 gene (SEQ ID NO: 69) from *Mesorhizobium* sp. BNC1 was chosen as a candidate from the first group of homologues having gene surroundings the same as the gene from *Polaromonas* sp. It has the weakest homology in the group (42% of amino acid identity_to Bpro_3686 gene from *Polaromonas* sp. JS666).

The Nmar_1240 gene (SEQ ID NO: 71) from *Nitrosopumilus maritimus* SCM1 (32% of amino acid identity) was chosen as a candidate from the second group of homologues having gene surroundings similar to the gene from *T. maritima*. In contrast to *T. maritima, Nitrosopumilus maritimus* is a non-thermophilic organism living at moderate temperature (25-40° C.).

The AZC_4388 gene (SEQ ID NO: 67) from *Azorhizobium caulinodans* ORS 571 (45% of amino acid identity to Bpro_3686 gene from *Polaromonas* sp. JS666) and the bll6567 gene (SEQ ID NO: 68) from *Bradyrhizobium japonicum* USDA 110 (35% of amino acid identity to Bpro_3686 gene from *Polaromonas* sp. JS666) were chosen as candidates from two groups of homologues. Both organisms are symbiotic nitrogen-fixing bacteria and would cause formation of nodules in plants. Nitrogen-fixing bacteria may be perspective objects for searching of aspartate dehydrogenases because of aspartic acid can be synthesized via reductive amination of oxaloacetic acid not only in the plant part of nodules but also in bacteroids (Kretovich W L, Kariakina T I, Weinova M K, Sidelnikova L I and Kazakova O W. The synthesis of aspartic acid in *Rhizobium lupini* bacteroids. Plant Soil 1981. 61: 145-156).

The cgR_1126 gene (SEQ ID NO: 70) encoding hypothetical protein from *Corynebacterium glutamicum* R and OG2516_00504 gene from *Oceanicola granulosus* were chosen among of the weak homologues (31% and 30% of amino acid identity to Bpro_3686 gene from *Polaromonas* sp. JS666, respectively).

To provide efficient translation of the above genes in *E. coli* and *P. ananatis*, the chemical synthesis and cloning of the DNA fragments containing the coding part of the aspartate dehydrogenase genes, in which all rare codons were substituted by the synonymous frequent codons, was ordered from Sloning BioTechnology, GmbH (German). The nucleotide sequences of genes that contain substitutions of all rare codons are shown in the SEQUENCE LISTING section. There are modified_RPB_0147 gene from *Rhodoseudomonas palustris* HaA2 (SEQ ID NO: 73), modified_RPB_3108_gene from *Rhodoseudomonas palustris* HaA2 (SEQ ID NO: 74), modified h16_B0736 gene from *Ralstonia eutropha* (SEQ ID NO: 75), modified AZC_4388 gene from *Azorhizobium caulinodans* ORS 571 (SEQ ID NO: 76), modified bll6567 gene from *Bradyrhizobium japonicum* USDA 110 (SEQ ID NO: 77), modified Meso_0824 gene from *Mesorhizobium* sp. BNC1 (SEQ ID NO: 78), modified cgR_1126 gene from *Corynebacterium glutamicum* R (SEQ ID NO: 79), modified Nmar_1240 gene from *Nitrosopumilus maritimus* SCM1 (SEQ ID NO: 80) and modified OG2516_00504 gene from *Oceanicola granulosus* (SEQ ID NO: 81).

Example 7

Purification and Characterization of the Aspartate Dehydrogenase from *Ralstonia eutropha* H16 (ADH-Re)

Cloning of the Novel Aspartate Dehydrogenase Gene h16_B0736 from *Ralstonia eutropha* H16

As described above (see, Example 2), the h16_B0736 gene from *Ralstonia eutropha* H16 was selected for analysis as the putative aspartate dehydrogenase gene. Its protein product has 31% of homology to the known TM1643 aspartate dehydrogenase from *Thermotoga maritma* and high level of homology (68% identity) to the found aspartate dehydrogenase from *Polaromonas* sp. To provide an effective translation of mRNA of the gene from *Ralstonia eutropha*, the variant of the gene with substituted rare codons was sub-cloned into the pET-15b vector under the T7 expression region containing a $P_{T7}$ promoter, a T7 transcription start, a $RBS_{\Phi 10}$, a His-Tag coding sequence followed by a thrombin site. For that, the pPCRScript_AspDH-Re plasmid was digested with NdeI and BamHI restrictases. The plasmid fragment comprising the ORF of the *Ralstonia eutropha* h16_B0736 gene with substituted rare codons was ligated with the pET-15b vector digested with the same endonucleases (NdeI and BamHI). The resulting plasmid was designated pET15-ADH-Re (FIG. 22). The primary structure of cloned fragment was proved by sequence analysis. The primers Seq-adh-P5 (SEQ ID NO: 23) and sys-3 (SEQ ID NO: 94) were used for sequencing.

Preliminary assay of specific aspartate dehydrogenase activity in crude extracts of the BL21(DE3) strain harboring the pET15-ADH-Re plasmid was performed. The strain harboring pET-15b vector was used as a negative control. Cells were cultivated in LB medium with ampicillin (120 mg/L) at +37° C. up to $OD_{595}$=0.9. After that, 1 mM IPTG was added and cells were cultivated for 2 hours. Assay was performed at room temperature. Reaction mixture contained 100 mM TRIS-HCl, pH 9.8, 2 mM NAD(P)+ and 10 mM sodium aspartate (pH 7.0). Cells from 1.5 ml were disrupted by sonication in the buffer containing 50 mM TRIS pH 7.5, 1 mM DTT and 1 mM EDTA. As it is represented in Table 15, the plasmid provides rather low level of aspartate dehydrogenase activity. NAD+ is a preferable cofactor, at least in the aspartate deamination reaction.

TABLE 15

Assay of aspartate dehydrogenase activity in crude extracts of the BL21(DE3) strain harboring the pET15b vector or the pET15-ADH-Re plasmid carrying the gene from *Ralstonia eutropha* at +28° C.

| Strain | clone | Sp. ADH activity, nmol/min/mg | |
|---|---|---|---|
| | | NAD+ | NADP+ |
| BL21(DE3)/pET15b | | 0 | 0 |
| BL21(DE3)/pET15-ADH-Re | 2 | 21 ± 2 | 0 |
| | 3 | 33 ± 5 | 0 |
| | 4 | 34 ± 4 | 0 |

SDS/PAAG electrophoresis of the soluble and insoluble fractions prepared from the crude extracts of the BL21(DE3) strain harboring the pET15-ADH-Re plasmid was performed. As shown in FIG. 23, high level accumulation of a protein with molecular mass of about 33 kDa was observed in the soluble fraction. This result was in agree with computational protein Mw.

The novel *Ralstonia eutropha* aspartate dehydrogenase was purified from *E. coli* BL21(DE3) strain harboring pET15-ADH-Re plasmid clone 4. The procedure for purification of the recombinant aspartate dehydrogenase expressed with a hexa-histidine fusion tag at the N terminus from soluble fraction of crude extract was based on affinity chromatography. The used procedure resulted in 4-fold ADH-Re purification with 20% yield. The homogeneity of the purified ADH-Re was assessed by SDS/PAGE and a major band with molecular mass of about 33-34 kDa was obtained (see FIG. 24).

pH Optimum

The pH optimum for *Ralstonia eutropha* ADH-Re catalysis of the oxaloacetate amination and the aspartate deamination reactions was observed in alkaline region (FIG. 25). The amination reaction was performed in (a) 0.1 M MES-NaOH buffer, pH 6 to 7 or (b) 0.1 M TRIS-HCl buffer, pH 7 to 9.8 or (c) 0.05 M Gly-NaOH buffer, pH 8 to 11 with 0.15 mM NADH, 100 mM NH4Cl and 20 mM oxaloacetate. The deamination reaction was performed in (d) 0.1 M TRIS-HCl buffer, pH 7 to 9.8 or (e) 0.05 M Gly-NaOH buffer, pH 9 to 12 with 2 mM NAD+ and 10 mM aspartate. The assays were done at least in duplicate, and the error bars indicate deviations between the measurements. The purified ADH-Re showed maximum activity for amination reaction at pH 9. The maximum ADH-Re activity for deamination reaction occurred at pH from 9.8 to 11. Thus, 0.1 M TRIS-HCl buffers at pH 9 and 9.8 were used for further characterization of the purified ADH-Re in amination and deamination reactions, respectively. It should be noted that high level of activity was detected only in amination reaction under physiological conditions at pH 7.0.

Kinetic Parameters

A detailed kinetic characterization was performed for the purified *Ralstonia eutropha* ADH-Re in amination and deamination reactions (Table 16). The determined $K_m$ value for ammonium (NH4Cl) is 12 mM. It is 3 times lower than $K_m$ value for NH4Cl (33 mM) determined for *Polaromonas* sp. ADH.

TABLE 16

Kinetic parameters of the *Ralstonia eutropha* ADH-Re

| Substrate | $V_{max}$ (μmol/min/mg)[a] | $K_m$ (mM)[a] | $k_{cat}$ (1/min)[d] | $k_{cat}/K_m$ (1/min/mM)[d] |
|---|---|---|---|---|
| Oxaloacetate reductive amination | | | | |
| Oxaloacetate[b] | 117 ± 5 | 3.3 ± 0.4 | 3500 ± 140 | 1100 |
| NH4Cl[b] | 113 ± 4 | 11.9 ± 1.1 | 3400 ± 120 | 280 |
| NADH[b] | 610 ± 40 | 0.870 ± 0.080 | 18200 ± 1100 | 21000 |
| NADPH[b] | 220 ± 30 | 0.900 ± 0.300 | 6400 ± 1000 | 7000 |
| NADPH[c] | 137 ± 8 | 0.390 ± 0.040 | 4100 ± 300 | 11000 |
| Aspartate oxidative deamination | | | | |
| Aspartate[b] | 23 ± 2 | 13 ± 3 | 690 ± 60 | 50 |
| NAD+ [b] | 37 ± 3 | 1.7 ± 0.4 | 1120 ± 90 | 700 |
| NADP+ [b] | 10.9 ± 0.6 | 2.7 ± 0.4 | 330 ± 20 | 120 |

[a] The kinetic analysis of ADH-Re in amination reaction was carried out by varying the substrate (oxaloacetate) concentration from 0.3 to 20 mM at 0.15 mM NADH and 50 mM NH4Cl, and by varying the ammonium (NH4Cl) concentration from 0.7 to 50 mM at 0.15 mM NADH and 20 mM oxaloacetate, and by varying the concentration of NADH from 0.040 to 0.800 mM at 20 mM oxaloacetate and 50 mM NH4Cl, and by varying the concentration of NADPH from 0.025 to 1.200 mM at 20 mM oxaloacetate and 50 mM NH4Cl. The kinetic analysis of ADH-Re in deamination reaction was carried out by varying the substrate (aspartate) concentration from 2.5 to 40 mM at 2 mM NAD+, and by varying the concentration of NAD+ from 0.2 to 8 mM at 40 mM aspartate, and by varying the concentration of NADP+ from 0.5 to 8 mM at 40 mM aspartate. All data-fitting procedures were performed with the Sigma Plot 8.0 program.
[b] The $K_m$ and $V_{max}$ parameters were determined from Michaelis-Menten kinetic equation plots.
[c] The kinetic parameters were determined from Hill kinetic equation plots because of sigmoidal curve was observed for this reaction. The calculated Hill coefficient was 1.6 ± 0.1.
[d] The $k_{cat}$ and $k_{cat}/K_m$ values were calculated according to the molecular mass of the ADH-Re is equal to 29.94 kDa.

It was found that NADPH-saturation curve was rather sigmoid with positive Hill's coefficient (1.6±0.1) than classic Michaelis-Menten's hyperbolas. On the other hand, both oxaloacetate- and ammonium-saturation curves were hyperbolas. It seems that the native ADH-Re has two zymophores binding to NADPH cooperatively. With regard to coenzyme specificity, the catalytic efficiency ($k_{cat}/K_m$) of ADH-Re for NADH was nearly 2-3 times higher than that for NADPH, and the catalytic efficiency for NAD+ was nearly 6 times higher than that for NADP+. So the ADH-Re has some better affinity for NADH than for NADPH in amination reaction and for NAD+ than for NADP+ in deamination reaction. When the amination and the deamination reactions were compared, the ADH-Re catalyzed the oxaloacetate amination with the oxidation of NADH or NADPH at rates nearly 30 times or 60-90 times higher than those for the aspartate deamination.

Summary

1. Reaction of aspartic acid synthesis in vitro is catalyzed by the *Ralstonia eutropha* L-ADH-Re more efficiently (30-90 times) than reverse reaction of aspartate deamination under alkaline conditions (at pH 9 and 9.8). Moreover, only amination reaction was detected under physiological conditions at pH 7.0.

2. The determined $K_m$ value for ammonium (NH4Cl) is 12 mM. It is 3 times lower than $K_m$ value for NH4Cl (33 mM) determined for *Polaromonas* sp. ADH.

3. NADH and NAD are some preferable (in 2-6 times) cofactors for *Ralstonia eutropha* ADH-Re in vitro.

4. The determined $K_m$ values for NADH and NADPH are 0.87 and 0.39-0.9 mM, respectively. These values are rather high in comparison with the typical intracellular concentrations (0.02 mM NADH and 0.15 mM NADPH within *E. coli* cells). So in vivo NAD(P)H excess may be needed for ADH-Re catalysis.

Example 8

Purification and Characterization of Novel Aspartate Dehydrogenase from *Bradyrhizobium japonicum* (ADH-Bj)

As described above (see, Example 6), the bll6567 from *Bradyrhizobium japonicum* USDA 110 was chosen as a putative aspartate dehydrogenase gene. Its protein product is the best homologue (73% identity) of the NADPH-dependent aspartate dehydrogenase ADH1-Rp from *Rhodopseudomonas palustris*. On the other hand, the genes surrounding of these genes in *B. japonicum* and *R. palustris* are different. (The *R. palustris* RPB_0147 gene is localized near genes coding for a transporter and a putative monovalent cation/H$^+$ antiporter. The *B. japonicum* bll6567 gene localizes near the LysR family transcriptional regulator). So we proposed that the enzyme from *B. japonicum* possesses new features.

To provide an effective translation of mRNA of the gene from *B. japonicum*, the variant of the bll6567 gene with substituted rare codons was sub-cloned from the pSlo3.1A_AspDH-Bj plasmid provided by Sloning BioTechnology GmbH (German) into the pET-15b vector under the T7 expression region containing $P_{T7}$ promoter, T7 transcription start, $RBS_{\Phi10}$, His-Tag coding sequence. For that, the XbaI-BamHI fragment of the pSlo3.1A_AspDH-Bj plasmid containing the ORF of the *B. japonicum* b116567 gene with substituted rare codons was ligated with the pET-15b vector digested with the same endonucleases (XbaI and BamHI). The resulting plasmid was designated pET15-ADH-Bj. The primary structure of cloned fragment was proved by sequence analysis. The primers Seq-adh-P5 (SEQ ID NO: 23) and sys-3 (SEQ ID NO: 94) were used for sequencing.

Preliminary assay of specific aspartate dehydrogenase activity in crude extracts of the BL21(DE3) strain harboring the pET15-ADH-Bj plasmid was performed. The strain harboring pET-15b vector was used as a negative control. Cells were cultivated in LB medium with ampicillin (200 mg/L) at +37° C. up to $OD_{595}$=1. After that, 1 mM IPTG was added and cells were cultivated for 2 hours. Cells from 1.5 ml were disrupted by sonication in a buffer containing 50 mM TRIS pH 7.5, 1 mM DTT. The NADP(H)-dependent aspartate dehydrogenase activity was observed at room temperature (+28° C.). SDS/PAAG electrophoresis showed high level accumulation of a protein with molecular mass of about 30 kDa in the soluble and insoluble fractions (FIG. 26). This result was in agreement with computational protein Mw (30.76 kDa).

The novel *Bradyrhizobium japonicum* ADH-Bj was purified from *E. coli* BL21(DE3) strain harboring pET15-ADH-Bj plasmid clone 1. IMAC was used for purification of the recombinant his6-tag-aspartate dehydrogenase. The used procedure resulted in 28-fold ADH-Bj purification with 53% yield. The homogeneity of the purified ADH-Bj was assessed by SDS/PAGE and a major band with molecular mass of about 30 kDa was obtained (FIG. 27). The determined molecular mass of the ADH-Bj corresponded to the value predicted from its sequence (30.76 kDa).

pH Optimum

The amination reaction was performed in (a) 0.1 M MES-NaOH buffer, pH 6 to 7 or (b) 0.1 M TRIS-HCl buffer, pH 7 to 9.8 or (c) 0.05 M Gly-NaOH buffer, pH 8 to 11 with 0.15 mM NADPH, 100 mM NH$_4$Cl and 20 mM oxaloacetate. The deamination reaction was performed in (d) 0.1 M TRIS-HCl buffer, pH 8 to 9.8 or (e) 0.05 M Gly-NaOH buffer, pH 9.8 to 11 with 2 mM NADP and 10 mM aspartate. The assays were done at least in duplicate, and the error bars indicate deviations between the measurements. The pH optimum for *Bradyrhizobium japonicum* ADH-Bj catalysis of the oxaloacetate amination reaction was observed in alkaline region (FIG. 28). The purified ADH-Bj showed maximum activity for amination reaction at pH from 8 to 9. So, 0.1 M TRIS-HCl buffer (pH 9) was used for further characterization of the purified ADH-Bj in amination reaction. The maximum aspartate dehydrogenase activity for deamination reaction occurred at pH 9.8 in 0.1 M TRIS-HCl buffer (FIG. 28). Thus, this buffer was used for further characterization of the purified ADH-Bj in the deamination reaction.

Kinetic Parameters

A detailed kinetic characterization was performed for the purified *Bradyrhizobium japonicum* ADH-Bj in amination and deamination reactions (Table 17). The $K_m$ and $V_{max}$ parameters were determined from Michaelis-Menten kinetic equation plots. The determined $K_m$ value for ammonium (NH$_4$Cl) is 4.3 mM. It is 8 times lower than $K_m$ value for NH$_4$Cl (33 mM) determined for *Polaromonas* sp. ADH. The determined $K_m$ value for NADPH is 0.032 mM. It is 5 times lower than the typical concentration of NADPH within *E. coli* cells (0.15 mM). So it could be proposed that in vivo *Bradyrhizobium japonicum* ADH-Bj could prefer NADPH as a cofactor in the oxaloacetate amination reaction. With regard to coenzyme specificity, the catalytic efficiency ($k_{cat}/K_m$) of ADH-Bj j for NADPH was nearly 12 times higher than that for NADH, and the catalytic efficiency for NAD$^+$ was nearly 160 times higher than that for NADP$^+$. So, the ADH-Bj has much better affinity for NADPH than for NADH in amination reaction and for NADP$^+$ than for NAD$^+$ in deamination reaction. When the amination and the deamination reactions were compared, the ADH-Bj catalyzed the oxaloacetate amination with the oxidation of NADPH or NADH at rates nearly 24 times or 310 times higher than those for the aspartate deamination.

TABLE 17

Kinetic parameters of the *Bradyrhizobium japonicum* ADH-Bj

| Substrate | $V_{max}$ (µmol/min/mg)[a] | $K_m$ (mM)[a] | $k_{cat}$ (1/min)[b] | $k_{cat}/K_m$ (1/min/mM)[b] |
|---|---|---|---|---|
| Oxaloacetate reductive amination | | | | |
| Oxaloacetate | 94 ± 11 | 21 ± 6 | 2900 ± 300 | 140 |
| NH$_4$Cl | 48 ± 2 | 4.3 ± 0.7 | 1480 ± 50 | 340 |
| NADPH | 79 ± 3 | 0.032 ± 0.005 | 2450 ± 100 | 77000 |
| NADH | 51 ± 3 | 0.25 ± 0.04 | 1570 ± 90 | 6200 |
| Aspartate oxidative deamination | | | | |
| Aspartate | 14.3 ± 0.9 | 27 ± 4 | 440 ± 30 | 17 |
| NADP$^+$ | 12.1 ± 0.5 | 0.12 ± 0.02 | 370 ± 20 | 3200 |
| NAD$^+$ | 6.5 ± 1.0 | 10 ± 3 | 200 ± 30 | 20 |

[a]The kinetic analysis of ADH-Bj in amination reaction was carried out by varying the substrate (oxaloacetate) concentration from 2 to 60 mM at 0.15 mM NADPH and 50 mM NH$_4$Cl, and by varying the ammonium (NH$_4$Cl) concentration from 1 to 100 mM at 0.15 mM NADH and 20 mM oxaloacetate, and by varying the concentration of NADPH from 0.012 to 0.400 mM at 30 mM oxaloacetate and 50 mM NH$_4$Cl, and by varying the concentration of NADH from 0.1 to 0.7 mM at 30 mM oxaloacetate and 50 mM NH$_4$Cl. The kinetic analysis of ADH-Bj in deamination reaction was carried out by varying the substrate (aspartate) concentration from 5 to 80 mM at 2 mM NADP$^+$, and by varying the concentration of NADP$^+$ from 0.015 to 2 mM at 100 mM aspartate, and by varying the concentration of NAD$^+$ from 2 to 16 mM at 100 mM aspartate. All data-fitting procedures were performed with the Sigma Plot 10.0 program.
[b]The $k_{cat}$ and $k_{cat}/K_m$ values were calculated according to the molecular mass of the ADH-Bj is equal to 30.76 kDa.

Summary

1. Reaction of aspartatic acid synthesis in vitro is catalyzed by the *Bradyrhizobium japonicum* ADH-Bj more efficiently (24-310 times) than reverse reaction of aspartate deamination under alkaline conditions (at pH 9 and 9.8). Moreover, only amination reaction was detected under physiological conditions at pH 7.0.

2. The determined $K_m$ value for ammonium (NH$_4$Cl) is 4 mM. It is 8 times lower than $K_m$ value for NH$_4$Cl (33 mM) determined for *Polaromonas* sp. ADH.

3. NADPH and NADP are more preferable (in 12 and 160 times) cofactors for *Bradyrhizobium japonicum* ADH-Bj in vitro.

4. The determined $K_m$ values for NADPH and NADH are 0.032 and 0.25 mM, respectively. The typical intracellular concentrations of NADPH and NADH are 0.15 mM and 0.02 mM NADH within *E. coli* cells. So in vivo *Bradyrhizobium japonicum* ADH-Bj may prefer NADPH as a cofactor in the oxaloacetate amination reaction.

Example 9

Determination of Products in the Aspartate Deamination Reactions Catalyzed by the Examined Aspartate Dehydrogenases, and Substrate Specificity of the Examined Aspartate Dehydrogenases To check enzymatic formation of oxaloacetic acid and ammonium from aspartatic acid and NADP$^+$, the capillary analysis of oxaloacetic acid and HPLC-analysis of ammonium (NH$_4^+$) in a set of reaction mixtures with purified aspartate dehydrogenases from *Polaromonas* sp (ADH), from *Rhodopseudomonas palustris* (ADH1-Rp), and from *Ralstonia eutropha* (ADH-Re) were performed (Table 18). Obtained values of ammonium were very good correlated with NADPH formation in the reactions. Determined values of oxaloacetic acid were some lower (in 1.5-2.5 times) than values of NADPH and ammonium. It may be caused that oxaloacetate is rather unstable and converted to pyruvate. Thus in vitro the purified enzymes from *Polaromonas* sp., *Rhodopseudomonas palustris* and *Ralstonia eutropha* catalyzed formation oxaloacetic acid and ammonium from L-aspartic acid coupled with NADP$^+$ reduction.

TABLE 18

Determination of products in the aspartate deamination reactions catalyzed by aspartate dehydrogenases from *Polaromonas* sp., *Rhodopseudomonas palustris* and *Ralstonia eutropha*

| Reaction time | Sample[a] | NADPH[b], mM | OAA[c], mM | NH$_4^{+}$[d], mM |
|---|---|---|---|---|
| 0 min | No. 1 - reaction with ADH1-Rp | nm | <0.05 | 0.03 |
| | No. 2 - reaction with ADH | nm | <0.05 | nm |
| | No. 3 - reaction with ADH-Re | nm | <0.05 | 0.06 |
| 90 min at 28° C. | No. 4 - reaction with ADH1-Rp | 0.28 | 0.15 | 0.25 |
| | No. 5 - control without enzyme | 0.05 | <0.05 | 0.02 |
| | No. 6 - control with ADH1-Rp without NADP | 0 | <0.05 | 0.01 |
| | No. 7 - control with ADH1-Rp without aspartate | 0.04 | <0.05 | 0.03 |
| | No. 8 - reaction with ADH | 0.28 | 0.12 | 0.25 |
| | No. 9 - control with ADH without NADP | 0 | <0.05 | 0.04 |
| | No. 10 - control with ADH without aspartate | 0.05 | <0.05 | 0.02 |
| | No. 11 - reaction with ADH-Re | 0.31 | 0.21 | 0.31 |
| | No. 12 - control with ADH-Re without NADP | 0 | <0.05 | 0.01 |
| | No. 13 - control with ADH-Re without aspartate | 0.05 | <0.05 | 0.06 |
| 60 min at 28° C. | No. 14 - reaction with ADH1-Rp | 0.24 | 0.09 | 0.21 |
| | No. 15 - reaction with ADH | 0.23 | 0.11 | 0.22 |
| | No. 16 - reaction with ADH-Re | 0.26 | 0.12 | 0.26 |

[a]Reaction mixture contained 0.05M TRIS-HCl buffer, pH 9.8. 5 mM NADP$^+$, 40 mM aspartate, 10 mkl purified enzyme in 1 ml of final volume.
[b]NADPH was determined spectrophotometrically by absorption increase at 340 nm.
[c]Oxaloacetic acid was determined by capillar phoresis.
[d]Ammonium (NH$_4^+$) was determined by HPLC.
nm—not measured Substrate specificity of four examined dehydrogenases with metabolically significant amino acid keto-precursors was determined (Tables 19, 20). Only the ADH1-Rp and ADH-Bj exhibited weak amination activity with α-ketoglutarate and pyruvate but the ADH and ADH-Re were strictly specific for oxaloacetate.

TABLE 19

Screening of substrate specificity of examined aspartate dehydrogenases in amination reaction

| | Amination activity, %[1] | | | |
|---|---|---|---|---|
| Substrate | ADH | ADH1-Rp | ADH-Re | ADH-Bj |
| oxaloacetate | 100 ± 3 | 100 ± 2 | 100 ± 3 | 100 ± 2 |
| α-ketoglutarate | na | 2.03 ± 0.05 | na | 1.39 ± 0.03 |
| pyruvate | na | 0.86 ± 0.09 | na | 0.40 ± 0.09 |
| α-ketobutyrate | na | na | na | na |
| ketoisovaleriate | na | na | na | na |
| ketomethylvaleriate | na | na | na | na |

[1]The results are presented as the percentages of activity measured with alternative substrate in relation to the activity measured with oxaloacatate. Reaction mixture contained 0.1M TRIS-HCl buffer (pH 9), 100 mM NH4Cl, 20 mM substrate, 0.15 mM NADPH for ADH1-Rp and ADH-Bj or 0.15 mM NADH for ADH-Re and ADH.
na—no activity (<0.2%)

TABLE 20

Screening of substrate specificity of examined aspartate dehydrogenases in deamination reactions

| | Deamination activity, %[1] | | | |
|---|---|---|---|---|
| Substrate | ADH | ADH1-Rp | ADH-Re | ADH-Bj |
| Aspartate | 100 | 100 ± 8 | 100 | 100 ± 11 |
| Glutamate | na | 4.5 ± 0.4 | na | 5.5 ± 1.1 |
| Alanine | na | na | na | na |

[1]The results are presented as the percentages of activity measured with alternative substrate in relation to the activity measured with aspartate. Reaction mixture contained 0.1M TRIS-HCl buffer (pH 9.8), 20 mM substrate, 2 mM NADP$^+$ for ADH1-Rp and ADH-Bj or 2 mM NAD$^+$ for ADH-Re and ADH.
na—no activity (<2%)

Example 10

Production of L-arginine by E. coli Strain 382 ilvA$^+$ P$_{nlp8\phi10}$-adh::ΔpepA::Km To test the effect of increasing activity of the aspartate dehydrogenase gene from *Bradyrhizobium japonicum* on L-arginine production, DNA fragments from the chromosome of the described below *E. coli* strain MG1655 P$_{nlp8\phi10}$-adh::ΔpepA::Km (see Reference Example 7) was transferred to the *E. coli* arginine-producing strain 382 ilvA$^+$ (see Reference Example 6) by P1 transduction (Miller, J. H. Experiments in Molecular Genetics, Cold Spring Harbor Lab. Press, 1972, Plainview, N.Y.) to obtain the strain 382 ilvA$^+$ P$_{nlp8\phi10}$-adh::ΔpepA::Km. The strains 382 ilvA$^+$ and 382 ilvA$^+$ ΔpepA::Cm (see Reference Example 6) were used as controls.

*E. coli* strains, 382 ilvA$^+$, 382 ilvA$^+$ ΔpepA::Cm and 382 ilvA$^+$ P$_{nlp8\phi10}$-adh::ΔpepA::Km were separately cultivated with shaking at 37° C. for 18 hours in 3 ml of nutrient broth, and 0.3 ml of the obtained cultures were inoculated into 2 ml of a fermentation medium in 20×200-mm test tubes and cultivated at 32° C. for 72 hours on a rotary shaker.

After the cultivation, the amount of L-arginine which accumulated in the medium was determined by paper chromatography using the following mobile phase: butanol:acetic acid:water=4:1:1 (v/v). A solution of ninhydrin (2%) in acetone was used as a visualizing reagent. A spot containing L-arginine was cut out, L-arginine was eluted with 0.5% water solution of CdCl$_2$, and the amount of L-arginine was estimated spectrophotometrically at 540 nm. The results of eight tube fermentations are shown in Table 21. As it can be seen from Table 15, the strain 382 ilvA$^+$ P$_{nlp8\phi10}$-adh::ΔpepA::Km with intergrated aspartate dehydrogenase gene was able to produce a higher amount of L-arginine as compared with both the parent L-arginine producing *E. coli* strain 382 ilvA$^+$ and the control *E. coli* strain 382 ilvA$^+$ ΔpepA::Cm.

The composition of the fermentation medium (g/l) is as follows:

| | |
|---|---|
| Glucose | 48.0 |
| (NH$_4$)$_2$SO$_4$ | 35.0 |
| KH$_2$PO$_4$ | 2.0 |
| MgSO$_4$·7H$_2$O | 1.0 |
| Thiamine HCl | 0.0002 |
| Yeast extract | 1.0 |
| CaCO$_3$ | 5.0 |

Glucose and magnesium sulfate are sterilized separately. CaCO$_3$ is dry-heat sterilized at 180 C for 2 hours. The pH is adjusted to 7.0.

TABLE 21

| Strain | OD$_{540}$ | Amount of arginine, g/l |
|---|---|---|
| 382 ilvA$^+$ | 22.1 ± 0.9 | 4.4 ± 0.2 |
| 382 ilvA$^+$ ΔpepA::Cm | 21.7 ± 1.5 | 4.8 ± 0.9 |
| 382 ilvA$^+$ P$_{nlp8\phi10}$-adh::ΔpepA::Km | 23.6 ± 3.2 | 8 ± 0.8 |

Reference Example 1

Construction of Strains

The method of λ Red-dependent integration (Datsenko, K. A. and Wanner, B. L., Proc. Natl. Acad. Sci. USA, 97(12), 6640-6645(2000)) of PCR-generated fragments followed by λInt/Xis-dependent removing of the antibiotic resistance marker used for selection of the integrants previously adjusted for use in *P. ananatis* (RU application 2006134574, WO2008/090770, US2010062496) was applied for construction of the strains. The used primers are listed in the Table 22.

TABLE 22

Primers used to construct gene deletions.

| Gene | Primers for generation of the integrative DNA fragments | Test primers |
|---|---|---|
| aspA | aspA-attR (SEQ ID NO: 46)<br>aspA-attL (SEQ ID NO: 47) | aspA-test1 (SEQ ID NO: 48)<br>aspA-test2 (SEQ ID NO: 49) |
| sucA | sucA-attR (SEQ ID NO: 50)<br>sucA-attL (SEQ ID NO: 51) | sucA-test1 (SEQ ID NO: 52)<br>sucA-test2 (SEQ ID NO: 53) |
| gltA | gltA-attR (SEQ ID NO: 54)<br>gltA-attL (SEQ ID NO: 55) | gltA-test1 (SEQ ID NO: 56)<br>gltA-test2 (SEQ ID NO: 57) |
| ppc | Dppc-5' (SEQ ID NO: 32)<br>Dppc-3' (SEQ ID NO: 28)<br>Mash1 (SEQ ID NO: 30)<br>Mash2 (SEQ ID NO: 31)<br>attR3-XbaI-HindIII (SEQ ID NO: 29)<br>Tthr5'-XbaI (SEQ ID NO: 33) | ppc-t1 (SEQ ID NO: 34)<br>ppc-t2 (SEQ ID NO: 35) |
| pykA | pykA-attR (SEQ ID NO: 58)<br>pykA-attL (SEQ ID NO: 59) | pykA-test1 (SEQ ID NO: 60)<br>pykA-test2 (SEQ ID NO: 61) |
| pykF | pykF-attR (SEQ ID NO: 62)<br>pykF-attL (SEQ ID NO: 63) | pykF-test1 (SEQ ID NO: 26)<br>pykF-test2 (SEQ ID NO: 27) |

To prepare the integrative DNA fragments, PCR-amplification of the DNA fragment containing kanamycin resistance gene flanked with attL and attR sites of phage λ with primers presented in Table 22 was performed. Primers used in the reaction carried 40 bp homologies with the target sites of *P. ananatis* genome on their 5'-ends. pMW118-(λattL-Km$^r$-λattR) plasmid (RU application 2006134574, WO2008/090770, US2010062496) was used as a template in all the reactions. The obtained DNA fragments were treated for two or three hours with DpnI restrictase recognizing methylated GATC site to eliminate pMW118-(λattL-Km$^r$-λattR).

P. ananatis strain SC17(0) (VKPM B-9246, RU application 2006134574) resistant to the expression of all three Red-genes from phage λ (gam, bet and exo) harboring the RSF-Red-TER plasmid was used as a recipient in the integration experiments. The strain SC17(0) has been deposited at the Russian National Collection of Industrial Microorganisms (VKPM), GNII Genetika (address: Russia, 117545 Moscow, 1 Dorozhny proezd. 1) on Sep. 21, 2005 with an accession number of VKPM B-9246, and then converted to international deposit under the Budapest Treaty on Oct. 13, 2006.

In order to obtain electrocompetent P. ananatis cells, the SC17(0) strain transformed with the RSF-Red-TER plasmid was grown overnight at 34° C. on LB medium with 50 μg/ml chloramphenicol. Then, the culture was diluted 100× with fresh LB medium containing 50 μg/ml of chloramphenicol and grown up to $OD_{600}$ of 0.3 at 34° C. under aeration. After that, IPTG was added to 1 mM and cultivation was continued up to $OD_{600}$=0.7. 10 ml samples were washed three times with an equal volume of deionized ice water and resuspended in 40 μl of 10% cold glycerol. Just before electroporation, 100-200 ng of the in vitro amplified DNA preparation dissolved in 5 μl of deionized water was added to the cell suspension. The procedure was performed using the device for bacterial electrotransformation ("BioRad", USA, catalog number 165-2089, version 2-89). The following pulse parameters were applied:electric field intensity of 20 kV/cm; pulse time of 5 msec. After electroporation, 1 ml of LB medium enriched with glucose (0.5%) was immediately added to the cell suspension. Then, the cells were grown under aeration at 34° C. for 2 h and plated on solid LB medium containing 40 μg/ml of kanamycin, followed by an overnight incubation at 34° C. To select the integrants among grown $Km^R$ clones, their chromosome structure was verified by PCR with the test primers presented in Table 22. To cure the selected $Km^R$-integrants from the RSF-Red-TER helper plasmid, they were streaked on the plates containing LB medium with the addition of IPTG (1 mM) and sucrose (5 g/L) at 34° C. and grown to form single colonies. $Km^R$, $Cm^S$ plasmid-less clones were isolated.

To eliminate kanamycin or tetracycline antibiotic resistance marker, pMW-IntXis-cat plasmid (see Reference Example 2) was electroporated to the selected plasmid-less integrant by the same procedure as for electroporation of the PCR-generated fragments. After electroporation the cells were plated on LB-agar containing 0.5% glucose, 0.5× M9 salt solution and chloramphenicol (50 mg/L) and incubated at 37° C. overnight to induce synthesis of the Int/Xis proteins. The grown clones were replica-plated on LB-plates with and without kanamycin to select $Km^S$ variants. The selected $Km^S$ clones were re-checked by PCR with corresponding test primers.

To eliminate chloramphenicol resistance marker, $Cm^R$, the pMW-IntXis helper plasmid (WO2005010175) was used. Selection of $Cm^S$ clones was performed as above. But in this case, cells after electroporation were plated on the medium containing 800 mg/L ampicillin.

To construct the strains carrying multiple mutations, the entire procedure was repeated with the corresponding pairs of primers. The thus constructed strain 5ΔS has the genes aspA, sucA, gltA, pykA, pykF deleted. Primers used to construct these gene deletions are listed in Table 22.

To construct ppc deletion, the kan gene flanked by λattR/L was amplified by PCR, using primers Dppc-3' (SEQ ID NO: 28) and attR3-XbaI-HindIII (SEQ ID NO: 29). Genomic DNA isolated from P. ananatis SC17(0) strain Ptac-lacZ (RU application 2006134574, WO2008/090770, US2010062496) was used as a template for PCR. In the P. ananatis SC17(0) strain Ptac-lacZ, a sequence which has λattL-Kmr-λattR and Ptac promoter ligated downstream (λattL-Km$^r$-λattR-Ptac) was integrated upstream from lacZ gene. In parallel, the fragment containing terminator of leader peptide of the E. coli threonine operon (Tthr) was constructed by PCR. To that, two pairs of oligonucleotides were used: mash1 (SEQ ID NO: 30), mash2 (SEQ ID NO: 31), and Dppc-5' (SEQ ID NO: 32), Tthr5'-XbaI (SEQ ID NO: 33). At first, mash1 (SEQ ID NO: 30) and mash2 (SEQ ID NO: 31) were annealed to each other. As a result, the terminator was generated. The obtained DNA fragment was used as template for PCR with Dppc-5' (SEQ ID NO: 32), Tthr5'-XbaI (SEQ ID NO: 33) primers to create the fragment with XbaI recognition site on its 5'-end necessary for joining of the integrative cassette and homologous arm for integration on the 3'-end. The fragments including Tthr and the removable $Km^R$ marker were digested by XbaI restrictase and then ligated. The ligated mixture was electroporated to the SC17(0)/RSFRedTER strain (RU application 2006134574, WO2008/090770, US2010062496) strain for integration according to the procedure for λRed-dependent integration described above. Integrants were selected on LB-agar plates with kanamycin (40 mg/l). The chromosome structure of the integrants was confirmed by PCR using ppc-t1 (SEQ ID NO: 34) and ppc-t2 (SEQ ID NO: 35) oligonucleotides as primers. The resulting strain was named SC17(0) Δppc.

The constructed deletion has been transferred to 5ΔS by the chromosome electroporation procedure. To that, 200 ng of genomic DNA isolated from SC17(0)Δppc using Genomic DNA Purification Kit provided by "Fermentas" was electro-transformed to 5Δ-S. The cultivation conditions were the same as for the Red-dependent integration procedure excepting IPTG addition. Preparation of the electrocompetent cells was the same as for Red-dependent integration. Pulse parameters were: E=12.5 kV/cm; pulse time, 10 msec. The obtained integrants were verified by PCR using ppc-t2 (SEQ ID NO: 34) and ppc-t2 (SEQ ID NO: 35) oligonucleotides as primers. The resulting strain was named 5ΔP.

After that, Mu-dependent integration of the E. coli ppc$^{K620S}$ gene encoding feedback-resistant PEP-carboxylase to 5ΔP was performed using the integrative plasmid pMIVK620S (see Reference Example 5). The integration procedure was performed as follows. The pMIVK620S plasmid was electroporated to 5ΔP strain harboring phMIV-1 helper plasmid (see Reference Example 3) providing expression of the Mu integrase. After electroporation, cells were incubated at 37° C. for induction of the integrase synthesis. Cells were plated on L-agar containing 25 mg/L chloramphenicol. The grown clones were replica-plated and $Ap^S$ clones were selected. The obtained integrants were cured from the helper plasmid. To that, cells were seeded in LB medium and incubated without agitation at 37° C. in 3 days. After that, cells were plated on L-agar with addition of chloramphenicol (25 mg/L) and incubated at 34° C. overnight. The grown clones were replica plated and $Tc^SCm^R$ variants were selected, the obtained integrants (59 independent clones) were named 5ΔP2. The clone No. 36 (5ΔP2-36) provided the highest aspartic acid and biomass accumulation in 48-hour test tube cultivation at increased L-Glu concentration (6.0 g/L) (Table 2, data for the 15 best clones are represented), and was chosen for further improvement. The high L-Glu concentration was used to simulate presence of the glutamate dehydrogenase. The selected strain was cured from the chloramphenicol resistance marker using λInt/Xis-dependent procedure (see above). The resultant strain was named 5ΔP2-36S.

5ΔP2R strain was obtained from 5ΔP2-36S as a spontaneous Asp$^R$ mutant selected on the M9 plates containing 10 g/L glucose and 30 g/L L-Asp, pH 5.5 having the same producing ability as the parental strain.

Then, the 5ΔP2RM strain was obtained by deleting the mdhA gene coding for malate dehydrogenase from the 5ΔP2R strain (WO2010038905). By deleting the mdhA gene, unproductive conversion of oxaloacetate to malate, fumarate and succinate can be prevented.

5ΔP2RMG-S strain was obtained from 5ΔP2RM strain. For that purpose, the gcd gene coding for glucose dehydrogenase was deleted in the 5ΔP2RM strain according to the described above λRed-dependent procedure using oligonucleotides gcd-attR (SEQ ID NO: 95) and gcd-attL (SEQ ID NO: 96) as primers for generation of the integrative DNA fragment; oligonucleotides gcd-test1 (SEQ ID NO: 97) and gcd-test2 (SEQ ID NO: 98) were used for PCR verification of the obtained integrants. The resulting strain 5ΔP2RM was cured from the kanamycin resistance marker using the described above λInt/Xis-dependent procedure and named as 5ΔP2RMG-S.

Reference Example 2

Construction of pMW-intxis-cat Vector

Figure 4:
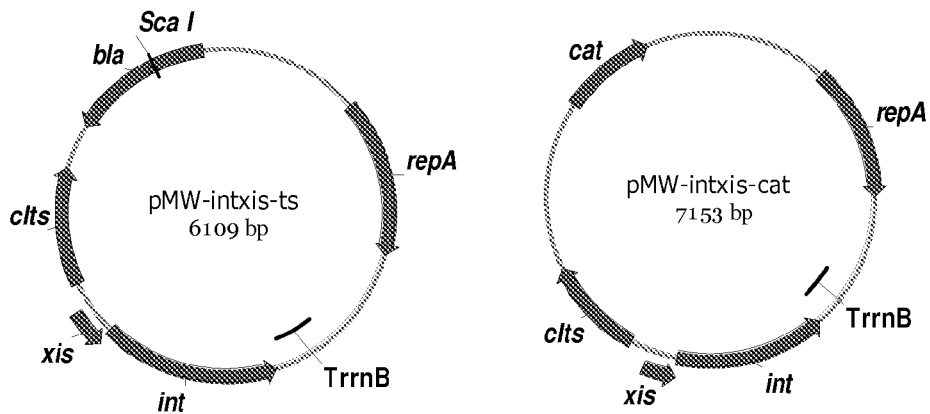
FIG. 4 shows construction of the pMW-intxis-cat plasmid vector.

To construct pMW-intxis-cat (FIG. 4), the DNA fragment containing cat gene was amplified by PCR with primers cat5'BglII (SEQ ID NO: 36) and cat3'SacI (SEQ ID NO: 37) and pACYC184 plasmid as a template. Pfu polymerase ("Fermentas") generating blunt ends was used in this reaction. The obtained DNA fragment was cloned in the unique ScaI recognition site (ScaI restriction endonuclease generates blunt ends) of the pMW-intxis plasmid (WO2005010175). Plasmid with orientation of cat gene shown on FIG. 4 was confirmed by restriction analysis using NcoI restrictase (lengths of necessary DNA fragments are 3758 and 3395 bp).

Reference Example 3

Construction of phMIV-1 Helper Plasmid

Figure 5:
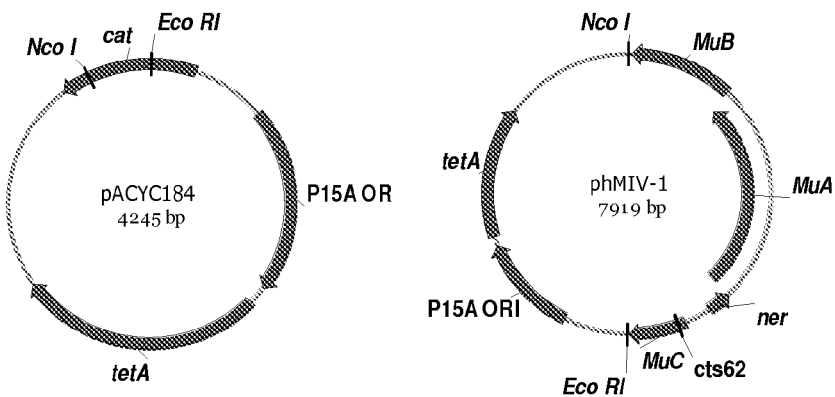
FIG. 5 shows construction of phMIV-1 helper plasmid

The DNA fragment comprising MuC (cts62), ner, MuA and MuB genes coding for the integrase and thermosensitive repressor was amplified by PCR using primers MuC5 (SEQ ID NO: 38) and MuB3 (SEQ ID NO: 39) and pMH10 plasmid (U.S. Pat. No. 6,960,455) as a template. Primer MuC5 contains site for EcoRI restrictase at the 5'-end thereof. Primer MuB3 contains site for NcoI restrictase at the 5'-end thereof. The obtained fragment was cloned into the EcoRI-NcoI recognition sites of the pACYC184 plasmid. Thus, phMIV-1 helper plasmid was obtained (FIG. 5).

Reference Example 4

Construction of E. coli Strain MG1655Δppc

1. Construction of an E. coli Strain Having Deletion of the ppc Gene

A strain having deletion of the ppc gene was constructed by the method initially developed by Datsenko, K. A. and Wanner, B. L. (Proc. Natl. Acad. Sci. USA, 2000, 97(12), 6640-6645) called "Red-driven integration". The DNA fragment containing the Cm$^R$ marker encoded by the cat gene was obtained by PCR, using primers pps-attR (SEQ ID NO: 40) and ppc-attL (SEQ ID NO: 41) and plasmid pMW118-attL-Cm-attR (WO2005010175) as a template. Primer pps-attR contains both a region complementary to the region located at the 5' end of the ppc gene and a region complementary to the attR region. Primer pps-attR contains both a region complementary to the region located at the 3' end of the ppc gene and a region complementary to the attL region.

A 1.7 kbp PCR product was obtained and purified in agarose gel and was used for electroporation of the E. coli strain MG1655 (ATCC 47076, ATCC 700926), which contains the plasmid pKD46 having a temperature-sensitive replication. The plasmid pKD46 (Datsenko, K. A. and Wanner, B. L., Proc. Natl. Acad. Sci. USA, 2000, 97:12:6640-45) includes a 2,154 nucleotide DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655.

Electrocompetent cells were prepared as follows: E. coli MG1655/pKD46 was grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 μl of cells and ≈100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 μg/ml) and grown at 37° C. to select Cm$^R$ recombinants. Then, to eliminate the pKD46 plasmid, two passages on L-agar with Cm at 42° C. were performed and the obtained colonies were tested for sensitivity to ampicillin.

2. Verification of the ppc Gene Deletion by PCR

The mutants having the ppc gene deleted and marked with the Cm resistance gene were verified by PCR. Locus-specific checking primers ppc-test1 (SEQ ID NO: 42) and ppc-test2 (SEQ ID NO: 43) were used in PCR for the verification. The PCR product obtained in the reaction with the cells of parental ppc$^+$ strain MG1655 as a template, was 2.8 kbp in length. The PCR product obtained in the reaction with the cells of mutant strain as the template was 1.7 kbp in length. The mutant strain was named MG1655Δppc::cat. Cm marker was excised from the chromosome using standard techniques (int-xis system) described in WO2005010175. Length of the DNA obtained in the PCR using primers ppc-test1 and ppc-test2 in the case when the Cm marker is excised was 280 bp.

Reference Example 5

Construction of the pMIVK620S Plasmid

Figure 6:
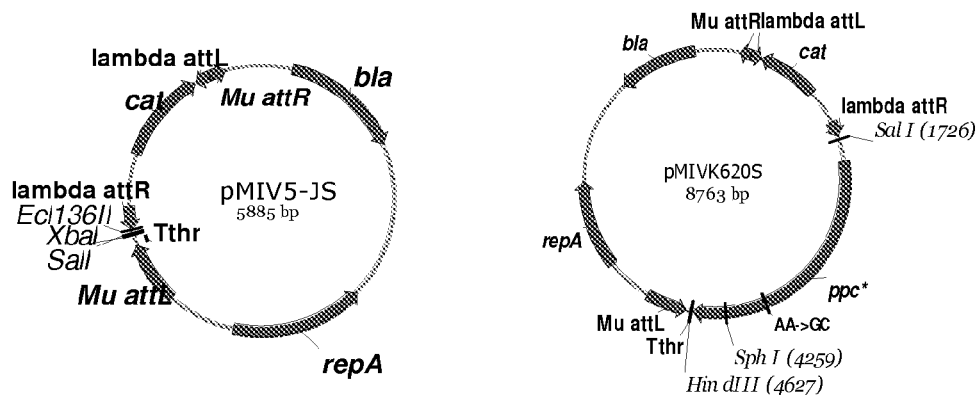
FIG. 6 shows construction of the pMIVK620S plasmid.
Figure 9:
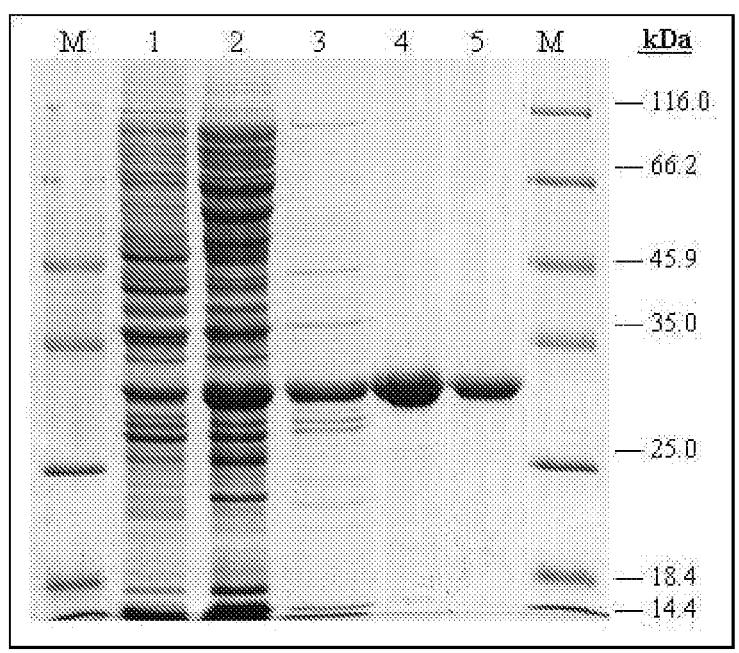
FIG. 9 is a photograph which shows analysis of the purification of *Polaromonas* sp. ADH by SDS-PAGE (10%).
M: Molecular weight protein marker;
Lane 1: Soluble fraction of crude cell extract from BL21 (DE3)/pET-ADH-P(S) (30 µg)
Lane 2: Fraction after precipitation in ammonium sulfate solution (30 µg)
Lane 3: Fraction after anion-exchange chromatography (4.6 µg);
Lanes 4, 5: Fraction after affinity chromatography (6.6 µg and 3.3 µg).

The E. coli ppcK620S gene coding for PEP-carboxylase resistant against inhibition by aspartic acid was sub-cloned from the plasmid pTK620S (Masato Yano and Katsura Izui, Eur. Biochem. FEBS, 247, 74-81, 1997) to the pMIV-5JS plasmid (RU patent application 2006132818, US2009197309) in two steps. At first, SalI-SphI fragment of pTK620S was sub-cloned into SalI-SphI recognition sites of pMIV5-JS. The obtained pMIV-ppc-5' plasmid carries large 5'-terminal portion of the ppcK620S gene. The 3'-proximal portion of the ppcK620S gene was amplified in PCR with primers ppc-SphI (SEQ ID NO: 44) and ppc-HindIII (SEQ ID NO: 45) and the pTK620S plasmid as template. The so obtained fragment and pMIV-ppc-5' were digested with SphI and HindIII restrictases and ligated. The ligated mixture was electroporated to E. coli strain MG1655Δppc (see Reference Example 4). Cells after transformation were plated on M9 glucose (5 g/l) minimal media with chloramphenicol (50 mg/l) to select the colonies harboring plasmids providing PEP-carboxylase activity. After isolation of plasmid DNA from the grown colonies and restriction analysis the plasmids of the expected structure (FIG. 6) have been selected.

Reference Example 6

Construction of the Parental Arginine-Producing Strain E. coli 382 ilvA$^+$ and the Control Strain E. coli 382 ilvA$^+$ ΔpepA::Cm The strain 382 ilvA$^+$ was obtained from the arginine-producing strain 382 (VKPM B-7926, EP 1170358A1) by P1 transduction wild type ilvA gene from E. coli K12 strain. The strain 382 was deposited at the VKPM (the Russian National Collection of Industrial Microorganisms, (Russia, 117545 Moscow, 1 Dorozhny proezd, 1) on Apr. 10, 2000 under the accession number VKPM B-7926.

Clones 382 ilvA were selected as good growing colonies on minimal agar plates. The strain 382 has been deposited in the Russian National Collection of Industrial Microorganisms (VKPM) (Russia, 117545 Moscow, 1$^{st}$ Dorozhny proezd, 1) on Apr. 10, 2000 under accession number VKPM B-7926 and then converted to a deposit under the Budapest Treaty on May 18, 2001. The strain 382 ilvA$^+$ ΔpepA::Cm with deleted pepA gene was constructed as follows:

Deleting the pepA gene in a bacterial strain was accomplished by the method initially developed by Datsenko, K. A. and Wanner, B. L. (Proc. Natl. Acad. Sci. USA, 2000, 97(12), 6640-6645) called "Red-driven integration". According to this procedure, the PCR primers P9 (SEQ ID NO: 90) and P10 (SEQ ID NO: 91), which are homologous to both the region adjacent to the pepA gene and the gene which confers antibiotic resistance in the template plasmid, were constructed. The plasmid pMW118-attL-Cm-attR (WO 05/010175) was used as the template in the PCR reaction. Conditions for PCR were as follows: initial DNA denaturation for 30 sec at 94° C., followed by 25 cycles of denaturation at 94° C. for 30 sec, annealing at 55° C. for 30 sec, elongation at 72° C. for 1 min 30 sec; and the final elongation for 2 min at 72° C.

The 1.7 kb PCR product was purified from an agarose gel and used for electroporation of the E. coli strain MG1655 (ATCC 700926), which contains the plasmid pKD46 which has a temperature-sensitive replication origin. The pKD46 plasmid (Datsenko, K. A. and Wanner, B. L., Proc. Natl. Acad. Sci. USA, 2000, 97:12:6640-45) includes a 2,154 nucleotide DNA fragment of phage λ (nucleotide positions 31088 to 33241, GenBank accession no. J02459), and contains genes of the λ Red homologous recombination system (γ, β, exo genes), which are under the control of the arabinose-inducible P$_{araB}$ promoter. The pKD46 plasmid is necessary for integration of the PCR product into the chromosome of the MG1655 strain.

Electrocompetent cells were prepared as follows: E. coli MG1655/pKD46 cells were grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells were grown with aeration at 30° C. to an OD$_{600}$ of ≈0.6 and then were made electrocompetent by concentrating 100-fold and washing three times with ice-cold deionized H$_2$O. Electroporation was performed using 70 µl of cells and ≈100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 µg/ml) and grown at 37° C. to select Cm$^R$ recombinants. Then, to eliminate the pKD46 plasmid, two passages on L-agar with Cm at 42° C. were performed and the colonies were tested for sensitivity to ampicillin.

Mutants in which the pepA gene has been deleted were marked with a Cm resistance gene and were verified by PCR using the locus-specific primers P11 (SEQ ID NO: 92) and P12 (SEQ ID NO: 93). For this purpose, a freshly isolated colony was suspended in 20 µl water and then 1 µl of the suspension was used for PCR. Conditions for PCR were as follows: initial DNA denaturation for 30 sec at 94° C.; then 30 cycles of denaturation at 94° C. for 30 sec, annealing at 55° C. for 30 sec and elongation at 72° C. for 2 min; the final elongation for 2 min at 72° C. The PCR product obtained in the PCR reaction using the cells of the parent pepA$^+$ strain MG1655 as the template was 1.65 kb in length. The PCR product obtained in the PCR reaction using the cells of the mutant MG1655 ΔpepA::Cm strain as the template was 1.71 kb nucleotides in length.

After that, DNA fragment from the chromosome of the E. coli strain MG1655 ΔpepA::Cm was transferred to the above-described E. coli arginine-producing strain 382 ilvA$^+$ by P1 transduction (Miller, J. H. Experiments in Molecular Genetics, Cold Spring Harbor Lab. Press, 1972, Plainview, N.Y.). The obtained strain was named 382 ilvA$^+$ ΔpepA::Cm.

Reference Example 7

Construction of the E. coli Strain MG1655 P$_{nlp8φ10}$-adh::ΔpepA::Km

The DNA fragment containing the promoter of the nlpD gene from E. coli was obtained using PCR. The chromosomal DNA of E. coli MG1655 strain was used as a template, and primers P1 (SEQ ID NO: 82) and P2 (SEQ ID NO: 83) were used for PCR. Conditions for PCR were as follows: denaturation step for 3 min at 95° C.; profile for two first cycles: 1 min at 95° C., 30 sec at 50° C., 40 sec at 72° C.; profile for the last 25 cycles: 20 sec at 94° C., 20 sec at 55° C., 15 sec at 72° C.; final step: 5 min at 72° C. The amplified DNA fragment was about 0.2 kb in size, and was purified by agarose gel electrophoresis. Then, the purified fragment was treated with endonucleases PaeI and SalI. The obtained DNA fragment was ligated with the plasmid pMIV-5JS (RU patent application 2006132818, EP1942183) which had been previously treated with endonucleases PaeI and SalI. The mixture for ligation was incubated at 4° C. overnight and was then used to transform E. coli MG1655 strain by electroporation. The resulting transformants were plated on plates with LB agar containing ampicillin (50 mg/l), and the plates were incubated at 37° C. overnight until individual colonies were visible. Plasmids were isolated from the obtained transformants and analyzed by restriction analysis. The obtained plasmid contains the promoter of the nlpD gene from E. coli, and was named pMIV-Pnlp0.

Then randomization of the −10 region of the promoter P$_{nlpD}$ and the selection of the P$_{nlp8}$ promoter were performed. The 3'-end of the promoter P$_{nlpD}$ was obtained using PCR amplification. The plasmid pMIV-Pn1p0 was used as a template, and primers P1 (SEQ ID NO: 82) and P7 (SEQ ID NO: 88) were used for PCR. Primer P7 has random nucleotides, which are depicted in SEQ ID NO: 88 by the letter "n" (for A or G or C or T). Conditions for PCR were as follows: denaturation step for 3 min at 95° C.; profile for two first cycles: 1 min at 95° C., 30 sec at 50° C., 40 sec at 72° C.; profile for the last 25 cycles: 20 sec at 94° C., 20 sec at 60° C., 15 sec at 72° C.; final step: 5 min at 72° C. 5'-end of promoter P$_{nlpD}$ was obtained using PCR amplification. The plasmid pMIV-Pn1p0 was used as a template, and primers P2 (SEQ ID NO: 83) and P8 (SEQ ID NO: 89) were used for PCR. Primer P8 has random nucleotides, which are depicted in SEQ ID NO: 89 by the letter "n" (for A or G or C or T). Conditions for PCR were as follows: denaturation step for 3 min at 95° C.; profile for two first cycles: 1 min at 95° C., 30 sec at 50° C., 40 sec at 72° C.; profile for the last 25 cycles: 20 sec at 94° C., 20 sec at 60° C., 15 sec at 72° C.; final step: 5 min at 72° C. Both amplified DNA fragments were purified by agarose gel electrophoresis. Then, the obtained DNA fragments were treated with endonuclease BglII followed by ligation of the fragments in equimolar proportion. The mixture for ligation was incubated at 4° C. overnight and was then used as a template for the next PCR procedure, and primers P1 (SEQ ID NO: 82) and P2 (SEQ ID NO: 83) were used for the PCR. Conditions for PCR were as follows: denaturation step for 3 min at 95° C.; profile for two first cycles: 1 min at 95° C., 30 sec at 50° C., 40 sec at 72° C.; profile for the last 12 cycles: 20 sec at 94° C., 20 sec at 60° C., 15 sec at 72° C.; final step: 5 min at 72° C. The amplified DNA fragment was about 0.2 kb in size, and was purified by agarose gel electrophoresis.

Then, the purified fragment was treated with Klenow fragment. The resulting DNA fragment was ligated in equimolar proportion with the plasmid pMW118-(λattL-Km$^r$-λattR) (RU application 2006134574) which had been previously treated with endonuclease XbaI followed by treatment with Klenow fragment. The mixture for ligation was incubated at 4° C. overnight and was then used to transform E. coli MG1655 strain by electroporation. The resulting transformants were plated on plates with LB agar containing kanamycin (20 mg/l), and the plates were incubated at 37° C. overnight until individual colonies were visible. Plasmids were isolated from the obtained transformants and analyzed by restriction analysis. The obtained plasmid containing P$_{nlp8}$ promoter was named pMW-Km-Pnlp8.

The DNA fragment containing the aspartate dehydrogenase gene from Bradyrhizobium japonicum was obtained using PCR. The plasmid DNA pET15-ADH-Bj was used as a template, and primers P3 (SEQ ID NO: 84) and P4 (SEQ ID NO: 85) were used for PCR. Conditions for PCR were as follows: denaturation step for 1 min at 95° C.; profile for the last 25 cycles: 1 min at 95° C., 30 sec at 55° C., 1 min at 72° C.;; final step: 2 min at 72° C. The amplified DNA fragment was about 1 kb in size (FIG. 21), and was purified by agarose gel electrophoresis.

The DNA fragment containing the λattL-Km-λattR-P$_{nlp8φ10}$ cassette was obtained using PCR. The plasmid DNA pMW-Km-Pnlp8 was used as a template, and primers P5 (SEQ ID NO: 86) and P6 (SEQ ID NO: 87) were used for PCR. Conditions for PCR were as follows: denaturation step for 1 min at 95° C.; profile for the last 25 cycles: 1 min at 95° C., 30 sec at 55° C., 1 min 40 sec at 72° C.; final step: 5 min at 72° C. The amplified DNA fragment was about 1.7 kb in size (FIG. 21), and was purified by agarose gel electrophoresis.

Then, the obtained DNA fragments (FIG. 21) with overlap regions were used as a template for the next PCR procedure, and primers P4 (SEQ ID NO: 85) and P5 (SEQ ID NO: 86) were used for the PCR. Conditions for PCR were as follows: denaturation step for 2 min at 95° C.; profile for the next 30 cycles: 30 sec at 94° C., 30 sec at 55° C., 2 min at 72° C.; final step: 5 min at 72° C. The amplified DNA fragment was about 2 kb in size, and was purified by agarose gel electrophoresis.

Obtained fragment contained exicible Km marker and the aspartate dehydrogenase gene from Bradyrhizobium japonicum under control of P$_{nlp8φ10}$ promoter. This fragment was integrated instead of the pepA gene into the chromosome of E. coli MG1655 by "Red-driven integration" developed by Datsenko, K. A. and Wanner, B. L. (Proc. Natl. Acad. Sci. USA, 2000, 97(12), 6640-6645) as described in Reference Example 6. Thus the strain E. coli MG1655 P$_{nlp8φ10}$-adh::ΔpepA::Km was obtained.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, in a method for producing L-aspartic acid or an L-aspartic acid-derived metabolite by fermentation using a microorganism belonging to the family Enterobacteriaceae, productivity of L-aspartic acid or an L-aspartic acid-derived metabolite can be improved.

The invention claimed is:

1. A method for producing L-aspartic acid or an L-aspartic acid-derived metabolite comprising:

cultivating a bacterium belonging to the genus *Pantoea* or *Escherichia*, which produces L-aspartic acid or an L-aspartic acid-derived metabolite, in a culture medium to produce and excrete the L-aspartic acid or the L-aspartic acid-derived metabolite into the medium, and collecting L-aspartic acid or said L-aspartic acid-derived metabolite from the medium, wherein said bacterium has been modified by introducing a gene encoding aspartate dehydrogenase derived from *Bradyrhizobium japonicum* wherein the gene encodes an amino acid sequence not less than 95% identical to the amino acid sequence encoded by SEQ ID NO: 68, and wherein said L-aspartic acid-derived metabolite is selected from the group consisting of L-threonine, L-lysine, L-arginine, L-methionine and L-homoserine.

2. The method according to claim 1, by which L-aspartic acid is produced.

3. The method according to claim 1, wherein said bacterium is *Pantoea ananatis*.

4. The method according to claim 1, wherein said bacterium is *Escherichia coli*.

5. The method according to claim 1, wherein the bacterium has been further modified to have at least:

decreased activity of α-ketoglutarate dehydrogenase by attenuating expression of a gene that encodes α-ketoglutarate dehydrogenase by modifying a promoter of such gene, or by disrupting a gene that encodes α-ketoglutarate dehydrogenase;

decreased activity of citrate synthase by attenuating expression of a gene that encodes citrate synthase by modifying a promoter of such gene, or by disrupting a gene that encodes citrate synthase;

increased activity of phosphoenolpyruvate carboxylase or pyruvate carboxylase by increasing copy number of a gene encoding phosphoenolpyruvate carboxylase or pyruvate carboxylase;

decreased activity of aspartate ammonia-lyase by attenuating expression of a gene that encodes aspartate ammonia-lyase by modifying a promoter of such gene, or by disrupting a gene that encodes aspartate ammonia-lyase; and decreased activity of pyruvate kinase by attenuating expression of a gene that encodes pyruvate kinase by modifying a promoter of such gene, or by disrupting a gene that encodes pyruvate kinase.

6. The method according to claim 1, wherein the bacterium has been further modified to have decreased activity of malate dehydrogenase by attenuating expression of a gene that encodes malate dehydrogenase by modifying a promoter of such gene, or by disrupting a gene that encodes malate dehydrogenase.

7. The method according to claim 1, wherein said amino acid sequence is identical to the amino acid sequence of SEQ ID NO: 68.

* * * * *

SEQUENCE LISTING

```
<160> NUMBER OF SEQ ID NOS: 113

<210> SEQ ID NO 1
<211> LENGTH: 726
<212> TYPE: DNA
<213> ORGANISM: Thermotoga maritima
<220> FEATURE:
<221> NAME/KEY: CDS
<222> LOCATION: (1)..(726)

<400> SEQUENCE: 1 atg act gtt ctg atc atc gga atg gga aat att ggg aaa aaa ctc gta    48
Met Thr Val Leu Ile Ile Gly Met Gly Asn Ile Gly Lys Lys Leu Val
1               5                   10                  15
```

-continued

```
gaa ctg gga aat ttc gag aaa atc tac gct tac gac agg att tca aaa    96
Glu Leu Gly Asn Phe Glu Lys Ile Tyr Ala Tyr Asp Arg Ile Ser Lys
         20                  25                  30 gac att ccg gga gtc gtt cgc ctc gat gaa ttc cag gtt cct tca gac   144
Asp Ile Pro Gly Val Val Arg Leu Asp Glu Phe Gln Val Pro Ser Asp
     35                  40                  45 gtc agc acg gtt gtc gaa tgc gct tct cca gaa gcc gtt aaa gaa tac   192
Val Ser Thr Val Val Glu Cys Ala Ser Pro Glu Ala Val Lys Glu Tyr
 50                  55                  60 tca ctt cag atc ctg aaa aac cct gtg aac tac atc ata atc agc acc   240
Ser Leu Gln Ile Leu Lys Asn Pro Val Asn Tyr Ile Ile Ile Ser Thr
65                  70                  75                  80 agc gct ttc gcg gac gaa gtt ttc agg gaa agg ttc ttc agc gaa ttg   288
Ser Ala Phe Ala Asp Glu Val Phe Arg Glu Arg Phe Phe Ser Glu Leu
                 85                  90                  95 aaa aat tca cca gcc agg gtc ttt ttc cca tcc ggt gcc atc ggc ggt   336
Lys Asn Ser Pro Ala Arg Val Phe Phe Pro Ser Gly Ala Ile Gly Gly
            100                 105                 110 ctc gat gtt ctc tct tcc atc aaa gat ttc gtc aaa aac gtc cgc ata   384
Leu Asp Val Leu Ser Ser Ile Lys Asp Phe Val Lys Asn Val Arg Ile
        115                 120                 125 gaa aca ata aaa cct cca aag agt ctc ggc ctg gat ttg aaa ggt aaa   432
Glu Thr Ile Lys Pro Pro Lys Ser Leu Gly Leu Asp Leu Lys Gly Lys
    130                 135                 140 aca gtc gtg ttc gaa gga agt gtt gag gaa gcg tca aaa cta ttt cca   480
Thr Val Val Phe Glu Gly Ser Val Glu Glu Ala Ser Lys Leu Phe Pro
145                 150                 155                 160 aga aac atc aac gta gcg tcg acc atc ggc ctt ata gtg ggc ttt gaa   528
Arg Asn Ile Asn Val Ala Ser Thr Ile Gly Leu Ile Val Gly Phe Glu
                165                 170                 175 aag gta aag gta aca ata gtg gca gat ccc gcc atg gat cac aac atc   576
Lys Val Lys Val Thr Ile Val Ala Asp Pro Ala Met Asp His Asn Ile
            180                 185                 190 cac att gta aga atc tcc tcc gct atc gga aac tac gaa ttc aaa ata   624
His Ile Val Arg Ile Ser Ser Ala Ile Gly Asn Tyr Glu Phe Lys Ile
        195                 200                 205 gag aat att cca tca cca gaa aac cca aaa aca agt atg cta aca gtc   672
Glu Asn Ile Pro Ser Pro Glu Asn Pro Lys Thr Ser Met Leu Thr Val
    210                 215                 220 tat tcg att ctc aga acc ttg aga aat ctc gaa tca aaa atc ata ttc   720
Tyr Ser Ile Leu Arg Thr Leu Arg Asn Leu Glu Ser Lys Ile Ile Phe
225                 230                 235                 240 gga tga                                                           726
Gly
```

<210> SEQ ID NO 2
<211> LENGTH: 241
<212> TYPE: PRT
<213> ORGANISM: Thermotoga maritima

<400> SEQUENCE: 2

```
Met Thr Val Leu Ile Ile Gly Met Gly Asn Ile Gly Lys Lys Leu Val
1               5                   10                  15

Glu Leu Gly Asn Phe Glu Lys Ile Tyr Ala Tyr Asp Arg Ile Ser Lys
            20                  25                  30

Asp Ile Pro Gly Val Val Arg Leu Asp Glu Phe Gln Val Pro Ser Asp
        35                  40                  45

Val Ser Thr Val Val Glu Cys Ala Ser Pro Glu Ala Val Lys Glu Tyr
    50                  55                  60
```

Ser Leu Gln Ile Leu Lys Asn Pro Val Asn Tyr Ile Ile Ser Thr
65                  70                  75                  80

Ser Ala Phe Ala Asp Glu Val Phe Arg Glu Arg Phe Phe Ser Glu Leu
            85                  90                  95

Lys Asn Ser Pro Ala Arg Val Phe Phe Pro Ser Gly Ala Ile Gly Gly
            100                 105                 110

Leu Asp Val Leu Ser Ser Ile Lys Asp Phe Val Lys Asn Val Arg Ile
            115                 120                 125

Glu Thr Ile Lys Pro Pro Lys Ser Leu Gly Leu Asp Leu Lys Gly Lys
130                 135                 140

Thr Val Val Phe Glu Gly Ser Val Glu Glu Ala Ser Lys Leu Phe Pro
145                 150                 155                 160

Arg Asn Ile Asn Val Ala Ser Thr Ile Gly Leu Ile Val Gly Phe Glu
                165                 170                 175

Lys Val Lys Val Thr Ile Val Ala Asp Pro Ala Met Asp His Asn Ile
                180                 185                 190

His Ile Val Arg Ile Ser Ser Ala Ile Gly Asn Tyr Glu Phe Lys Ile
            195                 200                 205

Glu Asn Ile Pro Ser Pro Glu Asn Pro Lys Thr Ser Met Leu Thr Val
            210                 215                 220

Tyr Ser Ile Leu Arg Thr Leu Arg Asn Leu Glu Ser Lys Ile Ile Phe
225                 230                 235                 240

Gly

<210> SEQ ID NO 3
<211> LENGTH: 804
<212> TYPE: DNA
<213> ORGANISM: Polaromonas sp.
<220> FEATURE:
<221> NAME/KEY: CDS
<222> LOCATION: (1)..(804)

<400> SEQUENCE: 3 atg ctg aaa att gcc atg att ggt tgc ggc gcg att ggc gcc agc gtg   48
Met Leu Lys Ile Ala Met Ile Gly Cys Gly Ala Ile Gly Ala Ser Val
1               5                   10                  15 ctg gag ttg ctg cat ggc gac tcc gac gtg gtg gtg gac cgg gtg atc   96
Leu Glu Leu Leu His Gly Asp Ser Asp Val Val Val Asp Arg Val Ile
                20                  25                  30 acg gtg ccg gag gcg cgt gac cgc acg gag atc gca gtc gcc cgc tgg   144
Thr Val Pro Glu Ala Arg Asp Arg Thr Glu Ile Ala Val Ala Arg Trp
            35                  40                  45 gcc ccg cgg gcc cgg gtg ctg gag gtg ctg gcc gcc gat gac gcg cct   192
Ala Pro Arg Ala Arg Val Leu Glu Val Leu Ala Ala Asp Asp Ala Pro
        50                  55                  60 gac ctg gtg gtc gag tgt gcg ggc cac ggc gcg att gcc gcg cat gtg   240
Asp Leu Val Val Glu Cys Ala Gly His Gly Ala Ile Ala Ala His Val
65                  70                  75                  80 gtg ccg gcg ctg gag cgc ggc att ccc tgc gtg gtg acc tcg gtg ggc   288
Val Pro Ala Leu Glu Arg Gly Ile Pro Cys Val Val Thr Ser Val Gly
                85                  90                  95 gcc ctg agc gcg ccc ggc atg gcg cag ctg ctg gag cag gcc gcg cgg   336
Ala Leu Ser Ala Pro Gly Met Ala Gln Leu Leu Glu Gln Ala Ala Arg
            100                 105                 110 cgc ggc aag acc cag gtg cag ctg ctc tct ggc gcc atc ggc ggg att   384
Arg Gly Lys Thr Gln Val Gln Leu Leu Ser Gly Ala Ile Gly Gly Ile
        115                 120                 125

```
gac gcg ctg gcc gcc gcg cgt gtg ggc ggg ctc gat tcg gtg gtg tac      432
Asp Ala Leu Ala Ala Ala Arg Val Gly Gly Leu Asp Ser Val Val Tyr
130             135                 140 acc ggc cgc aag cca ccg atg gcc tgg aag ggc acg ccg gcc gaa gcc      480
Thr Gly Arg Lys Pro Pro Met Ala Trp Lys Gly Thr Pro Ala Glu Ala
145                 150                 155                 160 gtc tgc gac ctc gac agc ctc acc gtc gcg cac tgc atc ttt gac ggc      528
Val Cys Asp Leu Asp Ser Leu Thr Val Ala His Cys Ile Phe Asp Gly
                165                 170                 175 agt gcc gag cag gcc gca cag ctc tac ccc aag aac gcc aat gtg gcg      576
Ser Ala Glu Gln Ala Ala Gln Leu Tyr Pro Lys Asn Ala Asn Val Ala
            180                 185                 190 gcc acg ctg tcg ctc gcg ggc ttg ggc ctg aag cgc acg cag gtg cag      624
Ala Thr Leu Ser Leu Ala Gly Leu Gly Leu Lys Arg Thr Gln Val Gln
        195                 200                 205 ctg ttt gcc gat ccg ggc gtc agc gaa aac gtt cac cac gtg gcg gcg      672
Leu Phe Ala Asp Pro Gly Val Ser Glu Asn Val His His Val Ala Ala
210                 215                 220 cac gga gct ttc ggc agc ttc gag ctg acg atg cgt ggc cgg ccg ctg      720
His Gly Ala Phe Gly Ser Phe Glu Leu Thr Met Arg Gly Arg Pro Leu
225                 230                 235                 240 gcg gcc aat cca aaa aca tcc gcg ctc acc gtt tac agc gtg gtg cgc      768
Ala Ala Asn Pro Lys Thr Ser Ala Leu Thr Val Tyr Ser Val Val Arg
                245                 250                 255 gcg ctg ctc aac cgg ggc cgc gcg ctc gtc atc tga                      804
Ala Leu Leu Asn Arg Gly Arg Ala Leu Val Ile
            260                 265

<210> SEQ ID NO 4
<211> LENGTH: 267
<212> TYPE: PRT
<213> ORGANISM: Polaromonas sp.

<400> SEQUENCE: 4

Met Leu Lys Ile Ala Met Ile Gly Cys Gly Ala Ile Gly Ala Ser Val
1               5                   10                  15

Leu Glu Leu Leu His Gly Asp Ser Asp Val Val Asp Arg Val Ile
            20                  25                  30

Thr Val Pro Glu Ala Arg Asp Arg Thr Glu Ile Ala Val Ala Arg Trp
        35                  40                  45

Ala Pro Arg Ala Arg Val Leu Glu Val Leu Ala Ala Asp Asp Ala Pro
    50                  55                  60

Asp Leu Val Val Glu Cys Ala Gly His Gly Ala Ile Ala Ala His Val
65                  70                  75                  80

Val Pro Ala Leu Glu Arg Gly Ile Pro Cys Val Val Thr Ser Val Gly
                85                  90                  95

Ala Leu Ser Ala Pro Gly Met Ala Gln Leu Leu Glu Gln Ala Ala Arg
            100                 105                 110

Arg Gly Lys Thr Gln Val Gln Leu Leu Ser Gly Ala Ile Gly Gly Ile
        115                 120                 125

Asp Ala Leu Ala Ala Ala Arg Val Gly Gly Leu Asp Ser Val Val Tyr
    130                 135                 140

Thr Gly Arg Lys Pro Pro Met Ala Trp Lys Gly Thr Pro Ala Glu Ala
145                 150                 155                 160

Val Cys Asp Leu Asp Ser Leu Thr Val Ala His Cys Ile Phe Asp Gly
                165                 170                 175

Ser Ala Glu Gln Ala Ala Gln Leu Tyr Pro Lys Asn Ala Asn Val Ala
            180                 185                 190
```

```
Ala Thr Leu Ser Leu Ala Gly Leu Gly Leu Lys Arg Thr Gln Val Gln
            195                 200                 205

Leu Phe Ala Asp Pro Gly Val Ser Glu Asn Val His His Val Ala Ala
    210                 215                 220

His Gly Ala Phe Gly Ser Phe Glu Leu Thr Met Arg Gly Arg Pro Leu
225                 230                 235                 240

Ala Ala Asn Pro Lys Thr Ser Ala Leu Thr Val Tyr Ser Val Val Arg
                245                 250                 255

Ala Leu Leu Asn Arg Gly Arg Ala Leu Val Ile
            260                 265

<210> SEQ ID NO 5
<211> LENGTH: 1581
<212> TYPE: DNA
<213> ORGANISM: Pantoea ananatis
<220> FEATURE:
<221> NAME/KEY: CDS
<222> LOCATION: (1)..(1581)

<400> SEQUENCE: 5 gtg atc tct gtt cgc gct tta ggg ctg ggt cag aat agg atc gtg ctc      48
Val Ile Ser Val Arg Ala Leu Gly Leu Gly Gln Asn Arg Ile Val Leu
1               5                  10                  15 acc cgc ctg aat acg gat aaa ata gcg gtt ctg gcg ctt ccc cac aaa      96
Thr Arg Leu Asn Thr Asp Lys Ile Ala Val Leu Ala Leu Pro His Lys
            20                  25                  30 aca aac aca tca tct gcg atg gtt agc agt gac aac aag aag gtt atc     144
Thr Asn Thr Ser Ser Ala Met Val Ser Ser Asp Asn Lys Lys Val Ile
        35                  40                  45 atg gcg aac aac att cgt atc gaa gaa gac ctg tta ggc atg cgc gaa     192
Met Ala Asn Asn Ile Arg Ile Glu Glu Asp Leu Leu Gly Met Arg Glu
    50                  55                  60 gtt ccg gcg gat gct tat tat ggc gtt cat act ttg cgt gcg att gaa     240
Val Pro Ala Asp Ala Tyr Tyr Gly Val His Thr Leu Arg Ala Ile Glu
65                  70                  75                  80 aac ttt tac atc agc aac agc aaa atc agt gat att cct gag ttt gtg     288
Asn Phe Tyr Ile Ser Asn Ser Lys Ile Ser Asp Ile Pro Glu Phe Val
                85                  90                  95 cgc ggc atg gtg atg gta aaa aaa gcg gcg gcg atg gcc aat aaa gag     336
Arg Gly Met Val Met Val Lys Lys Ala Ala Ala Met Ala Asn Lys Glu
            100                 105                 110 ctg caa acg ttg ccg cgt gac atc gcc aat acc att att cag gcc tgc     384
Leu Gln Thr Leu Pro Arg Asp Ile Ala Asn Thr Ile Ile Gln Ala Cys
        115                 120                 125 gat gaa gtg ctg aac aaa ggt cgc tgc atg gat cag ttc ccg gtc gat     432
Asp Glu Val Leu Asn Lys Gly Arg Cys Met Asp Gln Phe Pro Val Asp
    130                 135                 140 gtg tat caa ggc ggc gcg ggc acc tcg gtc aac atg aat acc aat gag     480
Val Tyr Gln Gly Gly Ala Gly Thr Ser Val Asn Met Asn Thr Asn Glu
145                 150                 155                 160 gtg ctg gcc aat att ggt ctg gag ctg atg gga cat cag aaa ggc gaa     528
Val Leu Ala Asn Ile Gly Leu Glu Leu Met Gly His Gln Lys Gly Glu
                165                 170                 175 tac cag tat ctg aat ccc aac gac cac gtg aat aaa tgc cag tcc acc     576
Tyr Gln Tyr Leu Asn Pro Asn Asp His Val Asn Lys Cys Gln Ser Thr
            180                 185                 190 aac gat gct tac ccg acc ggc ttt cgc atc gcc gtt tac agc tcg ctg     624
Asn Asp Ala Tyr Pro Thr Gly Phe Arg Ile Ala Val Tyr Ser Ser Leu
        195                 200                 205
```

```
ttg aaa ctg ctc gac ggc atc agc cag tta gcc gaa ggt ttc cag cgt      672
Leu Lys Leu Leu Asp Gly Ile Ser Gln Leu Ala Glu Gly Phe Gln Arg
    210                 215                 220 aaa gct gac gaa ttc cag acg att tta aaa atg ggc cgt act cag cta      720
Lys Ala Asp Glu Phe Gln Thr Ile Leu Lys Met Gly Arg Thr Gln Leu
225                 230                 235                 240 cag gat gcg gtg ccg atg acg ctg ggt cag gaa ttc cat gcg ttt agc      768
Gln Asp Ala Val Pro Met Thr Leu Gly Gln Glu Phe His Ala Phe Ser
                245                 250                 255 gtg ctc ctc aat gaa gag acg aaa agc att ttg cgc acc ggc gaa ctg      816
Val Leu Leu Asn Glu Glu Thr Lys Ser Ile Leu Arg Thr Gly Glu Leu
            260                 265                 270 ctg ctg gag gtt aac ctg ggc gcg acc gct att ggt act cgc ctg aat      864
Leu Leu Glu Val Asn Leu Gly Ala Thr Ala Ile Gly Thr Arg Leu Asn
        275                 280                 285 acg ccg gat ggc tac caa cac tta gcc gtt cag aaa ctg gca gaa gtc      912
Thr Pro Asp Gly Tyr Gln His Leu Ala Val Gln Lys Leu Ala Glu Val
    290                 295                 300 agt aac ctg gcg gtg gtg cca gcc gaa gat ctg atc gag gcc acc tcc      960
Ser Asn Leu Ala Val Val Pro Ala Glu Asp Leu Ile Glu Ala Thr Ser
305                 310                 315                 320 gac tgc ggc gcc tac gtt atg gtg cac tct tcg ctg aag cgt ctg gcc     1008
Asp Cys Gly Ala Tyr Val Met Val His Ser Ser Leu Lys Arg Leu Ala
                325                 330                 335 gtg aag ctt tct aaa att tgt aac gac ctt cgc ctg ctc tcg tcg ggt     1056
Val Lys Leu Ser Lys Ile Cys Asn Asp Leu Arg Leu Leu Ser Ser Gly
            340                 345                 350 ccg cgt gcc ggc ctg aac gaa att aac ctg cca gaa ttg cag gcc ggc     1104
Pro Arg Ala Gly Leu Asn Glu Ile Asn Leu Pro Glu Leu Gln Ala Gly
        355                 360                 365 tcc tca atc atg cct gcc aaa gtg aac ccg gtg gtg cct gag gtg gta     1152
Ser Ser Ile Met Pro Ala Lys Val Asn Pro Val Val Pro Glu Val Val
    370                 375                 380 aac cag gtg tgc ttc aaa gtg att ggc aac gat acc acg gtc acc atg     1200
Asn Gln Val Cys Phe Lys Val Ile Gly Asn Asp Thr Thr Val Thr Met
385                 390                 395                 400 gcg tcc gag gcc ggg cag ctg cag ctt aac gtt atg gaa ccg gtg att     1248
Ala Ser Glu Ala Gly Gln Leu Gln Leu Asn Val Met Glu Pro Val Ile
                405                 410                 415 ggc cag gcg ctg ttt gag tcg gtc agc atc ctg act aac gct tgc tac     1296
Gly Gln Ala Leu Phe Glu Ser Val Ser Ile Leu Thr Asn Ala Cys Tyr
            420                 425                 430 aac ctg ctg gaa aaa tgc gtt aac ggc atc aca gcc aac aaa gcg gtc     1344
Asn Leu Leu Glu Lys Cys Val Asn Gly Ile Thr Ala Asn Lys Ala Val
        435                 440                 445 tgt gaa gct tat gtg ttt aac tct att ggc atc gtc act tac ctg aac     1392
Cys Glu Ala Tyr Val Phe Asn Ser Ile Gly Ile Val Thr Tyr Leu Asn
    450                 455                 460 ccc tac att ggg cac cat aat ggc gat atc gtc ggt aaa att tgt gcc     1440
Pro Tyr Ile Gly His His Asn Gly Asp Ile Val Gly Lys Ile Cys Ala
465                 470                 475                 480 gaa acc ggt aaa agc gtt cgc gaa gtg gtg ctt gag cgc ggc ctg ctc     1488
Glu Thr Gly Lys Ser Val Arg Glu Val Val Leu Glu Arg Gly Leu Leu
                485                 490                 495 acc gaa agc gag ctg gac gat att ttc tct gtg caa aac ctg atg tat     1536
Thr Glu Ser Glu Leu Asp Asp Ile Phe Ser Val Gln Asn Leu Met Tyr
            500                 505                 510 ccg gtt tat aaa gcc aaa cgt tac acc gac gaa aac gaa cag taa         1581
Pro Val Tyr Lys Ala Lys Arg Tyr Thr Asp Glu Asn Glu Gln
        515                 520                 525
```

<210> SEQ ID NO 6
<211> LENGTH: 526
<212> TYPE: PRT
<213> ORGANISM: Pantoea ananatis

<400> SEQUENCE: 6

Val Ile Ser Val Arg Ala Leu Gly Leu Gly Gln Asn Arg Ile Val Leu
1               5                   10                  15

Thr Arg Leu Asn Thr Asp Lys Ile Ala Val Leu Ala Leu Pro His Lys
            20                  25                  30

Thr Asn Thr Ser Ser Ala Met Val Ser Ser Asp Asn Lys Lys Val Ile
        35                  40                  45

Met Ala Asn Asn Ile Arg Ile Glu Glu Asp Leu Leu Gly Met Arg Glu
    50                  55                  60

Val Pro Ala Asp Ala Tyr Tyr Gly Val His Thr Leu Arg Ala Ile Glu
65                  70                  75                  80

Asn Phe Tyr Ile Ser Asn Ser Lys Ile Ser Asp Ile Pro Glu Phe Val
                85                  90                  95

Arg Gly Met Val Met Val Lys Lys Ala Ala Met Ala Asn Lys Glu
            100                 105                 110

Leu Gln Thr Leu Pro Arg Asp Ile Ala Asn Thr Ile Ile Gln Ala Cys
        115                 120                 125

Asp Glu Val Leu Asn Lys Gly Arg Cys Met Asp Gln Phe Pro Val Asp
    130                 135                 140

Val Tyr Gln Gly Gly Ala Gly Thr Ser Val Asn Met Asn Thr Asn Glu
145                 150                 155                 160

Val Leu Ala Asn Ile Gly Leu Glu Leu Met Gly His Gln Lys Gly Glu
                165                 170                 175

Tyr Gln Tyr Leu Asn Pro Asn Asp His Val Asn Lys Cys Gln Ser Thr
            180                 185                 190

Asn Asp Ala Tyr Pro Thr Gly Phe Arg Ile Ala Val Tyr Ser Ser Leu
        195                 200                 205

Leu Lys Leu Leu Asp Gly Ile Ser Gln Leu Ala Glu Gly Phe Gln Arg
    210                 215                 220

Lys Ala Asp Glu Phe Gln Thr Ile Leu Lys Met Gly Arg Thr Gln Leu
225                 230                 235                 240

Gln Asp Ala Val Pro Met Thr Leu Gly Gln Glu Phe His Ala Phe Ser
                245                 250                 255

Val Leu Leu Asn Glu Glu Thr Lys Ser Ile Leu Arg Thr Gly Glu Leu
            260                 265                 270

Leu Leu Glu Val Asn Leu Gly Ala Thr Ala Ile Gly Thr Arg Leu Asn
        275                 280                 285

Thr Pro Asp Gly Tyr Gln His Leu Ala Val Gln Lys Leu Ala Glu Val
    290                 295                 300

Ser Asn Leu Ala Val Val Pro Ala Glu Asp Leu Ile Glu Ala Thr Ser
305                 310                 315                 320

Asp Cys Gly Ala Tyr Val Met Val His Ser Ser Leu Lys Arg Leu Ala
                325                 330                 335

Val Lys Leu Ser Lys Ile Cys Asn Asp Leu Arg Leu Leu Ser Ser Gly
            340                 345                 350

Pro Arg Ala Gly Leu Asn Glu Ile Asn Leu Pro Glu Leu Gln Ala Gly
        355                 360                 365

Ser Ser Ile Met Pro Ala Lys Val Asn Pro Val Val Pro Glu Val Val

```
                370                 375                 380
Asn Gln Val Cys Phe Lys Val Ile Gly Asn Asp Thr Thr Val Thr Met
385                 390                 395                 400

Ala Ser Glu Ala Gly Gln Leu Gln Leu Asn Val Met Glu Pro Val Ile
                405                 410                 415

Gly Gln Ala Leu Phe Glu Ser Val Ser Ile Leu Thr Asn Ala Cys Tyr
                420                 425                 430

Asn Leu Leu Glu Lys Cys Val Asn Gly Ile Thr Ala Asn Lys Ala Val
                435                 440                 445

Cys Glu Ala Tyr Val Phe Asn Ser Ile Gly Ile Val Thr Tyr Leu Asn
                450                 455                 460

Pro Tyr Ile Gly His His Asn Gly Asp Ile Val Gly Lys Ile Cys Ala
465                 470                 475                 480

Glu Thr Gly Lys Ser Val Arg Glu Val Val Leu Glu Arg Gly Leu Leu
                485                 490                 495

Thr Glu Ser Glu Leu Asp Asp Ile Phe Ser Val Gln Asn Leu Met Tyr
                500                 505                 510

Pro Val Tyr Lys Ala Lys Arg Tyr Thr Asp Glu Asn Glu Gln
                515                 520                 525

<210> SEQ ID NO 7
<211> LENGTH: 2808
<212> TYPE: DNA
<213> ORGANISM: Pantoea ananatis
<220> FEATURE:
<221> NAME/KEY: CDS
<222> LOCATION: (1)..(2808)

<400> SEQUENCE: 7 atg cag aac agc gcg atg aag ccc tgg ctg gac tcc tcc tgg ctg gcc       48
Met Gln Asn Ser Ala Met Lys Pro Trp Leu Asp Ser Ser Trp Leu Ala
1               5                   10                  15 ggc gcg aat cag tct tac ata gag caa ctc tat gag gat ttc ctg acc       96
Gly Ala Asn Gln Ser Tyr Ile Glu Gln Leu Tyr Glu Asp Phe Leu Thr
                20                  25                  30 gat cct gac tct gtg gat gca gtg tgg cgc tcg atg ttc caa cag tta      144
Asp Pro Asp Ser Val Asp Ala Val Trp Arg Ser Met Phe Gln Gln Leu
            35                  40                  45 cca ggc acg gga gtg aaa cct gag cag ttc cac tcc gca act cgc gaa      192
Pro Gly Thr Gly Val Lys Pro Glu Gln Phe His Ser Ala Thr Arg Glu
        50                  55                  60 tat ttc cgt cgc ctg gcg aaa gac gca tct cgt tac acc tcc tca gtt      240
Tyr Phe Arg Arg Leu Ala Lys Asp Ala Ser Arg Tyr Thr Ser Ser Val
65                  70                  75                  80 acc gat ccg gca acc aac tcc aaa caa gtg aaa gtg ctg cag ctg att      288
Thr Asp Pro Ala Thr Asn Ser Lys Gln Val Lys Val Leu Gln Leu Ile
                85                  90                  95 aac gcg ttt cgt ttc cgc gga cat cag gaa gca aat ctc gat ccg ctt      336
Asn Ala Phe Arg Phe Arg Gly His Gln Glu Ala Asn Leu Asp Pro Leu
                100                 105                 110 ggc ctg tgg aaa cag gac cgc gtt gcc gat ctc gat cct gcc ttt cac      384
Gly Leu Trp Lys Gln Asp Arg Val Ala Asp Leu Asp Pro Ala Phe His
            115                 120                 125 gat ctg acc gac gcc gat ttt cag gaa agc ttt aac gta ggt tct ttt      432
Asp Leu Thr Asp Ala Asp Phe Gln Glu Ser Phe Asn Val Gly Ser Phe
        130                 135                 140 gcc att ggc aaa gaa acc atg aag ctg gcc gat ctg ttc gac gcg ctg      480
Ala Ile Gly Lys Glu Thr Met Lys Leu Ala Asp Leu Phe Asp Ala Leu
145                 150                 155                 160
```

-continued

```
aag cag acc tac tgt ggc tcg att ggt gca gag tat atg cac atc aat     528
Lys Gln Thr Tyr Cys Gly Ser Ile Gly Ala Glu Tyr Met His Ile Asn
            165                 170                 175 aac acc gaa gag aaa cgc tgg atc cag cag cgt atc gaa tcc ggt gcg     576
Asn Thr Glu Glu Lys Arg Trp Ile Gln Gln Arg Ile Glu Ser Gly Ala
        180                 185                 190 agc cag acg tca ttc agt ggc gaa gag aaa aaa ggt ttc ctg aaa gag     624
Ser Gln Thr Ser Phe Ser Gly Glu Glu Lys Lys Gly Phe Leu Lys Glu
    195                 200                 205 ctg acc gcg gca gaa ggg ctg gaa aaa tat ctg ggc gcg aaa ttc ccg     672
Leu Thr Ala Ala Glu Gly Leu Glu Lys Tyr Leu Gly Ala Lys Phe Pro
210                 215                 220 ggt gca aaa cgt ttc tcg ctg gaa ggc ggt gat gcg ctg gtg ccg atg     720
Gly Ala Lys Arg Phe Ser Leu Glu Gly Gly Asp Ala Leu Val Pro Met
225                 230                 235                 240 ctg cgc gag atg att cgt cat gcg ggc aaa agc ggc aca cgt gaa gtg     768
Leu Arg Glu Met Ile Arg His Ala Gly Lys Ser Gly Thr Arg Glu Val
                245                 250                 255 gta ctg ggg atg gcg cac cgt ggc cgt ctt aac gta ctg att aac gta     816
Val Leu Gly Met Ala His Arg Gly Arg Leu Asn Val Leu Ile Asn Val
            260                 265                 270 ctg ggt aaa aag cca cag gat ctg ttc gac gaa ttc tcc ggt aaa cac     864
Leu Gly Lys Lys Pro Gln Asp Leu Phe Asp Glu Phe Ser Gly Lys His
        275                 280                 285 aaa gag cat ctg ggc acc ggt gat gtg aag tat cac atg ggc ttc tct     912
Lys Glu His Leu Gly Thr Gly Asp Val Lys Tyr His Met Gly Phe Ser
    290                 295                 300 tcg gat att gaa acc gaa ggt ggt ctg gtg cat ctg gcg ctg gcg ttt     960
Ser Asp Ile Glu Thr Glu Gly Gly Leu Val His Leu Ala Leu Ala Phe
305                 310                 315                 320 aac ccg tct cac ctg gaa att gtc agc ccg gtg gtc atg gga tcg gta    1008
Asn Pro Ser His Leu Glu Ile Val Ser Pro Val Val Met Gly Ser Val
                325                 330                 335 cgt gca cgt ctc gat cgt ctg gcc gaa ccg gtc agc aat aaa gtg ttg    1056
Arg Ala Arg Leu Asp Arg Leu Ala Glu Pro Val Ser Asn Lys Val Leu
            340                 345                 350 cct atc acc att cac ggt gat gcg gcg gtg att ggt cag ggc gtg gtt    1104
Pro Ile Thr Ile His Gly Asp Ala Ala Val Ile Gly Gln Gly Val Val
        355                 360                 365 cag gaa acc ctg aac atg tct cag gcg cgc ggc tac gaa gtg ggc ggc    1152
Gln Glu Thr Leu Asn Met Ser Gln Ala Arg Gly Tyr Glu Val Gly Gly
    370                 375                 380 acg gta cgt atc gtc att aac aac cag gtt ggt ttt acc acc tcc aac    1200
Thr Val Arg Ile Val Ile Asn Asn Gln Val Gly Phe Thr Thr Ser Asn
385                 390                 395                 400 ccg aaa gat gcg cgt tca acc ccg tac tgt act gac atc ggc aag atg    1248
Pro Lys Asp Ala Arg Ser Thr Pro Tyr Cys Thr Asp Ile Gly Lys Met
                405                 410                 415 gtg ctg gca ccg att ttc cac gtc aat gct gac gat ccg gaa gcg gtg    1296
Val Leu Ala Pro Ile Phe His Val Asn Ala Asp Asp Pro Glu Ala Val
            420                 425                 430 gcc ttt gtt acc cgc ctg gcg ctg gac tat cgc aac acc ttc aaa cgc    1344
Ala Phe Val Thr Arg Leu Ala Leu Asp Tyr Arg Asn Thr Phe Lys Arg
        435                 440                 445 gat gtg ttt atc gat ctg gtg tgc tat cgc cgt cat ggt cac aac gag    1392
Asp Val Phe Ile Asp Leu Val Cys Tyr Arg Arg His Gly His Asn Glu
    450                 455                 460 gcg gat gag cca agt gct acc cag ccg ttg atg tac cag aaa atc aaa    1440
Ala Asp Glu Pro Ser Ala Thr Gln Pro Leu Met Tyr Gln Lys Ile Lys
```

-continued

```
                465                 470                 475                 480
aag cat ccg acg ccg cgt aaa att tac gcc gat cgt ctg gaa ggc gaa      1488
Lys His Pro Thr Pro Arg Lys Ile Tyr Ala Asp Arg Leu Glu Gly Glu
                    485                 490                 495 ggt gtc gcg tcg cag gaa gat gcc acc gag atg gtg aac ctg tac cgc      1536
Gly Val Ala Ser Gln Glu Asp Ala Thr Glu Met Val Asn Leu Tyr Arg
            500                 505                 510 gat gcg ctc gat gcg ggc gaa tgc gtg gtg ccg gaa tgg cgt ccg atg      1584
Asp Ala Leu Asp Ala Gly Glu Cys Val Val Pro Glu Trp Arg Pro Met
        515                 520                 525 agc ctg cac tcc ttc acg tgg tcg cct tat ctg aac cac gaa tgg gat      1632
Ser Leu His Ser Phe Thr Trp Ser Pro Tyr Leu Asn His Glu Trp Asp
    530                 535                 540 gag cct tat ccg gca cag gtt gac atg aaa cgc ctg aag gaa ctg gca      1680
Glu Pro Tyr Pro Ala Gln Val Asp Met Lys Arg Leu Lys Glu Leu Ala
545                 550                 555                 560 ttg cgt atc agc cag gtc cct gag cag att gaa gtg cag tcg cgc gtg      1728
Leu Arg Ile Ser Gln Val Pro Glu Gln Ile Glu Val Gln Ser Arg Val
                565                 570                 575 gcc aag atc tat aac gat cgc aag ctg atg gcc gaa ggc gag aaa gcg      1776
Ala Lys Ile Tyr Asn Asp Arg Lys Leu Met Ala Glu Gly Glu Lys Ala
            580                 585                 590 ttc gac tgg ggc ggt gcc gag aat ctg gcg tac gcc acg ctg gtg gat      1824
Phe Asp Trp Gly Gly Ala Glu Asn Leu Ala Tyr Ala Thr Leu Val Asp
        595                 600                 605 gaa ggt att ccg gtt cgc ctc tcg ggt gaa gac tcc ggt cgt gga acc      1872
Glu Gly Ile Pro Val Arg Leu Ser Gly Glu Asp Ser Gly Arg Gly Thr
    610                 615                 620 ttc ttc cat cgc cac gcg gtc gtg cac aac cag gct aac ggt tca acc      1920
Phe Phe His Arg His Ala Val Val His Asn Gln Ala Asn Gly Ser Thr
625                 630                 635                 640 tat acg ccg ctg cac cat att cat aac agc cag ggc gag ttc aaa gtc      1968
Tyr Thr Pro Leu His His Ile His Asn Ser Gln Gly Glu Phe Lys Val
                645                 650                 655 tgg gat tcg gtg ctg tct gaa gaa gcg gtg ctg gcg ttt gaa tac ggt      2016
Trp Asp Ser Val Leu Ser Glu Glu Ala Val Leu Ala Phe Glu Tyr Gly
            660                 665                 670 tac gcc acg gct gag ccg cgc gtg ctg acc atc tgg gaa gcg cag ttt      2064
Tyr Ala Thr Ala Glu Pro Arg Val Leu Thr Ile Trp Glu Ala Gln Phe
        675                 680                 685 ggt gac ttt gcc aac ggt gct cag gtg gtg att gac cag ttc atc agc      2112
Gly Asp Phe Ala Asn Gly Ala Gln Val Val Ile Asp Gln Phe Ile Ser
    690                 695                 700 tct ggc gaa cag aag tgg ggc cgt atg tgt ggc ctg gtg atg ttg ctg      2160
Ser Gly Glu Gln Lys Trp Gly Arg Met Cys Gly Leu Val Met Leu Leu
705                 710                 715                 720 ccg cat ggc tac gaa ggt cag gga ccg gaa cac tcc tct gcc cgt ctg      2208
Pro His Gly Tyr Glu Gly Gln Gly Pro Glu His Ser Ser Ala Arg Leu
                725                 730                 735 gaa cgc tat ctg caa ctt tgc gcc gag cag aac atg cag gtt tgc gtc      2256
Glu Arg Tyr Leu Gln Leu Cys Ala Glu Gln Asn Met Gln Val Cys Val
            740                 745                 750 ccg tcg acg ccg gct cag gtg tat cac atg ctg cgc cgt cag gcg ctg      2304
Pro Ser Thr Pro Ala Gln Val Tyr His Met Leu Arg Arg Gln Ala Leu
        755                 760                 765 cgc ggg atg cgc cgt ccg ctg gtg gtg atg tcg ccg aag tcg ctg tta      2352
Arg Gly Met Arg Arg Pro Leu Val Val Met Ser Pro Lys Ser Leu Leu
    770                 775                 780 cgc cat cca ctg gcg atc tcg tcg ctg gat gaa ctg gca aac ggc agt      2400
Arg His Pro Leu Ala Ile Ser Ser Leu Asp Glu Leu Ala Asn Gly Ser
```

```
Arg His Pro Leu Ala Ile Ser Ser Leu Asp Glu Leu Ala Asn Gly Ser
785                 790                 795                 800 ttc cag ccg gcc att ggt gag atc gac gat ctg gat ccg cag ggc gtg          2448
Phe Gln Pro Ala Ile Gly Glu Ile Asp Asp Leu Asp Pro Gln Gly Val
            805                 810                 815 aaa cgc gtc gtg ctg tgc tcc ggt aag gtt tac tac gat ctg ctg gaa          2496
Lys Arg Val Val Leu Cys Ser Gly Lys Val Tyr Tyr Asp Leu Leu Glu
                820                 825                 830 cag cgt cgt aaa gac gag aaa acc gat gtt gcc atc gtg cgc atc gaa          2544
Gln Arg Arg Lys Asp Glu Lys Thr Asp Val Ala Ile Val Arg Ile Glu
            835                 840                 845 cag ctt tac ccg ttc ccg cat cag gcg gta cag gaa gca ttg aaa gcc          2592
Gln Leu Tyr Pro Phe Pro His Gln Ala Val Gln Glu Ala Leu Lys Ala
        850                 855                 860 tat tct cac gta cag gac ttt gtc tgg tgc cag gaa gag cct ctg aac          2640
Tyr Ser His Val Gln Asp Phe Val Trp Cys Gln Glu Glu Pro Leu Asn
865                 870                 875                 880 cag ggc gcc tgg tac tgt agc cag cat cat ttc cgt gat gtc gtg ccg          2688
Gln Gly Ala Trp Tyr Cys Ser Gln His His Phe Arg Asp Val Val Pro
            885                 890                 895 ttt ggt gcc acc ctg cgt tat gca ggt cgc ccg gca tcg gct tct ccg          2736
Phe Gly Ala Thr Leu Arg Tyr Ala Gly Arg Pro Ala Ser Ala Ser Pro
                900                 905                 910 gcc gtg ggt tat atg tcc gta cac caa caa cag cag caa gac ctg gtt          2784
Ala Val Gly Tyr Met Ser Val His Gln Gln Gln Gln Gln Asp Leu Val
            915                 920                 925 aat gac gca ctg aac gtc aat taa                                          2808
Asn Asp Ala Leu Asn Val Asn
    930                 935

<210> SEQ ID NO 8
<211> LENGTH: 935
<212> TYPE: PRT
<213> ORGANISM: Pantoea ananatis

<400> SEQUENCE: 8

Met Gln Asn Ser Ala Met Lys Pro Trp Leu Asp Ser Ser Trp Leu Ala
1               5                   10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Glu Gln Phe His Ser Ala Thr Arg Glu
    50                  55                  60

Tyr Phe Arg Arg Leu Ala Lys Asp Ala Ser Arg Tyr Thr Ser Ser Val
65                  70                  75                  80

Thr Asp Pro Ala Thr Asn Ser Lys Gln Val Lys Val Leu Gln Leu Ile
                85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
    130                 135                 140

Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
                165                 170                 175
```

```
Asn Thr Glu Glu Lys Arg Trp Ile Gln Gln Arg Ile Glu Ser Gly Ala
            180                 185                 190

Ser Gln Thr Ser Phe Ser Gly Glu Lys Lys Gly Phe Leu Lys Glu
        195                 200                 205

Leu Thr Ala Ala Glu Gly Leu Glu Lys Tyr Leu Gly Ala Lys Phe Pro
        210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
                245                 250                 255

Val Leu Gly Met Ala His Arg Gly Arg Leu Asn Val Leu Ile Asn Val
            260                 265                 270

Leu Gly Lys Lys Pro Gln Asp Leu Phe Asp Glu Phe Ser Gly Lys His
        275                 280                 285

Lys Glu His Leu Gly Thr Gly Asp Val Lys Tyr His Met Gly Phe Ser
        290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Val Met Gly Ser Val
                325                 330                 335

Arg Ala Arg Leu Asp Arg Leu Ala Glu Pro Val Ser Asn Lys Val Leu
            340                 345                 350

Pro Ile Thr Ile His Gly Asp Ala Ala Val Ile Gly Gln Gly Val Val
        355                 360                 365

Gln Glu Thr Leu Asn Met Ser Gln Ala Arg Gly Tyr Glu Val Gly Gly
        370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
                405                 410                 415

Val Leu Ala Pro Ile Phe His Val Asn Ala Asp Asp Pro Glu Ala Val
            420                 425                 430

Ala Phe Val Thr Arg Leu Ala Leu Asp Tyr Arg Asn Thr Phe Lys Arg
        435                 440                 445

Asp Val Phe Ile Asp Leu Val Cys Tyr Arg Arg His Gly His Asn Glu
        450                 455                 460

Ala Asp Glu Pro Ser Ala Thr Gln Pro Leu Met Tyr Gln Lys Ile Lys
465                 470                 475                 480

Lys His Pro Thr Pro Arg Lys Ile Tyr Ala Asp Arg Leu Glu Gly Glu
                485                 490                 495

Gly Val Ala Ser Gln Glu Asp Ala Thr Glu Met Val Asn Leu Tyr Arg
            500                 505                 510

Asp Ala Leu Asp Ala Gly Glu Cys Val Val Pro Glu Trp Arg Pro Met
        515                 520                 525

Ser Leu His Ser Phe Thr Trp Ser Pro Tyr Leu Asn His Glu Trp Asp
        530                 535                 540

Glu Pro Tyr Pro Ala Gln Val Asp Met Lys Arg Leu Lys Glu Leu Ala
545                 550                 555                 560

Leu Arg Ile Ser Gln Val Pro Glu Gln Ile Glu Val Gln Ser Arg Val
                565                 570                 575

Ala Lys Ile Tyr Asn Asp Arg Lys Leu Met Ala Glu Gly Glu Lys Ala
            580                 585                 590
```

```
Phe Asp Trp Gly Gly Ala Glu Asn Leu Ala Tyr Ala Thr Leu Val Asp
            595                 600                 605

Glu Gly Ile Pro Val Arg Leu Ser Gly Glu Asp Ser Gly Arg Gly Thr
    610                 615                 620

Phe Phe His Arg His Ala Val Val His Asn Gln Ala Asn Gly Ser Thr
625                 630                 635                 640

Tyr Thr Pro Leu His His Ile His Asn Ser Gln Gly Glu Phe Lys Val
                645                 650                 655

Trp Asp Ser Val Leu Ser Glu Glu Val Leu Ala Phe Glu Tyr Gly
            660                 665                 670

Tyr Ala Thr Ala Glu Pro Arg Val Leu Thr Ile Trp Glu Ala Gln Phe
        675                 680                 685

Gly Asp Phe Ala Asn Gly Ala Gln Val Val Ile Asp Gln Phe Ile Ser
690                 695                 700

Ser Gly Glu Gln Lys Trp Gly Arg Met Cys Gly Leu Val Met Leu Leu
705                 710                 715                 720

Pro His Gly Tyr Glu Gly Gln Gly Pro Glu His Ser Ser Ala Arg Leu
                725                 730                 735

Glu Arg Tyr Leu Gln Leu Cys Ala Glu Gln Asn Met Gln Val Cys Val
            740                 745                 750

Pro Ser Thr Pro Ala Gln Val Tyr His Met Leu Arg Arg Gln Ala Leu
        755                 760                 765

Arg Gly Met Arg Arg Pro Leu Val Val Met Ser Pro Lys Ser Leu Leu
770                 775                 780

Arg His Pro Leu Ala Ile Ser Ser Leu Asp Glu Leu Ala Asn Gly Ser
785                 790                 795                 800

Phe Gln Pro Ala Ile Gly Glu Ile Asp Asp Leu Asp Pro Gln Gly Val
                805                 810                 815

Lys Arg Val Val Leu Cys Ser Gly Lys Val Tyr Tyr Asp Leu Leu Glu
            820                 825                 830

Gln Arg Arg Lys Asp Glu Lys Thr Asp Val Ala Ile Val Arg Ile Glu
        835                 840                 845

Gln Leu Tyr Pro Phe Pro His Gln Ala Val Gln Glu Ala Leu Lys Ala
850                 855                 860

Tyr Ser His Val Gln Asp Phe Val Trp Cys Gln Glu Glu Pro Leu Asn
865                 870                 875                 880

Gln Gly Ala Trp Tyr Cys Ser Gln His His Phe Arg Asp Val Val Pro
                885                 890                 895

Phe Gly Ala Thr Leu Arg Tyr Ala Gly Arg Pro Ala Ser Ala Ser Pro
            900                 905                 910

Ala Val Gly Tyr Met Ser Val His Gln Gln Gln Gln Asp Leu Val
        915                 920                 925

Asn Asp Ala Leu Asn Val Asn
930                 935

<210> SEQ ID NO 9
<211> LENGTH: 1350
<212> TYPE: DNA
<213> ORGANISM: Pantoea ananatis
<220> FEATURE:
<221> NAME/KEY: CDS
<222> LOCATION: (1)..(1350)

<400> SEQUENCE: 9 atg caa cat gcg cgc gtt tca ggt gtc gaa aga tcc tta cct gcc caa    48
Met Gln His Ala Arg Val Ser Gly Val Glu Arg Ser Leu Pro Ala Gln
```

```
              1               5                    10                        15
ggc gct atg gag acg aaa atg aca gat aaa aaa gtg acg cta acc cta            96
Gly Ala Met Glu Thr Lys Met Thr Asp Lys Lys Val Thr Leu Thr Leu
             20                   25                      30 ccc gac gaa aag cct att gaa ctg aaa gtg ctg caa ggc acg ctg ggc           144
Pro Asp Glu Lys Pro Ile Glu Leu Lys Val Leu Gln Gly Thr Leu Gly
                 35                   40                  45 cag gat gtc gtc gat gtc cgc gaa ctg ggt tct aac ggc ctg ttt acc           192
Gln Asp Val Val Asp Val Arg Glu Leu Gly Ser Asn Gly Leu Phe Thr
         50                   55                   60 ttc gat cct ggt ttc acg tct acc gcg tcc tgc gag tca aaa atc acc           240
Phe Asp Pro Gly Phe Thr Ser Thr Ala Ser Cys Glu Ser Lys Ile Thr
65                   70                   75                   80 ttt atc gat ggc gat gaa ggt atc ctg ctt cac cgt ggt ttt ccc atc           288
Phe Ile Asp Gly Asp Glu Gly Ile Leu Leu His Arg Gly Phe Pro Ile
                     85                   90                  95 gat cag ttg gcc acc cac tct aac tac ctg gaa gtg tgc tat atc ctg           336
Asp Gln Leu Ala Thr His Ser Asn Tyr Leu Glu Val Cys Tyr Ile Leu
             100                  105                 110 ctg aat ggt gaa gcc ccg acg cag aaa cag ttt gaa gag ttc aaa gtc           384
Leu Asn Gly Glu Ala Pro Thr Gln Lys Gln Phe Glu Glu Phe Lys Val
         115                  120                  125 acc gtt acc cgc cac acc atg att cat gag cag atc acg cgt ctg ttc           432
Thr Val Thr Arg His Thr Met Ile His Glu Gln Ile Thr Arg Leu Phe
     130                  135                  140 cac ggc ttc cgt cgc gac tca cat cca atg gct gtg atg tgc ggc gtg           480
His Gly Phe Arg Arg Asp Ser His Pro Met Ala Val Met Cys Gly Val
145                  150                  155                  160 act ggc gcc ctg gcc gcg ttt tat cac gac tcg ctg gat gtg aac att           528
Thr Gly Ala Leu Ala Ala Phe Tyr His Asp Ser Leu Asp Val Asn Ile
                 165                  170                  175 gag cgc cat cgt gaa atc gcc gct ttc cgc ctg ctg tct aaa atg cct           576
Glu Arg His Arg Glu Ile Ala Ala Phe Arg Leu Leu Ser Lys Met Pro
             180                  185                  190 acc atg gca gcg atg tgt tac aag tat tca atc ggc cag ccg ttc gtt           624
Thr Met Ala Ala Met Cys Tyr Lys Tyr Ser Ile Gly Gln Pro Phe Val
         195                  200                  205 tat cca cgt aac gac ctt tcc tac gcc ggt aac ttc ctg cac atg atg           672
Tyr Pro Arg Asn Asp Leu Ser Tyr Ala Gly Asn Phe Leu His Met Met
     210                  215                  220 ttt gca acg cct tgt gaa gaa tac aag gtc aac cct gtg ctt gaa cgc           720
Phe Ala Thr Pro Cys Glu Glu Tyr Lys Val Asn Pro Val Leu Glu Arg
225                  230                  235                  240 gcc atg gat cgc att ctg att ctg cat gcc gat cac gag cag aac gcc           768
Ala Met Asp Arg Ile Leu Ile Leu His Ala Asp His Glu Gln Asn Ala
                 245                  250                  255 tca acc tca acc gtc cgt acg gca ggt tca tca ggc gct aac ccg ttt           816
Ser Thr Ser Thr Val Arg Thr Ala Gly Ser Ser Gly Ala Asn Pro Phe
             260                  265                  270 gcc tgt atc gcg gcc ggt atc gcc tcc ctg tgg gga ccg gcg cac ggt           864
Ala Cys Ile Ala Ala Gly Ile Ala Ser Leu Trp Gly Pro Ala His Gly
         275                  280                  285 ggc gca aac gaa gcc tgt ctg cgc atg ctg gaa gag atc agc acc gtt           912
Gly Ala Asn Glu Ala Cys Leu Arg Met Leu Glu Glu Ile Ser Thr Val
     290                  295                  300 gaa cac att cct gag ttc gta cgt cgt gca aaa gac aaa aac gac tcc           960
Glu His Ile Pro Glu Phe Val Arg Arg Ala Lys Asp Lys Asn Asp Ser
305                  310                  315                  320 ttc cgc ctg atg ggc ttt ggt cat cgc gtt tac aaa aac tat gac cca          1008
```

-continued

```
              Phe Arg Leu Met Gly Phe Gly His Arg Val Tyr Lys Asn Tyr Asp Pro
                              325                 330                 335 cgc gcg acc gtc atg cgt gaa acc tgt cat gaa gtg ctg aac gag ctg          1056
Arg Ala Thr Val Met Arg Glu Thr Cys His Glu Val Leu Asn Glu Leu
            340                 345                 350 ggc atg aaa gat gac ctg ctg gaa gtg gcg ctg gag ctg gaa cac att          1104
Gly Met Lys Asp Asp Leu Leu Glu Val Ala Leu Glu Leu Glu His Ile
        355                 360                 365 gcg ctg aac gac ccg tac ttc atc gag cgt aaa ctc tat cca aac gtg          1152
Ala Leu Asn Asp Pro Tyr Phe Ile Glu Arg Lys Leu Tyr Pro Asn Val
    370                 375                 380 gac ttc tac tcc ggt att atc ctg aaa gcc atg ggc att ccg tct tcc          1200
Asp Phe Tyr Ser Gly Ile Ile Leu Lys Ala Met Gly Ile Pro Ser Ser
385                 390                 395                 400 atg ttt acc gtg att ttt gcc atg gca cgt acc gtt ggc tgg att gcc          1248
Met Phe Thr Val Ile Phe Ala Met Ala Arg Thr Val Gly Trp Ile Ala
                405                 410                 415 cac tgg aaa gag atg cac gac gaa ggc atg aaa att gct ata cag ctg          1296
His Trp Lys Glu Met His Asp Glu Gly Met Lys Ile Ala Ile Gln Leu
            420                 425                 430 acg cgg acg gcc ggt tat acc gag cgc gac ttt acg tca cag ctg gat          1344
Thr Arg Thr Ala Gly Tyr Thr Glu Arg Asp Phe Thr Ser Gln Leu Asp
        435                 440                 445 aaa taa                                                                  1350
Lys
```

<210> SEQ ID NO 10
<211> LENGTH: 449
<212> TYPE: PRT
<213> ORGANISM: Pantoea ananatis

<400> SEQUENCE: 10

```
Met Gln His Ala Arg Val Ser Gly Val Glu Arg Ser Leu Pro Ala Gln
1               5                   10                  15

Gly Ala Met Glu Thr Lys Met Thr Asp Lys Lys Val Thr Leu Thr Leu
            20                  25                  30

Pro Asp Glu Lys Pro Ile Glu Leu Lys Val Leu Gln Gly Thr Leu Gly
        35                  40                  45

Gln Asp Val Val Asp Val Arg Glu Leu Gly Ser Asn Gly Leu Phe Thr
    50                  55                  60

Phe Asp Pro Gly Phe Thr Ser Thr Ala Ser Cys Glu Ser Lys Ile Thr
65                  70                  75                  80

Phe Ile Asp Gly Asp Glu Gly Ile Leu Leu His Arg Gly Phe Pro Ile
                85                  90                  95

Asp Gln Leu Ala Thr His Ser Asn Tyr Leu Glu Val Cys Tyr Ile Leu
            100                 105                 110

Leu Asn Gly Glu Ala Pro Thr Gln Lys Gln Phe Glu Glu Phe Lys Val
        115                 120                 125

Thr Val Thr Arg His Thr Met Ile His Glu Gln Ile Thr Arg Leu Phe
    130                 135                 140

His Gly Phe Arg Arg Asp Ser His Pro Met Ala Val Met Cys Gly Val
145                 150                 155                 160

Thr Gly Ala Leu Ala Ala Phe Tyr His Asp Ser Leu Asp Val Asn Ile
                165                 170                 175

Glu Arg His Arg Glu Ile Ala Ala Phe Arg Leu Leu Ser Lys Met Pro
            180                 185                 190

Thr Met Ala Ala Met Cys Tyr Lys Tyr Ser Ile Gly Gln Pro Phe Val
```

```
                    195                 200                 205
Tyr Pro Arg Asn Asp Leu Ser Tyr Ala Gly Asn Phe Leu His Met Met
    210                 215                 220

Phe Ala Thr Pro Cys Glu Glu Tyr Lys Val Asn Pro Val Leu Glu Arg
225                 230                 235                 240

Ala Met Asp Arg Ile Leu Ile Leu His Ala Asp His Glu Gln Asn Ala
                245                 250                 255

Ser Thr Ser Thr Val Arg Thr Ala Gly Ser Ser Gly Ala Asn Pro Phe
            260                 265                 270

Ala Cys Ile Ala Ala Gly Ile Ala Ser Leu Trp Gly Pro Ala His Gly
        275                 280                 285

Gly Ala Asn Glu Ala Cys Leu Arg Met Leu Glu Glu Ile Ser Thr Val
    290                 295                 300

Glu His Ile Pro Glu Phe Val Arg Arg Ala Lys Asp Lys Asn Asp Ser
305                 310                 315                 320

Phe Arg Leu Met Gly Phe Gly His Arg Val Tyr Lys Asn Tyr Asp Pro
                325                 330                 335

Arg Ala Thr Val Met Arg Glu Thr Cys His Glu Val Leu Asn Glu Leu
            340                 345                 350

Gly Met Lys Asp Asp Leu Leu Glu Val Ala Leu Glu Leu Glu His Ile
        355                 360                 365

Ala Leu Asn Asp Pro Tyr Phe Ile Glu Arg Lys Leu Tyr Pro Asn Val
    370                 375                 380

Asp Phe Tyr Ser Gly Ile Ile Leu Lys Ala Met Gly Ile Pro Ser Ser
385                 390                 395                 400

Met Phe Thr Val Ile Phe Ala Met Ala Arg Thr Val Gly Trp Ile Ala
                405                 410                 415

His Trp Lys Glu Met His Asp Glu Gly Met Lys Ile Ala Ile Gln Leu
            420                 425                 430

Thr Arg Thr Ala Gly Tyr Thr Glu Arg Asp Phe Thr Ser Gln Leu Asp
        435                 440                 445

Lys

<210> SEQ ID NO 11
<211> LENGTH: 1443
<212> TYPE: DNA
<213> ORGANISM: Pantoea ananatis
<220> FEATURE:
<221> NAME/KEY: CDS
<222> LOCATION: (1)..(1443)

<400> SEQUENCE: 11 atg tct cga cgt tta aga aga acc aaa atc gta act acc ctc ggc cca      48
Met Ser Arg Arg Leu Arg Arg Thr Lys Ile Val Thr Thr Leu Gly Pro
1               5                   10                  15 gcc act gac cgc gac aac aac ctc gaa aaa atc att gca gct ggc gcc      96
Ala Thr Asp Arg Asp Asn Asn Leu Glu Lys Ile Ile Ala Ala Gly Ala
            20                  25                  30 aac gtc gtg cgt ctt aac ttt tct cac ggc acg gct gaa gat cat cag     144
Asn Val Val Arg Leu Asn Phe Ser His Gly Thr Ala Glu Asp His Gln
        35                  40                  45 ttg cgt gct gat aaa gtc cgt cag att gcc gca aaa ctg gga cgt cat     192
Leu Arg Ala Asp Lys Val Arg Gln Ile Ala Ala Lys Leu Gly Arg His
    50                  55                  60 gtt gcc att ctg ggc gat ttg caa ggc cct aag atc cgt gtc tcg acc     240
Val Ala Ile Leu Gly Asp Leu Gln Gly Pro Lys Ile Arg Val Ser Thr
65                  70                  75                  80
```

```
ttc aaa gaa ggc aaa gtg ttc ctg aac gtc ggc gat cgt ttc ctg ctg       288
Phe Lys Glu Gly Lys Val Phe Leu Asn Val Gly Asp Arg Phe Leu Leu
                 85              90              95 gac gcg gcg atg ggt aaa ggc gaa ggc gac aaa gaa cgc gtg ggc atc       336
Asp Ala Ala Met Gly Lys Gly Glu Gly Asp Lys Glu Arg Val Gly Ile
            100             105             110 gat tat aaa ggt ctg cct gaa gac gtg gtg cct ggc gat att ctg ttg       384
Asp Tyr Lys Gly Leu Pro Glu Asp Val Val Pro Gly Asp Ile Leu Leu
            115             120             125 ctg gat gat ggt cgc gtt cag tta aag gtg ctg gaa gtt cag ggc gta       432
Leu Asp Asp Gly Arg Val Gln Leu Lys Val Leu Glu Val Gln Gly Val
        130             135             140 aaa gtc ttt act gaa gtt acg gta ggc ggc ccg ctc tcc aac aat aaa       480
Lys Val Phe Thr Glu Val Thr Val Gly Gly Pro Leu Ser Asn Asn Lys
145             150             155             160 ggg atc aac aaa ctg ggc ggc ggg tta tca gcc gaa gcc ctg acc gaa       528
Gly Ile Asn Lys Leu Gly Gly Gly Leu Ser Ala Glu Ala Leu Thr Glu
                165             170             175 aaa gac aaa gca gac atc atc acc gca gcc aaa atc aat gtg gat tac       576
Lys Asp Lys Ala Asp Ile Ile Thr Ala Ala Lys Ile Asn Val Asp Tyr
            180             185             190 ctg gcc gtt tct ttc ccg cgc tgt ggt gaa gac atg cac tat gcg cgc       624
Leu Ala Val Ser Phe Pro Arg Cys Gly Glu Asp Met His Tyr Ala Arg
            195             200             205 cgt ctg gcg cgc gac gca ggc tgt gat gcg ctg atg gtg gcg aag gtt       672
Arg Leu Ala Arg Asp Ala Gly Cys Asp Ala Leu Met Val Ala Lys Val
        210             215             220 gaa cgt gct gaa gcc gtt gcc tcg cag gag gcg atg gac gac atc att       720
Glu Arg Ala Glu Ala Val Ala Ser Gln Glu Ala Met Asp Asp Ile Ile
225             230             235             240 ctg gcc tca gac gtg gtc atg gtg gcc cgt ggc gat ctt ggc gtt gaa       768
Leu Ala Ser Asp Val Val Met Val Ala Arg Gly Asp Leu Gly Val Glu
                245             250             255 atc ggc gat ccg gag ctg gtg ggt att cag aag gcg ctt atc cgc cgc       816
Ile Gly Asp Pro Glu Leu Val Gly Ile Gln Lys Ala Leu Ile Arg Arg
            260             265             270 gcc cgt cag ctt aac cgt acc atc atc acg gca acc cag atg atg gaa       864
Ala Arg Gln Leu Asn Arg Thr Ile Ile Thr Ala Thr Gln Met Met Glu
            275             280             285 tcc atg att acc aat cca atg ccc acc cgc gct gaa gtc atg gac gtt       912
Ser Met Ile Thr Asn Pro Met Pro Thr Arg Ala Glu Val Met Asp Val
        290             295             300 gcc aac gcc gtg ctg gac ggc acc gat gcc gtg atg ctc tct gct gaa       960
Ala Asn Ala Val Leu Asp Gly Thr Asp Ala Val Met Leu Ser Ala Glu
305             310             315             320 acc gcc gca ggc cag tac ccg gct gaa acg gtc gcg gcg atg gca aaa      1008
Thr Ala Ala Gly Gln Tyr Pro Ala Glu Thr Val Ala Ala Met Ala Lys
                325             330             335 gtg tgt ctg ggt gca gaa aaa atc ccc agc gtg aac gtc tct aaa cac      1056
Val Cys Leu Gly Ala Glu Lys Ile Pro Ser Val Asn Val Ser Lys His
            340             345             350 cgc ctt gac gtg cag ttt gac aac atc gaa gaa gcc atc gcg atg tca      1104
Arg Leu Asp Val Gln Phe Asp Asn Ile Glu Glu Ala Ile Ala Met Ser
            355             360             365 gcc atg tac acg gcc aac cat ctg cag ggc gtg acc gcc att att acg      1152
Ala Met Tyr Thr Ala Asn His Leu Gln Gly Val Thr Ala Ile Ile Thr
        370             375             380 atg acg gaa tca ggc cgt acg ccg ttg atg acc tcg cgc atc acc tct      1200
Met Thr Glu Ser Gly Arg Thr Pro Leu Met Thr Ser Arg Ile Thr Ser
```

|     |     | 385 |     |     | 390 |     |     |     | 395 |     |     |     | 400 |     |     |      |
| --- | --- | --- | --- | --- | --- | --- | --- | --- | --- | --- | --- | --- | --- | --- | --- | ---- |
| ggc | ctg | ccg | att | ttc | gcc | atg | tcg | cgc | cac | gag | cgc | acg | ctg | aac | att | 1248 |
| Gly | Leu | Pro | Ile | Phe | Ala | Met | Ser | Arg | His | Glu | Arg | Thr | Leu | Asn | Ile |      |
|     |     | 405 |     |     |     |     |     | 410 |     |     |     |     |     | 415 |     |      |

| acg | gcg | ctg | ttc | cgt | ggc | gtg | acg | ccg | gtt | ttc | ttt | gac | agc | aat | aat | 1296 |
| --- | --- | --- | --- | --- | --- | --- | --- | --- | --- | --- | --- | --- | --- | --- | --- | ---- |
| Thr | Ala | Leu | Phe | Arg | Gly | Val | Thr | Pro | Val | Phe | Phe | Asp | Ser | Asn | Asn |      |
|     |     | 420 |     |     |     |     |     | 425 |     |     |     |     |     | 430 |     |      |

| gag | ggt | gta | gca | aac | gcg | cac | gac | gcg | gtt | aat | ctg | ctg | cgt | gat | aaa | 1344 |
| --- | --- | --- | --- | --- | --- | --- | --- | --- | --- | --- | --- | --- | --- | --- | --- | ---- |
| Glu | Gly | Val | Ala | Asn | Ala | His | Asp | Ala | Val | Asn | Leu | Leu | Arg | Asp | Lys |      |
|     |     | 435 |     |     |     |     |     | 440 |     |     |     |     |     | 445 |     |      |

| ggc | ttt | ctg | ctg | tcg | ggt | gac | ctt | gtc | gtg | gtc | acc | caa | ggt | gat | gtg | 1392 |
| --- | --- | --- | --- | --- | --- | --- | --- | --- | --- | --- | --- | --- | --- | --- | --- | ---- |
| Gly | Phe | Leu | Leu | Ser | Gly | Asp | Leu | Val | Val | Val | Thr | Gln | Gly | Asp | Val |      |
|     |     | 450 |     |     |     |     |     | 455 |     |     |     |     |     | 460 |     |      |

| atg | ggc | gca | acc | gga | aca | acc | aac | aca | ggt | cgt | gtg | ctg | cgc | gtc | gat | 1440 |
| --- | --- | --- | --- | --- | --- | --- | --- | --- | --- | --- | --- | --- | --- | --- | --- | ---- |
| Met | Gly | Ala | Thr | Gly | Thr | Thr | Asn | Thr | Gly | Arg | Val | Leu | Arg | Val | Asp |      |
| 465 |     |     |     |     | 470 |     |     |     |     | 475 |     |     |     |     | 480 |      |

| taa | 1443 |
| --- | ---- |

<210> SEQ ID NO 12
<211> LENGTH: 480
<212> TYPE: PRT
<213> ORGANISM: Pantoea ananatis

<400> SEQUENCE: 12

Met Ser Arg Arg Leu Arg Arg Thr Lys Ile Val Thr Thr Leu Gly Pro
1               5                   10                  15

Ala Thr Asp Arg Asp Asn Asn Leu Glu Lys Ile Ile Ala Ala Gly Ala
                20                  25                  30

Asn Val Val Arg Leu Asn Phe Ser His Gly Thr Ala Glu Asp His Gln
            35                  40                  45

Leu Arg Ala Asp Lys Val Arg Gln Ile Ala Ala Lys Leu Gly Arg His
        50                  55                  60

Val Ala Ile Leu Gly Asp Leu Gln Gly Pro Lys Ile Arg Val Ser Thr
65                  70                  75                  80

Phe Lys Glu Gly Lys Val Phe Leu Asn Val Gly Asp Arg Phe Leu Leu
                85                  90                  95

Asp Ala Ala Met Gly Lys Gly Glu Gly Asp Lys Glu Arg Val Gly Ile
                100                 105                 110

Asp Tyr Lys Gly Leu Pro Glu Asp Val Val Pro Gly Asp Ile Leu Leu
            115                 120                 125

Leu Asp Asp Gly Arg Val Gln Leu Lys Val Leu Glu Val Gln Gly Val
        130                 135                 140

Lys Val Phe Thr Glu Val Thr Val Gly Gly Pro Leu Ser Asn Asn Lys
145                 150                 155                 160

Gly Ile Asn Lys Leu Gly Gly Gly Leu Ser Ala Glu Ala Leu Thr Glu
                165                 170                 175

Lys Asp Lys Ala Asp Ile Ile Thr Ala Ala Lys Ile Asn Val Asp Tyr
            180                 185                 190

Leu Ala Val Ser Phe Pro Arg Cys Gly Glu Asp Met His Tyr Ala Arg
        195                 200                 205

Arg Leu Ala Arg Asp Ala Gly Cys Asp Ala Leu Met Val Ala Lys Val
        210                 215                 220

Glu Arg Ala Glu Ala Val Ala Ser Gln Glu Ala Met Asp Asp Ile Ile
225                 230                 235                 240

Leu Ala Ser Asp Val Val Met Val Ala Arg Gly Asp Leu Gly Val Glu
                245                 250                 255

-continued

```
Ile Gly Asp Pro Glu Leu Val Gly Ile Gln Lys Ala Leu Ile Arg Arg
            260                 265                 270

Ala Arg Gln Leu Asn Arg Thr Ile Ile Thr Ala Thr Gln Met Met Glu
        275                 280                 285

Ser Met Ile Thr Asn Pro Met Pro Thr Arg Ala Glu Val Met Asp Val
    290                 295                 300

Ala Asn Ala Val Leu Asp Gly Thr Asp Ala Val Met Leu Ser Ala Glu
305                 310                 315                 320

Thr Ala Ala Gly Gln Tyr Pro Ala Glu Thr Val Ala Ala Met Ala Lys
                325                 330                 335

Val Cys Leu Gly Ala Glu Lys Ile Pro Ser Val Asn Val Ser Lys His
            340                 345                 350

Arg Leu Asp Val Gln Phe Asp Asn Ile Glu Glu Ala Ile Ala Met Ser
        355                 360                 365

Ala Met Tyr Thr Ala Asn His Leu Gln Gly Val Thr Ala Ile Ile Thr
    370                 375                 380

Met Thr Glu Ser Gly Arg Thr Pro Leu Met Thr Ser Arg Ile Thr Ser
385                 390                 395                 400

Gly Leu Pro Ile Phe Ala Met Ser Arg His Glu Arg Thr Leu Asn Ile
                405                 410                 415

Thr Ala Leu Phe Arg Gly Val Thr Pro Val Phe Phe Asp Ser Asn Asn
            420                 425                 430

Glu Gly Val Ala Asn Ala His Asp Ala Val Asn Leu Leu Arg Asp Lys
        435                 440                 445

Gly Phe Leu Leu Ser Gly Asp Leu Val Val Val Thr Gln Gly Asp Val
    450                 455                 460

Met Gly Ala Thr Gly Thr Thr Asn Thr Gly Arg Val Leu Arg Val Asp
465                 470                 475                 480

<210> SEQ ID NO 13
<211> LENGTH: 1413
<212> TYPE: DNA
<213> ORGANISM: Pantoea ananatis
<220> FEATURE:
<221> NAME/KEY: CDS
<222> LOCATION: (1)..(1413)

<400> SEQUENCE: 13 atg aaa aag act aag atc gtt tgt aca atc ggc cca aaa acc gaa tcc     48
Met Lys Lys Thr Lys Ile Val Cys Thr Ile Gly Pro Lys Thr Glu Ser
1               5                   10                  15 gaa gag atg ctg act cag ctg ctt gaa gca ggc atg aac gtc atg cgt     96
Glu Glu Met Leu Thr Gln Leu Leu Glu Ala Gly Met Asn Val Met Arg
                20                  25                  30 ctt aac ttc tct cac ggt gac tat gca gaa cac ggt cag cgt att acc    144
Leu Asn Phe Ser His Gly Asp Tyr Ala Glu His Gly Gln Arg Ile Thr
            35                  40                  45 aac atg cgt gcc gtg acg aaa aaa acc ggc att cct gcg gct atc ctg    192
Asn Met Arg Ala Val Thr Lys Lys Thr Gly Ile Pro Ala Ala Ile Leu
    50                  55                  60 ctg gat acc aaa ggg ccg gaa atc cgc acc atg aag ctg gaa ggt ggc    240
Leu Asp Thr Lys Gly Pro Glu Ile Arg Thr Met Lys Leu Glu Gly Gly
65                  70                  75                  80 aac gat gtg tca ctg aaa gcc ggt caa acc ttt acc ttt acc acc gac    288
Asn Asp Val Ser Leu Lys Ala Gly Gln Thr Phe Thr Phe Thr Thr Asp
                85                  90                  95 cag agc gtg att ggt aac aac gag cgt gtt gcc gtg acc tac tca ggc    336
```

```
                Gln Ser Val Ile Gly Asn Asn Glu Arg Val Ala Val Thr Tyr Ser Gly
                            100                 105                 110 ttc gcg aac gat ctc aaa att ggt aac act gta ctg gtc gac gat ggt        384
Phe Ala Asn Asp Leu Lys Ile Gly Asn Thr Val Leu Val Asp Asp Gly
            115                 120                 125 ctg atc ggc atg cag gtc acc gaa gtc act gag aac agc gtt gtg tgt        432
Leu Ile Gly Met Gln Val Thr Glu Val Thr Glu Asn Ser Val Val Cys
    130                 135                 140 gaa gtg ctg aac aac ggc gat ctg ggc gaa aac aaa ggc gtg aac ctg        480
Glu Val Leu Asn Asn Gly Asp Leu Gly Glu Asn Lys Gly Val Asn Leu
145                 150                 155                 160 cct ggc gtt tcc atc cag ctg cct gca ctc gca gag aaa gac aag cgc        528
Pro Gly Val Ser Ile Gln Leu Pro Ala Leu Ala Glu Lys Asp Lys Arg
                165                 170                 175 gat ctg att ttt ggt tgt gag caa ggc gtg gat ttt gtt gca gcc tcg        576
Asp Leu Ile Phe Gly Cys Glu Gln Gly Val Asp Phe Val Ala Ala Ser
            180                 185                 190 ttt att cgt aaa cgc tca gac gtg ctg gaa att cgt gaa cac ctg aag        624
Phe Ile Arg Lys Arg Ser Asp Val Leu Glu Ile Arg Glu His Leu Lys
    195                 200                 205 cag cac ggt ggc gaa aac att caa atc atc tcc aag att gaa aac cag        672
Gln His Gly Gly Glu Asn Ile Gln Ile Ile Ser Lys Ile Glu Asn Gln
210                 215                 220 gaa ggc ctg aat aac ttc gac gaa atc ctc gaa gcc tcg gac ggc atc        720
Glu Gly Leu Asn Asn Phe Asp Glu Ile Leu Glu Ala Ser Asp Gly Ile
225                 230                 235                 240 atg gtt gcg cgt ggc gat ctg ggc gtt gaa atc ccg gtt gaa gaa gtg        768
Met Val Ala Arg Gly Asp Leu Gly Val Glu Ile Pro Val Glu Glu Val
                245                 250                 255 atc ttc gcg cag aag atg atg att aaa aaa tgt aat aaa gcc cgc aaa        816
Ile Phe Ala Gln Lys Met Met Ile Lys Lys Cys Asn Lys Ala Arg Lys
            260                 265                 270 gtt gtc atc acc gcg acg cag atg ctg gat tcc atg atc aag aac ccg        864
Val Val Ile Thr Ala Thr Gln Met Leu Asp Ser Met Ile Lys Asn Pro
    275                 280                 285 cgt cca acc cgc gct gaa gct ggc gac gtg gct aac gcc att ctg gat        912
Arg Pro Thr Arg Ala Glu Ala Gly Asp Val Ala Asn Ala Ile Leu Asp
290                 295                 300 gga acg gat gcg gtg atg ctg tct ggc gag agc gcg aaa ggc cgc tat        960
Gly Thr Asp Ala Val Met Leu Ser Gly Glu Ser Ala Lys Gly Arg Tyr
305                 310                 315                 320 ccg ctg gag tcg gtc acc atc atg gcg acc atc tgt gag cgt acc gac       1008
Pro Leu Glu Ser Val Thr Ile Met Ala Thr Ile Cys Glu Arg Thr Asp
                325                 330                 335 cgc gtg atg aag cca cgc atc gac gga caa aat gac agc cgt aag ctg       1056
Arg Val Met Lys Pro Arg Ile Asp Gly Gln Asn Asp Ser Arg Lys Leu
            340                 345                 350 cgc att acc gaa gcc gtt tgc cgc ggt gcc gtt gag aca gcc gag aaa       1104
Arg Ile Thr Glu Ala Val Cys Arg Gly Ala Val Glu Thr Ala Glu Lys
    355                 360                 365 ctg gaa gca cca ctg att gta gtc gcc aca gaa ggc ggt aaa tca gcc       1152
Leu Glu Ala Pro Leu Ile Val Val Ala Thr Glu Gly Gly Lys Ser Ala
370                 375                 380 aag gcc gtg cgt aag tat ttc cct aat gca acc atc ctg gca ctg acc       1200
Lys Ala Val Arg Lys Tyr Phe Pro Asn Ala Thr Ile Leu Ala Leu Thr
385                 390                 395                 400 acc aac gcc acc acg gcg cgc cag ttg att ctg agc aaa ggg atc gag       1248
Thr Asn Ala Thr Thr Ala Arg Gln Leu Ile Leu Ser Lys Gly Ile Glu
                405                 410                 415
```

```
acc cgt atg gtc agc gaa atc gcc tct acc gat gat ttc tat cac ctg    1296
Thr Arg Met Val Ser Glu Ile Ala Ser Thr Asp Asp Phe Tyr His Leu
        420                 425                 430 ggt aaa gaa gcg gcg ctg gaa agc ggt ttt gct cag aaa ggt gat gtt    1344
Gly Lys Glu Ala Ala Leu Glu Ser Gly Phe Ala Gln Lys Gly Asp Val
        435                 440                 445 gtt gtg ctg gtt tca ggt gcg ctg gta ccc agc gga acg acc aat acg    1392
Val Val Leu Val Ser Gly Ala Leu Val Pro Ser Gly Thr Thr Asn Thr
450                 455                 460 gca tcg gta cac gtt ctg taa                                        1413
Ala Ser Val His Val Leu
465                 470

<210> SEQ ID NO 14
<211> LENGTH: 470
<212> TYPE: PRT
<213> ORGANISM: Pantoea ananatis

<400> SEQUENCE: 14

Met Lys Lys Thr Lys Ile Val Cys Thr Ile Gly Pro Lys Thr Glu Ser
1               5                   10                  15

Glu Glu Met Leu Thr Gln Leu Leu Glu Ala Gly Met Asn Val Met Arg
            20                  25                  30

Leu Asn Phe Ser His Gly Asp Tyr Ala Glu His Gly Gln Arg Ile Thr
        35                  40                  45

Asn Met Arg Ala Val Thr Lys Lys Thr Gly Ile Pro Ala Ala Ile Leu
    50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Gln Ser Val Ile Gly Asn Asn Glu Arg Val Ala Val Thr Tyr Ser Gly
            100                 105                 110

Phe Ala Asn Asp Leu Lys Ile Gly Asn Thr Val Leu Val Asp Asp Gly
        115                 120                 125

Leu Ile Gly Met Gln Val Thr Glu Val Thr Glu Asn Ser Val Val Cys
    130                 135                 140

Glu Val Leu Asn Asn Gly Asp Leu Gly Glu Asn Lys Gly Val Asn Leu
145                 150                 155                 160

Pro Gly Val Ser Ile Gln Leu Pro Ala Leu Ala Glu Lys Asp Lys Arg
                165                 170                 175

Asp Leu Ile Phe Gly Cys Glu Gln Gly Val Asp Phe Val Ala Ala Ser
            180                 185                 190

Phe Ile Arg Lys Arg Ser Asp Val Leu Glu Ile Arg Glu His Leu Lys
        195                 200                 205

Gln His Gly Gly Glu Asn Ile Gln Ile Ser Lys Ile Glu Asn Gln
    210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Lys Lys Cys Asn Lys Ala Arg Lys
            260                 265                 270

Val Val Ile Thr Ala Thr Gln Met Leu Asp Ser Met Ile Lys Asn Pro
        275                 280                 285

Arg Pro Thr Arg Ala Glu Ala Gly Asp Val Ala Asn Ala Ile Leu Asp
```

```
                    290                 295                 300
Gly Thr Asp Ala Val Met Leu Ser Gly Glu Ser Ala Lys Gly Arg Tyr
305                 310                 315                 320

Pro Leu Glu Ser Val Thr Ile Met Ala Thr Ile Cys Glu Arg Thr Asp
                    325                 330                 335

Arg Val Met Lys Pro Arg Ile Asp Gly Gln Asn Asp Ser Arg Lys Leu
                340                 345                 350

Arg Ile Thr Glu Ala Val Cys Arg Gly Ala Val Glu Thr Ala Glu Lys
            355                 360                 365

Leu Glu Ala Pro Leu Ile Val Ala Thr Glu Gly Gly Lys Ser Ala
        370                 375                 380

Lys Ala Val Arg Lys Tyr Phe Pro Asn Ala Thr Ile Leu Ala Leu Thr
385                 390                 395                 400

Thr Asn Ala Thr Thr Ala Arg Gln Leu Ile Leu Ser Lys Gly Ile Glu
                    405                 410                 415

Thr Arg Met Val Ser Glu Ile Ala Ser Thr Asp Asp Phe Tyr His Leu
                420                 425                 430

Gly Lys Glu Ala Ala Leu Glu Ser Gly Phe Ala Gln Lys Gly Asp Val
            435                 440                 445

Val Val Leu Val Ser Gly Ala Leu Val Pro Ser Gly Thr Thr Asn Thr
        450                 455                 460

Ala Ser Val His Val Leu
465                 470

<210> SEQ ID NO 15
<211> LENGTH: 2652
<212> TYPE: DNA
<213> ORGANISM: Escherichia coli
<220> FEATURE:
<221> NAME/KEY: CDS
<222> LOCATION: (1)..(2652)

<400> SEQUENCE: 15 atg aac gaa caa tat tcc gca ttg cgt agt aat gtc agt atg ctc ggc       48
Met Asn Glu Gln Tyr Ser Ala Leu Arg Ser Asn Val Ser Met Leu Gly
1               5                   10                  15 aaa gtg ctg gga gaa acc atc aag gat gcg ttg gga gaa cac att ctt       96
Lys Val Leu Gly Glu Thr Ile Lys Asp Ala Leu Gly Glu His Ile Leu
            20                  25                  30 gaa cgc gta gaa act atc cgt aag ttg tcg aaa tct tca cgc gct ggc      144
Glu Arg Val Glu Thr Ile Arg Lys Leu Ser Lys Ser Ser Arg Ala Gly
        35                  40                  45 aat gat gct aac cgc cag gag ttg ctc acc acc tta caa aat ttg tcg      192
Asn Asp Ala Asn Arg Gln Glu Leu Leu Thr Thr Leu Gln Asn Leu Ser
    50                  55                  60 aac gac gag ctg ctg ccc gtt gcg cgt gcg ttt agt cag ttc ctg aac      240
Asn Asp Glu Leu Leu Pro Val Ala Arg Ala Phe Ser Gln Phe Leu Asn
65                  70                  75                  80 ctg gcc aac acc gcc gag caa tac cac agc att tcg ccg aaa ggc gaa      288
Leu Ala Asn Thr Ala Glu Gln Tyr His Ser Ile Ser Pro Lys Gly Glu
                85                  90                  95 gct gcc agc aac ccg gaa gtg atc gcc cgc acc ctg cgt aaa ctg aaa      336
Ala Ala Ser Asn Pro Glu Val Ile Ala Arg Thr Leu Arg Lys Leu Lys
            100                 105                 110 aac cag ccg gaa ctg agc gaa gac acc atc aaa aaa gca gtg gaa tcg      384
Asn Gln Pro Glu Leu Ser Glu Asp Thr Ile Lys Lys Ala Val Glu Ser
        115                 120                 125 ctg tcg ctg gaa ctg gtc ctc acg gct cac cca acc gaa att acc cgt      432
```

```
Leu Ser Leu Glu Leu Val Leu Thr Ala His Pro Thr Glu Ile Thr Arg
    130                 135                 140 cgt aca ctg atc cac aaa atg gtg gaa gtg aac gcc tgt tta aaa cag    480
Arg Thr Leu Ile His Lys Met Val Glu Val Asn Ala Cys Leu Lys Gln
145                 150                 155                 160 ctc gat aac aaa gat atc gct gac tac gaa cac aac cag ctg atg cgt    528
Leu Asp Asn Lys Asp Ile Ala Asp Tyr Glu His Asn Gln Leu Met Arg
                165                 170                 175 cgc ctg cgc cag ttg atc gcc cag tca tgg cat acc gat gaa atc cgt    576
Arg Leu Arg Gln Leu Ile Ala Gln Ser Trp His Thr Asp Glu Ile Arg
            180                 185                 190 aag ctg cgt cca agc ccg gta gat gaa gcc aaa tgg ggc ttt gcc gta    624
Lys Leu Arg Pro Ser Pro Val Asp Glu Ala Lys Trp Gly Phe Ala Val
        195                 200                 205 gtg gaa aac agc ctg tgg caa ggc gta cca aat tac ctg cgc gaa ctg    672
Val Glu Asn Ser Leu Trp Gln Gly Val Pro Asn Tyr Leu Arg Glu Leu
    210                 215                 220 aac gaa caa ctg gaa gag aac ctc ggc tac aaa ctg ccc gtc gaa ttt    720
Asn Glu Gln Leu Glu Glu Asn Leu Gly Tyr Lys Leu Pro Val Glu Phe
225                 230                 235                 240 gtt ccg gtc cgt ttt act tcg tgg atg ggc ggc gac cgc gac ggc aac    768
Val Pro Val Arg Phe Thr Ser Trp Met Gly Gly Asp Arg Asp Gly Asn
                245                 250                 255 ccg aac gtc act gcc gat atc acc cgc cac gtc ctg cta ctc agc cgc    816
Pro Asn Val Thr Ala Asp Ile Thr Arg His Val Leu Leu Leu Ser Arg
            260                 265                 270 tgg aaa gcc acc gat ttg ttc ctg aaa gat att cag gtg ctg gtt tct    864
Trp Lys Ala Thr Asp Leu Phe Leu Lys Asp Ile Gln Val Leu Val Ser
        275                 280                 285 gaa ctg tcg atg gtt gaa gcg acc cct gaa ctg ctg gcg ctg gtt ggc    912
Glu Leu Ser Met Val Glu Ala Thr Pro Glu Leu Leu Ala Leu Val Gly
    290                 295                 300 gaa gaa ggt gcc gca gaa ccg tat cgc tat ctg atg aaa aac ctg cgt    960
Glu Glu Gly Ala Ala Glu Pro Tyr Arg Tyr Leu Met Lys Asn Leu Arg
305                 310                 315                 320 tct cgc ctg atg gcg aca cag gca tgg ctg gaa gcg cgc ctg aaa ggc   1008
Ser Arg Leu Met Ala Thr Gln Ala Trp Leu Glu Ala Arg Leu Lys Gly
                325                 330                 335 gaa gaa ctg cca aaa cca gaa ggc ctg ctg aca caa aac gaa gaa ctg   1056
Glu Glu Leu Pro Lys Pro Glu Gly Leu Leu Thr Gln Asn Glu Glu Leu
            340                 345                 350 tgg gaa ccg ctc tac gct tgc tac cag tca ctt cag gcg tgt ggc atg   1104
Trp Glu Pro Leu Tyr Ala Cys Tyr Gln Ser Leu Gln Ala Cys Gly Met
        355                 360                 365 ggt att atc gcc aac ggc gat ctg ctc gac acc ctg cgc cgc gtg aaa   1152
Gly Ile Ile Ala Asn Gly Asp Leu Leu Asp Thr Leu Arg Arg Val Lys
    370                 375                 380 tgt ttc ggc gta ccg ctg gtc cgt att gat atc cgt cag gag agc acg   1200
Cys Phe Gly Val Pro Leu Val Arg Ile Asp Ile Arg Gln Glu Ser Thr
385                 390                 395                 400 cgt cat acc gaa gcg ctg ggc gag ctg acc cgc tac ctc ggt atc ggc   1248
Arg His Thr Glu Ala Leu Gly Glu Leu Thr Arg Tyr Leu Gly Ile Gly
                405                 410                 415 gac tac gaa agc tgg tca gag gcc gac aaa cag gcg ttc ctg atc cgc   1296
Asp Tyr Glu Ser Trp Ser Glu Ala Asp Lys Gln Ala Phe Leu Ile Arg
            420                 425                 430 gaa ctg aac tcc aaa cgt ccg ctt ctg ccg cgc aac tgg caa cca agc   1344
Glu Leu Asn Ser Lys Arg Pro Leu Leu Pro Arg Asn Trp Gln Pro Ser
        435                 440                 445
```

```
gcc gaa acg cgc gaa gtg ctc gat acc tgc cag gtg att gcc gaa gca    1392
Ala Glu Thr Arg Glu Val Leu Asp Thr Cys Gln Val Ile Ala Glu Ala
450                 455                 460 ccg caa ggc tcc att gcc gcc tac gtg atc tcg atg gcg aaa acg ccg    1440
Pro Gln Gly Ser Ile Ala Ala Tyr Val Ile Ser Met Ala Lys Thr Pro
465                 470                 475                 480 tcc gac gta ctg gct gtc cac ctg ctg ctg aaa gaa gcg ggt atc ggg    1488
Ser Asp Val Leu Ala Val His Leu Leu Leu Lys Glu Ala Gly Ile Gly
                485                 490                 495 ttt gcg atg ccg gtt gct ccg ctg ttt gaa acc ctc gat gat ctg aac    1536
Phe Ala Met Pro Val Ala Pro Leu Phe Glu Thr Leu Asp Asp Leu Asn
            500                 505                 510 aac gcc aac gat gtc atg acc cag ctg ctc aat att gac tgg tat cgt    1584
Asn Ala Asn Asp Val Met Thr Gln Leu Leu Asn Ile Asp Trp Tyr Arg
        515                 520                 525 ggc ctg att cag ggc aaa cag atg gtg atg att ggc tat tcc gac tca    1632
Gly Leu Ile Gln Gly Lys Gln Met Val Met Ile Gly Tyr Ser Asp Ser
530                 535                 540 gca aaa gat gcg gga gtg atg gca gct tcc tgg gcg caa tat cag gca    1680
Ala Lys Asp Ala Gly Val Met Ala Ala Ser Trp Ala Gln Tyr Gln Ala
545                 550                 555                 560 cag gat gca tta atc aaa acc tgc gaa aaa gcg ggt att gag ctg acg    1728
Gln Asp Ala Leu Ile Lys Thr Cys Glu Lys Ala Gly Ile Glu Leu Thr
                565                 570                 575 ttg ttc cac ggt cgc ggc ggt tcc att ggt cgc ggc ggc gca cct gct    1776
Leu Phe His Gly Arg Gly Gly Ser Ile Gly Arg Gly Gly Ala Pro Ala
            580                 585                 590 cat gcg gcg ctg ctg tca caa ccg cca gga agc ctg aaa ggc ggc ctg    1824
His Ala Ala Leu Leu Ser Gln Pro Pro Gly Ser Leu Lys Gly Gly Leu
        595                 600                 605 cgc gta acc gaa cag ggc gag atg atc cgc ttt aaa tat ggt ctg cca    1872
Arg Val Thr Glu Gln Gly Glu Met Ile Arg Phe Lys Tyr Gly Leu Pro
610                 615                 620 gaa atc acc gtc agc agc ctg tcg ctt tat acc ggg gcg att ctg gaa    1920
Glu Ile Thr Val Ser Ser Leu Ser Leu Tyr Thr Gly Ala Ile Leu Glu
625                 630                 635                 640 gcc aac ctg ctg cca ccg ccg gag ccg aaa gag agc tgg cgt cgc att    1968
Ala Asn Leu Leu Pro Pro Pro Glu Pro Lys Glu Ser Trp Arg Arg Ile
                645                 650                 655 atg gat gaa ctg tca gtc atc tcc tgc gat gtc tac cgc ggc tac gta    2016
Met Asp Glu Leu Ser Val Ile Ser Cys Asp Val Tyr Arg Gly Tyr Val
            660                 665                 670 cgt gaa aac aaa gat ttt gtg cct tac ttc cgc tcc gct acg ccg gaa    2064
Arg Glu Asn Lys Asp Phe Val Pro Tyr Phe Arg Ser Ala Thr Pro Glu
        675                 680                 685 caa gaa ctg ggc aaa ctg ccg ttg ggt tca cgt ccg gcg aaa cgt cgc    2112
Gln Glu Leu Gly Lys Leu Pro Leu Gly Ser Arg Pro Ala Lys Arg Arg
690                 695                 700 cca acc ggc ggc gtc gag tca cta cgc gcc att ccg tgg atc ttc gcc    2160
Pro Thr Gly Gly Val Glu Ser Leu Arg Ala Ile Pro Trp Ile Phe Ala
705                 710                 715                 720 tgg acg caa aac cgt ctg atg ctc ccc gcc tgg ctg ggt gca ggt acg    2208
Trp Thr Gln Asn Arg Leu Met Leu Pro Ala Trp Leu Gly Ala Gly Thr
                725                 730                 735 gcg ctg caa aaa gtg gtc gaa gac ggc aaa cag agc gag ctg gag gct    2256
Ala Leu Gln Lys Val Val Glu Asp Gly Lys Gln Ser Glu Leu Glu Ala
            740                 745                 750 atg tgc cgc gat tgg cca ttc ttc tcg acg cgt ctc ggc atg ctg gag    2304
Met Cys Arg Asp Trp Pro Phe Phe Ser Thr Arg Leu Gly Met Leu Glu
        755                 760                 765
```

-continued

```
atg gtc ttc gcc aaa gca gac ctg tgg ctg gcg gaa tac tat gac caa      2352
Met Val Phe Ala Lys Ala Asp Leu Trp Leu Ala Glu Tyr Tyr Asp Gln
770             775                 780 cgc ctg gta gac aaa gca ctg tgg ccg tta ggt aaa gag tta cgc aac      2400
Arg Leu Val Asp Lys Ala Leu Trp Pro Leu Gly Lys Glu Leu Arg Asn
785             790                 795                 800 ctg caa gaa gaa gac atc aaa gtg gtg ctg gcg att gcc aac gat tcc      2448
Leu Gln Glu Glu Asp Ile Lys Val Val Leu Ala Ile Ala Asn Asp Ser
                805                 810                 815 cat ctg atg gcc gat ctg ccg tgg att gca gag tct att cag cta cgg      2496
His Leu Met Ala Asp Leu Pro Trp Ile Ala Glu Ser Ile Gln Leu Arg
            820                 825                 830 aat att tac acc gac ccg ctg aac gta ttg cag gcc gag ttg ctg cac      2544
Asn Ile Tyr Thr Asp Pro Leu Asn Val Leu Gln Ala Glu Leu Leu His
        835                 840                 845 cgc tcc cgc cag gca gaa aaa gaa ggc cag gaa ccg gat cct cgc gtc      2592
Arg Ser Arg Gln Ala Glu Lys Glu Gly Gln Glu Pro Asp Pro Arg Val
    850                 855                 860 gaa caa gcg tta atg gtc act att gcc ggg att gcg gca ggt atg cgt      2640
Glu Gln Ala Leu Met Val Thr Ile Ala Gly Ile Ala Ala Gly Met Arg
865                 870                 875                 880 aat acc ggc taa                                                       2652
Asn Thr Gly
```

<210> SEQ ID NO 16
<211> LENGTH: 883
<212> TYPE: PRT
<213> ORGANISM: Escherichia coli

<400> SEQUENCE: 16

```
Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205
```

```
Val Glu Asn Ser Leu Trp Gln Gly Val Pro Asn Tyr Leu Arg Glu Leu
210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
                260                 265                 270

Trp Lys Ala Thr Asp Leu Phe Leu Lys Asp Ile Gln Val Leu Val Ser
                275                 280                 285

Glu Leu Ser Met Val Glu Ala Thr Pro Glu Leu Leu Ala Leu Val Gly
290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
                340                 345                 350

Trp Glu Pro Leu Tyr Ala Cys Tyr Gln Ser Leu Gln Ala Cys Gly Met
                355                 360                 365

Gly Ile Ile Ala Asn Gly Asp Leu Leu Asp Thr Leu Arg Arg Val Lys
370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
                420                 425                 430

Glu Leu Asn Ser Lys Arg Pro Leu Leu Pro Arg Asn Trp Gln Pro Ser
                435                 440                 445

Ala Glu Thr Arg Glu Val Leu Asp Thr Cys Gln Val Ile Ala Glu Ala
                450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
                500                 505                 510

Asn Ala Asn Asp Val Met Thr Gln Leu Leu Asn Ile Asp Trp Tyr Arg
                515                 520                 525

Gly Leu Ile Gln Gly Lys Gln Met Val Met Ile Gly Tyr Ser Asp Ser
530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
                580                 585                 590

His Ala Ala Leu Leu Ser Gln Pro Pro Gly Ser Leu Lys Gly Gly Leu
                595                 600                 605

Arg Val Thr Glu Gln Gly Glu Met Ile Arg Phe Lys Tyr Gly Leu Pro
610                 615                 620

Glu Ile Thr Val Ser Ser Leu Ser Leu Tyr Thr Gly Ala Ile Leu Glu
```

```
                625                 630                 635                 640
            Ala Asn Leu Leu Pro Pro Glu Pro Lys Glu Ser Trp Arg Arg Ile
                            645                 650                 655
            Met Asp Glu Leu Ser Val Ile Ser Cys Asp Val Tyr Arg Gly Tyr Val
                                660                 665                 670
            Arg Glu Asn Lys Asp Phe Val Pro Tyr Phe Arg Ser Ala Thr Pro Glu
                            675                 680                 685
            Gln Glu Leu Gly Lys Leu Pro Leu Gly Ser Arg Pro Ala Lys Arg Arg
                        690                 695                 700
            Pro Thr Gly Gly Val Glu Ser Leu Arg Ala Ile Pro Trp Ile Phe Ala
            705                 710                 715                 720
            Trp Thr Gln Asn Arg Leu Met Leu Pro Ala Trp Leu Gly Ala Gly Thr
                                725                 730                 735
            Ala Leu Gln Lys Val Val Glu Asp Gly Lys Gln Ser Glu Leu Glu Ala
                            740                 745                 750
            Met Cys Arg Asp Trp Pro Phe Phe Ser Thr Arg Leu Gly Met Leu Glu
                        755                 760                 765
            Met Val Phe Ala Lys Ala Asp Leu Trp Leu Ala Glu Tyr Tyr Asp Gln
                    770                 775                 780
            Arg Leu Val Asp Lys Ala Leu Trp Pro Leu Gly Lys Glu Leu Arg Asn
            785                 790                 795                 800
            Leu Gln Glu Glu Asp Ile Lys Val Val Leu Ala Ile Ala Asn Asp Ser
                                805                 810                 815
            His Leu Met Ala Asp Leu Pro Trp Ile Ala Glu Ser Ile Gln Leu Arg
                            820                 825                 830
            Asn Ile Tyr Thr Asp Pro Leu Asn Val Leu Gln Ala Glu Leu Leu His
                        835                 840                 845
            Arg Ser Arg Gln Ala Glu Lys Glu Gly Gln Glu Pro Asp Pro Arg Val
                    850                 855                 860
            Glu Gln Ala Leu Met Val Thr Ile Ala Gly Ile Ala Ala Gly Met Arg
            865                 870                 875                 880
            Asn Thr Gly

<210> SEQ ID NO 17
<211> LENGTH: 1263
<212> TYPE: DNA
<213> ORGANISM: T. maritima
<220> FEATURE:
<221> NAME/KEY: CDS
<222> LOCATION: (1)..(1263)

<400> SEQUENCE: 17 atg ttg agc atg act gtt ctg atc atc gga atg gga aat att ggg aaa      48
Met Leu Ser Met Thr Val Leu Ile Ile Gly Met Gly Asn Ile Gly Lys
 1               5                  10                  15 aaa ctc gta gaa ctg gga aat ttc gag aaa atc tac gct tac gac cgt      96
Lys Leu Val Glu Leu Gly Asn Phe Glu Lys Ile Tyr Ala Tyr Asp Arg
             20                  25                  30 att tca aaa gac att ccg gga gtc gtt cgc ctc gat gaa ttc cag gtt     144
Ile Ser Lys Asp Ile Pro Gly Val Val Arg Leu Asp Glu Phe Gln Val
         35                  40                  45 cct tca gac gtc agc acg gtt gtc gaa tgc gct tct cca gaa gcc gtt     192
Pro Ser Asp Val Ser Thr Val Val Glu Cys Ala Ser Pro Glu Ala Val
     50                  55                  60 aaa gaa tac tca ctt cag atc ctg aaa aac cct gtg aac tac atc atc     240
Lys Glu Tyr Ser Leu Gln Ile Leu Lys Asn Pro Val Asn Tyr Ile Ile
 65                  70                  75                  80
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | agc | acc | agc | gct | ttc | gcg | gac | gaa | gtt | ttc | cgt | gaa | cgt | ttc | ttc | 288  |
| Ile | Ser | Thr | Ser | Ala | Phe | Ala | Asp | Glu | Val | Phe | Arg | Glu | Arg | Phe | Phe |      |
|     |     |     |     | 85  |     |     |     |     | 90  |     |     |     |     | 95  |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agc | gaa | ttg | aaa | aat | tca | cca | gcc | cgt | gtc | ttt | ttc | cca | tcc | ggt | gcc | 336  |
| Ser | Glu | Leu | Lys | Asn | Ser | Pro | Ala | Arg | Val | Phe | Phe | Pro | Ser | Gly | Ala |      |
|     |     |     | 100 |     |     |     |     | 105 |     |     |     |     | 110 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | ggc | ggt | ctc | gat | gtt | ctc | tct | tcc | atc | aaa | gat | ttc | gtc | aaa | aac | 384  |
| Ile | Gly | Gly | Leu | Asp | Val | Leu | Ser | Ser | Ile | Lys | Asp | Phe | Val | Lys | Asn |      |
|     |     | 115 |     |     |     |     | 120 |     |     |     |     | 125 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtc | cgc | atc | gaa | aca | atc | aaa | cct | cca | aag | agt | ctc | ggc | ctg | gat | ttg | 432  |
| Val | Arg | Ile | Glu | Thr | Ile | Lys | Pro | Pro | Lys | Ser | Leu | Gly | Leu | Asp | Leu |      |
|     | 130 |     |     |     |     | 135 |     |     |     |     | 140 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aaa | ggt | aaa | aca | gtc | gtg | ttc | gaa | gga | agt | gtt | gag | gaa | gcg | tca | aaa | 480  |
| Lys | Gly | Lys | Thr | Val | Val | Phe | Glu | Gly | Ser | Val | Glu | Glu | Ala | Ser | Lys |      |
| 145 |     |     |     |     | 150 |     |     |     |     | 155 |     |     |     |     | 160 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | ttt | cca | cgt | aac | atc | aac | gta | gcg | tcg | acc | atc | ggc | ctt | atc | gtg | 528  |
| Leu | Phe | Pro | Arg | Asn | Ile | Asn | Val | Ala | Ser | Thr | Ile | Gly | Leu | Ile | Val |      |
|     |     |     |     | 165 |     |     |     |     | 170 |     |     |     |     | 175 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggc | ttt | gaa | aag | gta | aag | gta | aca | atc | gtg | gca | gat | cca | gcc | atg | gat | 576  |
| Gly | Phe | Glu | Lys | Val | Lys | Val | Thr | Ile | Val | Ala | Asp | Pro | Ala | Met | Asp |      |
|     |     |     | 180 |     |     |     |     | 185 |     |     |     |     | 190 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cac | aac | atc | cac | att | gta | cgt | atc | tcc | tcc | gct | atc | gga | aac | tac | gaa | 624  |
| His | Asn | Ile | His | Ile | Val | Arg | Ile | Ser | Ser | Ala | Ile | Gly | Asn | Tyr | Glu |      |
|     |     | 195 |     |     |     |     | 200 |     |     |     |     | 205 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttc | aaa | atc | gag | aat | att | cca | tca | cca | gaa | aac | cca | aaa | aca | agt | atg | 672  |
| Phe | Lys | Ile | Glu | Asn | Ile | Pro | Ser | Pro | Glu | Asn | Pro | Lys | Thr | Ser | Met |      |
|     | 210 |     |     |     |     | 215 |     |     |     |     | 220 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | aca | gtc | tat | tcg | att | ctc | cgt | acc | ttg | cgt | aat | ctc | gaa | tca | aaa | 720  |
| Leu | Thr | Val | Tyr | Ser | Ile | Leu | Arg | Thr | Leu | Arg | Asn | Leu | Glu | Ser | Lys |      |
| 225 |     |     |     |     | 230 |     |     |     |     | 235 |     |     |     |     | 240 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | atc | ttc | gga | tca | ctt | cag | atc | ctg | aaa | aac | cct | gtg | aac | tac | atc | 768  |
| Ile | Ile | Phe | Gly | Ser | Leu | Gln | Ile | Leu | Lys | Asn | Pro | Val | Asn | Tyr | Ile |      |
|     |     |     |     | 245 |     |     |     |     | 250 |     |     |     |     | 255 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | atc | agc | acc | agc | gct | ttc | gcg | gac | gaa | gtt | ttc | cgt | gaa | cgt | ttc | 816  |
| Ile | Ile | Ser | Thr | Ser | Ala | Phe | Ala | Asp | Glu | Val | Phe | Arg | Glu | Arg | Phe |      |
|     |     |     | 260 |     |     |     |     | 265 |     |     |     |     | 270 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttc | agc | gaa | ttg | aaa | aat | tca | cca | gcc | cgt | gtc | ttt | ttc | cca | tcc | ggt | 864  |
| Phe | Ser | Glu | Leu | Lys | Asn | Ser | Pro | Ala | Arg | Val | Phe | Phe | Pro | Ser | Gly |      |
|     |     | 275 |     |     |     |     | 280 |     |     |     |     | 285 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | atc | ggc | ggt | ctc | gat | gtt | ctc | tct | tcc | atc | aaa | gat | ttc | gtc | aaa | 912  |
| Ala | Ile | Gly | Gly | Leu | Asp | Val | Leu | Ser | Ser | Ile | Lys | Asp | Phe | Val | Lys |      |
|     | 290 |     |     |     |     | 295 |     |     |     |     | 300 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aac | gtc | cgc | atc | gaa | aca | atc | aaa | cct | cca | aag | agt | ctc | ggc | ctg | gat | 960  |
| Asn | Val | Arg | Ile | Glu | Thr | Ile | Lys | Pro | Pro | Lys | Ser | Leu | Gly | Leu | Asp |      |
| 305 |     |     |     |     | 310 |     |     |     |     | 315 |     |     |     |     | 320 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttg | aaa | ggt | aaa | aca | gtc | gtg | ttc | gaa | gga | agt | gtt | gag | gaa | gcg | tca | 1008 |
| Leu | Lys | Gly | Lys | Thr | Val | Val | Phe | Glu | Gly | Ser | Val | Glu | Glu | Ala | Ser |      |
|     |     |     |     | 325 |     |     |     |     | 330 |     |     |     |     | 335 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aaa | ctg | ttt | cca | cgt | aac | atc | aac | gta | gcg | tcg | acc | atc | ggc | ctt | atc | 1056 |
| Lys | Leu | Phe | Pro | Arg | Asn | Ile | Asn | Val | Ala | Ser | Thr | Ile | Gly | Leu | Ile |      |
|     |     |     | 340 |     |     |     |     | 345 |     |     |     |     | 350 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | ggc | ttt | gaa | aag | gta | aag | gta | aca | atc | gtg | gca | gat | cca | gcc | atg | 1104 |
| Val | Gly | Phe | Glu | Lys | Val | Lys | Val | Thr | Ile | Val | Ala | Asp | Pro | Ala | Met |      |
|     |     | 355 |     |     |     |     | 360 |     |     |     |     | 365 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gat | cac | aac | atc | cac | att | gta | cgt | atc | tcc | tcc | gct | atc | gga | aac | tac | 1152 |
| Asp | His | Asn | Ile | His | Ile | Val | Arg | Ile | Ser | Ser | Ala | Ile | Gly | Asn | Tyr |      |
|     | 370 |     |     |     |     | 375 |     |     |     |     | 380 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gaa | ttc | aaa | atc | gag | aat | att | cca | tca | cca | gaa | aac | cca | aaa | aca | agt | 1200 |
| Glu | Phe | Lys | Ile | Glu | Asn | Ile | Pro | Ser | Pro | Glu | Asn | Pro | Lys | Thr | Ser |      |

```
                385                 390                 395                 400
atg ctg aca gtc tat tcg att ctc cgt acc ttg cgt aat ctc gaa tca       1248
Met Leu Thr Val Tyr Ser Ile Leu Arg Thr Leu Arg Asn Leu Glu Ser
            405                 410                 415 aaa atc atc ttc gga                                                    1263
Lys Ile Ile Phe Gly
        420

<210> SEQ ID NO 18
<211> LENGTH: 421
<212> TYPE: PRT
<213> ORGANISM: T. maritima

<400> SEQUENCE: 18

Met Leu Ser Met Thr Val Leu Ile Ile Gly Met Gly Asn Ile Gly Lys
1               5                   10                  15

Lys Leu Val Glu Leu Gly Asn Phe Glu Lys Ile Tyr Ala Tyr Asp Arg
            20                  25                  30

Ile Ser Lys Asp Ile Pro Gly Val Val Arg Leu Asp Glu Phe Gln Val
        35                  40                  45

Pro Ser Asp Val Ser Thr Val Val Glu Cys Ala Ser Pro Glu Ala Val
    50                  55                  60

Lys Glu Tyr Ser Leu Gln Ile Leu Lys Asn Pro Val Asn Tyr Ile Ile
65                  70                  75                  80

Ile Ser Thr Ser Ala Phe Ala Asp Glu Val Phe Arg Glu Arg Phe Phe
                85                  90                  95

Ser Glu Leu Lys Asn Ser Pro Ala Arg Val Phe Phe Pro Ser Gly Ala
            100                 105                 110

Ile Gly Gly Leu Asp Val Leu Ser Ser Ile Lys Asp Phe Val Lys Asn
        115                 120                 125

Val Arg Ile Glu Thr Ile Lys Pro Pro Lys Ser Leu Gly Leu Asp Leu
130                 135                 140

Lys Gly Lys Thr Val Val Phe Glu Gly Ser Val Glu Glu Ala Ser Lys
145                 150                 155                 160

Leu Phe Pro Arg Asn Ile Asn Val Ala Ser Thr Ile Gly Leu Ile Val
                165                 170                 175

Gly Phe Glu Lys Val Lys Val Thr Ile Val Ala Asp Pro Ala Met Asp
            180                 185                 190

His Asn Ile His Ile Val Arg Ile Ser Ser Ala Ile Gly Asn Tyr Glu
        195                 200                 205

Phe Lys Ile Glu Asn Ile Pro Ser Pro Glu Asn Pro Lys Thr Ser Met
    210                 215                 220

Leu Thr Val Tyr Ser Ile Leu Arg Thr Leu Arg Asn Leu Glu Ser Lys
225                 230                 235                 240

Ile Ile Phe Gly Ser Leu Gln Ile Leu Lys Asn Pro Val Asn Tyr Ile
                245                 250                 255

Ile Ile Ser Thr Ser Ala Phe Ala Asp Glu Val Phe Arg Glu Arg Phe
            260                 265                 270

Phe Ser Glu Leu Lys Asn Ser Pro Ala Arg Val Phe Phe Pro Ser Gly
        275                 280                 285

Ala Ile Gly Gly Leu Asp Val Leu Ser Ser Ile Lys Asp Phe Val Lys
    290                 295                 300

Asn Val Arg Ile Glu Thr Ile Lys Pro Pro Lys Ser Leu Gly Leu Asp
305                 310                 315                 320

Leu Lys Gly Lys Thr Val Val Phe Glu Gly Ser Val Glu Glu Ala Ser
```

```
                          325                 330                 335
Lys Leu Phe Pro Arg Asn Ile Asn Val Ala Ser Thr Ile Gly Leu Ile
                340                 345                 350

Val Gly Phe Glu Lys Val Lys Val Thr Ile Val Ala Asp Pro Ala Met
                355                 360                 365

Asp His Asn Ile His Ile Val Arg Ile Ser Ser Ala Ile Gly Asn Tyr
            370                 375                 380

Glu Phe Lys Ile Glu Asn Ile Pro Ser Pro Glu Asn Pro Lys Thr Ser
385                 390                 395                 400

Met Leu Thr Val Tyr Ser Ile Leu Arg Thr Leu Arg Asn Leu Glu Ser
                405                 410                 415

Lys Ile Ile Phe Gly
                420

<210> SEQ ID NO 19
<211> LENGTH: 804
<212> TYPE: DNA
<213> ORGANISM: Polaromonas
<220> FEATURE:
<221> NAME/KEY: CDS
<222> LOCATION: (1)..(804)

<400> SEQUENCE: 19 atg ctg aaa att gcc atg att ggt tgc ggc gcg att ggc gcc agc gtg     48
Met Leu Lys Ile Ala Met Ile Gly Cys Gly Ala Ile Gly Ala Ser Val
1               5                   10                  15 ctg gag ttg ctg cat ggc gac tcc gac gtg gtg gtg gac cgt gtg atc     96
Leu Glu Leu Leu His Gly Asp Ser Asp Val Val Val Asp Arg Val Ile
                20                  25                  30 acg gtg ccg gag gcg cgt gac cgc acg gag atc gca gtc gcc cgc tgg    144
Thr Val Pro Glu Ala Arg Asp Arg Thr Glu Ile Ala Val Ala Arg Trp
            35                  40                  45 gcc ccg cgt gcc cgt gtg ctg gag gtg ctg gcc gcc gat gac gcg cct    192
Ala Pro Arg Ala Arg Val Leu Glu Val Leu Ala Ala Asp Asp Ala Pro
        50                  55                  60 gac ctg gtg gtc gag tgt gcg ggc cac ggc gcg att gcc gcg cat gtg    240
Asp Leu Val Val Glu Cys Ala Gly His Gly Ala Ile Ala Ala His Val
65                  70                  75                  80 gtg ccg gcg ctg gag cgc ggc att ccg tgc gtg gtg acc tcg gtg ggc    288
Val Pro Ala Leu Glu Arg Gly Ile Pro Cys Val Val Thr Ser Val Gly
                85                  90                  95 gcc ctg agc gcg ccg ggc atg gcg cag ctg ctg gag cag gcc gcg cgt    336
Ala Leu Ser Ala Pro Gly Met Ala Gln Leu Leu Glu Gln Ala Ala Arg
                100                 105                 110 cgc ggc aag acc cag gtg cag ctg ctc tct ggc gcc atc ggc ggg att    384
Arg Gly Lys Thr Gln Val Gln Leu Leu Ser Gly Ala Ile Gly Gly Ile
            115                 120                 125 gac gcg ctg gcc gcc gcg cgt gtg ggc ggg ctc gat tcg gtg gtg tac    432
Asp Ala Leu Ala Ala Ala Arg Val Gly Gly Leu Asp Ser Val Val Tyr
        130                 135                 140 acc ggc cgc aag cca ccg atg gcc tgg aag ggc acg ccg gcc gaa gcc    480
Thr Gly Arg Lys Pro Pro Met Ala Trp Lys Gly Thr Pro Ala Glu Ala
145                 150                 155                 160 gtc tgc gac ctc gac agc ctc acc gtc gcg cac tgc atc ttt gac ggc    528
Val Cys Asp Leu Asp Ser Leu Thr Val Ala His Cys Ile Phe Asp Gly
                165                 170                 175 agt gcc gag cag gcc gca cag ctc tac ccg aag aac gcc aat gtg gcg    576
Ser Ala Glu Gln Ala Ala Gln Leu Tyr Pro Lys Asn Ala Asn Val Ala
                180                 185                 190
```

```
gcc acg ctg tcg ctc gcg ggc ttg ggc ctg aag cgc acg cag gtg cag     624
Ala Thr Leu Ser Leu Ala Gly Leu Gly Leu Lys Arg Thr Gln Val Gln
        195                 200                 205 ctg ttt gcc gat ccg ggc gtc agc gaa aac gtt cac cac gtg gcg gcg     672
Leu Phe Ala Asp Pro Gly Val Ser Glu Asn Val His His Val Ala Ala
210                 215                 220 cac gga gct ttc ggc agc ttc gag ctg acg atg cgt ggc cgt ccg ctg     720
His Gly Ala Phe Gly Ser Phe Glu Leu Thr Met Arg Gly Arg Pro Leu
225                 230                 235                 240 gcg gcc aat cca aaa aca tcc gcg ctc acc gtt tac agc gtg gtg cgc     768
Ala Ala Asn Pro Lys Thr Ser Ala Leu Thr Val Tyr Ser Val Val Arg
            245                 250                 255 gcg ctg ctc aac cgt ggc cgc gcg ctc gtc atc tga                     804
Ala Leu Leu Asn Arg Gly Arg Ala Leu Val Ile
        260                 265
```

<210> SEQ ID NO 20
<211> LENGTH: 267
<212> TYPE: PRT
<213> ORGANISM: Polaromonas

<400> SEQUENCE: 20

```
Met Leu Lys Ile Ala Met Ile Gly Cys Gly Ala Ile Gly Ala Ser Val
1               5                   10                  15

Leu Glu Leu Leu His Gly Asp Ser Asp Val Val Asp Arg Val Ile
            20                  25                  30

Thr Val Pro Glu Ala Arg Asp Arg Thr Glu Ile Ala Val Ala Arg Trp
        35                  40                  45

Ala Pro Arg Ala Arg Val Leu Glu Val Leu Ala Ala Asp Ala Pro
50                  55                  60

Asp Leu Val Val Glu Cys Ala Gly His Gly Ala Ile Ala Ala His Val
65                  70                  75                  80

Val Pro Ala Leu Glu Arg Gly Ile Pro Cys Val Val Thr Ser Val Gly
                85                  90                  95

Ala Leu Ser Ala Pro Gly Met Ala Gln Leu Leu Glu Gln Ala Ala Arg
            100                 105                 110

Arg Gly Lys Thr Gln Val Gln Leu Leu Ser Gly Ala Ile Gly Gly Ile
        115                 120                 125

Asp Ala Leu Ala Ala Ala Arg Val Gly Gly Leu Asp Ser Val Val Tyr
130                 135                 140

Thr Gly Arg Lys Pro Pro Met Ala Trp Lys Gly Thr Pro Ala Glu Ala
145                 150                 155                 160

Val Cys Asp Leu Asp Ser Leu Thr Val Ala His Cys Ile Phe Asp Gly
                165                 170                 175

Ser Ala Glu Gln Ala Ala Gln Leu Tyr Pro Lys Asn Ala Asn Val Ala
            180                 185                 190

Ala Thr Leu Ser Leu Ala Gly Leu Gly Leu Lys Arg Thr Gln Val Gln
        195                 200                 205

Leu Phe Ala Asp Pro Gly Val Ser Glu Asn Val His His Val Ala Ala
210                 215                 220

His Gly Ala Phe Gly Ser Phe Glu Leu Thr Met Arg Gly Arg Pro Leu
225                 230                 235                 240

Ala Ala Asn Pro Lys Thr Ser Ala Leu Thr Val Tyr Ser Val Val Arg
            245                 250                 255

Ala Leu Leu Asn Arg Gly Arg Ala Leu Val Ile
        260                 265
```

```
<210> SEQ ID NO 21
<211> LENGTH: 51
<212> TYPE: DNA
<213> ORGANISM: Artificial sequence
<220> FEATURE:
<223> OTHER INFORMATION: primer AspP5S-Xba

<400> SEQUENCE: 21
aaaatctaga ggagggatca tatgctgaaa attgccatga ttggttgcgg c          51

<210> SEQ ID NO 22
<211> LENGTH: 45
<212> TYPE: DNA
<213> ORGANISM: Artificial sequence
<220> FEATURE:
<223> OTHER INFORMATION: primer AspP3-BH

<400> SEQUENCE: 22
aaaaaggatc ctcatgacag atgtcctcag atgacgagcg cgcgg                 45

<210> SEQ ID NO 23
<211> LENGTH: 20
<212> TYPE: DNA
<213> ORGANISM: Artificial sequence
<220> FEATURE:
<223> OTHER INFORMATION: primer Seq-adh-P5

<400> SEQUENCE: 23
agcaaccgca cctgtggcgc                                             20

<210> SEQ ID NO 24
<211> LENGTH: 20
<212> TYPE: DNA
<213> ORGANISM: Artificial sequence
<220> FEATURE:
<223> OTHER INFORMATION: primer Seq-adh-P3

<400> SEQUENCE: 24
cagccggatc tcagtggtgg                                             20

<210> SEQ ID NO 25
<211> LENGTH: 20
<212> TYPE: DNA
<213> ORGANISM: Artificial sequence
<220> FEATURE:
<223> OTHER INFORMATION: primer Seq-adh-Pm

<400> SEQUENCE: 25
agctgcacct gggtcttgcc                                             20

<210> SEQ ID NO 26
<211> LENGTH: 20
<212> TYPE: DNA
<213> ORGANISM: Artificial sequence
<220> FEATURE:
<223> OTHER INFORMATION: primer pykF-test1

<400> SEQUENCE: 26
catccatcac aacttacaga                                             20

<210> SEQ ID NO 27
<211> LENGTH: 20
<212> TYPE: DNA
<213> ORGANISM: Artificial sequence
<220> FEATURE:
<223> OTHER INFORMATION: primer pykF-test2
```

```
<400> SEQUENCE: 27
ttcctgaatc tgtattatga                                          20

<210> SEQ ID NO 28
<211> LENGTH: 68
<212> TYPE: DNA
<213> ORGANISM: Artificial sequence
<220> FEATURE:
<223> OTHER INFORMATION: primer Dppc-3'

<400> SEQUENCE: 28
cttgagcacg tgaacggtga agcagttcag cctgcagtac tgaagcctgc ttttttatac   60
taagttgg                                                            68

<210> SEQ ID NO 29
<211> LENGTH: 45
<212> TYPE: DNA
<213> ORGANISM: Artificial sequence
<220> FEATURE:
<223> OTHER INFORMATION: primer attR3-XbaI-HindIII

<400> SEQUENCE: 29
accgttaagc tttctagacg ctcaagttag tataaaaaag ctgaa                   45

<210> SEQ ID NO 30
<211> LENGTH: 68
<212> TYPE: DNA
<213> ORGANISM: Artificial sequence
<220> FEATURE:
<223> OTHER INFORMATION: primer mash1

<400> SEQUENCE: 30
ctagaaagct taacacagaa aaagcccgc acctgacagt gcgggctttt tttttcgacc   60
actgcagg                                                            68

<210> SEQ ID NO 31
<211> LENGTH: 68
<212> TYPE: DNA
<213> ORGANISM: Artificial sequence
<220> FEATURE:
<223> OTHER INFORMATION: primer mash2

<400> SEQUENCE: 31
gatccctgca gtggtcgaaa aaaaagccc gcactgtcag gtgcgggctt ttttctgtgt   60
taagcttt                                                            68

<210> SEQ ID NO 32
<211> LENGTH: 62
<212> TYPE: DNA
<213> ORGANISM: Artificial sequence
<220> FEATURE:
<223> OTHER INFORMATION: primer Dppc-5'

<400> SEQUENCE: 32
ggatttgata taagaataa cttatcccgc ttctccccta ggatccctgc agtggtcgaa   60
aa                                                                  62

<210> SEQ ID NO 33
<211> LENGTH: 28
<212> TYPE: DNA
<213> ORGANISM: Artificial sequence
<220> FEATURE:
```

<223> OTHER INFORMATION: primer Tthr5'-XbaI

<400> SEQUENCE: 33
aatgcatcta gaaagcttaa cacagaaa     28

<210> SEQ ID NO 34
<211> LENGTH: 21
<212> TYPE: DNA
<213> ORGANISM: Artificial sequence
<220> FEATURE:
<223> OTHER INFORMATION: primer ppc-t1

<400> SEQUENCE: 34
ccaggttgtg cagcatttct g     21

<210> SEQ ID NO 35
<211> LENGTH: 20
<212> TYPE: DNA
<213> ORGANISM: Artificial sequence
<220> FEATURE:
<223> OTHER INFORMATION: primer ppc-t2

<400> SEQUENCE: 35
gtgttacgca tgccagcagc     20

<210> SEQ ID NO 36
<211> LENGTH: 33
<212> TYPE: DNA
<213> ORGANISM: Artificial sequence
<220> FEATURE:
<223> OTHER INFORMATION: primer cat5'BglII

<400> SEQUENCE: 36
tagcgagatc tctgatgtcc ggcggtgctt ttg     33

<210> SEQ ID NO 37
<211> LENGTH: 32
<212> TYPE: DNA
<213> ORGANISM: Artificial sequence
<220> FEATURE:
<223> OTHER INFORMATION: primer cat3'SacI

<400> SEQUENCE: 37
aaaaagagct cttacgcccc gccctgccac tc     32

<210> SEQ ID NO 38
<211> LENGTH: 24
<212> TYPE: DNA
<213> ORGANISM: Artificial sequence
<220> FEATURE:
<223> OTHER INFORMATION: primer MuC5

<400> SEQUENCE: 38
atcgaattca tggttgttat acgg     24

<210> SEQ ID NO 39
<211> LENGTH: 30
<212> TYPE: DNA
<213> ORGANISM: Artificial sequence
<220> FEATURE:
<223> OTHER INFORMATION: primer MuB3

<400> SEQUENCE: 39
ctaccatgga agcttaatta cgcagcagcg     30

```
<210> SEQ ID NO 40
<211> LENGTH: 59
<212> TYPE: DNA
<213> ORGANISM: Artificial sequence
<220> FEATURE:
<223> OTHER INFORMATION: primer ppc-attR

<400> SEQUENCE: 40
tatgaacgaa caatattccg cattgcgtag taatgcgctc aagttagtat aaaaaagct      59

<210> SEQ ID NO 41
<211> LENGTH: 60
<212> TYPE: DNA
<213> ORGANISM: Artificial sequence
<220> FEATURE:
<223> OTHER INFORMATION: primer ppc-attL

<400> SEQUENCE: 41
ttagccggta ttacgcatac ctgccgcaat cccggctgaa gcctgctttt ttatactaag     60

<210> SEQ ID NO 42
<211> LENGTH: 18
<212> TYPE: DNA
<213> ORGANISM: Artificial sequence
<220> FEATURE:
<223> OTHER INFORMATION: primer ppc-test1

<400> SEQUENCE: 42
cacgagggtt tgcagaag                                                   18

<210> SEQ ID NO 43
<211> LENGTH: 18
<212> TYPE: DNA
<213> ORGANISM: Artificial sequence
<220> FEATURE:
<223> OTHER INFORMATION: primer ppc-test2

<400> SEQUENCE: 43
gcagcatttg acgtcacc                                                   18

<210> SEQ ID NO 44
<211> LENGTH: 20
<212> TYPE: DNA
<213> ORGANISM: Artificial sequence
<220> FEATURE:
<223> OTHER INFORMATION: primer ppc-SphI

<400> SEQUENCE: 44
gtctcggcat gctggagatg                                                 20

<210> SEQ ID NO 45
<211> LENGTH: 32
<212> TYPE: DNA
<213> ORGANISM: Artificial sequence
<220> FEATURE:
<223> OTHER INFORMATION: primer ppc-HindIII

<400> SEQUENCE: 45
ggtttgaagc ttcagaagag gaagattagc cg                                   32

<210> SEQ ID NO 46
<211> LENGTH: 60
<212> TYPE: DNA
<213> ORGANISM: Artificial sequence
<220> FEATURE:
<223> OTHER INFORMATION: primer aspA-attR
```

-continued

<400> SEQUENCE: 46
taggatcgtg ctcacccgcc tgaatacgga taaaatagcg cgctcaagtt agtataaaaa          60

<210> SEQ ID NO 47
<211> LENGTH: 68
<212> TYPE: DNA
<213> ORGANISM: Artificial sequence
<220> FEATURE:
<223> OTHER INFORMATION: primer aspA-attL

<400> SEQUENCE: 47
gatacatcag gttttgcaca gagaaaatat cgtccagctc tgaagcctgc ttttttatac          60
taagttgg                                                                  68

<210> SEQ ID NO 48
<211> LENGTH: 22
<212> TYPE: DNA
<213> ORGANISM: Artificial sequence
<220> FEATURE:
<223> OTHER INFORMATION: primer aspA-test1

<400> SEQUENCE: 48
gtaaggtgat ctctgttcgc gc                                                  22

<210> SEQ ID NO 49
<211> LENGTH: 28
<212> TYPE: DNA
<213> ORGANISM: Artificial sequence
<220> FEATURE:
<223> OTHER INFORMATION: primer aspA-test2

<400> SEQUENCE: 49
catcagtaag tacaattaag ccttactg                                            28

<210> SEQ ID NO 50
<211> LENGTH: 68
<212> TYPE: DNA
<213> ORGANISM: Artificial sequence
<220> FEATURE:
<223> OTHER INFORMATION: primer sucA-attR

<400> SEQUENCE: 50
ctgaccgatc ctgactctgt ggatgcagtg tggcgctcga cgctcaagtt agtataaaaa          60
agctgaac                                                                  68

<210> SEQ ID NO 51
<211> LENGTH: 68
<212> TYPE: DNA
<213> ORGANISM: Artificial sequence
<220> FEATURE:
<223> OTHER INFORMATION: primer sucA-attL

<400> SEQUENCE: 51
ctacgctact cattatcttt cctttaatt aattgacgtt tgaagcctgc ttttttatac           60
taagttgg                                                                  68

<210> SEQ ID NO 52
<211> LENGTH: 18
<212> TYPE: DNA
<213> ORGANISM: Artificial sequence
<220> FEATURE:
<223> OTHER INFORMATION: primer sucA-test1

<400> SEQUENCE: 52

```
ataacattgc ttaaggga                                                    18
```

<210> SEQ ID NO 53
<211> LENGTH: 18
<212> TYPE: DNA
<213> ORGANISM: Artificial sequence
<220> FEATURE:
<223> OTHER INFORMATION: primer sucA-test2

<400> SEQUENCE: 53

```
atgccggcac ttccagca                                                    18
```

<210> SEQ ID NO 54
<211> LENGTH: 68
<212> TYPE: DNA
<213> ORGANISM: Artificial sequence
<220> FEATURE:
<223> OTHER INFORMATION: primer gltA-attR

<400> SEQUENCE: 54

```
gctaaccctc cccgacgaaa agcctattga actgaaagtg cgctcaagtt agtataaaaa     60
agctgaac                                                              68
```

<210> SEQ ID NO 55
<211> LENGTH: 68
<212> TYPE: DNA
<213> ORGANISM: Artificial sequence
<220> FEATURE:
<223> OTHER INFORMATION: primer gltA-attL

<400> SEQUENCE: 55

```
aacggtacgt gccatggcaa aaatcacggt aaacatggaa tgaagcctgc ttttttatac     60
taagttgg                                                              68
```

<210> SEQ ID NO 56
<211> LENGTH: 22
<212> TYPE: DNA
<213> ORGANISM: Artificial sequence
<220> FEATURE:
<223> OTHER INFORMATION: primer gltA-test1

<400> SEQUENCE: 56

```
cgtttcaggt gtcgaaagat cc                                              22
```

<210> SEQ ID NO 57
<211> LENGTH: 19
<212> TYPE: DNA
<213> ORGANISM: Artificial sequence
<220> FEATURE:
<223> OTHER INFORMATION: primer gltA-test2

<400> SEQUENCE: 57

```
gtcgcgctcg gtataaccg                                                  19
```

<210> SEQ ID NO 58
<211> LENGTH: 68
<212> TYPE: DNA
<213> ORGANISM: Artificial sequence
<220> FEATURE:
<223> OTHER INFORMATION: primer pykA-attR

<400> SEQUENCE: 58

```
ttccaatggt aatacaggtg atgggaaaaa ggcggaatta cgctcaagtt agtataaaaa     60
``` agctgaac 68

<210> SEQ ID NO 59
<211> LENGTH: 68
<212> TYPE: DNA
<213> ORGANISM: Artificial sequence
<220> FEATURE:
<223> OTHER INFORMATION: primer pykA-attL

<400> SEQUENCE: 59
ggaatcccta tgtctcgacg tttaagaaga accaaaatcg tgaagcctgc ttttttatac    60
taagttgg    68

<210> SEQ ID NO 60
<211> LENGTH: 20
<212> TYPE: DNA
<213> ORGANISM: Artificial sequence
<220> FEATURE:
<223> OTHER INFORMATION: primer pykA-test1

<400> SEQUENCE: 60
cagtatctga tgggctaaca    20

<210> SEQ ID NO 61
<211> LENGTH: 20
<212> TYPE: DNA
<213> ORGANISM: Artificial sequence
<220> FEATURE:
<223> OTHER INFORMATION: primer pykA-test2

<400> SEQUENCE: 61
catctggcct ccttgtggaa    20

<210> SEQ ID NO 62
<211> LENGTH: 68
<212> TYPE: DNA
<213> ORGANISM: Artificial sequence
<220> FEATURE:
<223> OTHER INFORMATION: primer pykF-attR

<400> SEQUENCE: 62
gaggcgttaa acgcgatatt acagaacgtg taccgatgcc cgctcaagtt agtataaaaa    60
agctgaac    68

<210> SEQ ID NO 63
<211> LENGTH: 68
<212> TYPE: DNA
<213> ORGANISM: Artificial sequence
<220> FEATURE:
<223> OTHER INFORMATION: primer pykF-attL

<400> SEQUENCE: 63
cgaatccgaa gagatgctga ctcagctgct tgaagcaggc tgaagcctgc ttttttatac    60
taagttgg    68

<210> SEQ ID NO 64
<211> LENGTH: 819
<212> TYPE: DNA
<213> ORGANISM: Rhodopseudomonas palustris

<400> SEQUENCE: 64
atgcgcagcg gccgggcccc gcagcgcgtc gccattgccg ggctcggcgc catcggcaag    60
gcgatcgcgc gtgaactcga tcgcgggctc gacgggctga cgctcggcgc cgtcgccagc    120

```
ggcgacccgg agaagcatcg cgccttcctc gacggcctgc ggacgacgcc gccggtggtc      180
ccgctggatc agttgcacgc ccacgcagac ctcgtgatcg aggcggcgcc gagcaggctg      240
ctgcgcgcga tcgtcgagcc gttcgtcagc cgcggcagga ccgcgatcgt gctcagcgcc      300
gcggcgctgc tgcagaacga ggacctgatc gatctggcca atctgaacgg cggccagatc      360
atcgtgccga ccggcgcgct gatcgggctc gacgccgtca ctgccgccgc cgtcggcacg      420
attcattcgg tgcggatgat cacccgcaag ccggtcgatg gcctgcgcgg cgcgccgttc      480
atcgtcgaca acggcatcga cctcgacgga ttgcgcgaac cgctgaaact gttcgaaggc      540
accgcgcgcg aagccggcaa gggctttccg gccaatctca acgtcgcggt ggcgctgtcg      600
ctggccggca tcgggccgga tcgcaccatg gtggagatct gggccgatcc gggcgtcacc      660
cgcaacaccc accgcatcga ggtcgatgcg gattcggcgc ggttcgcgat gacgatcgag      720
aacgtgccgt ccgacaatcc ccgcaccggc ctgatcacgc cgctgtcggt gatcgcgctg      780
ctgcgcaagc aatccgccgc gctgcgggtc gggacctga                            819

<210> SEQ ID NO 65
<211> LENGTH: 774
<212> TYPE: DNA
<213> ORGANISM: Rhodopseudomonas palustris

<400> SEQUENCE: 65
ttgaagatcg ccgtgatcgg ctacggagcc atcggaaggt tcttgatcga gcagctcgat      60
gccgttccgg atttcgagat cgcagcggtc tattccgtgc cggcgccacc cgatcgcgcc      120
gagcgcgtgg tcgacgatct cgacgcgctg cttgcgaccc ggcccgacct ggtggtcgaa      180
tgcgccggcc atcgcgccct gtcggaatgc ggcgaggccg ttcttcgcag cggcgtcgat      240
ctgttggtgg tctcggtcgg cgccctcgcc gatcccgcgc tcgagcagca attacggaca      300
gccgcccggc acggggggccg cctgctgatc gccgcgggcg ccttgagcgg cctcgacgca      360
ctcagcacgg cgcgcgaggc cggcctggat tcggtgtcct atgtcggcaa gaaggcgcca      420
gcggcttgga ccaacacgcc cgcggaagac atggtggacc tgacatcgat cacgtcggcc      480
gtgacattcc tcgaatgcga cgcgcgtaca gccgcgctcc gcttcccaca gaacgccaac      540
gtggtcgcgg ccatcgcact ggccgggctc ggcttcgagc gcacgcaggt gagcctcgtc      600
gtcgatccgc cgtcgaacgg caacaatcac tccttcgtag cccgcggcgc attcggcgag      660
atcgccatga cgacgcgctc ggccacccctg cctgccaatc caagacatc catgctggcg      720 ccctacagtc tcgtgcagac catcaagaag cacgccggtt tgatcatcgt ttga           774

<210> SEQ ID NO 66
<211> LENGTH: 801
<212> TYPE: DNA
<213> ORGANISM: Ralstonia eutropha

<400> SEQUENCE: 66
atgctgcatg tgtccatggt tggctgcggc gcgatcggcc gcggcgtgat ggaattgctc      60
aagagcgatc ccgaggtggt gttcgacgtg gtgatcgtgc ggagcacac gatggacgag      120 gcccgcgacg cggtcaccgc gctggcgccg ggcgcccgcg tggcgacgca cctggacgac      180
cagcgtcccg acctgctggt cgagtgcgcc ggccaccatg cgctggaaga gcacatcgtg      240
ccggcgctgg aacgcggcat cccgtgcatg gtggtgtcgg tgggcgcgct gtccgagccc      300
ggcatggccg agcggctgga agcggccgcg cgccgcggcg gcacccaggt gcagctgttg      360
```

| | |
|---|---|
| tcaggtgcga tcggcgcgat cgatgcgctg gccgcggcgc gtgtcggcgg gctggacgaa | 420 |
| gtcatctaca ccggccgcaa gccggctcgc gcctgggccg gcacgccggc cgagcagctc | 480 |
| ttcgacctgg atgcgctgac cgaggcgacc gtgatcttcg aaggcacggc ccgcgacgcg | 540 |
| gcgcgtctgt atcccaagaa cgccaacgtg gccgccacgg tgtcgctggc aggcttgggg | 600 |
| ctggaccgca cctcggtcaa gctgctggcc gacccgcatg cggtggagaa cgtgcaccac | 660 |
| gtggaagcgc gcggcgcctt cggcggcttc gagctgacga tgcgcggcaa gccgctggcg | 720 |
| gccaatccca agacttccgc gctgaccgtg ttcagcgtgg tgcgcgcact gggaaaccgg | 780 |
| gcgcacgcgg tatcgatcta g | 801 |

<210> SEQ ID NO 67
<211> LENGTH: 792
<212> TYPE: DNA
<213> ORGANISM: Azorhizobium caulinodans

<400> SEQUENCE: 67

| | |
|---|---|
| atgaagatcg gcatcgtggg tcatggcgcc atggcgggcg cgctccgcgg cgtgttggcg | 60 |
| caggaaggcg cggcgcttgg cgcggttctg gtccggcccg cggcgcagaa cgggtacgg | 120 |
| gcggctctgc cggccgatgt tgcggtggcc gagaccttgg gcgatttcct cgccagcggc | 180 |
| gtgaccgtgg tggcggaatg cgcggggcat ggggcgctcc aggcccatgg gcccggcatc | 240 |
| ctcgctgcgg gtcgggatct cgtggtcgcg gccgtgggcg cgctggccga tccggagctg | 300 |
| gagacccgcc tgcgcgcggc ctcggcttgc ggcgggcggc tagtgattcc agcgggcgcc | 360 |
| gtgggcggcc tcgatgcgct ggctgctgcc cggcgggccg gcctttcgtc ggtgcgctat | 420 |
| gtctcgcgca agcccccggc cgcgtggctc ggcacgcccg ccgagcgggt ggccgatctg | 480 |
| tcggcactca ccgcggccgc cgcggtcttc accggcaccg cacgggaggc ggccctcgcc | 540 |
| ttcccgcaga atgccaatgt ggtggcggcc attgcgctgg cggggctcgg ctttgacgag | 600 |
| acgcaggtga cgctcatggc cgatccggcg gtgacgggaa tcgccacac gatcgaggcg | 660 |
| gagggcgcct cgggcgcat gtcggtgacg atggaaggcc gccgctgcc ggacaatccg | 720 |
| aagacgtcga tgctggcgcc ctacagcctt gcccgtgcgg ttctgaatct ggacgcgcgg | 780 |
| gtcgtcgtct ga | 792 |

<210> SEQ ID NO 68
<211> LENGTH: 843
<212> TYPE: DNA
<213> ORGANISM: Bradyrhizobium japonicum

<400> SEQUENCE: 68

| | |
|---|---|
| gtggatagaa ggtggaaggt gatgaccgat cagacagctt cgagcgaatt gcgggtggcc | 60 |
| atcgcaggcc tgggctcgat cggcaccaag atcgcggccg cgctcgatca gggcgagggg | 120 |
| ctgacactgt ccgccgtcgc cgtgcgcgat cccgccaagc atcaggcatt tctcaacggc | 180 |
| ctgcgtcgcc cgccgcaggt tctgccgatc gaccagctcg gtgaagccgc cgacatcgtg | 240 |
| gtcgagtgcg caccgagcag ccagctgcgc gcgatcgtcg agcggcagt gaagcgcggc | 300 |
| aaggccgctg tcgtcgtcag cgtcggcggg ctgctcgaca atttcgatct cgtcgatctc | 360 |
| gcccgtgcca atggcggccg catcatcgtg ccgaccggcg cgctgatcgg gctcgatgcc | 420 |
| gtcaacgccg ctgtgatcgg caccattcat tcggtgaaga tggtgacgcg caagccgatc | 480 |
| gacgggctga gggtgcgcc cttcatcgtt cacaacaaca tcgacatcga cacgctgcgc | 540 |
| gagccgctaa agctgttcga gggcacggcg cgcgaggccg caaaaggctt cccggccaat | 600 |

```
ctcaacgtcg cagtcgcgct gtcgctcgcg ggtgtcgggc ctgatcgcac ctccgtgcag    660
atctgggccg atccgaccgt cacgcgcaat gttcaccgca tcgaggtcga ggcggattcg    720
gcgcgcttct cgatgtcgat cgagaacatc ccgtccgaaa atcccaagac cgggctgatc    780
acggcgctgt cggtgatcgc gctgctgcgc aagcagcgcg ccacgctctg tgtcgggacg    840
taa                                                                  843

<210> SEQ ID NO 69
<211> LENGTH: 813
<212> TYPE: DNA
<213> ORGANISM: Mesorhizobium sp

<400> SEQUENCE: 69
gtgcatctgg gactgatcgg ctacggcaat atcgctcgca cgctgatggg gatactatcg     60
cgcgaaagcg ttccgctctc gcaggtgacc gtcgtttgcc cacgcgggtt cgcggatgaa    120
agccgcgtgc ggctggccag cgacttcgca gggccgggga ccgtcgtctg cgagacccaa    180
gcgctggtcg aagccgcgcc tgacctggtt gtcgagtgtg ccggccatga aggtgtccgc    240
cagcacgcca cggccgtgct ccaggcagga attgaaacga ttatcgtttc catcggttcg    300
ctggccgacc ggagcctgca cgaggcggtg atccaggcgg cgcgcgccgg gtcctcccgc    360
ttcatcctgc ccgccggcgc catcggcggc atcgatattc tctcggccct taaagtgtcc    420
gggatcgagg ccgtcaccta tacaggccgc aagcctccgc acgcgtggaa ggacacgccg    480
gccgcggcac tttatgatct ggatacgctt gcaaccgaaa ccgtcttctt ttcaggcaat    540
gcgcgcgagg cggcaacgca ataccccaag aatgccaatg ttgcggcaac gctcgcgctg    600
gccggcctag ggttcgaaaa gaccgatgta aggctcatcg cagacccgc cgccaagggc     660 aatgtgcacg aatacagcgt gcgctcggcc gccgccgact tcacgatgaa gatcgagggc    720
aggccgtctc cggataatcc gaaaacctcg gtgaccaccg tttattcgat cgcgcgggaa    780
gtcttcaacc gatgccggga gcaggccata tga                                 813

<210> SEQ ID NO 70
<211> LENGTH: 684
<212> TYPE: DNA
<213> ORGANISM: Corynebacterium glutamicum

<400> SEQUENCE: 70
atggtgggag tatcacttta tgatgccaac cttgaagagc tcatcgagtc ccacgatatc     60
gtagttgaat gcgctggcgt ttcggctgtg aaagaacatg gaccggcagt aattgcgagc    120
gacaaagatc tgctgttgac gtcggtgggt gcgctggcgg accctgatgc gcgccgggca    180
ctgttagccg gtcctgggaa agggcatgtc acctccggtg ctatcggtgg tttcgatttg    240
tgggcagctc ttgcagagtc ggatgcggtg acacggtaa agattaggac taccaagaat    300
gccgaagccc tcattcaaga ctggatgaat ggcaatgagc gcgctgaatt ggaaaacgca    360
acggaacctt ttcttctctt cggtggacgg cctagtgatg caattgtaaa attcccgggc    420
aacgtcaatg cctccatcgc gctgcgtgg gccacccgag gtagaggtgc cagtgacgat    480
gagctgctta agcgatcgct tgagcgagta tcggtgaaac ttgttgcctc tccgaatctg    540
gccgatacgc gtcatgacat cgaggtatca ggctctgccg gtactttttc tttggttagc    600
gaatctggac caaatcccgt gaatcccaaa acctctgcga ttacggcact gtcagttgcg    660
cacactttaa ggcacacgat ttaa                                           684
```

<210> SEQ ID NO 71
<211> LENGTH: 819
<212> TYPE: DNA
<213> ORGANISM: Nitrosopumilus maritimus

<400> SEQUENCE: 71

```
ttgaaacgaa tagctcttct tggatgcggt tcaatgggaa ctcaaattgc tcttgcaatt      60
gattcagaaa atttccctgc tactcttacc catgtatatg atgaatcaaa agatgcatcc     120
ttctccctta ctcaaaaact aaaaaacaaa ccagaaatcg ttgaaaattc tcatctctta     180
tcttctcaac caatcgatat tgttgtagag gcggcatcac aaaatgcagt aaaagatgtt     240
gcactaagtg ttatacaaaa caaaaaagac ttgatgataa tgagtgttgg tgcgttactt     300
gatgaatcaa tttatgatat tttatctgat gcatgtaatg atttaaaaa aacaatctat      360
cttccttctg gtgcaattgc aggattggat ggattaaaat cagtcaaaga cgaacttgaa     420
tccatatcta tcacaacaac aaaacatcca cgttctctga aggtgcaaa attctttgag     480
acttctgaca ttaacttgga tgaaattact tcttcaactg tcgtgtataa aggaactgca     540
aaagaagctg ttacactatt tcctgcaaac atcaacgttg cagcactatt gtcactaact     600
ggaattggta gtgaaaaaac tagtgtaaca attgttgcag atccaaatac tgacaagaac     660
acacaccaca ttgaggcttc aggaaagttc ggaacgatga cctttacaat agaaaatgtt     720
cctgattcaa ataatccaaa acaagtagaa ttggcaatct tgtctgcaat tgaaactctg     780
aaaaaatact gttcagatga tattcaaatt ggcacataa                            819
```

<210> SEQ ID NO 72
<211> LENGTH: 843
<212> TYPE: DNA
<213> ORGANISM: Oceanicola granulosus

<400> SEQUENCE: 72

```
atggacagca gcgaggcgga gcggatgcgg ggcgagaggt tgagggtggc cgtcggggc       60
ttcggcgcga tcggcaagcc ggtggtgcgg gcgctgcacg agggcatcga cgggctcgag     120
ctgacggccg tttcagcgcg cgacaccggg cgggccgaga cgtggatgac gcgcgagctc     180
ggccgggcct acccggcgat gccgctcgcg cggctcggcg aggtggcgga cgtggtggtc     240
gagtgcgcgc cgccgcagct gctcggcgag ctggcgcggc cggtgctgga ggcgggcaag     300
gtcgtggtcg cgctgagcgt gggcgcgctc ctgagcaacc ccgacctcgt gccgctcgcc     360
gcgcggaccg gcgggcgcat cctcgtgccg tcgggcgcgc tgctcgggct cgacgcggtg     420
caggcggccg cgcagggcga gatcgagagc gtcaccatcg tcacccgcaa accgcccgaa     480
agcctgcgcg cgcacaccgg cgatcgaggcg atgggcctcg atctcgacac cctgcgcgag    540
ccggtgcgct gcttcgcggg gccggcgtcg gaggcgatct cgagctttcc cgccaacctc     600
aacgtcgccg tcgcgctcgg cctcgccggg ttcgggacgg agcggacgat gctcgaggtc     660
tgggccgacc cgggcgtcag ccgcaatacg caccggatca gcgtcacgtc cgacagctcg     720
aacttcacca tgcagatcga gggcatcccg atcgaggaaa accgcgcac cgggcggctg       780
acgccgctga gcgtgatctc gaccctcaag cggctcaccg ccccgctggt gatcggcgcc     840
tga                                                                   843
```

<210> SEQ ID NO 73
<211> LENGTH: 819
<212> TYPE: DNA
<213> ORGANISM: Rhodopseudomonas palustris

<400> SEQUENCE: 73

```
atgcgcagcg gccgtgcccc gcagcgcgtc gccattgccg ggctcggcgc catcggcaag      60
gcgatcgcgc gtgaactcga tcgcgggctc gacgggctga cgctcggcgc cgtcgccagc     120
ggcgacccgg agaagcatcg cgccttcctc gacggcctgc gtacgacgcc gccggtggtc     180
ccgctggatc agttgcacgc ccacgcagac ctcgtgatcg aggcggcgcc gagccgtctg     240
ctgcgcgcga tcgtcgagcc gttcgtcagc cgcggccgta ccgcgatcgt gctcagcgcc     300
gcggcgctgc tgcagaacga ggacctgatc gatctggcca atctgaacgg cggccagatc     360
atcgtgccga ccgcgcgcgct gatcgggctc gacgccgtca ctgccgccgc cgtcggcacg     420
attcattcgg tgcgtatgat cacccgcaag ccggtcgatg gcctgcgcgg cgcgccgttc     480
atcgtcgaca acggcatcga cctcgacgga ttgcgcgaac cgctgaaact gttcgaaggc     540
accgcgcgcg aagccggcaa gggctttccg gccaatctca acgtcgcggt ggcgctgtcg     600
ctggccggca cgggccgga tcgcaccatg gtggagatct gggccgatcc gggcgtcacc     660
cgcaacaccc accgcatcga ggtcgatgcg gattcggcgc gtttcgcgat gacgatcgag     720
aacgtgccgt ccgacaatcc gcgcaccggc ctgatcacgc cgctgtcggt gatcgcgctg     780
ctgcgcaagc aatccgccgc gctgcgtgtc gggacctga                            819
```

<210> SEQ ID NO 74
<211> LENGTH: 804
<212> TYPE: DNA
<213> ORGANISM: Rhodopseudomonas palustris

<400> SEQUENCE: 74

```
atggtgcatt taccgggatc gcgttcgcca ttgaagatcg ccgtgatcgg ctacggagcc      60
atcggaaggt tcttgatcga gcagctcgat gccgttccgg atttcgagat cgcagcggtc     120
tattccgtgc cggcgccacc ggatcgcgcc gagcgcgtgg tcgacgatct cgacgcgctg     180
cttgcgaccc gtccggacct ggtggtcgaa tgcgccggcc atcgcgccct gtcggaatgc     240
ggcgaggccg ttcttcgcag cggcgtcgat ctgttggtgg tctcggtcgg cgccctcgcc     300
gatccggcgc tcgagcagca attacgtaca gccgcccgtc acgggggccg cctgctgatc     360
gccgcgggcg ccttgagcgg cctcgacgca ctcagcacgg cgcgcgaggc cggcctggat     420
tcggtgtcct atgtcggcaa gaaggcgcca gcggcttgga ccaacacgcc ggcggaagac     480
atggtggacc tgacatcgat cacgtcggcc gtgacattcc tcgaatgcga cgcgcgtaca     540
gccgcgctcc gcttcccaca gaacgccaac gtggtcgcgg ccatcgcact ggccgggctc     600
ggcttcgagc gcacgcaggt gagcctcgtc gtcgatccgg cgtcgaacgg caacaatcac     660
tccttcgtag cccgcggcgc attcggcgag atcgccatga cgacgcgctc ggccaccctg     720
cctgccaatc cgaagacatc catgctggcg ccgtacagtc tcgtgcagac catcaagaag     780
cacgccggtt tgatcatcgt ttga                                            804
```

<210> SEQ ID NO 75
<211> LENGTH: 861
<212> TYPE: DNA
<213> ORGANISM: Ralstonia eutropha

<400> SEQUENCE: 75

```
atgggcagca gccatcatca tcatcatcac agcagcggcc tggtgccgcg cggcagccat      60
atgctgcatg tgtccatggt tggctgcggc gcgatcggcc gcggcgtgat ggaattgctc     120
```

| | |
|---|---|
| aagagcgatc cggaggtggt gttcgacgtg gtgatcgtgc cggagcacac gatggacgag | 180 |
| gcccgcgacg cggtcaccgc gctggcgccg ggcgcccgcg tggcgacgca cctgacgac | 240 |
| cagcgtccgg acctgctggt cgagtgcgcc ggccaccatg cgctggaaga gcacatcgtg | 300 |
| ccggcgctgg aacgcggcat cccgtgcatg gtggtgtcgg tgggcgcgct gtccgagccg | 360 |
| ggcatggccg agcggctgga agcggccgcg cgccgcggcg gcacccaggt gcagctgttg | 420 |
| tcaggtgcga tcggcgcgat cgatgcgctg gccgcggcgc gtgtcggcgg gctggacgaa | 480 |
| gtcatctaca ccggccgcaa gccggctcgc gcctgggccg gcacgccggc cgagcagctc | 540 |
| ttcgacctgg atgcgctgac cgaggcgacc gtgatcttcg aaggcacggc ccgcgacgcg | 600 |
| gcgcgtctgt atccgaagaa cgccaacgtg gccgccacgg tgtcgctggc aggcttgggg | 660 |
| ctggaccgca cctcggtcaa gctgctggcc gacccgcatg cggtggagaa cgtgcaccac | 720 |
| gtggaagcgc gcggcgcctt cggcggcttc gagctgacga tgcgcggcaa gccgctggcg | 780 |
| gccaatccga agacttccgc gctgaccgtg ttcagcgtgg tgcgcgcact gggaaaccgg | 840 |
| gcgcacgcgg tatcgatcta g | 861 |

<210> SEQ ID NO 76
<211> LENGTH: 828
<212> TYPE: DNA
<213> ORGANISM: Azorhizobium caulinodans

<400> SEQUENCE: 76

| | |
|---|---|
| atgggcagca gccatcatca tcatcatcac agcagcggca agatcggcat cgtgggtcat | 60 |
| ggcgccatgg cgggcgcgct ccgcggcgtg ttggcgcagg aaggcgcggc gcttggcgcg | 120 |
| gttctggtcc ggccgggcgg cgcagaacgg gtacgggcgg ctctgccggc cgatgttgcg | 180 |
| gtggccgaga ccttgggcga tttcctcgcc agcggcgtga ccgtggtggc ggaatgcgcg | 240 |
| gggcatgggg cgctccaggc ccatgggccg ggcatcctcg ctgcgggtcg ggatctcgtg | 300 |
| gtcgcggccg tggcgcgct ggccgatccg gagctggaga cccgcctgcg cgcggcctcg | 360 |
| gcttgcggcg ggcggctagt gattccagcg ggcgccgtgg gcggcctcga tgcgctggct | 420 |
| gctgcccggc gggccggcct ttcgtcggtg cgctatgtct cgcgcaagcc gccggccgcg | 480 |
| tggctcggca cgccggccga gcgggtggcc gatctgtcgg cactcaccgc ggccgccgcg | 540 |
| gtcttcaccg gcaccgcacg ggaggcggcc ctcgccttcc cgcagaatgc caatgtggtg | 600 |
| gcggccattg cgctggcggg gctcggcttt gacgagacgc aggtgacgct catggccgat | 660 |
| ccggcggtga cgggaaatcg ccacacgatc gaggcggagg gcgccttcgg gcgcatgtcg | 720 |
| gtgacgatgg aaggccgccc gctgccggac aatccgaaga cgtcgatgct ggcgccgtac | 780 |
| agccttgccc gtgcggttct gaatctggac gcgcgggtcg tcgtctaa | 828 |

<210> SEQ ID NO 77
<211> LENGTH: 879
<212> TYPE: DNA
<213> ORGANISM: Bradyrhizobium japonicum

<400> SEQUENCE: 77

| | |
|---|---|
| atgggcagca gccatcatca tcatcatcac agcagcggcg atcgtcgttg gaaggtgatg | 60 |
| accgatcaga cagcttcgag cgaattgcgg gtggccatcg caggcctggg ctcgatcggc | 120 |
| accaagatcg cggccgcgct cgatcagggc gaggggctga cactgtccgc cgtcgccgtg | 180 |
| cgcgatccgc ccaagcatca ggcatttctc aacggcctgc gtcgcccgcc gcaggttctg | 240 |
| ccgatcgacc agctcggtga agccgccgac atcgtggtcg agtgcgcacc gagcagccag | 300 |

```
ctgcgcgcga tcgtcgagcc ggcagtgaag cgcggcaagg ccgctgtcgt cgtcagcgtc    360
ggcgggctgc tcgacaattt cgatctcgtc gatctcgccc gtgccaatgg cggccgcatc    420
atcgtgccga ccggcgcgct gatcgggctc gatgccgtca acgccgctgt gatcggcacc    480
attcattcgg tgaagatggt gacgcgcaag ccgatcgacg ggctgaaggg tgcgccgttc    540
atcgttcaca acaacatcga catcgacacg ctgcgcgagc cgctaaagct gttcgagggc    600
acggcgcgcg aggccgcaaa aggcttcccg gccaatctca acgtcgcagt cgcgctgtcg    660
ctcgcgggtg tcgggcctga tcgcacctcc gtgcagatct gggccgatcc gaccgtcacg    720
cgcaatgttc accgcatcga ggtcgaggcg gattcggcgc gcttctcgat gtcgatcgag    780
aacatcccgt ccgaaaatcc gaagaccggg ctgatcacgg cgctgtcggt gatcgcgctg    840
ctgcgcaagc agcgcgccac gctctgtgtc gggacgtaa                          879

<210> SEQ ID NO 78
<211> LENGTH: 849
<212> TYPE: DNA
<213> ORGANISM: Mesorhizobium sp.

<400> SEQUENCE: 78
atgggcagca gccatcatca tcatcatcac agcagcggcc atctgggact gatcggctac    60
ggcaatatcg ctcgcacgct gatgggggatt ctatcgcgcg aaagcgttcc gctctcgcag   120
gtgaccgtcg tttgcccacg cggggttcgcg gatgaaagcc gcgtgcggct ggccagcgac   180
ttcgcagggc cggggaccgt cgtctgcgag acccaagcgc tggtcgaagc cgcgcctgac   240
ctggttgtcg agtgtgccgg ccatgaaggt gtccgccagc acgccacggc cgtgctccag   300
gcaggaattg aaacgattat cgtttccatc ggttcgctgg ccgaccggag cctgcacgag   360
gcggtgatcc aggcggcgcg cgccgggtcc tcccgcttca tcctgccggc cggcgccatc   420
ggcggcatcg atattctctc ggcccttaaa gtgtccggga tcgaggccgt cacctataca   480
ggccgcaagc ctccgcacgc gtggaaggac acgccggccg cggcacttta tgatctggat   540
acgcttgcaa ccgaaaccgt cttctttcca ggcaatgcgc gcgaggcggc aacgcaatac   600
ccgaagaatg ccaatgttgc ggcaacgctc gcgctggccg gctagggtt cgaaaagacc    660 gatgtacgtc tcatcgcaga cccggccgcc aagggcaatg tgcacgaata cagcgtgcgc   720
tcggccgccg ccgacttcac gatgaagatc gagggccgtc cgtctccgga taatccgaaa   780
acctcggtga ccaccgtttta ttcgatcgcg cgggaagtct tcaaccgatg ccgggagcag   840
gccatataa                                                           849

<210> SEQ ID NO 79
<211> LENGTH: 720
<212> TYPE: DNA
<213> ORGANISM: Corynebacterium glutamicum

<400> SEQUENCE: 79
atgggcagca gccatcatca tcatcatcac agcagcggcg tgggagtatc actttatgat    60
gccaaccttg aagagctcat cgagtcccac gatatcgtag ttgaatgcgc tggcgtttcg   120
gctgtgaaag aacatggacc ggcagtaatt gcgagcgaca agatctgct gttgacgtcg   180 gtgggtgcgc tggcggaccc tgatgcgcgc cgggcactgt tagccggtcc tgggaaggg    240 catgtcacct ccggtgctat cggtggtttc gatttgtggg cagctcttgc agagtcggat   300
gcggtggaca cggtaaagat tcgtactacc aagaatgccg aagccctcat tcaagactgg   360
```

```
atgaatggca atgagcgcgc tgaattggaa aacgcaacgg aacctttct tctcttcggt      420 ggacggccta gtgatgcaat tgtaaaattc ccgggcaacg tcaatgcctc catcgcgctg      480
gcgtgggcca cccgaggtcg tggtgccagt gacgatgagc tgcttaagcg atcgcttgag      540
cgagtatcgg tggaacttgt tgcctctccg aatctggccg atacgcgtca tgacatcgag      600
gtatcaggct ctgccggtac ttttctttg gttagcgaat ctggaccaaa tccggtgaat      660
ccgaaaacct ctgcgattac ggcactgtca gttgcgcaca ctttacgtca cacgatttaa      720
```

<210> SEQ ID NO 80
<211> LENGTH: 855
<212> TYPE: DNA
<213> ORGANISM: Nitrosopumilus maritimus

<400> SEQUENCE: 80

```
atgggcagca gccatcatca tcatcatcac agcagcggca acgaatcgc tcttcttgga       60 tgcggttcaa tgggaactca aattgctctt gcaattgatt cagaaaattt ccctgctact      120
cttacccatg tatatgatga atcaaaagat gcatccttct cccttactca aaaactaaaa      180
aacaaaccag aaatcgttga aaattctcat ctcttatctt ctcaaccaat cgatattgtt      240
gtagaggcgg catcacaaaa tgcagtaaaa gatgttgcac taagtgttat ccaaaacaaa      300
aaagacttga tgatcatgag tgttggtgcg ttacttgatg aatcaattta tgatatttta      360
tctgatgcat gtaatgattt taaaaaaaca atctatcttc cttctggtgc aattgcagga      420
ttggatggat taaaatcagt caaagacgaa cttgaatcca tctctatcac aacaacaaaa      480
catccacgtt ctctgaaagg tgcaaaattc tttgagactt ctgacattaa cttggatgaa      540
attacttctt caactgtcgt gtataaagga actgcaaaag aagctgttac actatttcct      600
gcaaacatca acgttgcagc actattgtca ctaactggaa ttggtagtga aaaaactagt      660
gtaacaattg ttgcagatcc aaatactgac aagaacacac accacattga ggcttcagga      720
aagttcggaa cgatgacctt tacaatcgaa atgttcctg attcaaataa tccaaagaca      780 agtcgttgg caatcttgtc tgcaattgaa actctgaaaa aatactgttc agatgatatt      840
caaattggca cataa                                                       855
```

<210> SEQ ID NO 81
<211> LENGTH: 879
<212> TYPE: DNA
<213> ORGANISM: Oceanicola granulosus

<400> SEQUENCE: 81

```
atgggcagca gccatcatca tcatcatcac agcagcggcg acagcagcga ggcggagcgg       60
atgcggggcg agcgtttgcg tgtggccgtc ggggcttcg gcgcgatcgg caagccggtg      120
gtgcgggcgc tgcacgaggg catcgacggg ctcgagctga cggccgtttc agcgcgcgac      180
accgggcggg ccgagacgtg gatgacgcgc gagctcggcc gggcctaccc ggcgatgccg      240
ctcgcgcggc tcggcgaggt ggcggacgtg gtggtcgagt gcgcgccgcc gcagctgctc      300
ggcgagctgg cgcggccggt gctggaggcg ggcaaggtcg tggtcgcgct gagcgtgggc      360
gcgctcctga gcaacccgga cctcgtgccg ctcgccgcgc ggaccggcgg gcgcatcctc      420
gtgccgtcgg gcgcgctgct cgggctcgac gcggtgcagg cggccgcgca gggcgagatc      480
gagagcgtca ccatcgtcac cgcaaaccg ccggaaagcc tgcgcggcgc accggcgatc      540
gaggcgatgg gcctcgatct cgacaccctg cgcgagccgg tgcgctgctt cgcggggccg      600
gcgtcggagg cgatctcgag cttctccggcc aacctcaacg tcgccgtcgc gctcggcctc      660
```

```
gccgggttcg ggacggagcg gacgatgctc gaggtctggg ccgacccggg cgtcagccgc    720
aatacgcacc ggatcagcgt cacgtccgac agctcgaact tcaccatgca gatcgagggc    780
atcccgatcg aggaaaaccc gcgcaccggg cggctgacgc cgctgagcgt gatctcgacc    840
ctcaagcggc tcaccgcccc gctggtgatc ggcgcctaa                          879
```

```
<210> SEQ ID NO 82
<211> LENGTH: 36
<212> TYPE: DNA
<213> ORGANISM: Artificial sequence
<220> FEATURE:
<223> OTHER INFORMATION: primer P1

<400> SEQUENCE: 82
agctgagtcg acccccagga aaaattggtt aataac                              36

<210> SEQ ID NO 83
<211> LENGTH: 33
<212> TYPE: DNA
<213> ORGANISM: Artificial sequence
<220> FEATURE:
<223> OTHER INFORMATION: primer P2

<400> SEQUENCE: 83
agctgagcat gcttccaact gcgctaatga cgc                                 33

<210> SEQ ID NO 84
<211> LENGTH: 45
<212> TYPE: DNA
<213> ORGANISM: Artificial sequence
<220> FEATURE:
<223> OTHER INFORMATION: primer P3

<400> SEQUENCE: 84
taactttaag aaggagatat aatgggcagc agccatcatc atcat                    45

<210> SEQ ID NO 85
<211> LENGTH: 56
<212> TYPE: DNA
<213> ORGANISM: Artificial sequence
<220> FEATURE:
<223> OTHER INFORMATION: primer P4

<400> SEQUENCE: 85
ccgttaaacc cagcgcggtt taacaggaac tgtgccgcgg gatatccgga tatagt        56

<210> SEQ ID NO 86
<211> LENGTH: 64
<212> TYPE: DNA
<213> ORGANISM: Artificial sequence
<220> FEATURE:
<223> OTHER INFORMATION: primer P5

<400> SEQUENCE: 86
caccgccgtt gtctttaaga ttcaggagcg tagtgctgaa gcctgctttt ttatactaag    60
ttgg                                                                 64

<210> SEQ ID NO 87
<211> LENGTH: 61
<212> TYPE: DNA
<213> ORGANISM: Artificial sequence
<220> FEATURE:
<223> OTHER INFORMATION: primer P6
```

```
<400> SEQUENCE: 87
ttatatctcc ttcttaaagt taaacaaaat tattaggaaa aattggttat taaccagtga    60
c                                                                    61

<210> SEQ ID NO 88
<211> LENGTH: 59
<212> TYPE: DNA
<213> ORGANISM: Artificial sequence
<220> FEATURE:
<223> OTHER INFORMATION: primer P7
<220> FEATURE:
<221> NAME/KEY: misc_feature
<222> LOCATION: (25,27,28,46,49,51)
<223> OTHER INFORMATION: n = a, c, t or g

<400> SEQUENCE: 88
atcgtgaaga tcttttccag tgttnannag ggtgccttgc acggtnatna ngtcactgg     59

<210> SEQ ID NO 89
<211> LENGTH: 32
<212> TYPE: DNA
<213> ORGANISM: Artificial sequence
<220> FEATURE:
<223> OTHER INFORMATION: primer P8
<220> FEATURE:
<221> NAME/KEY: misc_feature
<222> LOCATION: (16)..(20)
<223> OTHER INFORMATION: n = a, c, t or g

<400> SEQUENCE: 89
tggaaaagat cttctnnnnn cgctgacctg cg                                  32

<210> SEQ ID NO 90
<211> LENGTH: 60
<212> TYPE: DNA
<213> ORGANISM: Artificial sequence
<220> FEATURE:
<223> OTHER INFORMATION: primer P9

<400> SEQUENCE: 90
caccgccgtt gtctttaaga ttcaggagcg tagtgccgct caagttagta taaaaaagct    60

<210> SEQ ID NO 91
<211> LENGTH: 60
<212> TYPE: DNA
<213> ORGANISM: Artificial sequence
<220> FEATURE:
<223> OTHER INFORMATION: primer P10

<400> SEQUENCE: 91
cgccgcatcc ggcaataaca gccttgcctg acgcaatgaa gcctgccttt ttatactaag    60

<210> SEQ ID NO 92
<211> LENGTH: 20
<212> TYPE: DNA
<213> ORGANISM: Artificial sequence
<220> FEATURE:
<223> OTHER INFORMATION: primer P11

<400> SEQUENCE: 92
agttcagtgc tgtgtaggtc                                                20

<210> SEQ ID NO 93
<211> LENGTH: 20
<212> TYPE: DNA
<213> ORGANISM: Artificial sequence
```

<220> FEATURE:
<223> OTHER INFORMATION: primer P12

<400> SEQUENCE: 93
atcgcaacag cggacatgag                                               20

<210> SEQ ID NO 94
<211> LENGTH: 19
<212> TYPE: DNA
<213> ORGANISM: Artificial sequence
<220> FEATURE:
<223> OTHER INFORMATION: primer svs-3

<400> SEQUENCE: 94
gctagttatt gctcagcgg                                                19

<210> SEQ ID NO 95
<211> LENGTH: 68
<212> TYPE: DNA
<213> ORGANISM: Artificial sequence
<220> FEATURE:
<223> OTHER INFORMATION: primer gcd-attR

<400> SEQUENCE: 95
ttacttctgg tcgggcagcg cataggcaat cacgtaatcg cgctcaagtt agtataaaaa   60
agctgaac                                                            68

<210> SEQ ID NO 96
<211> LENGTH: 68
<212> TYPE: DNA
<213> ORGANISM: Artificial sequence
<220> FEATURE:
<223> OTHER INFORMATION: primer gcd-attL

<400> SEQUENCE: 96
ggtcaacatt atggggaaaa actcctcatc ctttagcgtg tgaagcctgc ttttttatac   60
taagttgg                                                            68

<210> SEQ ID NO 97
<211> LENGTH: 20
<212> TYPE: DNA
<213> ORGANISM: Artificial sequence
<220> FEATURE:
<223> OTHER INFORMATION: primer gcd-test1

<400> SEQUENCE: 97
tgacaacaat ctatctgatt                                               20

<210> SEQ ID NO 98
<211> LENGTH: 20
<212> TYPE: DNA
<213> ORGANISM: Artificial sequence
<220> FEATURE:
<223> OTHER INFORMATION: primer gcd-test2

<400> SEQUENCE: 98
tgcgcctggt taagctggcg                                               20

<210> SEQ ID NO 99
<211> LENGTH: 804
<212> TYPE: DNA
<213> ORGANISM: Delftia acidovorans
<220> FEATURE:
<221> NAME/KEY: CDS
<222> LOCATION: (1)..(804)

<400> SEQUENCE: 99

```
atg acg atg aat att gct gtg att ggc tgc ggt gcg att ggc gcc agc        48
Met Thr Met Asn Ile Ala Val Ile Gly Cys Gly Ala Ile Gly Ala Ser
1               5                   10                  15 gtg ctc gaa ctg ctc aag ggc cat gcc gcg gtg cag gtg ggc tgg gtg        96
Val Leu Glu Leu Leu Lys Gly His Ala Ala Val Gln Val Gly Trp Val
                20                  25                  30 ctt gtg ccc gaa gtg acg gac gcc gtg cgc gcc acc ctg gcc cgg cat       144
Leu Val Pro Glu Val Thr Asp Ala Val Arg Ala Thr Leu Ala Arg His
            35                  40                  45 gcg ccc cag gcg cgc gca ctg cct gcg ctg acg att gaa gac cgg ccc       192
Ala Pro Gln Ala Arg Ala Leu Pro Ala Leu Thr Ile Glu Asp Arg Pro
        50                  55                  60 gac ctc att gtc gaa tgc gca ggc cat acc gcc atc gaa gag cat gtg       240
Asp Leu Ile Val Glu Cys Ala Gly His Thr Ala Ile Glu Glu His Val
65                  70                  75                  80 ctg ccc gcc ctg cgg cgc ggc att cct gcc gtc gtg gcc tcc atc ggc       288
Leu Pro Ala Leu Arg Arg Gly Ile Pro Ala Val Val Ala Ser Ile Gly
                85                  90                  95 gca ctc agc gcc ccc ggc atg gcc gag gcc gtg cag gcc gcg gcc gag       336
Ala Leu Ser Ala Pro Gly Met Ala Glu Ala Val Gln Ala Ala Ala Glu
            100                 105                 110 gcc gga ggc acc cag gtg caa ttg ctg tcg ggc gcc atc ggc ggc gtg       384
Ala Gly Gly Thr Gln Val Gln Leu Leu Ser Gly Ala Ile Gly Gly Val
        115                 120                 125 gat gcg ctg gcc gcc gcg cgc atc ggc ggc ctg gac gaa gtg gtc tac       432
Asp Ala Leu Ala Ala Ala Arg Ile Gly Gly Leu Asp Glu Val Val Tyr
130                 135                 140 acc ggc cgc aag ccg ccc ctg gcc tgg acc ggc acg ccc gca gaa cag       480
Thr Gly Arg Lys Pro Pro Leu Ala Trp Thr Gly Thr Pro Ala Glu Gln
145                 150                 155                 160 cgc tgc gac ctc gcc agc ctc aag gaa gcc ttc tgc atc ttc gaa ggc       528
Arg Cys Asp Leu Ala Ser Leu Lys Glu Ala Phe Cys Ile Phe Glu Gly
                165                 170                 175 agc gca cgc gag gcc gcc cag ctc tac ccc aag aac gcc aac gtg gcc       576
Ser Ala Arg Glu Ala Ala Gln Leu Tyr Pro Lys Asn Ala Asn Val Ala
            180                 185                 190 gcc acc ctg tcg ctg gcc ggc atg ggc ctg gac cgc acc acg gtg cgc       624
Ala Thr Leu Ser Leu Ala Gly Met Gly Leu Asp Arg Thr Thr Val Arg
        195                 200                 205 ctg tac gcc gac ccg gcc gtg gac gaa aac gtg cac cat gtg gcc gcg       672
Leu Tyr Ala Asp Pro Ala Val Asp Glu Asn Val His His Val Ala Ala
    210                 215                 220 cgc ggc gcc ttc ggg tcc atg gaa ttg acc atg cgc ggc aag ccg ctg       720
Arg Gly Ala Phe Gly Ser Met Glu Leu Thr Met Arg Gly Lys Pro Leu
225                 230                 235                 240 gag gcc aat ccc aag acc tcg gcc ctc acc gtc tac agc gtg gtg cgc       768
Glu Ala Asn Pro Lys Thr Ser Ala Leu Thr Val Tyr Ser Val Val Arg
                245                 250                 255 gcc gtg ctc aac cag gcc acg gcc atc gcc atc tga                       804
Ala Val Leu Asn Gln Ala Thr Ala Ile Ala Ile
            260                 265
```

<210> SEQ ID NO 100
<211> LENGTH: 267
<212> TYPE: PRT
<213> ORGANISM: Delftia acidovorans

<400> SEQUENCE: 100

```
Met Thr Met Asn Ile Ala Val Ile Gly Cys Gly Ala Ile Gly Ala Ser
1               5                   10                  15

Val Leu Glu Leu Leu Lys Gly His Ala Ala Val Gln Val Gly Trp Val
            20                  25                  30

Leu Val Pro Glu Val Thr Asp Ala Val Arg Ala Thr Leu Ala Arg His
        35                  40                  45

Ala Pro Gln Ala Arg Ala Leu Pro Ala Leu Thr Ile Glu Asp Arg Pro
    50                  55                  60

Asp Leu Ile Val Glu Cys Ala Gly His Thr Ala Ile Glu Glu His Val
65                  70                  75                  80

Leu Pro Ala Leu Arg Arg Gly Ile Pro Ala Val Val Ala Ser Ile Gly
                85                  90                  95

Ala Leu Ser Ala Pro Gly Met Ala Glu Ala Val Gln Ala Ala Ala Glu
            100                 105                 110

Ala Gly Gly Thr Gln Val Gln Leu Leu Ser Gly Ala Ile Gly Gly Val
        115                 120                 125

Asp Ala Leu Ala Ala Ala Arg Ile Gly Gly Leu Asp Glu Val Val Tyr
    130                 135                 140

Thr Gly Arg Lys Pro Pro Leu Ala Trp Thr Gly Thr Pro Ala Glu Gln
145                 150                 155                 160

Arg Cys Asp Leu Ala Ser Leu Lys Glu Ala Phe Cys Ile Phe Glu Gly
                165                 170                 175

Ser Ala Arg Glu Ala Ala Gln Leu Tyr Pro Lys Asn Ala Asn Val Ala
            180                 185                 190

Ala Thr Leu Ser Leu Ala Gly Met Gly Leu Asp Arg Thr Thr Val Arg
        195                 200                 205

Leu Tyr Ala Asp Pro Ala Val Asp Glu Asn Val His His Val Ala Ala
    210                 215                 220

Arg Gly Ala Phe Gly Ser Met Glu Leu Thr Met Arg Gly Lys Pro Leu
225                 230                 235                 240

Glu Ala Asn Pro Lys Thr Ser Ala Leu Thr Val Tyr Ser Val Val Arg
                245                 250                 255

Ala Val Leu Asn Gln Ala Thr Ala Ile Ala Ile
            260                 265

<210> SEQ ID NO 101
<211> LENGTH: 801
<212> TYPE: DNA
<213> ORGANISM: Comamonas testosteroni
<220> FEATURE:
<221> NAME/KEY: CDS
<222> LOCATION: (1)..(801)

<400> SEQUENCE: 101 atg aaa aat att gct ttg att ggc tgc ggc gcg att ggc tcc agt gtg    48
Met Lys Asn Ile Ala Leu Ile Gly Cys Gly Ala Ile Gly Ser Ser Val
1               5                   10                  15 ctg gag ctt ttg agc gga gat acc cag ttg cag gtg ggc tgg gta ctg    96
Leu Glu Leu Leu Ser Gly Asp Thr Gln Leu Gln Val Gly Trp Val Leu
            20                  25                  30 gtt ccc gag atc acg cca gcc gtg cgc gag acg gct gcc cgc ctg gcg   144
Val Pro Glu Ile Thr Pro Ala Val Arg Glu Thr Ala Ala Arg Leu Ala
        35                  40                  45 cca cag gca cag ctg ctg cag gcc ctg ccc ggc gat gcg gtg ccg gat   192
Pro Gln Ala Gln Leu Leu Gln Ala Leu Pro Gly Asp Ala Val Pro Asp
    50                  55                  60 ctt ctc gtg gaa tgc gca ggt cat gca gcc ata gag gaa cat gtg ttg   240
```

```
Leu Leu Val Glu Cys Ala Gly His Ala Ala Ile Glu Glu His Val Leu
 65                  70                  75                  80 ccg gcg ctg gcg cgc ggc att cct gcg gtc atc gca tcc ata ggc gcc      288
Pro Ala Leu Ala Arg Gly Ile Pro Ala Val Ile Ala Ser Ile Gly Ala
                 85                  90                  95 ttg agc gca ccg ggc atg gcc gag cgc gta cag gct gcg gcc gag acc      336
Leu Ser Ala Pro Gly Met Ala Glu Arg Val Gln Ala Ala Ala Glu Thr
            100                 105                 110 ggc aag acg cag gcc cag ctg ttg tcg ggc gcc atc ggc ggt att gat      384
Gly Lys Thr Gln Ala Gln Leu Leu Ser Gly Ala Ile Gly Gly Ile Asp
        115                 120                 125 gcc ctg gct gcg gcg cgt gtc ggc ggc ctg gag acg gtg ctc tat acg      432
Ala Leu Ala Ala Ala Arg Val Gly Gly Leu Glu Thr Val Leu Tyr Thr
    130                 135                 140 ggc cgc aag ccg ccc aag gca tgg agc ggc acc ccg gcc gag cag gtc      480
Gly Arg Lys Pro Pro Lys Ala Trp Ser Gly Thr Pro Ala Glu Gln Val
145                 150                 155                 160 tgc gat ctg gac ggc ctg acc gag gcc ttc tgc att ttc gag ggc tcg      528
Cys Asp Leu Asp Gly Leu Thr Glu Ala Phe Cys Ile Phe Glu Gly Ser
                165                 170                 175 gcg cgc gag gcc gca cag ctc tat ccc aag aat gcg aat gtg gcg gcc      576
Ala Arg Glu Ala Ala Gln Leu Tyr Pro Lys Asn Ala Asn Val Ala Ala
            180                 185                 190 acc ttg tcg ctg gcc gga ctg ggg ctg gac aag acc atg gtg cgt ttg      624
Thr Leu Ser Leu Ala Gly Leu Gly Leu Asp Lys Thr Met Val Arg Leu
        195                 200                 205 ttt gcc gat cct ggc gtt cag gag aac gtg cac cag gtc gag gcg cgg      672
Phe Ala Asp Pro Gly Val Gln Glu Asn Val His Gln Val Glu Ala Arg
    210                 215                 220 ggt gct ttc ggc gcc atg gaa ctg acc atg cgc ggc aag cct ctg gcg      720
Gly Ala Phe Gly Ala Met Glu Leu Thr Met Arg Gly Lys Pro Leu Ala
225                 230                 235                 240 gcc aat ccc aag acc tcg gcg ctg acc gtg tac agc gtg gtg cgc gcc      768
Ala Asn Pro Lys Thr Ser Ala Leu Thr Val Tyr Ser Val Val Arg Ala
                245                 250                 255 gtg ctc aac aac gtg gcg ccg ctg gcc atc tga                          801
Val Leu Asn Asn Val Ala Pro Leu Ala Ile
            260                 265

<210> SEQ ID NO 102
<211> LENGTH: 266
<212> TYPE: PRT
<213> ORGANISM: Comamonas testosteroni

<400> SEQUENCE: 102

Met Lys Asn Ile Ala Leu Ile Gly Cys Gly Ala Ile Gly Ser Ser Val
 1               5                  10                  15

Leu Glu Leu Leu Ser Gly Asp Thr Gln Leu Gln Val Gly Trp Val Leu
                20                  25                  30

Val Pro Glu Ile Thr Pro Ala Val Arg Glu Thr Ala Ala Arg Leu Ala
            35                  40                  45

Pro Gln Ala Gln Leu Leu Gln Ala Leu Pro Gly Asp Ala Val Pro Asp
        50                  55                  60

Leu Leu Val Glu Cys Ala Gly His Ala Ala Ile Glu Glu His Val Leu
 65                  70                  75                  80

Pro Ala Leu Ala Arg Gly Ile Pro Ala Val Ile Ala Ser Ile Gly Ala
                 85                  90                  95

Leu Ser Ala Pro Gly Met Ala Glu Arg Val Gln Ala Ala Ala Glu Thr
            100                 105                 110
```

| | | | | | | | | | | | | |
|---|---|---|---|---|---|---|---|---|---|---|---|---|
| Gly | Lys | Thr | Gln | Ala | Gln | Leu | Leu | Ser | Gly | Ala | Ile | Gly | Gly | Ile | Asp |
| | | 115 | | | | 120 | | | | 125 | | |

Ala Leu Ala Ala Ala Arg Val Gly Gly Leu Glu Thr Val Leu Tyr Thr
    130                    135                  140

Gly Arg Lys Pro Pro Lys Ala Trp Ser Gly Thr Pro Ala Glu Gln Val
145                  150                  155                  160

Cys Asp Leu Asp Gly Leu Thr Glu Ala Phe Cys Ile Phe Glu Gly Ser
                165                  170                  175

Ala Arg Glu Ala Ala Gln Leu Tyr Pro Lys Asn Ala Asn Val Ala Ala
            180                  185                  190

Thr Leu Ser Leu Ala Gly Leu Gly Leu Asp Lys Thr Met Val Arg Leu
            195                  200                  205

Phe Ala Asp Pro Gly Val Gln Glu Asn Val His Gln Val Glu Ala Arg
         210                  215                  220

Gly Ala Phe Gly Ala Met Glu Leu Thr Met Arg Gly Lys Pro Leu Ala
225                  230                  235                  240

Ala Asn Pro Lys Thr Ser Ala Leu Thr Val Tyr Ser Val Val Arg Ala
            245                  250                  255

Val Leu Asn Asn Val Ala Pro Leu Ala Ile
         260                  265

<210> SEQ ID NO 103
<211> LENGTH: 807
<212> TYPE: DNA
<213> ORGANISM: Ralstonia eutropha
<220> FEATURE:
<221> NAME/KEY: CDS
<222> LOCATION: (1)..(807)

<400> SEQUENCE: 103

```
atg tcc atg ctg cat gtg tcc atg gtg gga tgc ggc gcg atc ggc cgt      48
Met Ser Met Leu His Val Ser Met Val Gly Cys Gly Ala Ile Gly Arg
1               5                  10                  15 ggc gtg ctg gag ctg ctg aag gcg gat ccc gat gtc gcg ttc gac gtg      96
Gly Val Leu Glu Leu Leu Lys Ala Asp Pro Asp Val Ala Phe Asp Val
                20                  25                  30 gtg atc gtg ccg gaa ggc cag atg gat gag gca cgc agc gcg ctg tcc     144
Val Ile Val Pro Glu Gly Gln Met Asp Glu Ala Arg Ser Ala Leu Ser
            35                  40                  45 gcg ctc gcg ccc aac gtc cgt gtg gcc acg ggc ctc gac ggt cag cgc     192
Ala Leu Ala Pro Asn Val Arg Val Ala Thr Gly Leu Asp Gly Gln Arg
        50                  55                  60 ccc gac ctg ctg gtc gag tgc gcg ggc cac cag gcg ctc gaa gag cac     240
Pro Asp Leu Leu Val Glu Cys Ala Gly His Gln Ala Leu Glu Glu His
65                  70                  75                  80 atc gtg ccg gcg ctc gag cgc ggc atc ccg tgc atg gtg gtg tcg gtc     288
Ile Val Pro Ala Leu Glu Arg Gly Ile Pro Cys Met Val Val Ser Val
                85                  90                  95 ggc gcg ctg tcc gag ccg ggc ctg gtc gag cgg ctg gaa gcc gcc gcg     336
Gly Ala Leu Ser Glu Pro Gly Leu Val Glu Arg Leu Glu Ala Ala Ala
                100                 105                 110 cgc cgc ggc aac acg caa gtg caa ctg ctg tcc ggc gcg atc ggt gcg     384
Arg Arg Gly Asn Thr Gln Val Gln Leu Leu Ser Gly Ala Ile Gly Ala
            115                 120                 125 atc gac gcg ctg gcc gcg gca cgt gtg ggc ggc ctc gac gag gtc atc     432
Ile Asp Ala Leu Ala Ala Ala Arg Val Gly Gly Leu Asp Glu Val Ile
        130                 135                 140 tac acc ggc cgc aag ccg gcg cgc gcc tgg acc ggc acg ccg gcc gcc     480
```

```
Tyr Thr Gly Arg Lys Pro Ala Arg Ala Trp Thr Gly Thr Pro Ala Ala
145                 150                 155                 160 gag ctg ttc gac ctg gaa gcc ctg acc gag ccc acg gtg atc ttc gaa     528
Glu Leu Phe Asp Leu Glu Ala Leu Thr Glu Pro Thr Val Ile Phe Glu
                165                 170                 175 ggc acc gcg cgc gac gcg gcc cgc ctg tac ccg aag aac gcc aac gtg     576
Gly Thr Ala Arg Asp Ala Ala Arg Leu Tyr Pro Lys Asn Ala Asn Val
            180                 185                 190 gcg gcc acg gta tcg ctg gcc ggc ctc ggg ctg gat cgc act tcg gtg     624
Ala Ala Thr Val Ser Leu Ala Gly Leu Gly Leu Asp Arg Thr Ser Val
        195                 200                 205 cgg ctg ctg gcc gac ccg aat gcc gtg gag aac gtc cac cac atc gaa     672
Arg Leu Leu Ala Asp Pro Asn Ala Val Glu Asn Val His His Ile Glu
    210                 215                 220 gca cgt ggc gcg ttc ggc ggc ttc gag ctg acc atg cgc ggc aag ccg     720
Ala Arg Gly Ala Phe Gly Gly Phe Glu Leu Thr Met Arg Gly Lys Pro
225                 230                 235                 240 ctc gcg gcc aac ccc aag act tcg gcg ctg acg gtg ttc agc gtg gtg     768
Leu Ala Ala Asn Pro Lys Thr Ser Ala Leu Thr Val Phe Ser Val Val
                245                 250                 255 cgc gca ctg ggc aac cgg gcg cac gcg gta tcg atc tga                 807
Arg Ala Leu Gly Asn Arg Ala His Ala Val Ser Ile
            260                 265

<210> SEQ ID NO 104
<211> LENGTH: 268
<212> TYPE: PRT
<213> ORGANISM: Ralstonia eutropha

<400> SEQUENCE: 104

Met Ser Met Leu His Val Ser Met Val Gly Cys Gly Ala Ile Gly Arg
1               5                   10                  15

Gly Val Leu Glu Leu Leu Lys Ala Asp Pro Asp Val Ala Phe Asp Val
            20                  25                  30

Val Ile Val Pro Glu Gly Gln Met Asp Glu Ala Arg Ser Ala Leu Ser
        35                  40                  45

Ala Leu Ala Pro Asn Val Arg Val Ala Thr Gly Leu Asp Gly Gln Arg
    50                  55                  60

Pro Asp Leu Leu Val Glu Cys Ala Gly His Gln Ala Leu Glu Glu His
65                  70                  75                  80

Ile Val Pro Ala Leu Glu Arg Gly Ile Pro Cys Met Val Val Ser Val
                85                  90                  95

Gly Ala Leu Ser Glu Pro Gly Leu Val Glu Arg Leu Glu Ala Ala Ala
            100                 105                 110

Arg Arg Gly Asn Thr Gln Val Gln Leu Leu Ser Gly Ala Ile Gly Ala
        115                 120                 125

Ile Asp Ala Leu Ala Ala Ala Arg Val Gly Gly Leu Asp Glu Val Ile
    130                 135                 140

Tyr Thr Gly Arg Lys Pro Ala Arg Ala Trp Thr Gly Thr Pro Ala Ala
145                 150                 155                 160

Glu Leu Phe Asp Leu Glu Ala Leu Thr Glu Pro Thr Val Ile Phe Glu
                165                 170                 175

Gly Thr Ala Arg Asp Ala Ala Arg Leu Tyr Pro Lys Asn Ala Asn Val
            180                 185                 190

Ala Ala Thr Val Ser Leu Ala Gly Leu Gly Leu Asp Arg Thr Ser Val
        195                 200                 205

Arg Leu Leu Ala Asp Pro Asn Ala Val Glu Asn Val His His Ile Glu
```

```
                    210                 215                 220
Ala Arg Gly Ala Phe Gly Gly Phe Glu Leu Thr Met Arg Gly Lys Pro
225                 230                 235                 240

Leu Ala Ala Asn Pro Lys Thr Ser Ala Leu Thr Val Phe Ser Val Val
                245                 250                 255

Arg Ala Leu Gly Asn Arg Ala His Ala Val Ser Ile
            260                 265

<210> SEQ ID NO 105
<211> LENGTH: 804
<212> TYPE: DNA
<213> ORGANISM: Pseudomonas aeruginosa
<220> FEATURE:
<221> NAME/KEY: CDS
<222> LOCATION: (1)..(804)

<400> SEQUENCE: 105 atg ctg aat atc gtc atg atc ggc tgc ggc gcc atc ggc gcc ggc gtc      48
Met Leu Asn Ile Val Met Ile Gly Cys Gly Ala Ile Gly Ala Gly Val
1               5                   10                  15 ctg gaa ctg ttg gag aac gat ccg caa ctg agg gtc gat gcg gtg atc      96
Leu Glu Leu Leu Glu Asn Asp Pro Gln Leu Arg Val Asp Ala Val Ile
                20                  25                  30 gtt cct cgc gac tcc gag acc cag gtc cgc cat cgc ctg gcc agc ctg     144
Val Pro Arg Asp Ser Glu Thr Gln Val Arg His Arg Leu Ala Ser Leu
            35                  40                  45 cgc cgg ccg ccg cgg gta ctc agc gcg ctg ccg gcc gga gag cgc ccc     192
Arg Arg Pro Pro Arg Val Leu Ser Ala Leu Pro Ala Gly Glu Arg Pro
        50                  55                  60 gat ctt ctg gtg gag tgc gcc ggg cac cgc gcc atc gag cag cac gtg     240
Asp Leu Leu Val Glu Cys Ala Gly His Arg Ala Ile Glu Gln His Val
65                  70                  75                  80 ctg ccg gcg ctg gcc caa ggc att ccc tgc ctg gtg gtc tcg gtg ggc     288
Leu Pro Ala Leu Ala Gln Gly Ile Pro Cys Leu Val Val Ser Val Gly
                85                  90                  95 gcg ctg tcc gag ccg ggc ctg gtg gag cgc ctg gaa gcc gcg gcg cag     336
Ala Leu Ser Glu Pro Gly Leu Val Glu Arg Leu Glu Ala Ala Ala Gln
                100                 105                 110 gcc gga ggc agc cgc atc gag ctg ctg ccc ggc gcc atc ggc gcc atc     384
Ala Gly Gly Ser Arg Ile Glu Leu Leu Pro Gly Ala Ile Gly Ala Ile
            115                 120                 125 gat gcg ctg tcg gcg gcc agg gtc ggt ggc ctc gaa tcg gtg cgc tac     432
Asp Ala Leu Ser Ala Ala Arg Val Gly Gly Leu Glu Ser Val Arg Tyr
        130                 135                 140 acc ggg cgc aag ccg gcg agc gcc tgg ctg ggc acg cca ggc gag acg     480
Thr Gly Arg Lys Pro Ala Ser Ala Trp Leu Gly Thr Pro Gly Glu Thr
145                 150                 155                 160 gtc tgc gac ctg cag cgc ctg gag aag gcg cgg gtg atc ttc gac ggc     528
Val Cys Asp Leu Gln Arg Leu Glu Lys Ala Arg Val Ile Phe Asp Gly
                165                 170                 175 agc gcc cgc gag gcg gcg cgg ctc tat ccg aag aac gcc aat gtc gcc     576
Ser Ala Arg Glu Ala Ala Arg Leu Tyr Pro Lys Asn Ala Asn Val Ala
                180                 185                 190 gcc acc ctg tcg ctc gcc ggc ctc ggc ctg gac cgc acc cag gtg cgc     624
Ala Thr Leu Ser Leu Ala Gly Leu Gly Leu Asp Arg Thr Gln Val Arg
            195                 200                 205 ctg atc gcc gac ccc gaa agc tgc gag aac gtg cac cag gtg gaa gcc     672
Leu Ile Ala Asp Pro Glu Ser Cys Glu Asn Val His Gln Val Glu Ala
        210                 215                 220 agc ggc gcc ttc ggc ggc ttc gaa ctg acc ttg cgc ggc aaa ccg ctg     720
```

```
Ser Gly Ala Phe Gly Gly Phe Glu Leu Thr Leu Arg Gly Lys Pro Leu
225                 230                 235                 240 gcg gcc aac ccg aag aca tcg gcg ctg acc gtg tac agc gtg gtc cga      768
Ala Ala Asn Pro Lys Thr Ser Ala Leu Thr Val Tyr Ser Val Val Arg
                245                 250                 255 gcg ttg ggc aac cac gcc cac gcg att tcg atc tag                      804
Ala Leu Gly Asn His Ala His Ala Ile Ser Ile
                260                 265
```

<210> SEQ ID NO 106
<211> LENGTH: 267
<212> TYPE: PRT
<213> ORGANISM: Pseudomonas aeruginosa

<400> SEQUENCE: 106

```
Met Leu Asn Ile Val Met Ile Gly Cys Gly Ala Ile Gly Ala Gly Val
1               5                   10                  15

Leu Glu Leu Leu Glu Asn Asp Pro Gln Leu Arg Val Asp Ala Val Ile
                20                  25                  30

Val Pro Arg Asp Ser Glu Thr Gln Val Arg His Arg Leu Ala Ser Leu
            35                  40                  45

Arg Arg Pro Pro Arg Val Leu Ser Ala Leu Pro Ala Gly Glu Arg Pro
        50                  55                  60

Asp Leu Leu Val Glu Cys Ala Gly His Arg Ala Ile Glu Gln His Val
65                  70                  75                  80

Leu Pro Ala Leu Ala Gln Gly Ile Pro Cys Leu Val Val Ser Val Gly
                85                  90                  95

Ala Leu Ser Glu Pro Gly Leu Val Glu Arg Leu Glu Ala Ala Ala Gln
                100                 105                 110

Ala Gly Gly Ser Arg Ile Glu Leu Leu Pro Gly Ala Ile Gly Ala Ile
            115                 120                 125

Asp Ala Leu Ser Ala Ala Arg Val Gly Gly Leu Glu Ser Val Arg Tyr
        130                 135                 140

Thr Gly Arg Lys Pro Ala Ser Ala Trp Leu Gly Thr Pro Gly Glu Thr
145                 150                 155                 160

Val Cys Asp Leu Gln Arg Leu Glu Lys Ala Arg Val Ile Phe Asp Gly
                165                 170                 175

Ser Ala Arg Glu Ala Ala Arg Leu Tyr Pro Lys Asn Ala Asn Val Ala
                180                 185                 190

Ala Thr Leu Ser Leu Ala Gly Leu Gly Leu Asp Arg Thr Gln Val Arg
            195                 200                 205

Leu Ile Ala Asp Pro Glu Ser Cys Glu Asn Val His Gln Val Glu Ala
        210                 215                 220

Ser Gly Ala Phe Gly Gly Phe Glu Leu Thr Leu Arg Gly Lys Pro Leu
225                 230                 235                 240

Ala Ala Asn Pro Lys Thr Ser Ala Leu Thr Val Tyr Ser Val Val Arg
                245                 250                 255

Ala Leu Gly Asn His Ala His Ala Ile Ser Ile
                260                 265
```

<210> SEQ ID NO 107
<211> LENGTH: 828
<212> TYPE: DNA
<213> ORGANISM: Burkholderia cenocepacia
<220> FEATURE:
<221> NAME/KEY: CDS
<222> LOCATION: (1)..(828)

```
<400> SEQUENCE: 107 atg cat aac ggg caa aag cgg gcg cgc gcc ccc gtc gac gtc gcg atg        48
Met His Asn Gly Gln Lys Arg Ala Arg Ala Pro Val Asp Val Ala Met
1               5                   10                  15 atc ggc ttc ggc gcg atc ggc gcg gcc gtg tac cgc gcg gtc gag cac        96
Ile Gly Phe Gly Ala Ile Gly Ala Ala Val Tyr Arg Ala Val Glu His
                20                  25                  30 gat gcg tcg ttg cgc gtc gcg cac gtg atc gtg ccg gaa cac cag cgc       144
Asp Ala Ser Leu Arg Val Ala His Val Ile Val Pro Glu His Gln Arg
            35                  40                  45 gcg gcg gtg cag cgc gag ctc ggc ggc gcg gtg gag gtc gtg tcg tcg       192
Ala Ala Val Gln Arg Glu Leu Gly Gly Ala Val Glu Val Val Ser Ser
        50                  55                  60 gtc gac gcg ctg gct cgc cgc ccg gag ttc gcg ctc gaa tgc gcg ggc       240
Val Asp Ala Leu Ala Arg Arg Pro Glu Phe Ala Leu Glu Cys Ala Gly
65                  70                  75                  80 cac ggc gcg ctc gtc gat cac gtc gtg ccg ctg ctg aag gcc ggc acc       288
His Gly Ala Leu Val Asp His Val Val Pro Leu Leu Lys Ala Gly Thr
                85                  90                  95 gat tgc gcg gtc gcg tcg atc ggc gcg ctg tcc gat ctc gcg ctg ctc       336
Asp Cys Ala Val Ala Ser Ile Gly Ala Leu Ser Asp Leu Ala Leu Leu
            100                 105                 110 gac gtg ctg tcg cgg gcc gcc gac gaa ggc ggc acg act gtg acg ctg       384
Asp Val Leu Ser Arg Ala Ala Asp Glu Gly Gly Thr Thr Val Thr Leu
        115                 120                 125 ctg tcc ggc gcg atc ggc ggc atc gac gcg ctg gcg tcc gcg aag gag       432
Leu Ser Gly Ala Ile Gly Gly Ile Asp Ala Leu Ala Ser Ala Lys Glu
    130                 135                 140 ggc ggg ctc gac gaa gtg cgg tac gtc ggc cgc aag ccg ccg ctc ggc       480
Gly Gly Leu Asp Glu Val Arg Tyr Val Gly Arg Lys Pro Pro Leu Gly
145                 150                 155                 160 tgg ctc ggc acg ccg gcc gag gaa ttg tgc gac ctg cgc gcg atg acc       528
Trp Leu Gly Thr Pro Ala Glu Glu Leu Cys Asp Leu Arg Ala Met Thr
                165                 170                 175 gag gaa aag gtg atc ttc gaa ggc agc gcg cgc gac gcc gcg cgg ctg       576
Glu Glu Lys Val Ile Phe Glu Gly Ser Ala Arg Asp Ala Ala Arg Leu
            180                 185                 190 tat ccg aag aac gcg aac gtc gcg gcg acg gtg gcg ctc gcg ggc ctc       624
Tyr Pro Lys Asn Ala Asn Val Ala Ala Thr Val Ala Leu Ala Gly Leu
        195                 200                 205 ggc ctc gac gcg acg cac gtg cgg ctg atc gcc gat ccg gcc gtc gag       672
Gly Leu Asp Ala Thr His Val Arg Leu Ile Ala Asp Pro Ala Val Glu
    210                 215                 220 cgc aac gtg cac cgc atc acc gcg cgc ggt gca ttc ggc gag atg tcg       720
Arg Asn Val His Arg Ile Thr Ala Arg Gly Ala Phe Gly Glu Met Ser
225                 230                 235                 240 ctg gaa atg agc ggc aag ccg ctg ccc gac aac ccg aag acg tcc gcg       768
Leu Glu Met Ser Gly Lys Pro Leu Pro Asp Asn Pro Lys Thr Ser Ala
                245                 250                 255 ctg acg gcg tac agc gcg att cgc gcg ctg cgc aac cgc gcg gcc tgc       816
Leu Thr Ala Tyr Ser Ala Ile Arg Ala Leu Arg Asn Arg Ala Ala Cys
            260                 265                 270 tgc gtg atc tga                                                       828
Cys Val Ile
        275

<210> SEQ ID NO 108
<211> LENGTH: 275
<212> TYPE: PRT
<213> ORGANISM: Burkholderia cenocepacia
```

-continued

<400> SEQUENCE: 108

```
Met His Asn Gly Gln Lys Arg Ala Arg Ala Pro Val Asp Val Ala Met
1               5                   10                  15

Ile Gly Phe Gly Ala Ile Gly Ala Ala Val Tyr Arg Ala Val Glu His
            20                  25                  30

Asp Ala Ser Leu Arg Val Ala His Val Ile Val Pro Glu His Gln Arg
        35                  40                  45

Ala Ala Val Gln Arg Glu Leu Gly Gly Ala Val Glu Val Val Ser Ser
    50                  55                  60

Val Asp Ala Leu Ala Arg Arg Pro Glu Phe Ala Leu Glu Cys Ala Gly
65                  70                  75                  80

His Gly Ala Leu Val Asp His Val Val Pro Leu Leu Lys Ala Gly Thr
                85                  90                  95

Asp Cys Ala Val Ala Ser Ile Gly Ala Leu Ser Asp Leu Ala Leu Leu
            100                 105                 110

Asp Val Leu Ser Arg Ala Ala Asp Glu Gly Gly Thr Thr Val Thr Leu
        115                 120                 125

Leu Ser Gly Ala Ile Gly Gly Ile Asp Ala Leu Ala Ser Ala Lys Glu
    130                 135                 140

Gly Gly Leu Asp Glu Val Arg Tyr Val Gly Arg Lys Pro Pro Leu Gly
145                 150                 155                 160

Trp Leu Gly Thr Pro Ala Glu Glu Leu Cys Asp Leu Arg Ala Met Thr
                165                 170                 175

Glu Glu Lys Val Ile Phe Glu Gly Ser Ala Arg Asp Ala Ala Arg Leu
            180                 185                 190

Tyr Pro Lys Asn Ala Asn Val Ala Ala Thr Val Ala Leu Ala Gly Leu
        195                 200                 205

Gly Leu Asp Ala Thr His Val Arg Leu Ile Ala Asp Pro Ala Val Glu
    210                 215                 220

Arg Asn Val His Arg Ile Thr Ala Arg Gly Ala Phe Gly Glu Met Ser
225                 230                 235                 240

Leu Glu Met Ser Gly Lys Pro Leu Pro Asp Asn Pro Lys Thr Ser Ala
                245                 250                 255

Leu Thr Ala Tyr Ser Ala Ile Arg Ala Leu Arg Asn Arg Ala Ala Cys
            260                 265                 270

Cys Val Ile
        275

<210> SEQ ID NO 109
<211> LENGTH: 774
<212> TYPE: DNA
<213> ORGANISM: Rhodopseudomonas palustris
<220> FEATURE:
<221> NAME/KEY: CDS
<222> LOCATION: (1)..(774)

<400> SEQUENCE: 109 ttg aag atc gcc gtg atc ggc tac gga gcc atc gga agg ttc ttg atc      48
Leu Lys Ile Ala Val Ile Gly Tyr Gly Ala Ile Gly Arg Phe Leu Ile
1               5                   10                  15 gag cag ctc gat gcc gtt ccg gat ttc gag atc gca gcg gtc tat tcc      96
Glu Gln Leu Asp Ala Val Pro Asp Phe Glu Ile Ala Ala Val Tyr Ser
            20                  25                  30 gtg ccg gcg cca ccc gat cgc gcc gag cgc gtg gtc gac gat ctc gac     144
Val Pro Ala Pro Pro Asp Arg Ala Glu Arg Val Val Asp Asp Leu Asp
        35                  40                  45
```

```
gcg ctg ctt gcg acc cgg ccc gac ctg gtg gtc gaa tgc gcc ggc cat      192
Ala Leu Leu Ala Thr Arg Pro Asp Leu Val Val Glu Cys Ala Gly His
 50                  55                  60 cgc gcc ctg tcg gaa tgc ggc gag gcc gtt ctt cgc agc ggc gtc gat      240
Arg Ala Leu Ser Glu Cys Gly Glu Ala Val Leu Arg Ser Gly Val Asp
 65                  70                  75                  80 ctg ttg gtg gtc tcg gtc ggc gcc ctc gcc gat ccc gcg ctc gag cag      288
Leu Leu Val Val Ser Val Gly Ala Leu Ala Asp Pro Ala Leu Glu Gln
                 85                  90                  95 caa tta cgg aca gcc gcc cgg cac ggg ggc cgc ctg ctg atc gcc gcg      336
Gln Leu Arg Thr Ala Ala Arg His Gly Gly Arg Leu Leu Ile Ala Ala
            100                 105                 110 ggc gcc ttg agc ggc ctc gac gca ctc agc acg gcg cgc gag gcc ggc      384
Gly Ala Leu Ser Gly Leu Asp Ala Leu Ser Thr Ala Arg Glu Ala Gly
        115                 120                 125 ctg gat tcg gtg tcc tat gtc ggc aag aag gcg cca gcg gct tgg acc      432
Leu Asp Ser Val Ser Tyr Val Gly Lys Lys Ala Pro Ala Ala Trp Thr
130                 135                 140 aac acg ccc gcg gaa gac atg gtg gac ctg aca tcg atc acg tcg gcc      480
Asn Thr Pro Ala Glu Asp Met Val Asp Leu Thr Ser Ile Thr Ser Ala
145                 150                 155                 160 gtg aca ttc ctc gaa tgc gac gcg cgt aca gcc gcg ctc cgc ttc cca      528
Val Thr Phe Leu Glu Cys Asp Ala Arg Thr Ala Ala Leu Arg Phe Pro
                165                 170                 175 cag aac gcc aac gtg gtc gcg gcc atc gca ctg gcg ggg ctc ggc ttc      576
Gln Asn Ala Asn Val Val Ala Ala Ile Ala Leu Ala Gly Leu Gly Phe
            180                 185                 190 gag cgc acg cag gtg agc ctc gtc gtc gat ccg gcg tcg aac ggc aac      624
Glu Arg Thr Gln Val Ser Leu Val Val Asp Pro Ala Ser Asn Gly Asn
        195                 200                 205 aat cac tcc ttc gta gcc cgc ggc gca ttc ggc gag atc gcc atg acg      672
Asn His Ser Phe Val Ala Arg Gly Ala Phe Gly Glu Ile Ala Met Thr
210                 215                 220 acg cgc tcg gcc acc ctg cct gcc aat ccc aag aca tcc atg ctg gcg      720
Thr Arg Ser Ala Thr Leu Pro Ala Asn Pro Lys Thr Ser Met Leu Ala
225                 230                 235                 240 ccc tac agt ctc gtg cag acc atc aag aag cac gcc ggt ttg atc atc      768
Pro Tyr Ser Leu Val Gln Thr Ile Lys Lys His Ala Gly Leu Ile Ile
                245                 250                 255 gtt tga                                                              774
Val

<210> SEQ ID NO 110
<211> LENGTH: 257
<212> TYPE: PRT
<213> ORGANISM: Rhodopseudomonas palustris

<400> SEQUENCE: 110

Leu Lys Ile Ala Val Ile Gly Tyr Gly Ala Ile Gly Arg Phe Leu Ile
 1               5                  10                  15

Glu Gln Leu Asp Ala Val Pro Asp Phe Glu Ile Ala Ala Val Tyr Ser
             20                  25                  30

Val Pro Ala Pro Pro Asp Arg Ala Glu Arg Val Val Asp Asp Leu Asp
         35                  40                  45

Ala Leu Leu Ala Thr Arg Pro Asp Leu Val Val Glu Cys Ala Gly His
     50                  55                  60

Arg Ala Leu Ser Glu Cys Gly Glu Ala Val Leu Arg Ser Gly Val Asp
 65                  70                  75                  80
```

```
Leu Leu Val Val Ser Val Gly Ala Leu Ala Asp Pro Ala Leu Glu Gln
             85                  90                  95

Gln Leu Arg Thr Ala Ala Arg His Gly Gly Arg Leu Leu Ile Ala Ala
            100                 105                 110

Gly Ala Leu Ser Gly Leu Asp Ala Leu Ser Thr Ala Arg Glu Ala Gly
        115                 120                 125

Leu Asp Ser Val Ser Tyr Val Gly Lys Lys Ala Pro Ala Ala Trp Thr
    130                 135                 140

Asn Thr Pro Ala Glu Asp Met Val Asp Leu Thr Ser Ile Thr Ser Ala
145                 150                 155                 160

Val Thr Phe Leu Glu Cys Asp Ala Arg Thr Ala Ala Leu Arg Phe Pro
                165                 170                 175

Gln Asn Ala Asn Val Val Ala Ala Ile Ala Leu Ala Gly Leu Gly Phe
            180                 185                 190

Glu Arg Thr Gln Val Ser Leu Val Val Asp Pro Ala Ser Asn Gly Asn
        195                 200                 205

Asn His Ser Phe Val Ala Arg Gly Ala Phe Gly Glu Ile Ala Met Thr
    210                 215                 220

Thr Arg Ser Ala Thr Leu Pro Ala Asn Pro Lys Thr Ser Met Leu Ala
225                 230                 235                 240

Pro Tyr Ser Leu Val Gln Thr Ile Lys Lys His Ala Gly Leu Ile Ile
                245                 250                 255

Val

<210> SEQ ID NO 111
<211> LENGTH: 819
<212> TYPE: DNA
<213> ORGANISM: Rhodopseudomonas palustris
<220> FEATURE:
<221> NAME/KEY: CDS
<222> LOCATION: (1)..(819)

<400> SEQUENCE: 111 atg cgc agc ggc cgg gcc ccg cag cgc gtc gcc att gcc ggg ctc ggc     48
Met Arg Ser Gly Arg Ala Pro Gln Arg Val Ala Ile Ala Gly Leu Gly
1               5                  10                  15 gcc atc ggc aag gcg atc gcg cgt gaa ctc gat cgc ggg ctc gac ggg     96
Ala Ile Gly Lys Ala Ile Ala Arg Glu Leu Asp Arg Gly Leu Asp Gly
            20                  25                  30 ctg acg ctc ggc gcc gtc gcc agc ggc gac ccg gag aag cat cgc gcc    144
Leu Thr Leu Gly Ala Val Ala Ser Gly Asp Pro Glu Lys His Arg Ala
        35                  40                  45 ttc ctc gac ggc ctg cgg acg acg ccg gtg gtc ccg ctg gat cag        192
Phe Leu Asp Gly Leu Arg Thr Thr Pro Val Val Pro Leu Asp Gln
    50                  55                  60 ttg cac gcc cac gca gac ctc gtg atc gag gcg gcg ccg agc agg ctg    240
Leu His Ala His Ala Asp Leu Val Ile Glu Ala Ala Pro Ser Arg Leu
65                  70                  75                  80 ctg cgc gcg atc gtc gag ccg ttc gtc agc cgc ggc agg acc gcg atc    288
Leu Arg Ala Ile Val Glu Pro Phe Val Ser Arg Gly Arg Thr Ala Ile
                85                  90                  95 gtg ctc agc gcc gcg gcg ctg ctg cag aac gag gac ctg atc gat ctg    336
Val Leu Ser Ala Ala Ala Leu Leu Gln Asn Glu Asp Leu Ile Asp Leu
            100                 105                 110 gcc aat ctg aac ggc ggc cag atc atc gtg ccg acc ggc gcg ctg atc    384
Ala Asn Leu Asn Gly Gly Gln Ile Ile Val Pro Thr Gly Ala Leu Ile
        115                 120                 125 ggg ctc gac gcc gtc act gcc gcc gcc gtc ggc acg att cat tcg gtg    432
```

```
Gly Leu Asp Ala Val Thr Ala Ala Val Gly Thr Ile His Ser Val
    130                 135                 140 cgg atg atc acc cgc aag ccg gtc gat ggc ctg cgc ggc gcg ccg ttc      480
Arg Met Ile Thr Arg Lys Pro Val Asp Gly Leu Arg Gly Ala Pro Phe
145                 150                 155                 160 atc gtc gac aac ggc atc gac ctc gac gga ttg cgc gaa ccg ctg aaa      528
Ile Val Asp Asn Gly Ile Asp Leu Asp Gly Leu Arg Glu Pro Leu Lys
                    165                 170                 175 ctg ttc gaa ggc acc gcg cgc gaa gcc ggc aag ggc ttt ccg gcc aat      576
Leu Phe Glu Gly Thr Ala Arg Glu Ala Gly Lys Gly Phe Pro Ala Asn
                180                 185                 190 ctc aac gtc gcg gtg gcg ctg tcg ctg gcc ggc atc ggg ccg gat cgc      624
Leu Asn Val Ala Val Ala Leu Ser Leu Ala Gly Ile Gly Pro Asp Arg
            195                 200                 205 acc atg gtg gag atc tgg gcc gat ccg ggc gtc acc cgc aac acc cac      672
Thr Met Val Glu Ile Trp Ala Asp Pro Gly Val Thr Arg Asn Thr His
        210                 215                 220 cgc atc gag gtc gat gcg gat tcg gcg cgg ttc gcg atg acg atc gag      720
Arg Ile Glu Val Asp Ala Asp Ser Ala Arg Phe Ala Met Thr Ile Glu
225                 230                 235                 240 aac gtg ccg tcc gac aat ccc cgc acc ggc ctg atc acg ccg ctg tcg      768
Asn Val Pro Ser Asp Asn Pro Arg Thr Gly Leu Ile Thr Pro Leu Ser
                245                 250                 255 gtg atc gcg ctg ctg cgc aag caa tcc gcc gcg ctg cgg gtc ggg acc      816
Val Ile Ala Leu Leu Arg Lys Gln Ser Ala Ala Leu Arg Val Gly Thr
                260                 265                 270 tga                                                                   819

<210> SEQ ID NO 112
<211> LENGTH: 272
<212> TYPE: PRT
<213> ORGANISM: Rhodopseudomonas palustris

<400> SEQUENCE: 112

Met Arg Ser Gly Arg Ala Pro Gln Arg Val Ala Ile Ala Gly Leu Gly
1               5                   10                  15

Ala Ile Gly Lys Ala Ile Ala Arg Glu Leu Asp Arg Gly Leu Asp Gly
                20                  25                  30

Leu Thr Leu Gly Ala Val Ala Ser Gly Asp Pro Glu Lys His Arg Ala
            35                  40                  45

Phe Leu Asp Gly Leu Arg Thr Thr Pro Pro Val Val Pro Leu Asp Gln
        50                  55                  60

Leu His Ala His Ala Asp Leu Val Ile Glu Ala Ala Pro Ser Arg Leu
65                  70                  75                  80

Leu Arg Ala Ile Val Glu Pro Phe Val Ser Arg Gly Arg Thr Ala Ile
                85                  90                  95

Val Leu Ser Ala Ala Leu Leu Gln Asn Glu Asp Leu Ile Asp Leu
                100                 105                 110

Ala Asn Leu Asn Gly Gly Gln Ile Ile Val Pro Thr Gly Ala Leu Ile
            115                 120                 125

Gly Leu Asp Ala Val Thr Ala Ala Val Gly Thr Ile His Ser Val
        130                 135                 140

Arg Met Ile Thr Arg Lys Pro Val Asp Gly Leu Arg Gly Ala Pro Phe
145                 150                 155                 160

Ile Val Asp Asn Gly Ile Asp Leu Asp Gly Leu Arg Glu Pro Leu Lys
                165                 170                 175

Leu Phe Glu Gly Thr Ala Arg Glu Ala Gly Lys Gly Phe Pro Ala Asn
```

```
            180                 185                 190
Leu Asn Val Ala Val Ala Leu Ser Leu Ala Gly Ile Gly Pro Asp Arg
            195                 200                 205

Thr Met Val Glu Ile Trp Ala Asp Pro Gly Val Thr Arg Asn Thr His
    210                 215                 220

Arg Ile Glu Val Asp Ala Asp Ser Ala Arg Phe Ala Met Thr Ile Glu
225                 230                 235                 240

Asn Val Pro Ser Asp Asn Pro Arg Thr Gly Leu Ile Thr Pro Leu Ser
                245                 250                 255

Val Ile Ala Leu Leu Arg Lys Gln Ser Ala Ala Leu Arg Val Gly Thr
            260                 265                 270

<210> SEQ ID NO 113
<211> LENGTH: 280
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (44)..(48)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(63)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(73)
<223> OTHER INFORMATION: Xaa can be any naturally occurring amino acid
<220> FEATURE:
<221> NAME/KEY: misc_feature
<222> LOCATION: (84)..(84)
```

-continued

```
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (172)..(173)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (183)..(184)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
```

```
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid

<400> SEQUENCE: 113

Xaa Xaa Xaa Xaa Xaa Xaa Xaa Xaa Xaa Xaa Leu Xaa Ile Ala Met
1               5                   10                  15

Ile Gly Cys Gly Ala Ile Gly Ala Ser Val Leu Glu Leu Leu Xaa Gly
                20                  25                  30

Asp Xaa Xaa Leu Xaa Val Xaa Xaa Val Ile Val Xaa Xaa Xaa Xaa
        35                  40                  45

Asp Xaa Xaa Arg Xaa Xaa Leu Ala Xaa Leu Xaa Xaa Xaa Xaa Xaa Val
50                  55                  60

Leu Xaa Ala Leu Xaa Xaa Xaa Xaa Pro Asp Leu Val Val Glu Cys
65                  70                  75                  80

Ala Gly His Xaa Ala Ile Xaa Glu His Val Leu Pro Ala Leu Xaa Arg
                85                  90                  95

Gly Ile Pro Xaa Val Val Val Ser Val Gly Ala Leu Ser Asp Pro Gly
                100                 105                 110

Leu Xaa Glu Xaa Leu Xaa Ala Ala Ala Xaa Xaa Gly Gly Thr Gln Val
            115                 120                 125

Xaa Leu Leu Ser Gly Ala Ile Gly Gly Ile Asp Ala Leu Ala Ala Ala
130                 135                 140

Arg Val Gly Gly Leu Asp Ser Val Val Tyr Thr Gly Arg Lys Pro Pro
145                 150                 155                 160

Xaa Ala Trp Xaa Gly Thr Pro Ala Glu Xaa Val Xaa Xaa Cys Asp Leu
                165                 170                 175

Xaa Ser Leu Thr Glu Ala Xaa Xaa Ile Phe Glu Gly Ser Ala Arg Glu
            180                 185                 190

Ala Ala Arg Leu Tyr Pro Lys Asn Ala Asn Val Ala Ala Thr Leu Ser
            195                 200                 205

Leu Ala Gly Leu Gly Leu Asp Arg Thr Xaa Val Arg Leu Ile Ala Asp
        210                 215                 220

Pro Ala Val Xaa Glu Asn Val His Xaa Val Xaa Ala Arg Gly Ala Phe
225                 230                 235                 240

Gly Xaa Phe Glu Leu Thr Met Arg Gly Lys Pro Leu Ala Ala Asn Pro
            245                 250                 255

Lys Thr Ser Ala Leu Thr Val Tyr Ser Val Val Arg Ala Leu Xaa Asn
            260                 265                 270

Xaa Ala Xaa Ala Ile Xaa Ile Xaa
        275                 280
```